(12) United States Patent
Chilkoti et al.

(10) Patent No.: US 11,648,200 B2
(45) Date of Patent: May 16, 2023

(54) GENETICALLY ENCODED LIPID-POLYPEPTIDE HYBRID BIOMATERIALS THAT EXHIBIT TEMPERATURE TRIGGERED HIERARCHICAL SELF-ASSEMBLY

(71) Applicant: Duke University, Durham, NC (US)

(72) Inventors: Ashutosh Chilkoti, Durham, NC (US); Davoud Mozhdehi, Durham, NC (US); Kelli M. Luginbuhl, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/477,229

(22) PCT Filed: Jan. 12, 2018

(86) PCT No.: PCT/US2018/013611
§ 371 (c)(1),
(2) Date: Jul. 11, 2019

(87) PCT Pub. No.: WO2018/132732
PCT Pub. Date: Jul. 19, 2018

(65) Prior Publication Data
US 2019/0328662 A1    Oct. 31, 2019

Related U.S. Application Data

(60) Provisional application No. 62/445,504, filed on Jan. 12, 2017, provisional application No. 62/479,977, filed on Mar. 31, 2017.

(51) Int. Cl.
| | |
|---|---|
| *A61K 47/42* | (2017.01) |
| *C07K 14/78* | (2006.01) |
| *A61K 38/00* | (2006.01) |
| *A61K 9/107* | (2006.01) |
| *C12N 1/20* | (2006.01) |
| *C12N 9/10* | (2006.01) |
| *C12P 21/00* | (2006.01) |

(52) U.S. Cl.
CPC ............ *A61K 9/1075* (2013.01); *A61K 47/42* (2013.01); *C07K 14/78* (2013.01); *C12N 1/20* (2013.01); *C12N 9/1029* (2013.01); *C12P 21/00* (2013.01); *C12Y 203/01097* (2013.01); *A61K 38/00* (2013.01); *C07K 2319/033* (2013.01); *C07K 2319/735* (2013.01); *C07K 2319/90* (2013.01); *C12N 2501/00* (2013.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Felgner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |

(Continued)

FOREIGN PATENT DOCUMENTS

| | | |
|---|---|---|
| AU | 2007265628 B2 | 12/2012 |
| CA | 2327325 A1 | 11/1999 |

(Continued)

OTHER PUBLICATIONS

Marilyn D. Resh, Curr Biol. May 20, 2013; 23(10): R431-R435. (Year: 2013).*

Radzicka, Comparing the Polarities of the Amino Acids: Side-Chain Distribution Coefficients between the Vapor Phase, Cyclohexane, 1—Octanol, and Neutral Aqueous Solution, Biochemistry 1988, 27, 1664-1670 (Year: 1988).*

(Continued)

*Primary Examiner* — Thomas S Heard

(74) *Attorney, Agent, or Firm* — Michael Best & Friedrich LLP

(57) ABSTRACT

Disclosed herein are conjugates including a fatty acid, a self-assembly domain, and a polypeptide, where the conjugates have phase transition behavior. Further disclosed are methods of using the conjugates to treat disease, methods of delivering an agent, and methods of preparing the conjugates.

13 Claims, 87 Drawing Sheets

Specification includes a Sequence Listing.

(56) References Cited

U.S. PATENT DOCUMENTS

| | | |
|---|---|---|
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,179 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 7/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO 2003/040165 A2 | 10/2002 |
| WO | WO 2004/096124 A2 | 11/2004 |
| WO | WO 2006/004778 A2 | 1/2006 |

(56) References Cited

FOREIGN PATENT DOCUMENTS

| | | | |
|---|---|---|---|
| WO | 2006/110292 A2 | 10/2006 |
| WO | WO 2007/073486 A2 | 6/2007 |
| WO | WO 2007/108013 A2 | 9/2007 |
| WO | WO 2007/134245 A2 | 11/2007 |
| WO | 2008/012543 A1 | 1/2008 |
| WO | 2008/030968 A2 | 3/2008 |
| WO | WO 2009/067584 A1 | 5/2009 |
| WO | WO 2010/054699 A1 | 5/2010 |
| WO | WO 2010/057154 A1 | 5/2010 |
| WO | WO 2010/096422 A1 | 8/2010 |
| WO | 2011/025572 A1 | 3/2011 |
| WO | WO 2011/123813 A2 | 10/2011 |
| WO | 2012/162426 A1 | 11/2012 |
| WO | WO2013/049234 A2 | 4/2013 |
| WO | WO 2013/065009 A1 | 5/2013 |
| WO | WO2013/106715 A1 | 7/2013 |
| WO | WO2014/037373 A1 | 3/2014 |
| WO | WO 2014/194244 A1 | 12/2014 |
| WO | 2015/011231 A1 | 1/2015 |
| WO | WO 2015/130846 A2 | 9/2015 |
| WO | WO 2016/065273 A1 | 4/2016 |
| WO | WO2016/065300 A1 | 4/2016 |
| WO | WO 2016/090103 A1 | 6/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |
| WO | 2017/192449 A1 | 11/2017 |
| WO | WO2018/115401 A1 | 6/2018 |
| WO | WO 2018/144854 A1 | 8/2018 |
| WO | WO2019/103744 A1 | 5/2019 |
| WO | 2019/147954 A1 | 8/2019 |
| WO | 2020/037214 A1 | 2/2020 |
| WO | WO2020/160472 A1 | 8/2020 |

OTHER PUBLICATIONS

U.S. Appl. No. 62/506,593, filed May 15, 2017.
U.S. Appl. No. 62/534,442, filed Jun. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019.
U.S. Appl. No. 62/767,736, filed Nov. 15, 2018.
PCT/US2019/061144, Nov. 13, 2019.
U.S. Appl. No. 62/622,249, filed Jan. 26, 2018.
PCT/US2019/015176, Jan. 25, 2019, WO2019/147954, Aug. 1, 2019.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 62/700,939, filed Jul. 20, 2018.
U.S. Appl. No. 62/873,306, filed Jul. 12, 2019.
U.S. Appl. No. 62/713,752, filed Aug. 2, 2018.
PCT/US2019/044911, Aug. 2, 2019.
U.S. Appl. No. 62/985,174, filed Mar. 4, 2020.
U.S. Appl. No. 62/985,179, filed Mar. 4, 2020.
Park et al., "Protein stitchery: Design of a protein for selective binding to a specific DNA sequence," PNAS, 1992, vol. 89:9094-9096.
Olafsen et al., "Covalent disulfide-linked anti-CEA diabody allows site-specific conjugation and radiolabeling for tumor targeting applications," Protein Engineering, Design & Selection, 2004, 17(1):21-27.
Hu et al., "Nanografting De Novo Proteins onto Gold Surfaces," Langmuir, 2005, vol. 21:9103-9109.
McDaniel, "Assembly of Highly Asymmetric Genetically-Encoded Amphiphiles for Thermally Targeted Delivery of Therapeutics," Dissertation, 2013, 295 pages.
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
United States Patent Office Action for U.S. Appl. No. 16/058,924 dated Nov. 26, 2019 (23 pages).
Aaron et al., "Elastin as a Random-Network Elastomer—a Mechanical and Optical Analysis of Single Elastin Fibers," Biopolymers, 1981, 20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic," Bioeng Transl Med, Jun. 2016, 1(1):10-29.
Arami et al., "In vivo delivery, pharmacokinetics, biodistribution and toxicity of iron oxide nanoparticles," Chem Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3):198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.
Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.

(56) References Cited

OTHER PUBLICATIONS

Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci U S A, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6):1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell-material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci U S A, 2013, 110(33):13392-13397.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Ehlerding et al., "Biodegradable and Renal Clearable Inorganic Nanoparticles," Adv Sci (Weinh), Feb. 2016, 3(2):1500223.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.

Elsabahy et al., "Design of polymeric nanoparticles for biomedical delivery applications," Chem Soc Rev, 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.
Farokhzad et al., "Targeted nanoparticle-aptamer bioconjugates for cancer chemotherapy in vivo," Proc Natl Acad Sci U S A, 2006, 103(16):6315-20.
Franzmann et al., "Phase separation of a yeast prion protein promotes cellular fitness," Science, Jan. 2018, 359(6371):eaao5654.
Garcia Quiroz et al., "Syntax of Phase Transition Peptide Polymers with LCST and UCST Behavior," Jan. 1, 2013, Retrieved from the Internet: URL: https://dukespace.lib.duke.edu/dspace/bitstream/handle/10161/7256/GarciaQuirozduke0066D 11972.pdf?sequence=1&isAllowed=y.
Geng et al., Shape effects of filaments versus spherical particles in flow and drug delivery, Nat Nanotechnol, 2007, 2(4):249-55.
Gilbreth et al., "Structural insights for engineering binding proteins based on non-antibody scaffolds," Curr Opin Struct Biol, 2012, 22(4):413-20.
Gillies et al., "Dendrimers and dendritic polymers in drug delivery," Drug Discovery Today, 2005, 10(1):35-43.
Goldsmith et al., "Enzyme engineering: reaching the maximal catalytic efficiency peak," Curr Opin Struct Biol, Dec. 2017, 47:140-150.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, 2008, 105(33):11613-8.
Gu et al., "Precise engineering of targeted nanoparticles by using self-assembled biointegrated block copolymers," Proc Natl Acad Sci U S A, 2008, 105(7):2586-91.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al.,"Functional Implications of Intracellular Phase Transitions," Biochemistry, May 2018, 57(17):2415-2423.
Huber et al., "Designer amphiphilic proteins as building blocks for the intracellular formation of organelle-like compartments," Nat Mater, Jan. 2015, 14(1):125-132.
Jiang et al., "Nanoparticle-mediated cellular response is size-dependent," Nat Nanotechnol, 2008, 3(3):145-50.
Jokerst et al., "Nanoparticle PEGylation for imaging and therapy," Nanomedicine (Lond), 2011, 6(4):715-28.
Jurney et al., "Unique size and shape-dependent uptake behaviors of non-spherical nanoparticles by endothelial cells due to a shearing flow," J Control Release, Jan. 2017, 245:170-176.
Kamaly et al., "Targeted polymeric therapeutic nanoparticles: design, development and clinical translation," Chem Soc Rev, 2012, 41(7):2971-3010.
Karagoz et al., "Polymerization-Induced Self-Assembly (PISA)—control over the morphology of nanoparticles for drug delivery applications," Polym. Chem., Jan. 2014, 5(2):350-355.
Kataoka et al., "Block copolymer micelles for drug delivery: Design, characterization and biological significance," Advanced Drug Delivery Reviews, 2001, 47:113-131.
Kelly et al., "Shape-specific, monodisperse nano-molding of protein particles," J Am Chem Soc, 2008, 130(16):5438-9.
Kesharwani et al., "Dendrimer as nanocarrier for drug delivery," Progress in Polymer Science, Feb. 2014, 39(2):268-307.
Kulkarni et al., "Design of lipid nanoparticles for in vitro and in vivo delivery of plasmid DNA," Nanomedicine, May 2017, 13(4):1377-1387.
Lee et al., "Polymersomes for drug delivery: design, formation and characterization," J Control Release, 2012, 161(2):473-83.
Lewis et al., "Use of digitized video microscopy with a fluorogenic enzyme substrate to demonstrate cell-and compartment-specific gene expression in *Salmonella* enteritidis and Bacillus subtilis," Molecular microbiology, 1994, 13:655-662.

(56) References Cited

OTHER PUBLICATIONS

Li et al., "Phase transitions in the assembly of multivalent signalling proteins," Nature, 2012, 483(7389):336-340.
Li et al., "Tunable Assembly of Protein-Microdomains in Living Vertebrate Embryos," Advanced Biosystems, Oct. 2018, 2(10):1800112.
Lin et al., "Formation and Maturation of Phase-Separated Liquid Droplets by RNA-Binding Proteins," Mol Cell, Oct. 2015, 60(2):208-219.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Liong et al., "Multifunctional inorganic nanoparticles for imaging, targeting, and drug delivery," ACS Nano, 2008, 2(5):889-96.
Liu et al., "Integrin $\alpha_v\beta_3$-Targeted Cancer Therapy," Drug Dev Res, 2008, 69(6):329-339.
Loh et al., "Utilising inorganic nanocarriers for gene delivery," Biomater Sci, Jan. 2016, 4(1):70-86.
LoPresti et al., "Polymersomes: nature inspired nanometer sized compartments," Journal of Materials Chemistry 2009, 19(22):3576-3590.
Lukyanov et al., "Tumor-targeted liposomes: doxorubicin-loaded long-circulating liposomes modified with anti-cancer antibody," J Control Release, 2004, 100(1):135-44.
Lyons et al., "Comparisons of Recombinant Resilin-like Proteins: Repetitive Domains Are Sufficient to Confer Resilin-like Properties," Biomacromolecules, 2009, 10(11):3009-3014.
Lyons et al., "Design and facile production of recombinant resilin-like polypeptides: Gene construction and a rapid protein purification method," Protein Engineering Design & Selection, 2007, 20(1):25-32.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Malam et al., "Liposomes and nanoparticles: nanosized vehicles for drug delivery in cancer," Trends Pharmacol Sci 2009, 30(11):592-9.
Manders et al., "Dynamics of three-dimensional replication patterns during the S-phase, analysed by double labelling of DNA and confocal microscopy," Journal of cell science, 1992, 103(Pt 3):857-862.
Mao et al., "Net charge per residue modulates conformational ensembles of intrinsically disordered proteins," Proc Natl Acad Sci U S A, 2010, 107(18):8183-8188.
Masood, "Polymeric nanoparticles for targeted drug delivery system for cancer therapy," Mater Sci Eng C Mater Biol Appl, Mar. 2016, 60:569-578.
Mastria et al., "Nanoparticle formulation improves doxorubicin efficacy by enhancing host antitumor immunity," J Control Release, Jan. 2018, 269:364-373.
McKenzie et al., "Multivalent Binding of a Ligand-Coated Particle: Role of Shape, Size, and Ligand Heterogeneity," Biophys J, Apr. 2018, 114(8):1830-1846.
Meng et al., "Stimuli-responsive polymersomes for programmed drug delivery," Biomacromolecules, 2009, 10(2):197-209.
Merkel et al., "Using mechanobiological mimicry of red blood cells to extend circulation times of hydrogel microparticles," Proc Natl Acad Sci U S A, 2011, 108(2):586-91.
Mitragotri et al., "Physical approaches to biomaterial design," J. Nat Mater, 2009, 8(1):15-23.
Modery et al., "Heteromultivalent liposomal nanoconstructs for enhanced targeting and shear-stable binding to active platelets for site-selective vascular drug delivery," Biomaterials, 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Muiznieks et al., "Proline periodicity modulates the self-assembly properties of elastin-like polypeptides," J Biol Chem, 2010, 285(51):39779-39789.
Muro, "Challenges in design and characterization of ligand-targeted drug delivery systems," J Control Release, 2012, 164(2):125-37.
Napier et al., "Nanoparticle drug delivery platform," Journal of Macromolecular Science, Part C: Polymer Reviews, 2007, 47(3):321-327.
Nayeem et al., "Engineering enzymes for improved catalytic efficiency: a computational study of site mutagenesis in epothilone-B hydroxylase," Protein Eng Des Sel, 2009, 22(4):257-266.
Ni et al., "Engineering of inorganic nanoparticles as magnetic resonance imaging contrast agents," Chem Soc Rev, Nov. 2017, 46(23):7438-7468.
Niu et al., "The role of adhesion molecules, $\alpha v\beta 3$, $\alpha v\beta 5$ and their ligands in the tumor cell and endothelial cell adhesion," Eur J Cancer Prev, 2007, 16(6):517-27.
Nott et al., "Phase transition of a disordered nuage protein generates environmentally responsive membraneless organelles," Mol Cell, Mar. 2015, 57(5):936-947.
Ortega et al., "Hydrodynamic properties of rodlike and dislike particles in dilute solution," The Journal of Chemical Physics, 2003, 119(18):9914-9919.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Pardridge, "The blood-brain barrier: bottleneck in brain drug development," NeuroRx, 2005, 2(1):3-14.
Parker et al., "Antibody mimics based on human fibronectin type three domain engineered for thermostability and high-affinity binding to vascular endothelial growth factor receptor two," Protein Eng Des Sel, 2005, 18(9):435-44.
Pastuszka et al., "A tunable and reversible platform for the intracellular formation of genetically engineered protein microdomains," Biomacromolecules, 2012, 13(11):3439-3444.
Peng et al., "Length-dependent prediction of protein intrinsic disorder," BMC Bioinformatics, 2006, 7:208.
Petros et al., "Strategies in the design of nanoparticles for therapeutic applications," Nat Rev Drug Discov, 2010, 9(8):615-27.
Qamar et al., "FUS Phase Separation Is Modulated by a Molecular Chaperone and Methylation of Arginine Cation-pi Interactions," Cell, Apr. 2018, 173(3):720-734.e15.
Quiroz et al., "Intrinsically disordered proteins access a range of hysteretic phase separation behaviors," Scientific advances, Oct. 2019, 5(10):eaax5177.
Ravikumar et al., "Mimicking adhesive functionalities of blood platelets using ligand-decorated liposomes," Bioconjugate chemistry, 2012, 23(6):1266-1275.
Rolland et al., "Direct fabrication and harvesting of monodisperse, shape-specific nanobiomaterials," J Am Chem Soc, 2005, 127(28):10096-100.
Rosenholm et al., "Towards multifunctional, targeted drug delivery systems using mesoporous silica nanoparticles—opportunities & challenges," Nanoscale, 2010, 2(10):1870-83.

(56) References Cited

OTHER PUBLICATIONS

Rösler et al., "Advanced drug delivery devices via self-assembly of amphiphilic block copolymers," Advanced Drug Delivery Reviews, 2001, 53:95-108.
Ryu et al., "Elastin-like polypeptide for improved drug delivery for anticancer therapy: preclinical studies and future applications," Expert Opinion on Drug Delivery, 2014, 12(4):653-667.
Sanna et al., "Targeted therapy using nanotechnology: focus on cancer," Int J Nanomedicine, Jan. 2014, 9:467-83.
Schnell et al., "Expression of integrin $\alpha v\beta 3$ in gliomas correlates with tumor grade and is not restricted to tumor vasculature," Brain Pathol, 2008, 18(3):378-86.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, 2010, 147(3):408-412.
Shi et al., "Triggered sorting and co-assembly of genetically engineered protein microdomains in the cytoplasm," Adv Mater, 2014, 26(3):449-454.
Shin et al., "Liquid phase condensation in cell physiology and disease," Science, Sep. 2017, 357(6357):eaaf4382.
Sickmeier et al., "DisProt: the Database of Disordered Proteins," Nucleic Acids Res, 2007, 35:D786-793.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Skerra, "Alternative non-antibody scaffolds for molecular recognition," Curr Opin Biotechnol, 2007, 18(4):295-304.
Smits et al., "Elastin-Like Polypeptide Based Nanoparticled: Design Rationale Toward Nanomedicine," Macromolecular Bioscience, 2014, 15(1):36-51.
Steichen et al., "A Review of Current Nanoparticle and Targeting Moieties for the Delivery of Cancer Therapeutics," Eur J Pharm Sci, 2013, 48(3):416-27.
Strulson et al., "RNA catalysis through compartmentalization," Nat Chem, 2012, 4(11):941-946.
Suk et al., "PEGylation as a Strategy for Improving Nanoparticle-Based Drug and Gene Delivery," Adv Drug Deliv Rev, Apr. 2016, 99(Pt A):28-51.
Swider et al., "Customizing Poly(lactic-Co-Glycolic Acid) Particles for Biomedical Applications," Acta Biomater, Jun. 2018, 73:38-51.
Talelli et al., "Core-Crosslinked Polymeric Micelles: Principles, Preparation, Biomedical Applications and Clinical Translation," Nano Today, Feb. 2015, 10(1):93-117.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, 2013, 1(1):624360.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, 2011, 32(33):8462-73.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, 2010, 1804(6):1231-1264.

Vazquez-Lombardi et al., "Challenges and Opportunities for Non-Antibody Scaffold Drugs," Drug Discov Today, Oct. 2015, 20(10):1271-83.
Venkataraman et al., "The Effects of Polymeric Nanostructure Shape on Drug Delivery," Adv Drug Deliv Rev, 2011, 63(14-15):1228-46.
Verma et al., "Effect of surface properties on nanoparticle-cell interactions," Small, 2010, 6(1):12-21.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, 2006, 78(3):620-8.
Vrhovski et al., "Coacervation Characteristics of Recombinant Human Tropoelastin," European Journal of Biochemistry, 1997, 250(1):92-98.
Wang et al., "A Molecular Grammar Governing the Driving Forces for Phase Separation of Prion-like RNA Binding Proteins," Cell, Jul. 2018, 174(3):688-699.e616.
Wang et al., "More effective nanomedicines through particle design," Small, 2011, 7(14):1919-31.
Wang et al., "Nanoparticle delivery of cancer drugs," Annu Rev Med, 2012, 63:185-98.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Wechsel et al., "Renal Cell Carcinoma: Immunohistological Investigation of Expression of the Integrin $\alpha v\beta 3$," Anticancer research, 1999, 19(2C):1529-1532.
Weis et al., "$\alpha$V Integrins in Angiogenesis and Cancer," Cold Spring Harb Perspect Med, 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wilkins et al., "Hydrodynamic Radii of Native and Denatured Proteins Measured by Pulse Field Gradient NMR Techniques," Biochemistry, 1999, 38(50):16424-16431.
Wimley et al., "Experimentally determined hydrophobicity scale for proteins at membrane interfaces," Nature Structural & Molecular Biology, 1996, 3(10):842-848.
Wright et al., "Intrinsically disordered proteins in cellular signalling and regulation," Nat Rev Mol Cell Biol, Jan. 2015, 16(1):18-29.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, 2011, 155(2):248-61.
Xu et al., "Inorganic nanoparticles as carriers for efficient cellular delivery," Chemical Engineering Science, 2006, 61(3):1027-1040.
Zhao et al., "Cellular uptake, intracellular trafficking, and cytotoxicity of nanomaterials," Small, 2011, 7(10):1322-37.
Zhao et al., "Tumor $\alpha v\beta 3$ Integrin Is a Therapeutic Target for Breast Cancer Bone Metastases," Cancer Res, 2007, 67(12):5821-30.
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
U.S. Appl. No. 62/534,442, filed Jul. 19, 2017.
U.S. Appl. No. 16/332,865, filed Mar. 13, 2019, 2020/0164082, May 28, 2020.
U.S. Appl. No. 16/625,899, filed Dec. 23, 2019, 2020/0148724, May 14, 2020.
PCT/US2019/050077, Sep. 6, 2019, WO2020/051541, Mar. 12, 2020.

(56) References Cited

OTHER PUBLICATIONS

PCT/US2019/061144, Nov. 13, 2019, WO2020/102324, May 22, 2020.
U.S. Appl. No. 16/964,832, filed Jul. 24, 2020.
U.S. Appl. No. 16/927,982, filed Jul. 13, 2020.
PCT/US2019/044911, Aug. 2, 2019, WO2020/028806, Feb. 6, 2020.
U.S. Appl. No. 62/898,353, filed Sep. 12, 2019.
U.S. Appl. No. 17/015,315, filed Sep. 9, 2020.
Chockalingam et al., "Design and application of stimulus-responsive peptide systems," Protein Engineering, Design & Selection, 2007, 20(4):155-161.
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US2019/061144 dated May 21, 2020 (15 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
United States Patent Office Action for U.S. Appl. No. 15/749,797 dated Oct. 20, 2020 (16 pages).
U.S. Appl. No. 61/138,847, filed Mar. 26, 2015.
PCT/US2016/024202, Mar. 25. 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
U.S. Appl. No. 15/561,799, filed Sep. 26, 2017, 2018/0258157, Sep. 13, 2018.
U.S. Appl. No. 16/525,374, filed Jul. 29, 2019.
U.S. Appl. No. 16/335,734, filed Mar. 22, 2019.
PCT/US2019/023583, Mar. 22, 2019.
PCT/US2019/030022, Apr. 30, 2019.
AACR, "AACR Cancer Progress Report 2016," Clin Cancer Res, 2016, 22, 143 pages.
Abbruzzese et al., "A phase I clinical, plasma, and cellular pharmacology study of gemcitabine," J. Chin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overconr the pathophysiological barriers of pancreatic cancer," Nat Rev Clin Oncol, 2016, 13, 750-765.
Aladini et al., "Chemical Synthesis and Characterization of Elastin-Like Polypeptides (ELPs) With Variable Guest Residues," J Pept Sci, 2016, 22(5):334-342.
Alarcon et al., "Exenclin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., 2012, 14, 1-16.
Alconcel et al., "FDA-approved poly(ethylene glycol)-protein conjugate drugs," Polym. Chem. 2, 2011, 1442-1448.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, 2012, 13, 2645-2654.
American Diabetes Association (2018) Standards of medical care in diabetes—2018. Diabetes Care 41(Suppl 1):S1-S159.
Amiram et al., "A depot-forming glucagon-like peptide-1 fusion protein reduces blood glucose for five days with a single injection," J. Control. Release, 2013, 172, 144-151.
Amiram et al., "Injectable protease-operated depots of glucagon-like peptide-1 provide extended and tunable glucose control," Proc. Natl. Acad. Sci. 110, 2013, 2792-2797.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Antos et al., "Lipid Modification of Proteins through Sortase-Catalyzed Transpeptidation," J. Am. Chem. Soc. 2008, 130, 16338-16343.
Antos et al., "Site-Specific N- and C-Terminal Labeling of a Single Polypeptide Using Sortases of Different Specificity," J. Am. Chem. Soc. 2009, 131, 10800-10801.
Arias et al., "Superior preclinical efficacy of gemcitabine developed as chitosan nanoparticulate system," Biomacromolecules 2011, 12, 97-104.
Armstrong et al., "Antibody against poly(ethylene glycol) adversely affects PEG-asparaginase therapy in acute lymphoblastic leukemia patients," Cancer 110, 2007, 103-111.
Armstrong et al., "The Hydrodynamic Radii of Macromolecules and Their Effect on Red Blood Cell Aggregation," Biophys. J., 2004, 87, 4259-4270.

(56) References Cited

OTHER PUBLICATIONS

Arner et al., "FGF21 attenuates lipolysis inhuman adipocytes—a possible link to improved insulin sensitivity," FEBS Lett, 2008, 582(12):1725-1730.

Arnida et al., "Geometry and surface characteristics of gold nanoparticles influence their biodistribution and uptake by macrophages," Eur J Pharm Biopharm, 2011, 77, 417-423.

Asai et al., "Protein polymer hydrogels by in situ, rapid and reversible self-gelation," Biomatetials, 2012, 33, 5451-5458.

Atun et al., "Expanding global access to radiotherapy," Lancet Oncol, 2015, 16, 1153-1186.

Averick et al., "ATRP under biologically relevant conditions: grafting from a protein," ACS Macro. Lett. 1, 2012, 6-10.

Averick et al., "Protein-polymer hybrids: conducting ARGET ATRP from a genetically encoded cleavable ATRP initiator," Eur. Polym. J. 49, 2013, 2919-2924.

Awai et al., "Studies of the metabolism of I-131-labeled human transferrin," J. Lab. Clin. Med. 61, 1963, 363-396.

Awasthi et al., "Comparative benefits of Nab-paclitaxel over gemcitabine or polysorbate-based docetaxel in experimental pancreatic cancer," Carcinogenesis, 2013, 34, 2361-2369.

Awasthi et al., "Evaluation of combination treatment benefits of nab-paclitaxel in experimental pancreatic cancer," Journal of Clinical Oncology, 2012, 30, 170.

Axup et al., "Synthesis of site-specific antibody-thug conjugates using unnatural amino acids," Proc Natl Acad Sci USA, 2012, 109(40):16101-16106.

Azhdarinia et al., "Regional radiochemotherapy using in situ hydrogel," Pharm Res., 2005, 22, 776-783.

Bache et al., "Investigating the accuracy of microstereotactic-body-radiotherapy utilizing anatomically accurate 3D printed rodent-morphic dosimeters," Medical Physics, 2015, 42, 846-855.

Badi, "Non-linear PEG-based thermoresponsive polymer systems," Progress in Polymer Science, 2017, 66, 54-79.

Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.

Baggio et al., "Biology of Incretins: GLP-1 and GIP," Gastroenterology, 2007, 132(6):2131-2157.

Bailey et al., "Genomic analyses identify molecular subtypes of pancreatic cancer," Nature, 2016, 531, 47-52.

Bamford et al., "'The COSMIC (Catalogue of Somatic Mutations in Cancer) database and website," British Journal of Cancer, 2004, 91, 355-358.

Banga et al., "Parenteral controlled delivery and parmacokinetics of therapeutic peptides and proteins," (CRC Press, Boca Raton, FL, 2005).

Bansal et al., "PEGylation improves pharmacokinetic profile, liver uptake and efficacy of Interferon gamma in liver fibrosis," J. Control. Release 2011, 154, 233-240.

Barbuti et al., "Paclitaxel through the ages of anticancer therapy: Exploring its role in chemoresistance and radiation therapy," Cancers, 2015, 7, 2360-2371.

Barnett et al., "Normal tissue reactions to radiotherapy: towards tailoring treatment dose by genotype," Nat Rev Cancer, 2009, 9, 134-142.

Barton et al., "Estimating the demand for radiotherapy form the evidence: a review of changes from 2003 to 2012," Radiother Oncol, 2014, 112, 140-144.

Baskar et al., "Cancer and Radiation Therapy: Current Advances and Future Directions," Int. J. Med. Sci., 2012, 9, 193-199.

Bedford et al., "WW domain-mediated interactions reveal a spliceosome-associated protein that binds a third class of proline-rich motif: The proline glycine and methionine-rich motif," PNAS, 1998, 95: 10602-10607.

Beenken et al., "The FGF family: biology, pathophysiology and therapy," Nat Rev Drug Discov, 2009, 8(3):235-253.

Begg et al., "Strategies to improve radiotherapy with targeted drugs," Nat Rev Cancer, 2011, 11, 239-253.

Bellucci et al., "A noncanonical function of sortase enables site-specific conjugation of small molecules to lysine residues in proteins," Angew. Chem. Int. Ed. 54, 2015, 441-445.

Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.

Bender et al., "Synthesis, Crystallization, and Biological Evaluation of an Orally Active Prodrug of Gemcitabine," J. Med. Chem. 2009, 52, 6958-6961.

Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.

Bernacki et al., "Length-dependent aggregation of uninterrupted polyalanine peptides," Biochemistry, 2011, 50, 9200-9211.

Berndt et al., "Synthetic lipidation of peptides and amino acids: Monolayer structure and properties," J. Am. Chem. Soc., 1995, 117, 9515-9522.

Bessa et al., "Thermoresponsive self-assembled elastin-based nanoparticles for delivery of BMPs," Journal of Controlled Release, 2010, 142, 312-318.

Bhattacharyya et al., "A paclitaxel-loaded recombinant polypeptide nanoparticle outperforms Abraxane in multiple murine cancer models," Nat. Commun. 2015, 6, 7939.

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, 2017, 27(12):1-9.

Bidwell et al., "Development of elastin-like polypeptide for thermally targeted delivery of doxorubicin," Biochemical Pharmacology, 2007, 73(5):620-631.

Blasko et al., "Brachytherapy for carcinoma of the prostate: Techniques, patient selection, and clinical outcomes," Seminars in Radiation Oncology, 2002, 12, 81-94.

Blasko et al., "The role of external beam radiotherapy with I-125/Pd-103 brachytherapy for prostate carcinoma," Radiother Oncol, 2000, 57, 273-278.

Blasko et al., "Transperineal percutaneous iodine-125 implantation for prostatic carcinoma using transrectal ultrasound and template guidance," Endocurietherapy/Hyperthermia Oncology, 1987, 3, 131-139.

Bley et al., "Microtubule stabilising agents and ionising radiation: Multiple exploitable mechanisms for combined treatment," Eur J Cancer, 2013, 49, 245-253.

Bobo et al., "Nanoparticle-based medicines: a review of FDA-approved materials and clinical trials to date." Pharmaceutical research 33.10 (2016): 2373-2387.

Bocci et al., "The pharmacological bases of the antiangiogenic activity of paclitaxel," Angiogenesis, 2013, 16, 481-492.

Bochicchio et al., "Investigating by CD the molecular mechanism of elasticity of elastomeric proteins," Chirality, 2008, 20, 985-994.

Boekhorst et al., "Genome-wide detection and analysis of cell wall-bound proteins with LPxTG-like sorting motifs," J. Bacteriol. 187, 2005, 4928-4934.

Boldt, "Use of albumin: an update," Br J. Anaesth., 2010, 104 (3), 276-284.

Bond, "Exenatide (Byetta) as a novel treatment option for type 2 diabetes mellitus," Proc. (Bayl. Univ. Med. Cent.) 19, 2006, 281-284.

Bontempo et al., "Streptavidin as a macroinitiator for polymerization: in situ protein-polymer conjugate formation," J. Am. Chem. Soc., 2005, 6508-6509.

Boyer et al., "Well-Defined Protein-Polymer Conjugates via in Situ RAFT Polymerization," J. Am. Chem. Soc. 2007, 129, 7145-7154.

Branco et al., "Self-assembling materials for therapeutic delivery," Acta Biomaterialia, 2009, 5(3): p. 817-831.

Broyer et al., "Emerging synthetic approaches for protein-polymer conjugations," Chem. Commun. 2011, 47, 2212.

Brusa et al., "Antitumor activity and pharmacokinetics of liposomes containing lipophilic gemcitabine prodrugs," Anticancer Res. 2007, 27, 195-199.

Burchard, "Light Scattering Techniques," Physical techniques for the study of food biopolymers, 1994, 151-213.

(56) References Cited

OTHER PUBLICATIONS

Burnouf, "Modern plasma fractionation," Transfus. Med. Rev., 2007, 21 (2), 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechmlogy, 2011, 6, 815-823.
Cabrera et al., "Automated, High-Throughput Assays for Evaluation of Human Pancreatic Islet Function," Cell Transplant, 2008, 16(10):1039-1048.
Cabrera et al., "Glutamate Is a Positive Autocrine Signal for Glucagon Release," Cell Metab, 2008, 7(6):545-554.
Cai et al., "Long-acting preparations of exenatide," Drug Des. Dev. Ther. 7, 2013, 963-970.
Caliceti et al., "Pharmacokirctic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, 2012, 12, 2165-2170.
Camilloni et al., "Determination of secondary structure populations in disordered states of proteins using nuclear magnetic resonance chemical shifts," Biochemistry, 2012, 51, 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.
Cardenes et al., "Locally advanced pancreatic cancer: Current therapeutic approach," The Oncologist, 2006, 11, 612-623.
Carrico et al., "Introducing genetically encoded aldehydes into proteins," Nat Chem Biol, 2007, 3(6):321-322.
Cataldo et al., "Radiation-induced crosslinking of collagen gelatin into a stable hydrogel," Journal of Radioanalytical and Nuclear Chemistry, 2008, 275, 125-131.
Centers for Disease Control and Prevention (2017) National Diabetes Statistics Report, 2017. ed U.S. Dept of Health and Human Services (Atlanta).
Ceska et al., "A new and rapid inethod for the clinical determination of α-amylase activities in human serum and urine. Optimal conditions," Clinica Chimica Acta, 1969, 26, 437-444.
Chakrabartty et al., "Stability of α-Helices," Adv Protein Chem, 1995, 46, 141-176.
Chang et al., "Tumor-stroma interaction in orthotopic primary pancreatic cancer xenografts during hedgehog pathway inhibition," Int. J. Cancer, 2013, 133, 225-235.
Chatterjee et al., "Type 2 diabetes," The Lancet, 2017, 389(10085): 2239-2251.
Chaudhury et at, "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, 2012, 89, 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am. Chem. Soc., 2009, 132(13):4577-4579.
Chen et al., "Rheology of Soft Materials," Annual Review of Condensed Matter Physics, 2010, 1, 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials 34, 2013, 8776-8785.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, 2006, 10(6):652-657.
Chilkoti et al., "Targeted drug delivery by thermally responsive polymers," Advanced Drug Delivery Reviews, 2002, 54:613-630.
Chithrani et al., "Determining the size and shape dependence of gold nanoparlicle uptake into mammalian cells," Nano Lett, 2006, 6, 662-668.
Chitkara et al., "Self-Assembling Amphiphilic Polymer-Gemcitabine Conjugate Shows Enhanced Antitumor Efficacy Against Human Pancreatic Adenocarcinoma," Bioconjug. Chem. 2013, 24, 1161-1173.
Cho et al., "Effects of hofmeister anions on the phase transition temperature of elastin-like polypeptides," J. Phys. Chem. B., 2008, 112, 13765-13771.
Cho et al., "Hydrogen bonding of β-turn structure is stabilized in D(2)O," J Am Chem Soc, 2009, 131, 15188-15193.
Cho et al., "Therapeutic nanoparticles for drug delivery in cancer," Clin. Cancer Res., 2008, 14, 1310-1316.
Choi et al., "Renal Clearance of Nanoparticles," Nature biotechnology, 2007, 25(10): p. 1165-1170.
Chow et al., "Peptide-based biopolymers in biomedicine and biotechnology," Mater. Sci. Eng. R Reports, 2008, 62, 125-155.
Chow et al., "Ultra-High Expression of a Thermally Responsive Recombinant Fusion Protein in E. coli," Biotechnology Progress, 2006, 22(3):638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, 2009, 18:1377-1387.
Christensen et al., "Predicting Transition Temperatures of Elastin-Like Polypeptide Fusion Proteins," Biomacromolecules, 2013, 14(5): p. 1514-1519.
Cid-Arregui et al., "Perspectives in the treatment of pancreatic adenocarcinoma," World Journal of Gastroenterology, 2015, 21, 9297-9316.
Ciezki et al., "Brachytherapy or surgery? A composite view," Oncology, 2009, 23, 960-964.
Cima, "AVMA Guidelines for the Euthanasia of Animal: 2013 Edition," Journal of the American Veterinary Medical Association, 2013, 242, 102 pages.
Cirulis et al., "Viscoelastic properties and gelation of an elastin-like polypeptide," Journal of Rheology, 2009, 53, 1215-1228.
Clarke et al., "Tropoelastin massively associates during coacervation to form quantized protein spheres," Biochemistry, 2006, 45, 9989-9996.
Clavé et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., 2007, 2, 3247.
Colomb et al., "Radiation-Convertible Polymers from Norbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, 2011, 9, 22-31.
Coskun et al., "Fibroblast Growth Factor 21 Corrects Obesity in Mice," Endocrinology, 2008, 149(12):6018-6027.
Craik et al., "The future of peptide-based drugs," Chemical biology & drug design 81, 2013, 136-147.

(56) References Cited

OTHER PUBLICATIONS

Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalla Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.
Darzynkiewicz et al., "DNA content measurement for DNA ploidy and cell cycle analysis," Current Protocols in Cytometry, 2001, 7.5.1-7.5.24.
Dasgupta et al., "Isopeptide Ligation Catalyzed by Quintessential Sortase A: Mechanistic Cues From Cyclic and Branched Oligomers of Indolicidin," the Journal of Biological Chemistry, 2011, vol. 286, No. 27, pp. 23996-24006, Supplemental Information.
Day et al., "A new glucagon and GLP-1 co-agonist eliminates obesity in rodents," Nat Chem Biol, 2009, 5:749.
De et al., "Temperature-Regulated Activity of Responsive Polymer-Protein Conjugates Prepared by Grafting-from via RAFT Polymerization," J. Am. Chem. Soc. 2008, 130, 11288-11289.
De Simone et al., "Accurate random coil chemical shifts from an analysis of loop regions in native states of proteins," J Am Chem Soc, 2009, 131, 16332-16333.
Deer et at., "Phenotype and genotype of pancreatic cancer cell lines," Pancreas, 2010, 39, 425-435.
Dejana et al., "The role of adherens junctions and VE-cadherin in the control of vascular permeability," J Cell Sci, 2008, 121, 2115-2122.
Delaglio et al., "NMRPipe: A multidimensional spectral processing systembased on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression" PNAS, 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: a viable and potentially superior alternative to PEGylation for stabilizing biologics," Acta Biomater. 2009, 5, 560-569.
Deshayes et al., "Radium 223 dichloride for prostate cancer treatment," Drug Des Devel Ther, 2017, 11, 2643-2651.
DeYoung et al., "Encapsulation of exenatide in poly-(D,L-lactide-co-glycolide) microspheres produced an investigational long-acting once-weekly formulation for type 2 diabetes," Diabetes Technol Ther, 2011, 13, 1145-1154.
Diana et al., "Prognostic role and correlation of CA9, CD31, CD68 and CD20 with the desmoplastic stroma in pancreatic ductal adenocarcinoma," Oncotarget, 2016, 7, 72819-72832.
Diehl et al., "A Good Practice Guide to the Administration of Substances and Removal of Blood Including Routes and Volumes," J Appl Toxicol, 2001, 21, 15-23.
Ding et al., "Mechanism for the alpha-helix to beta-hairpin transition" Proteins, 2003, 53, 220-228.
Ding et al., "βKlotho Is Required for Fibroblast Growth Factor 21 Effects on Growth and Metabolism," Cell Metab, 2012, 16(3):387-393.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. 2008, 130, 687-694.
Dreher et al., "Thermal cycling enhances the accumulation of a temperature-sensitive biopolymer in solid tumors," Cancer Res, 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm, 2007, 341, 207-214.
Drucker "Mechanisms of Action and Therapeutic Application of Glucagon-like Peptide-1," Cell Metab, 2018, 27(4):740-756.
Drucker et al., "The incretin system: glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, 2013, 62, 3316-3323.
Du et al., "Endoscope-assisted brachytherapy for pancreatic cancer: From tumor killing to pain relief and drainage," Journal of interventional gastroenterology, 2011, 1, 23-27.
Du et al., "Tailor-made dual pH-sensitive polymer-doxorubicin nanoparticles for efficient anticancer drug delivery," J. Am. Chem. Soc., 2011, 133, 17560-17563.
Duan et al., "Fibronectin type III domain based monobody with high activity," Biochemistry, 2007 46(44):12656-12664.
Dubey et al., "Development and evaluation of folate functionalized albumin nanoparticles for targeted delivery of gemcitabine," Int J Pharm., 2015, 492(1-2):80-91.
Ducreux et al., "Radiation plus docetaxel and cisplatin in locally advanced pancreatic carcinoma: A non-comparative randomized phase II trial," Digestive and Liver Disease, 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, 2017, 45, 228-247.
El-Assaad et al., "Saturated Fatty Acids Synergize with Elevated Glucose to Cause Pancreatic β-Cell Death," Endocrinology, 2003, 144(9):4154-4163.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.

(56) References Cited

OTHER PUBLICATIONS

Farmer et al., "Conformational behavior of chemically reactive alanine-rich repetitive protein polymers," Biomacromolecules, 2005, 6, 1531-1539.
Feng et al., "Protein resistant surfaces: comparison of acrylate graft polymers bearing oligo-ethylene oxide and phosphorylcholine side chains," Biointerphases, 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, 2015, 16, 3389-3398.
Finan et al., "A rationally designed monomeric peptide triagonist corrects obesity and diabetes in rodents," Nat Med, 2015, 21:27-36.
Finan et al., "Unimolecular Dual Incretins Maximize Metabolic Benefits in Rodents, Monkeys, and Humans," Sci Transl Med, 2013, 5(209):209ra151.
Fluegel et al., "Chain stiffness of elastin-like polypeptides," Biomacromolecules 2010, 11, 3216-3218.
Fosgerau et al., "Peptide therapeutics: current status and future directions," Drug Discovery Today, 2015, 20, 122-128.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.
Friedman et al., "Directed Evolution to Low Nanomolar Affinity of a Tumor-Targeting Epidermal Growth Factor Receptor-Binding Affibody Molecule," J. Mol. Biol., 2008, 376, 1388-1402.
Frilling et al., "Recommendations for management of patients with neuroendocrine liver metastases," The lancet oncology, 2014, 15, e8-21.
Fu et al., Recent Patents on Anti-Cancer Drug Discovery, 2009. 4(3): p. 262-272.
Fujiwara et al., "Modulating effect of the PI3-kinase inhibitor LY294002 on cisplatin in human pancreatic cancer cells," Journal of Experimental & Clinical Cancer Research, 2008, 27, 76.
Furgeson et al., "Structural optimization of a "smart" doxorubicin-polypeptide conjugate for thermally targeted delivery to solid tumors," Journal of Controlled Release, 2006, 110:362-369.
Furumoto et al., "Effect of coupling of albumin onto surface of PEG liposome on its In vivo disposition," International Journal of Pharmaceutics, 2007, 329(1-2): p. 110-116.
Gaberc-Porekar et al., "Obstacles and pitfalls in the PEGylation of therapeutic proteins," Curr. Opin. Drug Discov. Devel. 11, 2008, 242-250.
Gabizon et al., "Prolonged circulation time and enhanced accumulation in malignant exudates of doxorubicin encapsulated in poly-ethylene-glycol coated liposomes," Cancer Res. 1994, 54, 987-992.
Gaich et al., "The Effects of LY2405319, an FGF21 Analog, in Obese Human Subjects with Type 2 Diabetes," Cell Metab, 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Ganson et al., "Pre-existing anti-polyethylene glycol antibody linked to first-exposure allergic reactions to pegnivacogin, a PEGylated RNA aptamer," J Allergy Clin Immunol, 2016, 137(5): 1610-1613, e1617.
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009, 15231-15236.
Gao, "Site-specific andin situgrowth of stealth polymer conjugates of proteins with significally improved pharmacology," Journal of Controlled Release, 2013, 172(1):e116-e117.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and in patients treated with PEG-conjugated agents," Expert Opinion. Drug Deliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (2017).
Ghoorchian et al., "Molecular architecture influences the thermally induced aggregation behavior of elastin-like polypeptides," Biomacromolecules, 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, 2009, 27, 607-612.
Gibson et al., "Enzymatic assembly of DNA molecules up to several hundred kilobases," Nat Methods, 2009, 6, 343-345.
Gilroy et al., "Fusion of fibroblast growth factor 21 to a thermally responsive biopolymer forms an injectable depot with sustained anti-diabetic action," J Control Release, 2018, 277:154-164.
Glassman et al., "Toughening of Thermoresponsive Arrested Networks of Elastin-Like Polypeptides To Engineer Cytocompatible Tissue Scaffolds," Biomacromolecules, 2016, 17, 415-426.
Gluck et al., "Single Vector System for Efficient N-myristoylation of Recombinant Proteins in E. coli," Plos One. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, 2008, 633-648.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin, 2003, 31(3): 529-540.
Greenfield, "Using circular dichroism spectra to estimate protein secondary structure," Nat. Protoc., 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, 2018, 19, 3525-3535.

(56) References Cited

OTHER PUBLICATIONS

Gu et al., "Photocontrolled micellar aggregation of amphiphilic DNA-azobenzene conjugates," Colloids Surfaces B: Biointerfaces, 2015, 135, 126-132.
Güngör et al., "Pancreatic cancer," British Journal of Pharmacology, 2014, 171, 849-858.
Guo et al., "Nanoparticles escaping RES and endosome: challenges for siRNA delivery for cancer therapy," J. Nanomaterials, 2011, 1-12.
Gustafsson, "Nonlinear structured-illumination microscopy: widefield fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.
Ha et al., "ImmunoglobulinFc Heterodimer Platform Technology: From Design to Applications in Therapeutic Antibodies and Proteins," Front Immunol, 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, 2013, vol. 4, Article 331, 7 pages.
Hamidi et al., "Pharmacokinetic Consequences of Pegylation," Drug Deliv. 2006, 13, 399-409.
Hamley, "Self-assembly of amphiphilic peptides," Soft Matter, 2011, 7, 4122.
Hampp et al., "Use of Antidiabetic Drugs in the U.S., 2003-2012," Diabetes Care, 2014, 37: 1367-1374.
Han et al., "Survival of patients with advanced pancreatic cancer after iodine[125] seeds implantation brachytherapy: A meta-analysis," Medicine, 2017, 96, e5719.
Harmon et al., "A Model for Hysteresis Observed in Phase Transitions of Thermally Responsive Instrinsically Disordered Protein Polymers," Biophysical Journal, 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, 2015, 48, 4183-4195.
Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.
Hassouneh et al., "Fusions of elastin-like polypeptides to pharmaceutical proteins," Methods Enzymol., 2012, 502, 215-37.
Hassouneh et al., "Unexpected Multivalent Display of Proteins by Temperature Triggered Self-assembly of Elastin-like Polypeptide Block Copolymers," Biomacromolecules, 2012, vol. 13, Issue 4, pp. 1598-1605.
Hathout et al., "Analysis of seed loss and pulmonary seed migration in patients treated with virtual needle guidance and robotic seed delivery," American journal of clinical oncology, 2011, 34, 449-453.
He et al., "Comparative genomics of elastin: Sequence analysis of a highly repetitive protein," Matrix Biology, 2007, 26:524-540.
He et al., "Improving protein resistance of α-Al2O3 membranes by modification with POEGMA brushes," Applied Surface Science, 2011, 258 (3), 1038-1044.
Heagerty et al., Biometrics, "Time-dependent ROC curves for censored survival data and a diagnostic marker," 2000, 56(2):337-44.
Heal et al., "N-Myristoyl transferase-mediated protein labelling in vivo," Org. Biomol. Cham., 2008, 6(13):2308-2315.
Heal et al., "Site-specific N-terminal labelling of proteins in vitro and in vivo using N-myristoyl transferase and bioorthogonal ligation chemistry," Chem. Commun., 2008, 3, 480-482.
Heredia et al., "In Situ Preparation of Protein-"Smart" Polymer Conjugates with Retention of Bioactivity," J. Am. Chem. Soc. 2005, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, 2014, R63.
Hidalgo, "Pancreatic Cancer," N Engl J Med, 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, 2016, 22, 2848-2854.
Ho et al., "Chemoenzymatic Labeling of Proteins for Imaging in Bacterial Cells," J. Am. Chem. Soc., 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, 2007, pp. 40-47.
Hochkoeppler, "Expanding the landscape of recombinant protein production in *Escherichia coli*," Biotechnol. Lett., 2013, 35, 1971-1981.
Holehouse et al., "CIDER: Classification of Intrinsically Disordered Ensemble Regions," Biophysical Journal, 2015, vol. 108, Issue 2, Supplement 1, p. 228a.
Holm et al., "Transperineal [125]iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011, 42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.
Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.

(56) References Cited

OTHER PUBLICATIONS

Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Ito et al., "Impaired negative feedback suppression of bile acid synthesis in mice lacking βKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.
Jia et al., "Preparation, physicochemical characterization and cytotoxicity in vitro of gemcitabine-loaded PEG-PDLLA nanovesicles," World J. Gastroenterol. 2010, 16(8):1008-1013.
Jiang et al "The internal structure of self-assembled peptide amphiphiles nanofibers," Soft Matter, 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, 2009, 137(5):1795-1804.
Jonsson et al., "Engineering of a femtomolar affinity binding protein to human serum albumin," Protein Engineering Design and Selection, 2008, 21(8): 515-527.
Junutula et al., "Site-specific conjugation of a cytotoxic drug to an antibody improves the therapeutic index," Nat Biotechnol, 2008, 26(8):925-932.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanoski et al., "The role of nausea in food intake and body weight suppression by peripheral GLP-1 receptor agonists, exendin-4 and liraglutide," Neuropharmacology 62, 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, 2013, 18, 807-817.
Katakura, "Nuclear Data Sheets for A=125," Nuclear Data Sheets, 2011, 112, 495-705.
Kato et al., "Acidic extracellular microenvironment and cancer," Cancer Cell Int, 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism" Biochim. Byophys. Acta—Proteins Proteomics, 2005, 1751(2):119-39.
Keten et al., "Nanoconfinement controls stiffness, strength and mechanical toughness of β-sheet crystals in silk," Nat Mater, 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, 2015, 26(11):608-617.
Kharitonenkov et al., "Fibroblast growth factor 21 night watch: advances and uncertainties in the field," J Intern Med, 2016, 281(3):233-246.
Kharitonenkov et al., "Inventing new medicines: the FGF21 story," Mol Metab, 2014, 3(3):221-229.
Khazov et al., "Nuclear Data Sheets for A=131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcriptionby ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, 2007, 30, 1487-93.
Kim et al., "Recombinant elastin-mimetic biomaterials: Emerging applications in medicine," Adv Drug Deliv Rev, 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem. 2012, 23, 2214-2220.
Kim et al., "Ultrasensitive Carbon nanotube-based biosensors using antibody-binding fragments," Analytical Biochemistry, 2008, 381, 193-198.

(56) References Cited

OTHER PUBLICATIONS

Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., 2015, 26(10):2153-2160.
Kulkarni et al., "Selective functionalization of the protein N terminus with N-myristoyl transferase for bioconjugation in cell lysate," ChemBioChem, 2013, 14, 1958-1962.
Kumar et al., "N-Terminal Region of the Catalytic Domain of Human N-Myristoyltransferase 1 Acts as an Inhibitory Module," PLoS One, 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of βKlotho and Fibroblast Growth Factor (FGF) Receptor Isoforms Determines Metabolic Activity of FGF19 and FGF21," J Biol Chem, 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, 2007, 50(4):752-763.

Le Droumaguet et al., "Recent advances in the design of bioconjugates from controlled/living radical polymerization," Polym. Chem. 2010, 1, 563-598.
Le Meins et al., "Hybrid polymer/lipid vesicles: State of the art and future perspectives," Mater. Today, 2013, 16, 397-402.
Leader et al., "Protein therapeutics: a summary and pharmacological classification," Nat. Rev. Drug Discov. 7, 2008, 21-39.
Lee et al., "Atomistic molecular dynamics simulations of peptide amphiphile self-assembly into cylindrical nanofibers," J. Am. Chem. Soc., 2011, 133, 3677-3683.
Lee et al., "Immunohistochemical analysis of claudin expression in pancreatic cystic tumors," Oncology Reports, 2011, 25(4): 971-978.
Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (2017): 198-208.
Lee et al., "Phase transition and elasticity of protein-based hydrogels," J. Biomater. Sci. Polymer Edn, 2001, 12, 229-242.
Lee et al., "Structures of β-klotho reveal a 'zip code'-like mechanism for endocrine FGF signaling," Nature, 2018, 553:501-505.
Lee et al., "Theranostic nanoparticles with controlled release of gemcitabine for targeted therapy and MRI of pancreatic cancer," ACS Nano 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., 2011, 77(22):8114-28.
Leung et al., "Bio-Click Chemistry: Enzymatic Functionalization of PEGylated Capsules for Targeting Applications**," Angew. Chem. Ink. Ed. 2012, 51, 7132-7136.
Le Vine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS One, 2014, 9(2): e87704, 9 pages.
Li et al., "Elastin is an essential determinant of arterial morphogenesis," Nature, 1998, 393, 276-280.
Li et al., "Molecular description of the LCST behavior of an elastin-like polypeptide," Biomacromolecules, 2014, 15, 3522-3530.
Li et al., "Nanoparticles Evading The Reticuloendothelial System: Role of The Supported Bilayer," Biochim. Biophys. Acta, 2009, 1788 (10), 2259-2266.
Li et al., "Pancreatic cancer," Lancet, 2004, 363, 1049-1057.
Li et al., "Prediction of solvent-induced morphological changes of polyelectrolyte diblock copolymer micelles," Soft Matter, 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., 2015, 36(1):90-95.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering 2010, 1:149-173.
Lillie et al., "The viscoelastic basis for the tensile strength of elastin," Int J Biol Macromol, 2002, 30, 119-127.

(56) References Cited

OTHER PUBLICATIONS

Lim et al., "Improved Non-Chromatographic Purification of a Recombinant Protein by Cationic Elastin-like Polypeptides" Biomacromolecules, 2007, 8(5): 1417-1424.
Lim et al., "In situ cross-linking of elastin-like polypeptide block copolymers for tissue repair," Biomacromolecules, 2008, 9, 222-230.
Lim et al., "In vivo post-translational modifications of recombinant mussel adhesive protein in insect cells," Biotechnol. Prog., 2011, 27, 1390-1396.
Lin et al., "Adiponectin Mediates the Metabolic Effects of FGF21 on Glucose Homeostasis and Insulin Sensitivity in Mice," Cell Metab, 2013, 17(5):779-789.
Lin et al., "Functional expression of a biologically active fragment of soluble gp130 as an ELP-fusion protein in transgenic plants: purification via inverse transition cycling," Biochem J, 2006, 398(3):577-583.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, 2012, 134(26):10749-10752.
Litiere et al., "RECIST—learning from the past to build the future," Nat Rev Clin Oncol, 2017, 14, 187-192.
Liu et al., "Brachytherapy using injectable seeds that are self-assembled from genetically encoded polypeptides in situ," Cancer Res, 2012, 72, 5956-5965.
Liu et al., "Hydrophobic modifications of cationic polymers for gene delivery," Prog. In Polym. Sci., 2010, 35, 1144-1162.
Liu et al., "In Situ Formation of Protein-Polymer Conjugates through Reversible Addition Fragmentation Chain Transfer Polymerization**," Angew. Chem. Int. Ed. 2007, 46, 3099-3103.
Liu et al., "Injectable intratumoral depot of thermally responsive polypeptide-radionuclide conjugates delays tumor progression in a mouse model," J. Control Release, 2010, 144(1):2-9.
Liu et al., "Tracking the in vivo fate of recombinant polypeptides by isotopic labeling" Journal of Controlled Release, 2006, 114, 184-192.
Liu et al., "Tumor accumulation, degradation and pharmacokinetics of elastin-like polypeptides in nude mice," Journal of Controlled Release, 2006, 116, 170-178.
Livingstone, "Theoretical property predictions. Curr Top Med Chem Field Full Journal Title: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, 2009, 262-269.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng., 2017, 1, 0078.
Luginbuhl et al., "Recombimnt Synthesis of Hybrid Lipid-Peptide Polymer Fusions that Self-Assemble and Encapsulate Hydrophobic Drugs," Angew Chem Int Ed Engl., 2017, 56: 13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, 2006, 39, 893-896.
Ma et al., "Non-fouling oligo(ethylene glycol)-functionalized polymer brushes synthesized by surface-initiated atom transfer radical polymerization," Advanced Materials 2004, 16 (4), 338.
Ma et al., "Protein-resistant polymer coatings on silicon oxide by surface-initiated atom transfer radical polymerization," Langmuir: the ACS journal of surfaces and colloids, 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.
MacEwan et al., "Applications of elastin-like polypeptides in drug delivery," Journal of Controlled Release, 2014, 190: p. 314-330.
MacEwan et al., "Controlled apoptosis by a thermally toggled nanoscale amplifier of cellular uptake," Nano Letters, 2014, 14, 2058-2064.
MacEwan et al., "Digital switching of local arginine density in a genetically encoded self-assembled polypeptide nanoparticle controls cellular uptake," Nano Lett., 2012, 12, 3322-3328.
MacEwan et al., "Elastin-like polypeptides: Biomedical applications of tunable biopolymers," Biopolymers, 2010, 94, 60-77.
MacEwan et al., "Non-chromatographic Purification of Recombinant Elastin-like Polypeptides and their Fusions with Peptides and Proteins from *Escherichia coli*," 2014, 88, p. e51583.
MacEwan et al., "Phase Behavior and Self-Assembly of Perfectly Sequence-Defined and Monodisperse Multiblock Copolypeptides," Biomacromolecules, 2017, 18(2):599-609.
Mack et al., "Antiobesity action of peripheral exenatide (exendin-4) in rodents: effects on food intake, body weight, metabolic status and side-effect measures," Int. J. Obes. 30, 2006, 1332-1340.
MacKay et al., "Self-assembling chimeric polypeptide-doxorubicin conjugate nanoparticles the abolish tumors after single injection," Nat Mater, 2009, 8(12):993-999.
Maeda et al., "Tumor vascular permeability and the EPR effect in macromolecular therapeutics: a review," J. Control. Release, 2000, 65(1-2)271-284.
Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, 2010, 671-678.
Magnusson et al., "Ion-Sensitive "Isothermal" Responsive Polymers Prepared in Water," Journal of the American Chemical Society, 2008, 130, 10852-10853.
Maitra et al., "Pancreatic Cancer," Annu Rev Pathol Mech Dis, 2008, 3, 157-188.
Malik et al., "Recent advances in protein and peptide drug delivery systems," Curr. Drug Deliv. 2, 2007, 141-151.
Mann et al., "Proteomic analysis of post-translational modifications," Nat Biotechnol., 2003, 21, 255-61.
Manzoor et al., "Overcoming limitations in nanoparticle drug delivery: triggered, intravascular release to improve drug penetration into tumors," Cancer Res, 2012, 72, 5566-5575.
Mao et al., "DNA repair by nonhomologous end joining and homologous recombination during cell cycle in human cells," Cell cycle, 2008, 7, 2902-2906.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, 2006, 70(1):192-221.
Mariam et al., "Albumin corona on nanoparticles—a strategic approach in drug delivery," Drug Deliv., 2016, 23 (8), 2668-2676.
Marr et al., "Effect of Temperature on the Composition of Fatty Acids in *Escherichia coli*," J Bacteriol., 1962, 84(6):1260-7.
Marten et al., "A randomized multicentre phase II trial comparing adjuvant therapy inpatients with interferon alpha-2b and 5-FU alone or in combination with either external radiation treatment and

(56) References Cited

OTHER PUBLICATIONS cisplatin (CapRI) or radiation alone regarding event-free survival—CapRI-2," BMC Cancer, 2009, 9, 1-8.
Maskarinec et al., "Protein engineering approaches to biomaterials design," Cut. Opin. Biotechnol., 2005, 16, 422-426.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, 2015, 208:52-8.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, 2012, 64, 710-719.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, 2008, 93(12):4810-4817.
Matyjaszewski et al., "Atom transfer radical polymerization," Chem. Rev. 101, 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, 2010, 457-469.
McDaniel et al., "A unified model for de novo design of elastin-like polypeptides with tunable inverse transition temperatures," Biomacromolecules, 2013, 14(8):2866-2872.
McDaniel et al., "Actively targeting solid tumours with thermoresponsive drug delivery systems that respond to mild hyperthermia," Int J Hyperthermia, 2013, 29, 501-510.
McDaniel et al., "Doxorubicin-conjugated chimeric polypeptide nanoparticles that respond to mild hyperthermia," Control. Release, 2012, 159 (3), 362-367.
McDaniel et al., "Drug delivery to solid tumors by elastin-like polypeptides," Adc. Drug Deliver. Rev., 2010, 62(15):1456-1467.
McDaniel et al., "Noncanonical Self-Assembly of Highly Asymmetric Genetically Encoded Polypeptide Amphiphiles into Cylindrical Micelles," Nano Lett., 2014, 14(11):6590-6598.
McDaniel et al., "Rational design of "heat seeking" drug loaded polypeptide nanoparticles that thermally target solid tumors," Nano Letters, 2014, 14, 2890-2895.
McDaniel et al., "Recursive Directional Ligation by Plasmid Reconstruction Allows Rapid and Seamless Cloning of Oligomeric Genes," Biomacromolecules, 2010, 11(4):944-952.
McDaniel et al., "Self-assembly of thermally responsive nanoparticles of a genetically encoded peptide polymer by drug conjugation," Chem. Int. Ed. 2013, 52, 1683-1687.
McHale et al., "Synthesis and in vitro evaluation of enzymatically cross-linked elastin-like polypeptide gels for cartilaginous tissue repair," Tissue Eng., 2005, 11, 1768-1779.

McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
Meier et al., "Determination of Optimal Sample Size for Quantification of β-Cell Area, Amyloid Area and β-Cell Apoptosis in Isolated Islets," J Histochem Cytochem, 2015, 63(8):663-673.
Mejuch et al., "Synthesis of lipidated proteins," Bioconjug. Chem. 27, 2016, 1771-1783.
Mero et al., "Transglutaminase-mediated PEGylation of proteins: direct identification of the sites protein medification by mass spectrometry using a novel monodisperse PEG," Bioconjug Chem, 2009, 20(2):384-389.
Merrick et al., "Seed fixity in the prostate/periprostatic region following brachytherapy," International journal of radiation oncology, biology, physics, 2000, 46, 215-220.
Methods and Welfare Considerations in Behavioral Research with Animal. (2002).
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, 2013, 62, 317-326.
Micsonai et al. "Accurate secondary structure prediction and fold recognition for circular dichroism spectroscopy," Proc Natl Acad Sci U S A, 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Mosbach et al., "Formation of proinsulin by immobilized Bacillus subtilis," Nature, 1983, 302, 543-545.
Mu et al., "FGF21 Analogs of Sustained Action Enabled by Orthogonal Biosynthesis Demonstrate Enhanced Antidiabetic Pharmacology in Rodents," Diabetes, 2012, 61(2):505-512.
Muiznieks et al., "Structural changes and facilitated association of tropoelastin," Archives of Biochemistry and Biophysics, 2003, 410, 317-323.
Muiznies et al., "Modulated growth, stability and interactions of liquid-like coacervate assemblies of elastin," Matrix Biology 36, 2014, pp. 39-50.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and

(56) References Cited

OTHER PUBLICATIONS

Rational Modification of the Helical Content of Natural Peptides," Journal of Molecular Biology, 1995, 245, 275-296.

Muñoz et al., "Elucidating the folding problem of helical peptides using empirical parameters. III. Temperature and pH dependence," J Mol Biol, 1995, 245, 297-308.

Muralidharan et al., "Protein Ligation: an Enabling Technology for the Biophysical Analysis of Proteins," Nature Methods, 2006, vol. 3, No. 6, pp. 429-438.

Murphy et al., "A dosimetric model of duodenal toxicity after stereotactic body radiotherapy for pancreatic cancer," Int J Radiation Oncology Biol Phys, 2010, 78, 1420-1426.

Na et al., "Thermoresponsive pore structure of biopolymer microspheres for a smart drug carrier," Langmuir, 2010, 26, 11165-11169.

Nagarsekar et al., "Genetically Engineered Polymers for Drug Delivery," Journal of Drug Targeting, 1999, 7(1):11-32.

Nahire et al., "Multifunctional Polymersomes for Cytosolic Delivery of Gemcitabine and Doxorubicin to Cancer Cells," Biomaterials 2014, 35(24):6482-6497.

Nairn et al., "A Synthetic Resilin Is Largely Unstructured," Biophysical Journal, 2008, vol. 95 3358-3365.

Nakaoka et al., "Prolongation of the serum half-life period of superoxide dismutase by poly(ethylene glycol) modification," Journal of Controlled Release, 1997, 46(3):253-261.

Nanoprecision Medical, "Pipeline, Type II Diabetes," <http://www.nanoprecisionmedical.com/pipeline/diabetes> webpage available as early as Aug. 2018.

Nauck "Glucagon-like Peptide 1 (GLP-1) in the Treatment of Diabetes," Horm Metab Res, 2004, 36(11/12):852-858 (in English).

Neidigh et al., "Exendin-4 and glucagon-like-peptide-q: NMR structural comparisons in the solution and micelle-associated states," Biochemistry 40, 2001, 13188-13200.

Nettles et al., "Applications of elastin-like polypeptides in tissue engineering," Adv Drug Deliv Rev, 2010, 62, 1479-1485.

Nettles et al., "In situ crosslinking elastin-like polypeptide gels for application to articular cartilage repair in a goat osteochondral defect model," Tissue Eng Part A, 2008, 14, 1133-1140.

Newcomb et al., "Advances in cryogenic transmission electron microscopy for the characterization of dynamic self-assembling nanostructures," Current Opinion in Colloid and Interface Science, 2012, 17, 350-359.

Newton et al., "Commissioning a small-field biological irradiator using point, 2D, and 3D dosimetry techniques," Medical Physics, 2011, 38, 6754-6762.

Nichols et al., "Claudin 4 protein expression in primary and metastatic pancreatic cancer," Am J Clin Pathol, 2004, 121, 226-230.

Nicolas et al., "Fluorescently tagged polymer bioconjugates from protein derived macroinitiators," Chem. Commun. 2006, 45, 4697-4699.

Nie, "Understanding and overcoming major barriers in cancer nanomedicine," Nanomedicine (Lond) 2010, 5 (4), 523-528.

Nielsen, "Incretin mimetics and DPP-IV inhibitors for the treatment of type 2 diabetes," Drug Discov. Today 10, 2005, 703-710.

Nies et al., "Fibroblast Growth Factor Signaling in Metabolic Regulation," Front Endocrinol, 2016, 6(193) (in English).

Nilvebrant et al., "The albumin-binding domain as a scaffold for protein engineering," Computational and Structural Biotechnology Journal, 2013, 6: e201303009, 8 pages.

Nucci et al., "The therapeutic value of poly(ethylene glycol)-modified proteins," Adv. Drug Deliv. Rev., 1991, 6(2):133-151.

Nuhn et al., "Secondary structure formation and LCST behavior of short elastin-like peptides," Biomacromolecules, 2008, 9, 2755-2763.

O'Day et al., "Therapeutic Protein-polymer Conjugates: Advancing beyond PEGylation," J. Am. Chem. Soc., 2014, vol. 136, pp. 14323-14332.

Ogawara et al., "Pre-coating with serum albumin reduces receptor-mediated hepatic disposition of polystyrene nanosphere: implications for rational design of nanoparticles," Journal of Controlled Release, 2004, 100(3): 451-455.

Ortony et al., "Internal dynamics of a supramolecular nanofibre," Nat. Mater., 2014, 13, 1-5.

Ozer et al., "Site-Specific and Stoichiometric Stealth Polymer Conjugates of Therapeutic Peptides and Proteins," Bioconjug Chem, 2017, 28(3):713-723.

Pace et al., "How to measure and predict the molar absorption coefficient of a protein" Protein Science 1995, 4: 2411-2423.

Pagani et al., "International guidelines for management of metastatic breast cancer: can metastatic breast cancer be cured?," Journal of the National Cancer Institute, 2010, 102, 456-463.

Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (Anchor) Study," International Journal of Radiation Oncology • Biology • Physics, 2016, 96, S204-S205.

Palva et al., "Secretion of interferon by Bacillus subtilis," Gene, 1983, 22, 229-235.

Pang et al., "A Modular Method for the High-Yield Synthesis of Site-Specific Protein-Polymer Therapeutics," Angew Chem Int Ed Engl, 2016, 55, 10296-10300.

Paolino et al., "Folate-targeted supramolecular vesicular aggregates as a new frontier for effective anticancer treatment in in vivo model," Eur. J. Pharm. Biopharm. 2012, 82(1):94-102.

Paolino et al., "Gemcitabine-loaded PEGylated unilamellar liposomes vs GEMZAR: biodistribution, pharmacokinetic features and in vivo antitumor activity," J. Control. Release 2010, 144(2):144-150.

Paoloni et al., "Translation of new cancer treatments from pet dogs to humans," Nat. Rev. Cancer 2008, 8 (2), 147-156.

Papa et al., "PEGylated Liposomal Gemcitabine: Insights Into a Potential Breast Cancer Therapeutic," Cell Oncol. (Dordr) 2013, 36(6):449-457.

Paramonov et al., "Self-assembly of peptide-amphiphile nanofibers: The roles of hydrogen bonding and amphiphilic packing" J. Am. Chem. Soc., 2006, 128, 7291-7298.

Park et al., "Exendin-4 and exercise improve hepatic glucose homeostasis by promoting insulin signaling in diabetic rats," Metabolism, 2010, 59, 123-133.

Park et al., "Formulation optimization and in vivo proof-of-concept study of thermosensitive liposomes balanced by phospholipid, elastin-like polypeptide, and cholesterol," PLoS One, 2014, 9: e103116, 13 pages.

Parkes et al. "Discovery and development of exenatide: the first antidiabetic agent to leverage the multiple benefits of the incretin hormone, GLP-1," Expert Opinion. Drug Deliv. 8, 2012, 219-244.

Parveen et al., "Nanomedicine," Clinical Pharmacokinetics, 2006, 45(10):965-988.

Patil et al., "Cellular delivery of doxorubicin via pH-controlled hydrazone linkage using multifunctional nano vehicle based on poly(beta-1-malic acid)," Int J Mol Sci, 2012, 13, 11681-11693.

Peeler et al., "Genetically encoded initiator for polymer growth from proteins," J. Am. Chem. Soc. 132, 2010, 13575-13577.

Peters, "Serum albumin," Adv. Protein Chem. 37, 1985, 161-245.

Petitdemange et al., "Tuning Thermoresponsive Properties of Cationic Elastin-like Polypeptides by Varying Counterions and Side-Chains," Bioconjug. Chem., 2017, 28(5):1403-1412.

Phan et al., "Temperature-responsive self-assembly of charged and uncharged hydroxyethylcellulose-graft-poly(N-isopropylacrylamide) copolymer in aqueous solution," Colloid Polym. Sci., 2011, 289 (9), 993-1003.

Pinkas et al., "Tunable, post-translational hydroxylation of collagen domains in *Escherichia coli*," ACS Chem. Biol., 2011, 6, 320-324.

Pliarchopoulou et al., "Pancreatic cancer: Current and future treatment strategies," Cancer Treatment Reviews, 2009, 35, 431-436.

Poitout et al., "Glucolipotoxicity: Fuel Excess and β-Cell Dysfunction," Endocr Rev, 2008, 29(3):351-366.

Pometun et al., "Quantitative observation of backbone disorder in native elastin," J Biol Chem, 2004, 279, 7982-7987.

(56) References Cited

OTHER PUBLICATIONS

Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve The Properties Of Cytokines," PNAS, 2011, vol. 108, No. 8, pp. 3169-3174.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et at, "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1 regulator of endothelial junctional integrity," Cell Tissue Res, 2014, 355, 607-619.
Prostate Seed Center, "Brachytherapy seed pre-plan rendering" <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21, 418-429.
Provenzano et al., "Hyaluronan, fluid pressure, and stromal resistance in pancreas cancer," Br J Cancer, 2013, 108, 1-8.
Pulaski et al., "Mouse 4T1 breast tumor model," Cuff. Protoc. Immunol., 2001, Chapter 20, Unit 20.2.
Qi et al., "A brush-polymer conjugate of exendin-4 reduces blood glucose for up to five days and eliminates poly(ethylene glycol) antigenicity," Nat Biomed Eng, 2016, 1:0002.
Qi et al., Dataset for A brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: a biomedical perspective," Polym. Chem. 5, 2014, 266-276.
Qi et al., "Protein-polymer conjugation—moving beyond PEGylation," Curr. Opin. Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Development of Orthotopic Pancreatic Tumor Mouse Models," Methods Mol Biol, 2013, 980: 215-223.
Qiu et al., "Polymer Architecture and Drug Delivery," Pharmaceutical Research, 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Sequence heuristics to encode phase behaviour in intrinsically disordered protein polymers," Nat. Mater., 2015, 14, 1164-1171.
Rabotyagova et al., "Protein-based block copolymers," Biomacromolecules, 2011, 12, 269-289.
Radivojac et al., "Intrinsic Disorder and Functional Proteomics," Biophysical Journal, 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, 2016, 76.
Rankine et al., "Investigating end-to-end accuracy of image guided radiation treatment delivery using a micro-irradiator," Physics in Medicine and Biology, 2013, 58, 7791-7801.
Rao et al., "Synthetic namparticles camouflaged with biometric erythrocyte membranes for reduced reticuloendothelial system uptake," Nanotechnology, 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for bionnterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Rauscher et al. "Proline and Glycine Control Protein Self-Organization into Elastomeric or Amyloid Fibrils," Structure, 2006, 14:1667-1676.
Ray et al., "Aptamer-mediated delivery of chemotherapy to pancreatic cancer cells." Nucleic acid therapeutics, 2012, 22(5): 295-305.
Regier et al., American Heart Association 2014 Scientific Sessions, 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Engineered fibronectin type III domain with a RGDWE sequence binds with enhanced affinity and specificity to human $\alpha v\beta 3$ integrin," J Mol Biol, 2003, 326(5):1475-1488.
Richards et al., "Man's best friend: what can pet dogs teach us about non-Hodgkin lymphoma?" Inmunol Rev., 2016, 263 (1), 173-191.
Riddles et al., "Ellman's reagent: 5,5'-dithiobis(2-nitrobenzoic acid)—a reexamination," Anal Biochem 1979, 94(1):75-81.
Riedel et al., "Engineered glucagon-like peptide-1-producing hepatocytes lower plasma glucose levels in mice," Am J Physiol Endocrinol Metab, 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, 2015, 17, 661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Diaz et al., "Alpha cells secrete acetylcholine as a non-neuronal paracrine signal priming beta cell function in humans," Nat Med, 2011, 17:888-892.
Römer et al., "The elaborate structure of spider silk: structure and function of a natural high performance fiber," Prion 2, 2008, 154-161.
Roopenian et al., "FcRn: the neonatal Fc receptor comes of age," Nat. Rev. Immunol., 2007, vol. 7, No. 9, 715-725.

(56) References Cited

OTHER PUBLICATIONS

Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabire); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, 2016, 12, 669-685.
Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Saifer et al., "Selectivity of binding of PEGs and PEG-like oligomers to anti-PEG antibodies induced by methoxyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schellenberger et al., "A recombinant polypeptide extends the in vivo half-life of peptides and proteins in a tunable manner," Nat. Biotechnol. 27, 2009, 1186-1188.
Schlaff et al., "Bringing the heavy: carbon ion therapy in the radiobiological clinical context," Radiation Oncology, 2014, 9, 1-18.
Schneider et al., "NIH Image to ImageJ: 25 years of image analysis," Nature Methods, 2012, 9, 671-675.
Schwendeman et al., "Injectable controlled release depots for large molecules," J Control Release, 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shadwick, "Mechanical design in arteries," J Exp, Biol, 1999, 202, 3305-3313.
Shang et al., "pH-Dependent Protein Conformational Changes in Albumin:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Shen et al., "Conjugation site modulates the in vivo stability and thearpeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.
Sherman et al., "Next-Generation PEGylation Enables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.
Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Shusharina et al., "Micelles of Diblock Copolymers with Charged and Neutral Blocks: Scaling and Mean-Field Lattice Approaches," Macromolecules, 2000, 33(10): 3892-3901.
Siegel et al., "Absorbed fractions for electrons and beta particles in spheres of various sizes," J Nucl Med, 1994, 35, 152-156.
Siegwart et al., "ATRP In The Design Of Functional Materials For Biomedical Applications," Prog Polymer Science, 2012, vol. 37, No. 1, pp. 18-37.
Silberstein et al., "The SNM Practice Guideline for Therapy of Thyroid Disease with $^{131}$I, 3.0," J Nucl Med, 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Singhal et al., "Fibroblast Growth Factor 21 (FGF21) Protects against High Fat Diet Induced Inflammation and Islet Hyperplasia in Pancreas," PLoS One, 2016, 11(2):e0148252.
Sisson et al., "Radiation safety in the treatment of patients with thyroid diseases by radioiodine 131I: practice recommendations of the American Thyroid Association," Thyroid, 2011, 21, 335-346.
Smith et al., "The Role of Beta Cell Glucagon-like Peptide-1 Signaling in Glucose Regulation and Response to Diabetes Drugs," Cell Metab, 2014, 19(6):1050-1057.
Sonawane et al., "Hydrazo linkages in pH responsive drug delivery systems," European Journal Pharmaceutical Sciences, 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, 2016, 234:83-89.
Sriraman et al., "Barriers to drug delivery in solid tumors," Tissue Barriers, 2014, 2, 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, 2017, 158(5):1314-1327.
Stefl et al., "RNA sequence-and shape-dependent recognition by proteins in the ribonucleoprotein particle" EMBO reports (2005) 6(1):33-38.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.

(56) References Cited

OTHER PUBLICATIONS

Strohmaier et al., "Comparison of $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, 2015, 10, 1-17.
Sumerlin, "Proteins as Initiators of Controlled Radical Polymerization: Grafting-from via ATRP and RAFT," ACS Macro Lett. 2012, 1, 141-145.
Sun et al., "Autofluorescence Imaging of Living Pancreatic Islets Reveals Fibroblast Growth Factor-21 (FGF21)-Induced Metabolism," Biophys J, 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, 2013, 46, 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, 2014, 42, 1508-1516.
Swee et al., "Sortase-mediated modification of αDEC205 affords optimization of antigen presentation and immunization against a set of viral epitopes," Proc Natl Acad Sci USA, 2013, 110(4):1428-1433.
Swers et al., Multivalent Scaffold Proteins as Superagonists of TRAIL Receptor 2-Induced Apoptosis, Mol Cancer Ther, 2013, 12, 1235-1244.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, 2016, 23(3):427-440.
Tamburro et al., "Dissection of human tropoelastin exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., 2016, 15, 419-424.
Tang et al., "Enzymatic Polymerization of High Molecular Weight DNA Amphiphiles That Self-Assemble into Star-Like Micelles," Advanced Materials, 2014, 26(19): 3050-3054.
Tang et al., "High-Molecular-Weight Polynucleotides by Transferase-Catalyzed Living Chain-Growth Polycondensation," Angew. Chem., 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., 2016, 15, 469-476.
Tedja et al., "Effect of TiO2 mnoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Teicher, "In vivo/ex vivo and in situ assays used in cancer research: a brief review," Toxicol. Pathol., 2009, 37 (1), 114-122.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, 2010, 107(4):1666-71.
Tompa et al., "Fuzzy complexes: polymorphism and structural disorder in protein-protein interactions," Trends Biochem Sci, 2008, 33, 2-8.
Tong et al., "Protein Modification with Amphiphilic Block Copoly(2-oxazoline)s as a New Platform for Enhanced Cellular Delivery," Mol. Pharm, 2010, vol. 7, No. 4, pp. 984-992.
Ton-That et al., "Assembly of pili on the surface of Corylabacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa-Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, 2014, 24, 140-147.
Trieu et al., "P0157 Preclinical evaluation of NBN-paclitaxel in pancreatic cancer xenograft models," Eur J Cancer, 2014, 50, e53.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, 2016, 24(1):51-62.
Tsume et al., "The development of orally administrable gemcitabine prodrugs with D-enantiomer amino acids: Enhanced membrane permeability and enzymatic stability," Eur. J. Pharm. Biopharm. 2014, 86(3):514-523.
Tu et al., "Stages in tropoelastin coalescence during synthetic elastin hydrogel formation," Micron, 2010, 41, 268-272.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Tward et al., "Survival of men with clinically localized prostate cancer treated with prostatectomy, brachytherapy, or no definitive treatment: impact of age at diagnosis," Cancer, 2006, 107, 2392-2400, doi:10.1002/cncr.22261.

(56) References Cited

OTHER PUBLICATIONS

Uchida et al., "Potential of adenovirus-mediated REIC/Dkk-3 gene therapy for use in the treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, 1992, 57(1):23-57.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.
Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., 2011, vol. 22, pp. 976-986.
Vlieghe et al., "Synthetic therapeutic peptides: science and market," Drug Discovery Today, 2010, 15, 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry of tropoelastin," Eur J Biochem, 1998, 258, 1-18.
Vrignaud et al., "Strategies for the nanoencapsulation of hydrophilic molecules in polymer-based nanoparticles," Biomaterials 2011, 32(33):8593-8604.
Walczak, "Death Receptor—Ligand Systems in Cancer, Cell Death, and Inflammation," Cold Spring Harb. Perspect. Biol., 2013, 5, a008698.
Wali et al., "Measuring Death of Pancreatic Beta Cells in Response to Stress and Cytotoxic T Cells," Methods in Molecular Biology, 2015, 1292:165-176.
Walsh et al., "Post-translational modifications in the context of therapeutic proteins," Nat. Biotechnol., 2006, 24, 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm. 2014, 11, 1140-1150.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparficles in Endo-Lysosomes by Local pH," Nano Lett., 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Wei et al., "Fibroblast growth factor 21 promotes bone loss by potentiating the effects of peroxisome proliferator-activated receptor γ," Proc Natl Acad Sci USA, 2012, 109(8):3143-3148.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic β-Cell Function and Survival by Activation of Extracellular Signal-Regulated Kinase 1/2 and Akt Signaling Pathways," Diabetes, 2006, 55(9):2470-2478.
Werle et al., "Strategies to improve plasma half life time of peptide and protein drugs," Amino Acids 30, 2006, 351-367.
Wienkers et al., "Predicting in vivo drug interactions from in vitro drug discovery data," Nat. Rev. Drug. Discov. 2005, 4(10):825-833.
Williams et al., "Targeted radionuclide therapy," Medical Physics, 2008, 35, 3062-3068.
Williamson et al., "Efficient N-terminal labeling of proteins by use of sortase," Angew Chem Int ed Engl, 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.

(56) References Cited

OTHER PUBLICATIONS

Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, 2016, 79, 405-412.
Xia et al., "Tunable self-assembly of genetically engineered silk—elastin-like protein polymers," Biomacromolecules, 2011, 12, 3844-3850.
Xiaodong et al., "FGF21 Is Not a Major Mediator for Bone Homeostasis or Metabolic Actions of PPARα and PPARγ Agonists," J Bone Miner Res, 2017, 32(4):834-845.
Xu et al., "A quality by design (QbD) case study on liposomes containing hydrophilic API: II. Screening of critical variables, and establishment of design space at laboratory scale," Int. J. Pharm. 2012, 423(2):543-553.
Xu et al., "Downregulation of GLP-1 and GIP Receptor Expression by Hyperglycemia," Diabetes, 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, 2009, 58(1):250-259.
Xu et al., "Genetically engineered block copolymers: influence of the length and structure of the coiled-coil blocks on hydrogel self-assembly," Pharm Res, 2008, 25, 674-682.
Xu et al., "Role of pancreatic stellate cells in pancreatic cancer metastasis," Am J of Pathology, 2010, 177, 2585-2596.
Xu et al., "Self-assembly behavior of peptide amphiphiles (PAs) with different length of hydrophobic alkyl tails," Colloids Surfaces B Biointerfaces, 2010, 81, 329-335.
Yamamoto et al., "ATRP Synthesis of Thermally Responsive Molecular Brushes from Oligo(ethylene oxide) Methacrylates," Macromolecules, 2007, 40, 9348-9353.
Yang et al., "Long Term Exendin-4 Treatment Reduces Food Intake and Body Weight and Alters Expression of Brain Homeostatic and Reward Markers," Endocrinology, 2014, 155, 3473-3483.
Yang et al., "Poly(carboxybetaine) nanomaterials enable long circulation and prevent polymer-specific antibody production," Nano Today, 2014, 9(1):10-16.
Yates et al., "Contemporary management of patients with high-risk non-muscle-invasive bladder cancer who fail intravesical BCG therapy," World journal of urology, 2011, 29, 415-422.
Yeo et al., "Coacervation of tropoelastin," Adv Colloid Interface Sci, 2011, 167, 94-103.
Yokoe et al., "Albumin-conjugated PEG liposome enhances tumor distribution of liposomal doxorubicin in rats," International Journal of Pharmaceutics, 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release 117, 2007, 371-379.
Yousefpour et al., "Co-opting biology to deliver drugs," Biotechnol Bioeng, 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett. 2018, 18(12): 7784-7793.
Yu et al., "Effectiveness and security of CT-guided percutaneous implantation of (125)I seeds in pancreatic carcinoma," The British journal of radiology, 2014, 87, 20130642, 7 pages.
Yusta et al., "GLP-1 receptor activation improves β cell function and survival following induction of endoplasmic reticulum stress," Cell Metab, 2006, 4(5):391-406.
Zhang et al., "A self-assembly pathway to aligned monodomain gels," Nat. Mater., 2010, 9, 594-601.
Zhang et al., "In Depth Analysis on the Unusual Multistep Aggregation Process of Oligo(ethylene glycol) Methacrylate-Based Polymers in Water," Macromolecules, 2014, 47, 4728-4737.
Zhang et al., "Nanoparticles in medicine: therapeutic applications and developments," Clin. Pharmacol. Ther. 2008, 83(5):761-769.
Zhang et al., "Novel agents for pancreatic ductal adenocarcinoma: emerging therapeutics and future directions," Jounral of Hematology & Oncology, 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "A new Bliss Independence model to analyze drug combination data," J Biomol Screen, 2014, 19, 817-821.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, 2011, 60, 1055-1065.
Zong et al., "Crystal structures of Staphylococcus aureus sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).

(56) References Cited

OTHER PUBLICATIONS

United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using Revolve System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The No. of operations required for completing breast reconstruction," Plast Reconstr Surg Glob Open, 2012, 2: e242.
Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4:232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.

Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush As a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.

(56) References Cited

OTHER PUBLICATIONS

Chu et al., "Controllable monodisperse multiple emulsions," Angew Chem Int Ed Engl, 2007, 46: 8970-8974.

Costa et al., "Photo-crosslinkable unnatural amino acids enable facile synthesis of thermoresponsive nano- to microgels of intrinsically disordered polypeptides," Adv Mater, 2018, 30(5): 1704878.

Darling et al., "Viscoelastic properties of zonal articular chondrocytes measured by atomic force microscopy," Osteoarthritis Cartilage, 2006, 14: 571-579.

Griffin et al., "Accelerated wound healing by injectable microporous gel scaffolds assembled from annealed building blocks," Nat Mater, 2015, 14: 737-744.

Hutter et al., "Calibration of atomic-force microscope tips," Review of Scientific Instruments, 1993, 64: 1868-1873.

Hwang et al., "Differentially degradable janus particles for controlled release applications," Macromol Rapid Commun, 2012, 33: 1178-1183.

Jang et al., "Engineering Globular Protein Vesicles through Tunable Self-Assembly of Recombinant Fusion Proteins," Small, 2017, 13(36): 1700399.

Khademhosseini et al., "Micromolding of photocrosslinkable hyaluronic acid for cell encapsulation and entrapment," J Biomed Mater Res A, 2006, 79: 522-532.

Kim et al., "Generation of core-shell microcapsules with three-dimensional focusing device for efficient formation of cell spheroid," Lab Chip, 2011, 11: 246-252.

Liu, L. et al., "Monodisperse core-shell chitosan microcapsules for pH-responsive burst release of hydrophobic drugs," Soft Matter, 2011, 7: 4821-4827.

Ma et al., "Core-shell hydrogel microcapsules for improved islets encapsulation," Adv Healthc Mater, 2013, 2: 667-672.

Matsunaga et al., "Molding cell beads for rapid construction of macroscopic 3D tissue architecture," Adv Mater, 2011, 23: H90-94.

Oh et al., "The development of microgels/nanogels for drug delivery applications," Progress in Polymer Science, 2008, 33(4): 448-477.

Panda et al., "Stop-flow lithography to generate cell-laden microgel particles," Lab Chip, 2008, 8: 1056-1061.

Paulsen et al., "Optofluidic fabrication for 3D-shaped particles," Nat Commun, 2015, 6: 6976.

Roberts et al., "Injectable tissue integrating networks from recombinant polypeptides with tunable order," Nature Materials, 2018, 17(12): 1154-1163.

Rodriguez-Cabello et al., "Elastin-like polypeptides in drug delivery," Adv Drug Deliv Rev, 2016, 97: 85-100.

Song et al., "Budding-like division of all-aqueous emulsion droplets modulated by networks of protein nanofibrils," Nat Commun, 2018, 9: 2110.

Srinivas et al., "Aptamer-functionalized microgel particles for protein detection," Anal Chem, 2011, 83: 9138-9145.

Tsuda et al., "Monodisperse cell-encapsulating peptide microgel beads for 3D cell culture," Langmuir, 2010, 26: 2645-2649.

Utada et al., "Monodisperse double emulsions generated from a microcapillary device," Science, 2005, 308: 537-541.

Uversky, "Protein intrinsic disorder-based liquid-liquid phase transitions in biological systems: Complex coacervates and membrane-less organelles," Adv Colloid Interface Sci, 2017, 239: 97-114.

Volodkin et al., "One-Step Formulation of Protein Microparticles with Tailored Properties: Hard Templating at Soft Conditions," Advanced Functional Materials, 2012, 22: 1914-1922.

Wang et al., "Functional polymeric microparticles engineered from controllable microfluidic emulsions," Acc Chem Res, 2014, 47: 373-384.

Yeh et al., "Micromolding of shape-controlled, harvestable cell-laden hydrogels," Biomaterials, 2006, 27: 5391-5398.

United States Patent Office Action for U.S. Appl. No. 16/305,696 dated Jan. 28, 2021 (15 pages).

United States Patent Office Notice of Allowance for U.S. Appl. No. 16/332,865 dated Apr. 2, 2021 (10 pages).

Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.

Amanat et al., "A serological assay to detect SARS-CoV-2 seroconversion in humans," Nat Med, 2020, 26(7): 1033-1036.

American Hospital Association, "AHA Hospital Statistics," 2020 edition. Available at: <https://www.aha.org/statistics/fast-facts-us-hospitals>.

Armbruster et al., "Limit of blank, limit of detection and limit of quantitation," Clin Biochem Rev, 2008, 29 Suppl 1: S49-52.

Arshavsky-Graham et al., "Lab-on-a-Chip Devices for Point-of-Care Medical Diagnostics," Advances in Biochemical Engineering/Biotechnology, 2020, 19 pages.

Atyeo et al., "Distinct Early Serological Signatures Track with SARS-CoV-2 Survival," Immunity, 2020, 53: 524-532.

Baraf et al., "Infusion-related reactions with pegloticase, a recombinant uricase for the treatment of chronic gout refractory to conventional therapy," J Clin Rheumatol, 2014, 20: 427-432.

Benn et al., "Physiology of Hyperuricemia and Urate-Lowering Treatments," Front Med (Lausanne), 2018, 5: 160, 28 pages.

Berry et al., "Development and characterisation of neutralising monoclonal antibody to the SARS-coronavirus," J Virol Methods, 2004, 120: 87-96.

Bryant et al., "Serology for SARS-CoV-2: Apprehensions, opportunities, and the path forward," Sci Immunol, 2020, 5: eabc6347, 4 pages.

Calabrese et al., "Frequency, distribution and immunologic nature of infusion reactions in subjects receiving pegloticase for chronic refractory gout," Arthritis Res Ther, 2017, 19: 191, 7 pages.

Caves et al., "Thermal inactivation of uricase (urate oxidase): mechanism and effects of additives," Biochemistry, 2013, 52: 497-507.

Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.

Chen et al., "Real-world patterns of pegloticase use for treatment of gout: descriptive multidatabase cohort study," BMJ Open, 2020, 10: e041167, 6 pages.

Chen et al., "The influence of polymer topology on pharmacokinetics: differences between cyclic and linear PEGylated poly(acrylic acid) comb polymers," J Control Release, 2009, 140: 203-209.

Chu et al., "Molecular Diagnosis of a Novel Coronavirus (2019-nCoV) Causing an Outbreak of Pneumonia," Clin Chem, 2020, 66(4): 549-555.

Cong et al., "Nucleocapsid Protein Recruitment to Replication-Transcription Complexes Plays a Crucial Role in Coronaviral Life Cycle," J Virol, 2020, 94: e01925-19, 21 pages.

Crowther, "The ELISA guidebook," Methods Mol Biol, 2000, 149(III-IV): 1-413.

Dincer et al., "Multiplexed Point-of-Care Testing—xPOCT," Trends Biotechnol, 2017, 35(8): 728-742.

Dong et al., "An interactive web-based dashboard to track COVID-19 in real time," Lancet Infect Dis, 2020, 20: 533-534.

Dutta et al., "The Nucleocapsid Protein of SARS-CoV-2: a Target for Vaccine Development," J Virol, 2020, 94(13): e00647-20, 2 pages.

Ekladious et al., "Polymer-drug conjugate therapeutics: advances, insights and prospects," Nature Reviews Drug Discovery, 2019, 18: 273-294.

Fathallah et al., "Immunogenicity of Subcutaneously Administered Therapeutic Proteins—a Mechanistic Perspective," The AAPS Journal, 2013, 15(4): 897-900.

Fox et al., "Soluble polymer carriers for the treatment of cancer: the importance of molecular architecture," Acc Chem Res, 2009, 42(8): 1141-1151.

Garay et al., "Therapeutic perspectives on uricases for gout," Joint Bone Spine, 2012, 79: 237-242.

Harris et al., "Effect of pegylation on pharmaceuticals," Nature Reviews Drug Discovery, 2003, 2: 214-221.

(56) References Cited

OTHER PUBLICATIONS

Heggestad et al., "In Pursuit of Zero 2.0: Recent Developments in Nonfouling Polymer Brushes for Immunoassays," Adv Mater, 2020, 32: e1903285.

Hermanson et al., "Peginesatide for the treatment of anemia due to chronic kidney disease—an unfulfilled promise," Expert Opin Drug Saf, 2016, 15(10): 1421-1426.

Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.

Huang et al., "Clinical features of patients infected with 2019 novel coronavirus in Wuhan," China. Lancet, 2020, 395: 497-506.

Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.

Jiang et al., "Neutralizing Antibodies against SARS-CoV-2 and Other Human Coronaviruses," Trends Immunol, 2020, 41(5): 355-359.

Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.

Joh et al., "Inkjet-printed point-of-care immunoassay on a nanoscale polymer brush enables subpicomolar detection of analytes in blood," Proc Natl Acad Sci U S A, 2017, 114: E7054-E7062.

Kang et al., "Crystal structure of SARS-CoV-2 nucleocapsid protein RNA binding domain reveals potential unique drug targeting sites," Acta Pharm Sin B, 2020, 10(7): 1228-1238.

Khailany et al., "Genomic characterization of a novel SARS-CoV-2," Gene Rep, 2020, 9: 100682, 6 pages.

Kozel et al., "Point-of-care testing for infectious diseases: past, present, and future," J Clin Microbiol, 2017, 55: 2313-2320.

Kozma et al., "Anti-PEG antibodies: Properties, formation, testing and role in adverse immune reactions to PEGylated nanobiopharmaceuticals," Adv Drug Deliv Rev, 2020, 154-155, 163-175.

Krammer et al., "Serology assays to manage COVID-19," Science, 2020, 368: 1060-1061.

Kuo et al., "Global epidemiology of gout: prevalence, incidence and risk factors," Nature Reviews Rheumatology, 2015, 11: 649-662.

Laing et al., "A dynamic COVID-19 immune signature includes associations with poor prognosis," Nat Med, 2020, 26:1623-1635.

Lieberman et al., "Comparison of Commercially Available and Laboratory-Developed Assays for In Vitro Detection of SARS-CoV-2 in Clinical Laboratories," J Clin Microbiol, 2020, 58(8):e00821-20.

Lipsitch et al., "Antibody testing will enhance the power and accuracy of COVID-19-prevention trials," Nat Med, 2020, 26: 818-819.

Lipsky et al., "Pegloticase immunogenicity: the relationship between efficacy and antibody development in patients treated for refractory chronic gout," Arthritis Res Ther, 2014, 16: R60.

Lisboa Bastos et al., "Diagnostic accuracy of serological tests for covid-19: systematic review and meta-analysis," BMJ, 2020, 370: m2516.

Liu et al., "High neutralizing antibody titer in intensive care unit patients with COVID-19," Emerg Microbes Infect, 2020, 9: 1664-1670.

Liu et al., "Semi-permeable coatings fabricated from comb-polymers efficiently protect proteins in vivo," Nature Communications, 2014, 5: 5526.

Liu et al., "The experiences of health-care providers during the COVID-19 crisis in China: a qualitative study," Lancet Glob Health, 2020, 8: e790-e798.

Lu et al., "Genomic characterisation and epidemiology of 2019 novel coronavirus: implications for virus origins and receptor binding," Lancet, 2020, 395: 565-574.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McElvaney et al., "A linear prognostic score based on the ratio of interleukin-6 to interleukin-10 predicts outcomes in COVID-19," EBioMedicine, 2020, 61: 103026, 8 pages.

Mejía-Salazar et al., "Microfluidic Point-of-Care Devices: New Trends and Future Prospects for eHealth Diagnostics," Sensors, 2020, 20: 1951, 19 pages.

Miller et al., "Disease and healthcare burden of COVID-19 in the United States," Nat Med, 2020, 26: 1212-1217.

Nalla et al., "Comparative Performance of SARS-CoV-2 Detection Assays Using Seven Different Primer-Probe Sets and One Assay Kit," J Clin Microbiol, 2020, 58: e00557-20, 6 pages.

Norman et al., "Ultrasensitive high-resolution profiling of early seroconversion in patients with COVID-19," Nat Biomed Eng, 2020, 11 pages.

Nunn et al., "Crystal Structure of Tobacco Etch Virus Protease Shows the Protein C Terminus Bound within the Active Site," Journal of Molecular Biology, 2005, 350: 145-155.

Nyborg et al., "A Therapeutic Uricase with Reduced Immunogenicity Risk and Improved Development Properties," PLoS One, 2016, 11(12): e0167935, 23 pages.

Okba et al., "Severe Acute Respiratory Syndrome Coronavirus 2-Specific Antibody Responses in Coronavirus Disease Patients," Emerg Infect Dis, 2020, 26: 1478-1488.

Ozer et al., "Effect of Molecular Architecture on Cell Interactions and Stealth Properties of PEG," Biomacromolecules, 2017, 18: 2699-2710.

Pecoraro et al., "A systematic evaluation of immunoassay point-of-care testing to define impact on patients' outcomes," Ann Clin Biochem, 2017, 54(4): 420-431.

Ponti et al., "Biomarkers associated with COVID-19 disease progression," Crit Rev Clin Lab Sci, 2020, 57, 11 pages.

Posthuma-Trumpie et al., "Lateral flow (immuno)assay: its strengths, weaknesses, opportunities and threats. A literature survey," Anal Bioanal Chem, 2009, 393: 569-582.

Ravichandran et al., "Antibody signature induced by SARS-CoV-2 spike protein immunogens in rabbits," Sci Transl Med, 2020, 10.1126/scitranslmed.abc3539, 9 pages.

Rogers et al., "Isolation of potent SARS-CoV-2 neutralizing antibodies and protection from disease in a small animal model," Science, 2020, 369: 956-963.

Rosadas et al., "Testing for responses to the wrong SARS-CoV-2 antigen," Lancet, 2020, 396: e23.

Rothe et al., "Transmission of 2019-nCoV Infection from an Asymptomatic Contact in Germany," N Engl J Med, 2020, 382: 10, 2 pages.

Seow et al., "Longitudinal evaluation and decline of antibody responses in SARS-CoV-2 infection," medRxiv, 2020, 24 pages.

Sundy et al., "Efficacy and tolerability of pegloticase for the treatment of chronic gout in patients refractory to conventional treatment: two randomized controlled trials," Jama, 2011, 306(7): 711-720.

Sundy et al., "Pharmacokinetics and pharmacodynamics of intravenous PEGylated recombinant mammalian urate oxidase in patients with refractory gout," Arthritis Rheum, 2007, 56(3): 1021-1028.

Tang et al., "Laboratory Diagnosis of COVID-19: Current Issues and Challenges," J Clin Microbiol, 2020, 58: e00512-20, 9 pages.

Turner et al., "Challenges and Opportunities for the Subcutaneous Delivery of Therapeutic Proteins," Journal of Pharmaceutical Sciences, 2018, 107(5): 1247-1260.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Vaninov, "In the eye of the COVID-19 cytokine storm," Nat Rev Immunol, 2020, 20: 277, 1 page.

Vashist et al., "Emerging Technologies for Next-Generation Point-of-Care Testing," Trends Biotechnol, 2015, 33(11): 692-705.

(56) References Cited

OTHER PUBLICATIONS

Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Whitman et al., "Evaluation of SARS-CoV-2 serology assays reveals a range of test performance," Nat Biotechnol, 2020, 38: 1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581: 465-469.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.

(56) References Cited

OTHER PUBLICATIONS

Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).

* cited by examiner

GENETICALLY ENCODED LIPID-POLYPEPTIDE HYBRID BIOMATERIALS THAT EXHIBIT TEMPERATURE TRIGGERED HIERARCHICAL SELF-ASSEMBLY

CROSS-REFERENCE TO RELATED APPLICATIONS

This patent application is the U.S. national stage entry, under 35 U.S.C. 371, of International Application Number PCT/US2018/013611, filed Jan. 12, 2018, which claims priority to U.S. Provisional Patent Application No. 62/445,504, filed Jan. 12, 2017 and U.S. Provisional Patent Application No. 62/479,977, filed Mar. 31, 2017, the entire contents of which are hereby incorporated by reference.

STATEMENT REGARDING FEDERALLY SPONSORED RESEARCH

This invention was made with government support under grant DMR-1121107 awarded by the National Science Foundation and grant R01 GM-061232 awarded by the National Institutes of Health. The government has certain rights in the invention.

SEQUENCE LISTING

The sequence listing is filed with the application in electronic format only and is incorporated by reference herein. The sequence listing text file "028193-9260-WO01_As_Filed_Sequence Listing.txt" was created on Jan. 11, 2018, and is 33,076 bytes in size.

FIELD

This disclosure relates to conjugates of lipids and polypeptides, such as fatty acid-modified elastin-like polypeptides, that are thermally responsive and can form aggregates.

INTRODUCTION

Developing new biomaterials is an active area of research, with applications in tissue engineering, regenerative medicine, and drug-delivery. In particular, protein- and peptide-based materials are attractive candidates for these applications because of their well-defined composition (e.g., sequence and length), their lack of toxicity, and their biodegradability. However, compared to synthetic polymers, the precision offered by recombinant expression is offset by their limited compositional repertoire that consists of the twenty canonical amino acids.

One strategy to expand the diversity of protein-based materials is post-translational modification (PTM), a large and diverse class of chemical transformations carried out on proteins within cells after their expression that nature uses to diversify the proteome. PTMs play an important role in modifying the function and localization of polypeptides in the cellular environment, as well as the material properties of structural proteins and biological matrices. Post-translational modification (PTM) of proteins is a strategy employed in biological systems to expand the diversity of the proteome and to tailor the function and localization of proteins within cells as well as the material properties of structural proteins and matrices. Despite their ubiquity in biology, with a few exceptions, such as the recombinant expression of collagen and mussel foot protein, there is still a need for the use of PTMs to synthesize hybrid biomaterials with properties suitable for applications such as tissue engineering, regenerative medicine, and drug-delivery.

SUMMARY

In an aspect, provided is a conjugate comprising: a fatty acid; a self-assembly domain comprising a sequence of 5 to 10 amino acids that is a substrate of a lipid enzyme transferase and that adopts a secondary structure at about 25° C., a pH of about 7, and a salt concentration of about 150 mM; and a polypeptide, wherein the fatty acid is N-terminal to the self-assembly domain, the polypeptide is C-terminal to the self-assembly domain, and the conjugate has a first phase transition at a transition temperature ($T_t$) and a second phase transition at a critical temperature ($T_c$), the $T_c$ being higher than the $T_t$. In some embodiments, the fatty acid is selected from myristic acid, palmitic acid, lauric acid, arachidic acid, strearic acid, erucic acid, oleic acid, arachidonic acid, linoleic acid, and linolenic acid. In some embodiments, the fatty acid is myristic acid. In some embodiments, the self-assembly domain comprises a glycine at the N-terminus. In some embodiments, the self-assembly domain comprises an amino acid sequence of $(G[XZ]_n)$ (SEQ ID NO:1) wherein X is an amino acid, Z is an amino acid more polar than X, and n is an integer from 2 to 5. In some embodiments, the self-assembly domain comprises an amino acid sequence of (GAGA), (GAGAS) (SEQ ID NO:2), (GAGAGAY) (SEQ ID NO:3), or (GLSLS) (SEQ ID NO:4). In some embodiments, the self-assembly domain adopts a beta-sheet secondary structure at about 25° C., a pH of about 7, and a salt concentration of about 150 mM. In some embodiments, the conjugate further comprises a linker in between the self-assembly domain and the polypeptide. In some embodiments, the linker comprises an amino acid sequence selected from (GGC), ($[GGC]_8$) (SEQ ID NO:5), ($[G_4S]_3$) (SEQ ID NO:6), and ($[GGS]_n$) (SEQ ID NO:7) wherein n is an integer from 1 to 10. In some embodiments, the polypeptide comprises a repeated unstructured polypeptide or a non-repeated unstructured polypeptide. In some embodiments, the polypeptide comprises a zwitterionic polypeptide. In some embodiments, the polypeptide comprises an amino acid sequence of $[GVGVP]_n$ (SEQ ID NO:8), wherein n is an integer from 10 to 120. In some embodiments, the conjugate self-assembles into aggregates above the $T_t$ of the conjugate.

In some embodiments, the conjugate self-assembles into aggregates in three phases relative to the $T_t$ and the $T_c$ of the conjugate, wherein the three phases comprise: (1) a first phase at a temperature below the $T_t$, wherein the conjugate is soluble and self-assembles into nanoscale aggregates; (2) a second phase at a temperature above the $T_t$ and below the $T_c$, wherein the conjugate forms micron-sized aggregates; and (3) a third phase at a temperature greater than the $T_c$, wherein the conjugate forms macroscale aggregates that are visible to the naked eye. In some embodiments, the aggregate comprises a micelle. In some embodiments, the aggregate comprises a rod-like structure. In some embodiments, the aggregate comprises a sheet.

In a further aspect, provided is a drug delivery composition including a plurality of conjugates as detailed herein, self-assembled into a micelle; and an agent encapsulated within the micelle.

In another aspect, provided is a method of treating a disease in a subject in need thereof, the method comprising administering a drug delivery composition as detailed herein to the subject.

In a further aspect, provided is a method of delivering an agent to a subject, the method including encapsulating the agent in a micelle, the micelle comprising a plurality of conjugates as detailed herein; and administering the micelle to the subject. In some embodiments, encapsulating comprises mixing the conjugates and agent and raising the temperature above the $T_t$ of the conjugates.

In a further aspect, provided is a method of increasing the maximum tolerated dose of an agent, the method including encapsulating the agent in a micelle comprising a plurality of conjugates as detailed herein; and administering the agent-encapsulated micelle to a subject. In some embodiments, the agent is hydrophobic. In some embodiments, the agent comprises a small molecule, a polypeptide, a polynucleotide, a lipid, a carbohydrate, or a combination thereof.

In a further aspect, provided is a method of preparing a conjugate as detailed herein, the method including (a) transforming a bacteria with a recombinant expression vector comprising a first polynucleotide encoding a first polypeptide and a second polynucleotide encoding a second polypeptide, wherein the first polypeptide comprises an N-myristoyl transferase (NMT), and wherein the second polypeptide comprises the self-assembly domain; and (b) culturing the transformed bacteria to express the first and second polypeptides and adding myristic acid to the N-terminus of the self-assembly domain. In some embodiments, the bacteria comprise $E.\ coli$. In some embodiments, the bacteria is cultured in media comprising myristic acid. In some embodiments, the vector further comprises a single polynucleotide encoding a single antibiotic selection marker. In some embodiments, the bacteria is cultured in media comprising the antibiotic. In some embodiments, the NMT comprises NMT from $S.\ cerevisiae$. In some embodiments, the NMT comprises an amino acid sequence consisting of residues 36-455 of NM_001182082.1 ($S.\ cerevisiae$ NMTΔ36-455). In some embodiments, the method further includes (c) isolating the conjugate.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A: Structure of a prototypical FAME, consisting of two domains, including a peptide amphiphile (PA)-like domain (a fatty acid conjugated to a short structure-directing peptide) and an ELP domain. The molecular structure of M-B$_1$-ELP is shown as an example. FIG. 1B: The approach involves one-pot expression and PTM by tandem expression of NMT and an ELP bearing a de novo designed NMT recognition sequence.

FIG. 2A: B$_1$-ELP; FIG. 2B, FIG. 2C: M-B$_1$-ELP; FIG. 2D: B$_2$-ELP; FIG. 2E, FIG. 2F: M-B$_2$-ELP; FIG. 2G: B$_3$-ELP; and FIG. 2H, FIG. 2I: M-B$_3$-ELP. 100 µM (solid line), 50 µM (dotted line), 25 µM (dashed line). The arrows denote the onset of hysteretic behavior and morphogenesis of M-B$_2$-ELP and M-B$_3$-ELP into macroscopic structures.

FIG. 3A: Shift in the dynamic light scattering (DLS) autocorrelation functions to longer timescales confirms the nano-aggregation of FAMEs even below the $T_t$. Error bars represent the mean±standard error of the mean calculated from 12 measurements (shown as a shaded band around each line). FIG. 3B: Secondary structure of ELPs and FAMEs bear significant similarities and myristoylation does not result in major changes in the secondary structure content. FIG. 3C: Fourier-transform-infrared (FT-IR) is consistent with the circular dichroism (CD) data, but also reveals differences in the internal dynamics of the control canonical PAs (grey solid line in each panel). FIG. 3D Static Thioflavin T (ThT) fluorescence quantifies the propensity to form β-sheets below the $T_t$. Error bars represent mean±standard deviations calculated from three measurements. FIG. 3E: Dynamic ThT fluorescence assay demonstrates that the temperature-triggered phase transition of ELPs is a convenient trigger for the self-assembly of PA-like domains. Arrows in (E) mark the final stage in the hierarchical self-assembly of M-B$_2$-ELP and M-B$_3$-ELP. FIG. 3F: variable temperature ATR-IR of FAMEs.

FIG. 4A, FIG. 4B and FIG. 4C: M-B$_1$-ELP transitions into liquid-like coacervates similar to canonical ELPs. FIG. 4D, FIG. 4E and FIG. 4F: M-B$_2$-ELP transitions into short disordered fiber-like structures before transitioning into a highly-packed network of fibers at higher temperatures. FIG. 4G, FIG. 4H and FIG. 4I: M-B$_3$-ELP transitions into a network of long kinetically trapped fibers.

FIG. 5A: M-B$_1$, FIG. 5B: M-B$_2$, and FIG. 5C: M-B$_3$. Cryo-TEM of the FAMEs, including FIG. 5D: M-B$_1$-ELP, FIG. 5E: M-B$_2$-ELP, and FIG. 5F: M-B$_3$-ELP.

FIG. 24A: Temperature-programmed turbidimetry assay of ELP. FIG. 24B: Temperature-programmed turbidimetry assay of M-ELP.

FIG. 25A: M-$B_1$-ELP; FIG. 25B: M-$B_2$-ELP; FIG. 25C: M-$B_3$-ELP. Each construct was prepared at 100 μM.

FIG. 26A: M-$B_1$-ELP; FIG. 26B: M-$B_2$-ELP; FIG. 26C: M-$B_3$-ELP. Each construct was prepared prepared at 50 μM.

FIG. 29B: M-ELP is reversible up to 50° C. Each construct was prepared at 50 μM.

FIG. 37A, FIG. 37B and FIG. 37C: Control ELP transitions into liquid-like coacervates at temperatures above its $T_t$ (~40° C. at 100 μM).

FIG. 41A: M-$B_1$-ELP; FIG. 41B: M-$B_2$-ELP; FIG. 41C: M-$B_3$-ELP. Spinning disk confocal laser microscopy (SDCLM) characterization of constructs at ~4° C. (T<$T_t$) to 30° C. ($T_c$>T>$T_t$): FIG. 41D: M-$B_1$-ELP; FIG. 41E: M-$B_2$-ELP; FIG. 41F: M-$B_3$-ELP. SDCLM characterization of constructs at above 50° C. (T>$T_c$): FIG. 41H: M-$B_1$-ELP; FIG. 41I: M-$B_2$-ELP; FIG. 41J: M-$B_3$-ELP.

FIG. 42A: M-$B_2$-ELP and FIG. 42B: M-$B_3$-ELP.

DETAILED DESCRIPTION

Figure 1A:
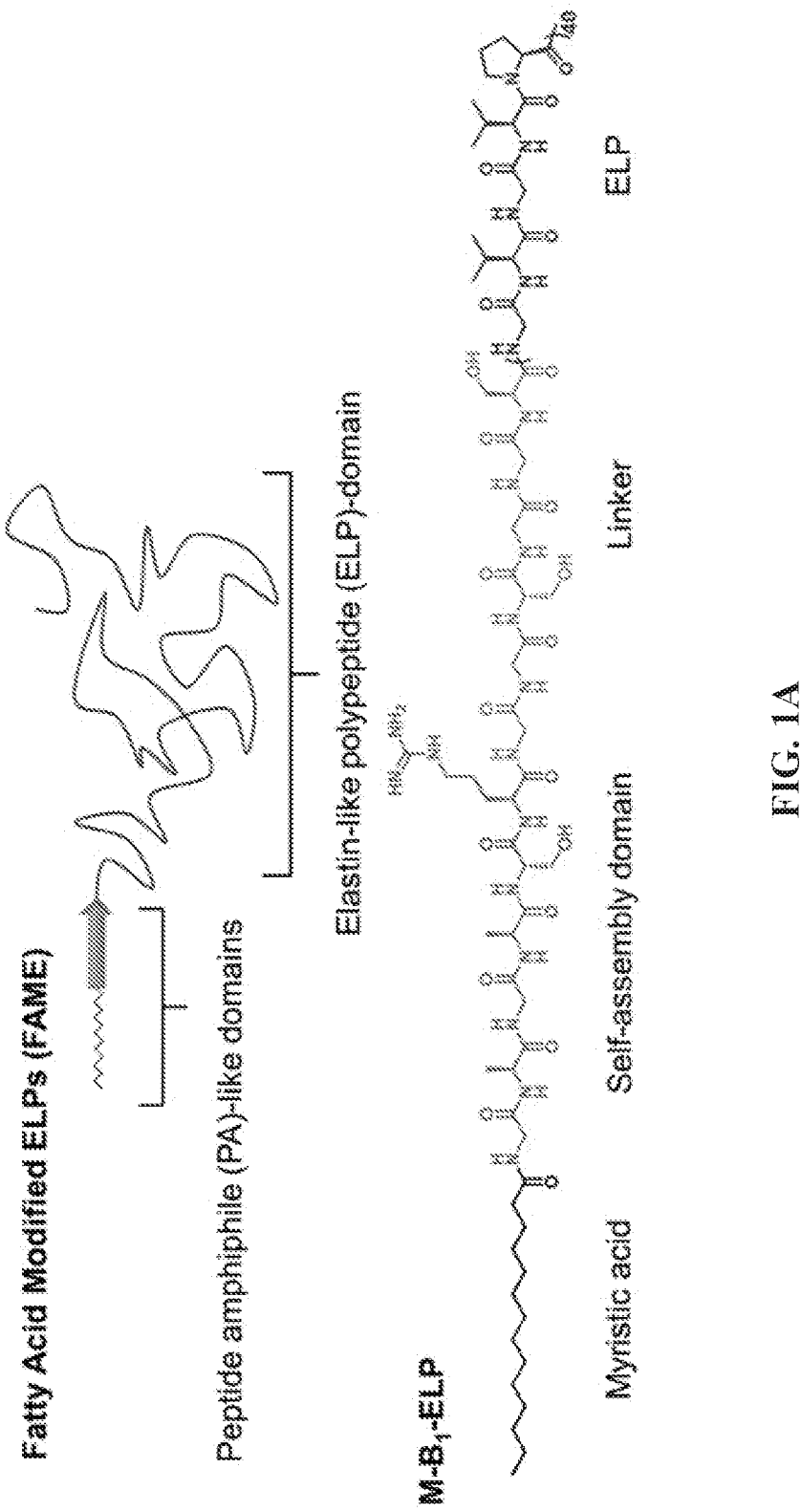
FIG. 1A-B. Schematic of the structure and the synthesis of Fatty Acid Modified Elastin-like peptides (FAMEs) through PTM of elastin-like peptides (ELPs).

Described herein are conjugates that include a fatty acid-modified polypeptide. The conjugates are thermally responsive and exhibit temperature-triggered hierarchical self-assembly into aggregates. The aggregates have a varied structure and material properties that can be tailored at the sequence level. The conjugates may be easily tailored and expressed recombinantly using a post-translational lipidation methodology, such that the synthesis of the conjugates may be easily regulated and amplified for commercial manufacturing. The control over the self-assembly of the aggregates conferred by the responsiveness of the conjugates to temperature makes the conjugates attractive for a range of applications, such as injectable biomaterials, and provides the ability to trigger the self-assembly of the conjugates on demand.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term 'about' refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44). Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof.

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a polypeptide, conjugate, or target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described conjugates. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Zwitterionic" or "zwitterion" refers to a molecule with net charge of zero, but including negative and positive charges on independent individual atoms within the molecule. The charged atoms are joined by one or more covalent bonds. A polypeptide may be zwitterionic.

2. Conjugates

Provided herein are conjugates including a fatty acid, a self-assembly domain, and a polypeptide. The self-assembling domain may adopt a secondary structure at physiological conditions, such as about 25° C., a pH of about 7, and a salt concentration of about 150 mM, and may be a substrate of a lipid enzyme transferase, where the lipid enzyme transferase can conjugate the fatty acid to the self-assembly domain. The conjugate may have at least two phase transitions at two distinct temperatures. For example, the conjugate may have a first phase transition at about a transition temperature ($T_t$—which is further described below) and a second phase transition at about a critical temperature ($T_c$—which is further described below), the $T_c$ being higher than the $T_t$. The phase transitions of the conjugate can result in the conjugate forming different aggregate structures.

a. Fatty Acid

The conjugates may include at least one fatty acid. Fatty acids include a carboxylic acid head and an aliphatic hydrocarbon chain tail. The hydrocarbon chain may be saturated or unsaturated. In some embodiments, the hydrocarbon chain comprises 2 carbon atoms to 28 carbon atoms (e.g., C2-C28), such as C2-C20, C4-C28 or C6-C18. In some embodiments, the hydrocarbon chain comprises an even number of carbon atoms. In some embodiments, the hydrocarbon chain is branched. In some embodiments, the hydrocarbon chain is linear with no branches. The fatty acid may be any substrate of a lipid enzyme transferase. In some embodiments, the fatty acid may be a substrate of N-myristoyl transferase (NMT), including natural substrates and unnatural substrates. The fatty acid may be selected from, for example, myristic acid, and natural and unnatural analogues thereof. In some embodiments, the fatty acid comprises myristic acid. In some embodiments, the fatty acid is myristic acid.

In addition, the fatty acid may have a melting temperature when not part of the disclosed conjugate (e.g., as an individual molecule not conjugated to the self-assembling domain). The melting temperature of the unconjugated fatty acid may correspond to an upper limit of the $T_c$ of the conjugate. For example, the $T_c$ of the conjugate may not be greater than the melting point of the unconjugated fatty acid.

b. Self-Assembly Domain

The conjugate may include a self-assembly domain. The self-assembling domain may serve as a substrate for a lipid enzyme transferase to conjugate a fatty acid thereto. For example, the self-assembling domain may serve as a substrate for N-myristoyl transferase to conjugate myristic acid thereto. In addition, the self-assembly domain is a polypeptide that can adopt a secondary structure under physiological conditions, such as at about 25° C., a pH of about 7, and a salt concentration of about 150 mM (e.g., the conditions found in phosphate buffered saline). For example, the self-assembly domain may form a β-sheet secondary structure at about 25° C., a pH of about 7, and a salt concentration of about 150 mM.

The self-assembly domain may be 2 to 20 amino acids in length, such as 2 to 18 or 5 to 10 amino acids in length. In some embodiments, the self-assembly domain comprises 5-6 amino acids. The self-assembly domain may comprise alternating polar and non-polar amino acids. In some embodiments, the self-assembly domain comprises an amino acid sequence of (G[XZ]$_n$) (SEQ ID NO:1) wherein X is an amino acid, Z is an amino acid more polar than X, and n is an integer from 2 to 5. Z may participate in hydrogen bonds as a proton donor or acceptor. Z may be charged positive or negative, or may be uncharged or neutral. Z may include Gln, Asn, Cys, Gly, Ser, Thr, Tyr, Arg, Asp, Glu, Lys, His, and Trp. In some embodiments, Z is selected from the group consisting of Gln, Asn, Cys, Gly, Ser, Thr, Tyr, Arg, Asp, Glu, Lys, His, and Trp. X may be hydrophobic. X may be uncharged or neutral. X may include Ala, Ile, Leu, Met, Phe, Val, Pro, Gly, and Trp. In some embodiments, X is selected from the group consisting of Ala, Ile, Leu, Met, Phe, Val, Pro, Gly, and Trp. In some embodiments, the self-assembly domain comprises a glycine at the N-terminal end. In some embodiments, the self-assembly domain comprises an amino acid sequence of (GAGA), (GAGAS) (SEQ ID NO:2), (GAGAGAY) (SEQ ID NO:3), or (GLSLS) (SEQ ID NO:4), or a combination thereof. In some embodiments, the conjugate may further include an arginine residue at the N-terminal end of the self-assembly domain. The arginine may facilitate tryptic digest of the conjugate.

c. Polypeptide

The conjugate may include a polypeptide. In some embodiments, the polypeptide comprises a repeated unstructured polypeptide, a non-repeated unstructured polypeptide, or a zwitterionic polypeptide, or a combination thereof. The unconjugated polypeptide (e.g., the polypeptide as an individual molecule not conjugated to the self-assembling domain) has phase transition behavior, wherein the unconjugated polypeptide changes phase at a transition temperature $T_t$. The $T_t$ of the unconjugated polypeptide may affect the $T_t$ of the conjugate.

In some embodiments, the polypeptide comprises an amino acid sequence of [GVGVP]$_n$ (SEQ ID NO:8), wherein n is an integer from 1 to 200. In some embodiments, the polypeptide comprises an amino acid sequence of [GVGVP]$_n$ (SEQ ID NO:8), wherein n is an integer from 10 to 120. In some embodiments, the polypeptide comprises an amino acid sequence of [GVGVP]$_n$ (SEQ ID NO:8), wherein n is an integer from 20 to 60.

(1) Repeated Unstructured Polypeptide

The polypeptide may comprise a repeated unstructured polypeptide. The repeated unstructured polypeptide may comprise any polypeptide that has minimal or no secondary structure as observed by CD, having phase transition behavior, and comprising a repeated amino acid sequence.

In some embodiments, the repeated unstructured polypeptide comprises an amino acid sequence that is rich in proline and glycine. In some embodiments, the repeated unstructured polypeptide comprises a PG motif. In some embodiments, the repeated unstructured polypeptide comprises a plurality of repeated PG motifs. A PG motif comprises an amino acid sequence selected from PG, P(X)$_n$G (SEQ ID NO:9), and (U)$_m$P(X)$_n$G(Z)$_p$ (SEQ ID NO: 10), or a combination thereof, wherein m, n, and p are independently an integer from 1 to 15, and wherein U, X, and Z are independently any amino acid. P(X)$_n$G (SEQ ID NO:9) may include PXG, PXXG, PXXXG (SEQ ID NO:11), PXXXXG (SEQ ID NO:12), PXXXXXG (SEQ ID NO:13), PXXXXXXG (SEQ ID NO:14), PXXXXXXXG (SEQ ID NO:15), PXXXXXXXXG (SEQ ID NO:16), PXXXXXXXXXG (SEQ ID NO:17), PXXXXXXXXXXG (SEQ ID NO:18), PXXXXXXXXXXXG (SEQ ID NO:19), PXXXXXXXXXXXXG (SEQ ID NO:20), PXXXXXXXXXXXXXG (SEQ ID NO:21), PXXXXXXXXXXXXXXG (SEQ ID NO:22), and/or PXXXXXXXXXXXXXXXG (SEQ ID NO:23). The repeated unstructured polypeptide may further include additional amino acids at the C-terminal and/or N-terminal end of the PG motif. These amino acids surrounding the PG motif may also be part of the overall repeated motif. The amino acids that surround the PG motif may balance the overall hydrophobicity and/or charge so as to control the T$_t$ of the repeated unstructured polypeptide.

In some embodiments, the repeated unstructured polypeptide comprises an amino acid sequence of [GVGVP]$_n$ (SEQ ID NO:8), wherein n is an integer from 1 to 200.

In some embodiments, the repeated unstructured polypeptide comprises one or more thermally responsive polypeptides. Thermally responsive polypeptides may include, for example, elastin-like polypeptides (ELP). "ELP" refers to a polypeptide comprising the pentapeptide repeat sequence (VPGXG)$_n$ (SEQ ID NO:24), wherein X is any amino acid except proline and n is an integer greater than or equal to 1. The repeated unstructured polypeptide may comprise an amino acid sequence consisting of (VPGXG)$_n$ (SEQ ID NO:24). In some embodiments, X is not proline. In some embodiments, n is 20, 30, 40, 50, 60, 70, 80, 90, 100, 110, 120, 130, 140, 150, 160, 170, 180, 190, 200, 210, 220, 230, 240, 250, 260, 270, 280, 290, or 300. In some embodiments, n may be less than 500, less than 400, less than 300, less than 200, or less than 100. In some embodiments, n may be from 1 and 500, from 1 and 400, from 1 and 300, or from 1 and 200. In some embodiments, n is 60, 120, or 180.

In other embodiments, the thermally responsive polypeptide comprises a resilin-like polypeptide (RLP). RLPs are derived from Rec1-resilin. Rec1-resilin is environmentally responsive and exhibits a dual phase transition behavior. The thermally responsive RLPs can have LCST and UCST (Li et. al, *Macromol. Rapid Commun.* 2015, 36, 90-95). Additional examples of suitable thermally responsive polypeptides are described in U.S. Patent Application Publication Nos. US 2012/0121709, filed May 17, 2012, and US 2015/0112022, filed Apr. 23, 2015.

(2) Non-Repeated Unstructured Polypeptide

The polypeptide may comprise a non-repetitive unstructured polypeptide. In some embodiments, the non-repeated unstructured polypeptide comprises a sequence of at least 60 amino acids, wherein at least about 10% of the amino acids are proline (P), and wherein at least about 20% of the amino acids are glycine (G). In some embodiments, the non-repeated unstructured polypeptide comprises a sequence wherein at least about 40% of the amino acids are selected from the group consisting of valine (V), alanine (A), leucine (L), lysine (K), threonine (T), isoleucine (I), tyrosine (Y), serine (S), and phenylalanine (F). In some embodiments, the non-repeated unstructured polypeptide comprises a sequence that does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G). As used herein, the term "subsequence" refers to a sequence of contiguous amino acids that occurs within another sequence of contiguous amino acids. A subsequence includes at least two amino acids. In some embodiments, a subsequence is 2 to 20, 2 to 15, or 2 to 10 sequential amino acids in length. In some embodiments, a subsequence includes 3, 4, 5, 6, 7, 8, 9, or 10 sequential amino acids. In some embodiments, the non-repeated unstructured polypeptide comprises a sequence of at least 60 amino acids, wherein at least about 10% of the amino acids are proline (P), wherein at least about 20% of the amino acids are glycine (G), wherein at least about 40% of the amino acids are selected from the group consisting of valine (V), alanine (A), leucine (L), lysine (K), threonine (T), isoleucine (I), tyrosine (Y), serine (S), and phenylalanine (F), wherein the sequence does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G).

(3) Zwitterionic Polypeptide

The polypeptide may comprise a zwitterionic polypeptide (ZiPP). ZiPPs are overall neutral polypeptides that include both amino acids with negative charge and amino acids with positive charge. ZiPPs may comprise one or more charged motifs. The charged motif includes one or more positively charged amino acids and one or more negatively charged amino acids, wherein the positively charged amino acids and negatively charged amino acids are present in a ratio of 1:1. In some embodiments, the net charge of the motif is neutral. In some embodiments, the charged motif is a zwitterionic motif. The positively charged amino acids within one motif may be the same or different. The negatively charged amino acids within one motif may be the same or different. As used herein, the charge of an amino acid (positive and/or negative) refers to the charge of the amino acid side chain. A charged amino acid is positively and/or negatively charged at neutral pH, at physiological pH, or at the local pH within the protein fold, or a combination thereof. The charged motif may further include one or more uncharged amino acids. In some embodiments, the charged motif has an amino acid sequence of VPX$_1$X$_2$G (SEQ ID NO:25), wherein X$_1$ is a negatively or positively charged amino acid, and wherein X$_2$ is the other of a negatively or positively charged amino acid.

In some embodiments, the zwitterionic polypeptide comprises a plurality of charged motifs. The plurality of charged motifs may be repeated. In some embodiments, the zwitterionic polypeptide comprises the amino acid sequence of $(VPX_1X_2G)_n$, wherein $X_1$ is a negatively or positively charged amino acid, $X_2$ is the other of a negatively or positively charged amino acid, and n is an integer greater than or equal to 1. For example, $X_1$ may not be the same charge as $X_2$. $X_1$ may be the same or different between adjacent motifs. $X_2$ may be the same or different between adjacent motifs. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprises the amino acid sequence of $(VPX_1X_2G)_n$ (SEQ ID NO:25), wherein $X_1$ is a negatively or positively charged amino acid, $X_2$ is the other of a negatively or positively charged amino acid, and n is an integer greater than or equal to 1, may be referred to as a homopolymer.

In some embodiments, the zwitterionic polypeptide includes one or more uncharged motifs in addition to the one or more charged motifs. The uncharged motif includes uncharged amino acids. In some embodiments, the uncharged motif does not include any charged amino acids. In some embodiments, the uncharged motif has an amino acid sequence consisting of VPGXG (SEQ ID NO:26), wherein X is any amino acid except proline.

A plurality of uncharged motifs may be repeated in tandem. In some embodiments, the zwitterionic polypeptide comprises the amino acid sequence of $(VPGXG)_n$ (SEQ ID NO:24) in addition to the one or more charged motifs, wherein X is any amino acid except proline, and n is an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, zwitterionic polypeptides comprising an uncharged motif having an amino acid sequence consisting of $(VPGXG)_n$ (SEQ ID NO:24) in addition to the one or more charged motifs, wherein X is any amino acid except proline, and n is an integer greater than or equal to 1, are referred to as elastin-like polypeptides (ELP).

The motifs of the zwitterionic polypeptide can be arranged in any number of possible ways. Examples of possible arrangements and architectures include a homopolymer, a diblock polymer, and a multiblock polymer. A homopolymer is wherein each unit is a repeat of the pentapeptide sequence $VPX_1X_2G$, or charged motif. In a diblock architecture, one block of polymer is made with a repeating charged motif, while the other part includes a repeating uncharged motif. In a multiblock polymer, the charged motifs and uncharged motifs are placed at different sites to increase diversity of the polymer. The particular number, identity, and arrangement of motifs may be designed and varied. In some embodiments, one or more uncharged motifs are positioned between at least two adjacent charged motifs of the zwitterionic polypeptide. In some embodiments, the zwitterionic polypeptide includes a plurality of charged motifs repeated in tandem and a plurality of uncharged motifs repeated in tandem. In some embodiments, the plurality of charged motifs repeated in tandem are positioned C-terminal to the plurality of uncharged motifs repeated in tandem. In some embodiments, the plurality of charged motifs repeated in tandem are positioned N-terminal to the plurality of uncharged motifs repeated in tandem.

In some embodiments, the zwitterionic polypeptide comprises the amino acid sequence of $(VPX_1X_2G)_n(VPGXG)_m$ (SEQ ID NO:27), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprising the amino acid sequence of $(VPX_1X_2G)_n(VPGXG)_m$ (SEQ ID NO:27), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the zwitterionic polypeptide comprises the amino acid sequence of $(VPGXG)_m(VPX_1X_2G)_n$ (SEQ ID NO:28), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprising the amino acid sequence of $(VPGXG)_m(VPX_1X_2G)_n$ (SEQ ID NO:28), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the zwitterionic polypeptide comprises the amino acid sequence of $\{(VPX_1X_2G)(VPGXG)\}_b$ (SEQ ID NO:29), wherein $X_1$ is a negatively or positively charged amino acid, $X_2$ is the other of a negatively or positively charged amino acid, X is any amino acid except proline, and b is an integer greater than or equal to 1. In some embodiments, b is an integer less than or equal to about 100, 200, or 300. In some embodiments, b is an integer greater than or equal to about 1, 10, 50, 100, 150, or 200. In some embodiments, b is an integer from about 10 to about 300, from about 10 to about 200, from about 10 to about 100, from about 10 to about 50, from about 1 to about 300, from about 1 to about 200, from about 1 to about 100, or from about 1 to about 50. In some embodiments, b is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300. In some embodiments, a zwitterionic polypeptide comprising the amino acid sequence of $\{(VPX_1X_2G)(VPGXG)\}_b$ (SEQ ID NO:29), wherein $X_1$ is a negatively or positively charged amino acid, $X_2$ is the other of a negatively or positively charged amino acid, X is any amino acid except proline, and b is an integer greater than or equal to 1, may be referred to as a multiblock polymer.

In some embodiments, $X_1$ is a negatively charged amino acid, and $X_2$ is a positively charged amino acid. In some embodiments, $X_1$ is a positively charged amino acid, and $X_2$ is a negatively charged amino acid. In some embodiments, the negatively charged amino acid is independently selected from glutamatic acid and aspartic acid. In some embodiments, the positively charged amino acid is independently selected from lysine and arginine. In some embodiments, X is selected from arginine, histidine, lysine, aspartic acid, glutamic acid, serine, threonine, asparagine, glutamine, cysteine, selenocysteine, glycine, alanine, valine, leucine, isoleucine, methionine, phenylalanine, tyrosine, and tryptophan. In some embodiments, X is selected from glycine and valine.

iv) Linker

In some embodiments, the conjugate comprises a linker in between the self-assembly domain and the polypeptide. In some embodiments, the conjugate comprises a linker at the C-terminal end of the polypeptide. The linker may comprise a variety of amino acid sequences suitably known in the art. The linker may comprise, for example, an amino acid sequence selected from (GGC), ([GGC]$_8$) (SEQ ID NO:30), ([G$_4$S]$_3$) (SEQ ID NO:31), and ([GGS]$_n$) (SEQ ID NO:32) wherein n is an integer from 1 to 10).

d. Phase Transition into Aggregates

"Phase transition" or "transition" may refer to the aggregation of the conjugate, which occurs sharply and in some instances reversibly at a specific temperature. Examples of specific temperatures include the $T_t$ and the $T_c$ of the conjugate. Below the $T_t$, for example, the conjugate may be highly soluble. Upon heating above the transition temperature, for example, the conjugate may hydrophobically collapse and aggregate, forming a separate, phase. As mentioned above, the $T_t$ of the conjugate may be dependent on the $T_t$ of the unconjugated polypeptide. In some embodiments, the $T_t$ of the conjugate is about 15° C. to about 20° C. lower than the $T_t$ of the unconjugated polypeptide. The $T_t$ can be adjusted by varying the amino acid sequence of the polypeptide, by varying the length of the polypeptide, or a combination thereof.

The conjugate may have a $T_t$ from about 0° C. to about 100° C., such as from about 10° C. to about 50° C., or from about 20° C. to about 42° C. In some embodiments, the conjugate has a $T_t$ between room temperature (about 25° C.) and body temperature (about 37° C.). In some embodiments, the conjugate has its $T_t$ below body temperature or above body temperature at the concentration at which the conjugate is administered to a subject.

The $T_t$ may be a LCST. The $T_t$ may be a UCST. LCST is the temperature below which the conjugate is miscible. UCST is the temperature above which the conjugate is miscible. In some embodiments, the conjugate has only UCST behavior. In some embodiments, the conjugate has only LCST behavior. In some embodiments, the conjugate has both UCST and LCST behavior.

As mentioned above, the conjugate may also have a $T_c$, which refers to a critical temperature at which the conjugate can undergo a second phase transition. The $T_c$ is a higher temperature than the $T_t$ of the conjugate. In some embodiments, the $T_c$ is a temperature that is above the $T_t$ and below the melting point of the unconjugated fatty acid. In some embodiments, the $T_c$ is about 10° C. to about 40° C. higher than the $T_t$, such as about 15° C. to about 35° C. or about 20° C. to about 30° C. higher than the $T_t$.

The phase of the conjugate may be described as, for example, soluble or an aggregate. The aggregate may be a variety of forms. The form and size of the aggregate may depend on the temperature, the sequence of the polypeptide, the sequence of the linker, or the fatty acid, or a combination thereof. The aggregate may be a micelle, a rod-like structure, a sheet, or a particle, or a combination thereof.

The aggregate may have a varying size depending on the phase or temperature. The aggregate may be, for example, nanoscale aggregates, micron-sized aggregates, or macroscale aggregates. In some embodiments, at a temperature below the $T_t$ the aggregate has a diameter or length of about 20 to about 100 nm. In some embodiments, at a temperature above the $T_t$ the aggregate has a diameter or length of about 1 μm to about 1 cm. At the $T_t$, the aggregate may change from soluble to an aggregate form, from an aggregate form to a soluble form, from a nanoscale aggregate to a micron-sized aggregate, from a nanoscale aggregate to a macroscale aggregate, from a micron-sized aggregate to a nanoscale aggregate, from a macroscale aggregate to a nanoscale aggregate, from a micron-sized aggregate to a macroscale aggregate, or from a macroscale aggregate to a micron-sized aggregate. In some embodiments, the conjugate is soluble below the $T_t$. In some embodiments, the conjugate is soluble above the $T_t$. In some embodiments, the conjugate is in the form of an aggregate below the $T_t$. In some embodiments, the conjugate is in the form of an aggregate above the $T_t$.

The conjugate can self-assemble into varying types of aggregates at different temperature phases dependent on the $T_t$ and the $T_c$ of the conjugate. The three phases may include a first phase, a second phase, and a third phase. The first phase may be at a temperature below the $T_t$, wherein the conjugate is soluble and self-assembles into nanoscale aggregates. The second phase may be above the $T_t$ and below the $T_c$, wherein the conjugate forms micron-sized aggregates. The third phase may be at a temperature greater than the $T_c$, wherein the conjugate forms macroscale aggregates that are visible to the naked eye. In some embodiments, the conjugate can reversibly go from one phase to another phase (e.g., phase 1 to phase 2 to phase 1; or phase 1 to phase 2 to phase 3 to phase 2, etc.). In some embodiments, the conjugate upon entering phase 3 cannot reversibly transition to phase 1 or phase 2. In some embodiments, the conjugate can reversibly transition from phase 1 to phase 2 and vice versa, but upon entering phase 3 cannot reversibly transition to phase 1 or phase 2.

The conjugate can phase transition at varying temperatures. In some embodiments, the conjugate may comprise two individual phase transitions that occur from about 0° C. to about 100° C., such as from about 20° C. to about 65° C., from about 25° C. to about 60° C., or from about 30° C. to about 55° C. For example, the conjugate may phase transition from the first phase to the second phase at a temperature of about 30° C. to about 50° C. In addition, the conjugate may phase transition from the second phase to the third phase at a temperature of greater than 50° C.

In some embodiments, in a first phase, at a temperature below the $T_t$, the hydrophobic collapse of the fatty acid drives the initial formation of nanoscale aggregates, such as spherical or cylindrical micelles. In some embodiments, in a second phase, at a temperature above the $T_t$ but below the $T_c$, as the temperature is increased to just above the $T_t$ of the polypeptide, the interactions among portions of the polypeptide bring the structures into proximity to one another. In some embodiments, in a third phase, at a temperature above the $T_c$, the desolvation of the polypeptide is intricately coupled to the final stages of self-assembly and morphogenesis of the final structure of the aggregate.

Phase transition behavior may be used to form drug depots within a tissue of a subject for controlled (slow) release of the conjugate. Phase transition behavior may also enable purification of the conjugate using inverse transition cycling, thereby eliminating the need for chromatography. "Inverse transition cycling" refers to a protein purification method for polypeptides having phase transition behavior, and the method may involve the use of the conjugate's reversible phase transition behavior to cycle the solution through soluble and insoluble phases, thereby removing contaminants and eliminating the need for chromatography.

In the above description of the phase transitions of the conjugate, the conjugate may have a varying concentration. For example, the conjugate may phase transition at a concentration of about 5 μM to about 1 M, such as about 10 μM to about 500 μM, about 15 μM to about 250 μM, about 20 μM to about 150 μM, or about 25 μM to about 100 μM. In some embodiments, the conjugate may phase transition at a concentration that is suitable for administration to a subject.

e. Agent

In some embodiments, the conjugate may encapsulate an agent upon forming an aggregate. In some embodiments, the conjugate may release an agent upon resolubilizing out of the aggregate form. The agent may be a therapeutic. The agent may be a drug. In some embodiments, the agent is selected from a small molecule, nucleotide, polynucleotide, protein, polypeptide, lipid, carbohydrate, and a combination thereof. In some embodiments, the agent comprises a small molecule. In some embodiments, the agent comprises a protein. In some embodiments, the agent comprises a cancer therapeutic. In some embodiments, the agent comprises an antibody. In some embodiments, the agent is attached to a cysteine of the polypeptide of the conjugate. In some embodiments, the agent is hydrophobic.

In some embodiments, the conjugates detailed herein may form a drug delivery composition. The drug delivery composition may include a plurality of conjugates as detailed herein self-assembled into a micelle, with an agent encapsulated within the micelle. One or more agents may be encapsulated within the micelle.

f. Polynucleotides

Further provided are polynucleotides encoding the conjugates detailed herein. A vector may include the polynucleotide encoding the conjugates detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding a conjugate as detailed herein. Bacterial expression systems for expressing the protein are available in, e.g., *E. coli, Bacillus* sp., and *Salmonella* (Paiva et al., *Gene* 1983, 22, 229-235; Mosbach et al., *Nature* 1983, 302, 543-545). Kits for such expression systems are commercially available. Eukaryotic expression systems for mammalian cells, yeast, and insect cells are well known in the art and are also commercially available. Retroviral expression systems can be used in the present invention.

The conjugate may be expressed recombinantly in a host cell according to one of skill in the art. The conjugate may be purified by any means known to one of skill in the art. For example, the conjugate may be purified using chromatography, such as liquid chromatography, size exclusion chromatography, or affinity chromatography, or a combination thereof. In some embodiments, the conjugate is purified without chromatography. In some embodiments, the conjugate is purified using inverse transition cycling.

g. Administration

A composition may comprise the conjugate. The conjugates as detailed herein can be formulated into a composition in accordance with standard techniques well known to those skilled in the pharmaceutical art. The composition may be prepared for administration to a subject. Such compositions comprising a conjugate can be administered in dosages and by techniques well known to those skilled in the medical arts taking into consideration such factors as the age, sex, weight, and condition of the particular subject, and the route of administration.

The conjugate can be administered prophylactically or therapeutically. In prophylactic administration, the conjugate can be administered in an amount sufficient to induce a response. In therapeutic applications, the conjugates are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugate can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997). The conjugate can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The conjugates can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidural routes. In some embodiments, the conjugate is administered intravenously, intraarterially, or intraperitoneally to the subject.

h. Methods (1) Method of Preparing a Conjugate

The present invention is directed to a method of preparing a conjugate as detailed herein. The method may include (a) transforming a bacteria with a recombinant expression vector comprising a first polynucleotide encoding a first polypeptide and a second polynucleotide encoding a second polypeptide, wherein the first polypeptide comprises an N-myristoyl transferase (NMT), and wherein the second polypeptide comprises the self-assembly domain; and (b) culturing the transformed bacteria to express the first and second polypeptides and add myristic acid to the N-terminus of the self-assembly domain. In some embodiments, the method further includes (c) isolating the conjugate. In some embodiments, the bacteria comprise *E. coli*. In some embodiments, the bacteria is cultured in media comprising myristic acid. The myristic acid may be present in a concentration of about 0 to about 100 µM, about 0 to about 200 µM, about 1 µM to about 100 µM, or about 1 µM to about 200 µM. In some embodiments, the bacteria is cultured in media comprising the antibiotic. In some embodiments, the vector further comprises a single polynucleotide encoding a single antibiotic selection marker.

In some embodiments, the NMT comprises NMT from *S. cerevisiae*. In some embodiments, the NMT comprises an amino acid sequence consisting of residues 36-455 of NM_001182082.1 (*S. cerevisiae* NMTΔ36-455).

Providing the disclosed conjugates by genetic methods (rather than chemical synthesis) may provide useful advantages, such as, but not limited to providing higher molecular weight conjugates. For example, the conjugate may have a molecular weight of about 12 kDa to about 30 kDa, such as about 15 kDa to about 25 kDa or about 15 kDa to about 20 kDa.

(2) Method of Treating a Disease

The present invention is directed to a method of treating a disease in a subject in need thereof. The method may include administering a drug delivery composition as detailed herein to the subject.

(3) Method of Delivering an Agent

The present invention is also directed to a method of delivering an agent to a subject. The method may include encapsulating the agent in a micelle, the micelle comprising a plurality of conjugates as detailed herein, and administering the micelle to the subject. In some embodiments, encapsulating comprises mixing the conjugates and agent and raising the temperature above the transition temperature ($T_t$) of the conjugates.

(4) Method of Increasing the Maximum Tolerated Dose of an Agent

The present invention is directed to a method of increasing the maximum tolerated dose of an agent. The method may include encapsulating the agent in a micelle comprising a plurality of conjugates as detailed herein, and administering the agent-encapsulated micelle to a subject.

3. Examples

Example 1

Materials and Methods

Materials

The pETDuet-1 vector was purchased from EMD Millipore (Billerica, Mass.). All the restriction enzymes, ligase, and corresponding buffers were purchased from New England Biolabs (Ipswich, Mass.). Chemically competent Eb5alpha and BL21(DE3) cells were purchased from Edge Bio (Gaithersburg, Md.). DNA extraction and purification kits were purchased from Qiagen (Valencia, Calif.). Terrific broth medium (TB) was purchased from Amresco (Solon, Ohio). Isopropyl β-D-1-thiogalactopyranoside (IPTG) was purchased from Bioline USA (Boston, Mass.). Myristic acid, N,N-diisopropylethylamine (DIPEA), 4-methylmorpholine, triisopropylsilane, alpha-cyano-4-hydroxycinnamic acid, and trifluoroacetic acid (TFA) were purchased from Sigma-Aldrich (St. Louis, Mo.). SnakeSkin™ Dialysis Tubing featuring 3.5K nominal molecular weight cut off (MWCO), mass spectroscopy grade Pierce™ trypsin protease, Alexa Fluor® 488 NHS ester, and anhydrous dimethyl sulfoxide (DMSO) were purchased from Thermo Fisher Scientific (Waltham, Mass.). Rink amide resin (200-400 mesh, 0.6 meq/g), Fmoc-protected amino acids, O-benzotriazole-N,N, N',N'-tetramethyluronium hexafluoro-phosphate (HBTU), and O-(6-Chlorobenzotriazol-1-yl)-N,N,N',N'-tetramethyluronium hexafluoro-phosphate (HCTU) were purchased from Chem-Impex (Wood Dale, Ill.). Diethyl ether, dichloromethane (DCM), and high performance liquid chromatography-(HPLC) grade acetonitrile were purchased from VWR International (Radnor, Pa.) and were used as received without further purification. Anhydrous dimethylformamide (DMF) was purchased from EMD Millipore and was further dried over t.h.e.® Desiccant (EMD Millipore) before use. Deionized water was obtained from a Milli-Q® system (Thermo Scientific, CA).

ABIL® EM 90 and TEGOSOFT® DEC surfactants were purchased from Evonik Industries (Essen, Germany). Mineral oil was purchased from Sigma-Aldrich (St. Louis, Mo.). A single emulsion droplet chip was purchased from Dolomite Microfluidics (Royston, United Kingdom). Syringe pumps were purchased from Chemyx Inc. (Stafford, Tex.).

Recognition Sequence

In the design of our NMT recognition sequences, we checked the feasibility of myristoylation using an myristoylation predictor. The sequences and the predictor score are summarized in Table 1. We did not observe any myristoylation for the last recognition sequence, GVEVERGGSGGSGGS, consistent with the predictor score.

TABLE 1

Myristoylation predictor scores for various sequences in this study

| Recognition Sequence | Query | NMT-The MYR Predictor Score |
|---|---|---|
| $B_1$ | GAGASRGGSG GSGVGVPGVG VP (SEQ ID NO: 30) | 2.183 (Reliable site) |
| $B_2$ | GAGAGAYRGG SGGSGGSGVG VPGVGVP (SEQ ID NO: 31) | -1.045 (Twilight zone, Likely site) |
| $B_3$ | GLSLSRGGSG GSGVGVPGVG VP (SEQ ID NO: 32) | 1.407 (reliable site) |
|  | GVEVERGGSG GSGGSGVGVP GVGVP (SEQ ID NO: 33) | -5.095 (no site for myristoylation) |

As shown in Table 1, three out of four designed recognition sequences were myristoylated in our system. In our experiments, the MYR predictor appeared to be a reliable indicator of myristoylation for de novo designed sequences.

β-Sheet Propensity of PA-Domain

We used two beta sheet propensity scales (Table 2). We are mindful that beta sheet propensities are context-dependent but in our system, we have used these relative propensities to score recognition sequences based on their propensity to form β-sheets ($B_1<B_2<B_3$) by comparing the first 8 amino acids, where the sequences are divergent. We have used this rough estimate also as an indirect surrogate for the stability of PA-domains. We point out that this treatment ignores secondary interactions such as the possible hydrogen bonds between the serine side chains.

TABLE 2

Experimentally observed thermodynamic scales for β-sheet forming tendencies of amino acids in the FAME sequence

| Amino Acid | ΔΔG (kcal/mol) | ΔG (kcal/mol) |
|---|---|---|
| Gly | 1.2 | 1.21 |
| Ala | 0 | 0 |
| Leu | -0.51 | -0.45 |
| Ser | -0.70 | -0.87 |
| Tyr | -0.96 | -1.63 |
| Arg | -0.45 | -0.40 |
| Val | -0.82 | -0.94 |
| Pro | >3 | Not determined |

With alanine chosen as the reference, the more negative ΔΔG values imply higher preference for β-sheet formation.

ELP Domain

Our preliminary work demonstrated that myristoylation reduces the transition temperature ($T_t$) of ELPs by ~15° C. We have chosen the length of the ELP with the following two considerations: 1) we aimed to maintain the transition temperature of FAMEs approximately around 20-25° C. and thus aimed to choose ELP with original $T_t$ of ~40° C., $(GVGVP)_{40}$ has a $T_t$ of ~39° C. at the concentration of 100 μM. 2) We also aimed to select an ELP segment as to avoid coacervation during the expression inside E. coli. Initially, we hypothesized that coacervation of the ELP may preclude the in situ enzymatic modification.

Gene Synthesis

Construction of the Expression Vector.

Figure 6:
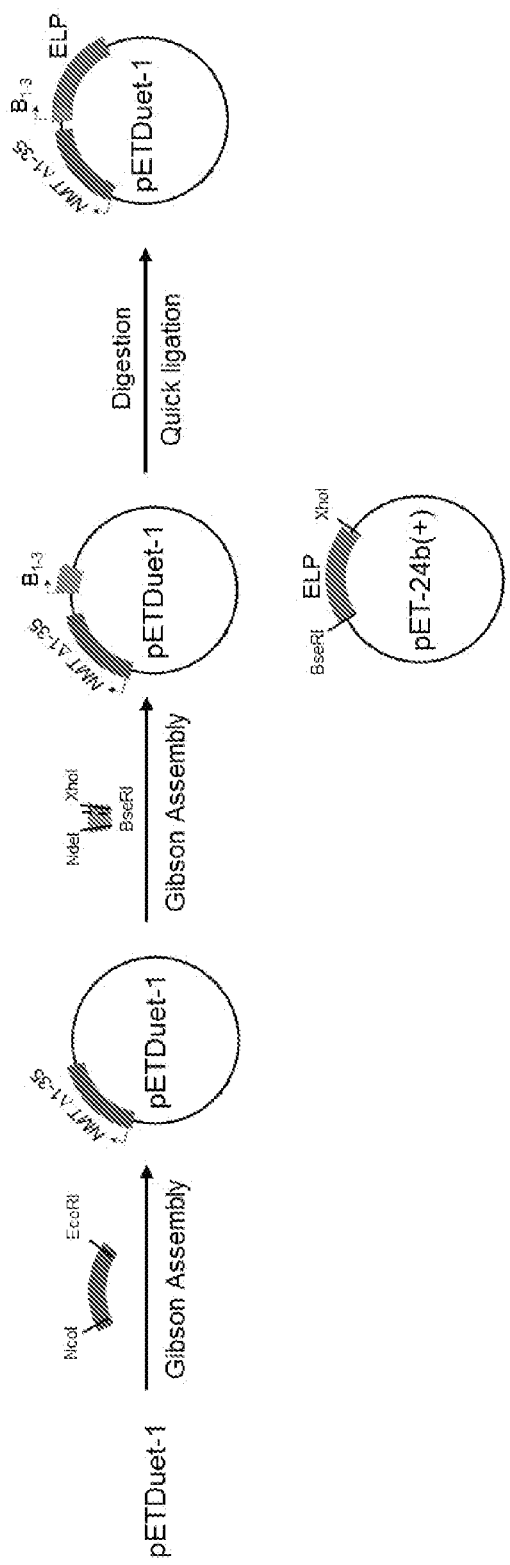
FIG. 6. Schematic of the process used to construct the dual expression vector used in the study.

FIG. 6. To generate a single vector dual expression system, we purchased pETDuet-1 DNA from EMD Millipore. This vector contains an ampicillin resistance gene and two multiple cloning sites (MCS), each of which is preceded by its own T7 promoter, lac operator, and ribosomal binding site. The following codon optimized double stranded genes were purchased from Integrated DNA Technologies and coded for an MGSSHHHHHH leader, followed by residues 36 to 455 of the S. cerevisiae NMT enzyme (Swiss-Prot accession number P14743). This cDNA (shown in green) was then flanked on each end by a 40-80 bp segment that corresponded to the pETDuet-1 sequences upstream and downstream of the MCS 1 (shown in black in the gene sequence below) in addition to cleavage sites for NcoI and EcoRI (underlined). After cutting and gel purifying pETDuet-1 DNA with NcoI and EcoRI-HF, the NMT gene was inserted into MCS 1 using the Gibson Assembly® Master Mix (New England Biolabs) according to the manufacturer's instructions. Ligated DNA (3 µL) was transformed into EB5alpha (25 µL) competent cells (EdgeBio) and spread onto agar plates containing 100 µg/mL ampicillin. Positive clones were identified with Sanger sequencing (Eton Biosciences) using the universal T7 Promoter primer.

(SEQ ID NO: 34)
5'-CAATGGTATATCTTCCGGGCGCTATCATGCCATACCTTTTTATA<u>CCA
TGGGCAGCAGCCATCACCATCATCACCAC</u>AAAGACCACAAATTTTGGCGT
ACCCAGCCGGTTAAAGATTTTGATGAAAAAGTTCTTGAAGAAGGTCCGAT
CGACAAACCGAAAACACCGGAAGATATTAGCGATAAACCGCTGCCGCTGC
TGAGCAGCTTTGAATGGTGTAGCATTGATGTGGACAACAAAAAACAGCTG
GAAGATGTTTTTGTGCTGCTGAACGAAAACTATGTGGAAGATCGTGATGC
AGGTTTTCGGTTCAATTATACCAAAGAGTTTTTCAACTGGGCACTGAAAA
GTCCGGGTTGGAAAAAAGATTGGCATATTGGTGTTCGTGTGAAAGAAACC
CAGAAACTGGTTGCATTTATTAGCGCAATTCCGGTTACCCTGGGTGTGCG
TGGTAAACAGGTTCCGAGCGTTGAAATTAACTTTCTGTGTGTTCATAAAC
AGCTGCGTAGCAAACGTCTGACACCGGTTCTGATTAAAGAAATCACCCGT
CGTGTGAACAAATGCGATATTTGGCATGCACTGTATACCGCAGGTATTGT
TCTGCCTGCACCGGTTAGCACCTGTCGTTATACCCATCGTCCGCTGAACT
GGAAAAAACTGTATGAAGTTGATTTCACCGGTCTGCCGGATGGTCATACC
GAAGAAGATATGATTGCAGAAAATGCACTGCCTGCAAAAACCAAACCGC
AGGTCTGCGTAAACTGAAAAAAGAGGACATCGATCAGGTCTTTGAGCTGT
TTAAACGTTATCAGAGCCGCTTTGAACTGATCCAGATTTTTACCAAAGAA
GAGTTCGAGCACAACTTTATTGGTGAAGAAAGCCTGCCGCTGGATAAACA
GGTCATTTTTAGCTATGTTGTTGAACAGCCGGATGGCAAAATTACCGATT
TTTTCAGCTTTTATAGCCTGGCGTTTACCATTCTGAACAACACCAAATAC
AAAGACCTGGGCATTGGCTATCTGTATTATTACGCAACCGATGCCGATTT
CCAGTTTAAAGATCGTTTTGATCCGAAAGCAACCAAAGCCCTGAAAACCC
GTCTGTGCGAACTGATTTATGATGCATGTATTCTGGCCAAAAACGCCAAC
ATGGATGTTTTTAATGCACTGACCAGCCAGGATAATACCCTGTTTCTGGA
TGATCTGAAATTTGGTCCGGGTGATGGTTTTCTGAATTTCTACCTGTTTA
ACTATCGTGCCAAACCGATTACCGGTGGTCT<u>GAATCC</u>GGATAATAGCAAT
GATATTAAACGTCGCAGCAATGTTGGTGTGGTTATGCTGTGATAATGATA
ATGATCTTCTGAATTCCCGTCATATCCGCTGAGCAATAACTAGCATAACC
CCTTATACGTTACAT-3'

This NMT(+) vector was then modified with the cDNA (see below) of each of the three de novo designed NMT signal sequences ($B_{1-3}$) using the same Gibson Assembly method. The following genes (Integrated DNA Technologies) were ligated into MCS 2 after digesting the NMT(+) pETDuet-1 vector with NdeI and XhoI and purification of linearized vector. Importantly, these cDNA for NMT signal (recognition) sequence were designed to contain a BseRI recognition sequence which was engineered to cut directly after the peptide substrate gene. BseRI is a type IIS restriction enzyme that enables seamless cloning with our available in-house ELPs, many of which have been designed using the cloning system developed by McDaniel et al. (McDaniel, et al. *Biomacromolecules* 2010, 11, 944). After Gibson Assembly, these new ligated vectors were transformed into competent cells and we identified positive clones with T7 Terminator sequencing. The recognition sequences for NdeI and XhoI enzymes are underlined in the sequences below.

NMT Recognition Sequence $B_1$: (GAGASRGGSGGS)
(SEQ ID NO: 35)
(SEQ ID NO: 36)
ATCTTAGTATATTAGTTAAGTATAAGAAGGAGATATA<u>CATATG</u>GGGGCGG
GCGCATCTCGTGGTGGCAGTGGTGGGAGCGGcTAATGATCTCCTCTATGA
GGATCC<u>GCTCGAG</u>TCTGGTAAAGAAACCGCTGCTGCGAAATTTGAA NMT Recogntion Sequence $B_2$: (GAGAGAYRGGSGGSGGS)
(SEQ ID NO: 37)
(SEQ ID NO: 38)
CATCTTAGTATATTAGTTAAGTATAAGAAGGAGATATA<u>CATATG</u>GGAGCG
GGTGCAGGTGCCTATAGAGGTGGGTCGGGAGGCAGTGGAGGCTCAGGCTA
ATGATCTCCTCAATGAG<u>CTCGAG</u>TCTGGTAAAGAAACCGCTGCTGCGAAA
TTTGAACG NMT Recognition Sequence $B_3$: (GLSLSRGGSGGS)
(SEQ ID NO: 39)
(SEQ ID NO: 40)
ATCTTAGTATATTAGTTAAGTATAAGAAGGAGATATA<u>CATATG</u>GGGCTGA
GCCTGTCTCGTGGTGGCAGTGGTGGGAGCGGCTAATGATCTCCTCAATGA
G<u>CTCGAG</u>TCTGGTAAAGAAACCGGTGCTGCGAAATTTGAA The final plasmid was constructed by digesting a plasmid containing the ELP gene and each NMT (+) vector (now containing NMT in MCS 1 and one of the three recognition sequences in MCS 2) with BseRI and XhoI. After gel purification, the ELP was ligated into each vector and transformed into EB5alpha cells. After confirming positive clones with T7 Terminator sequencing, the DNA was transformed into BL21(DE3) competent cells for expression.

Construction of Control Plasmids.

Figure 7:
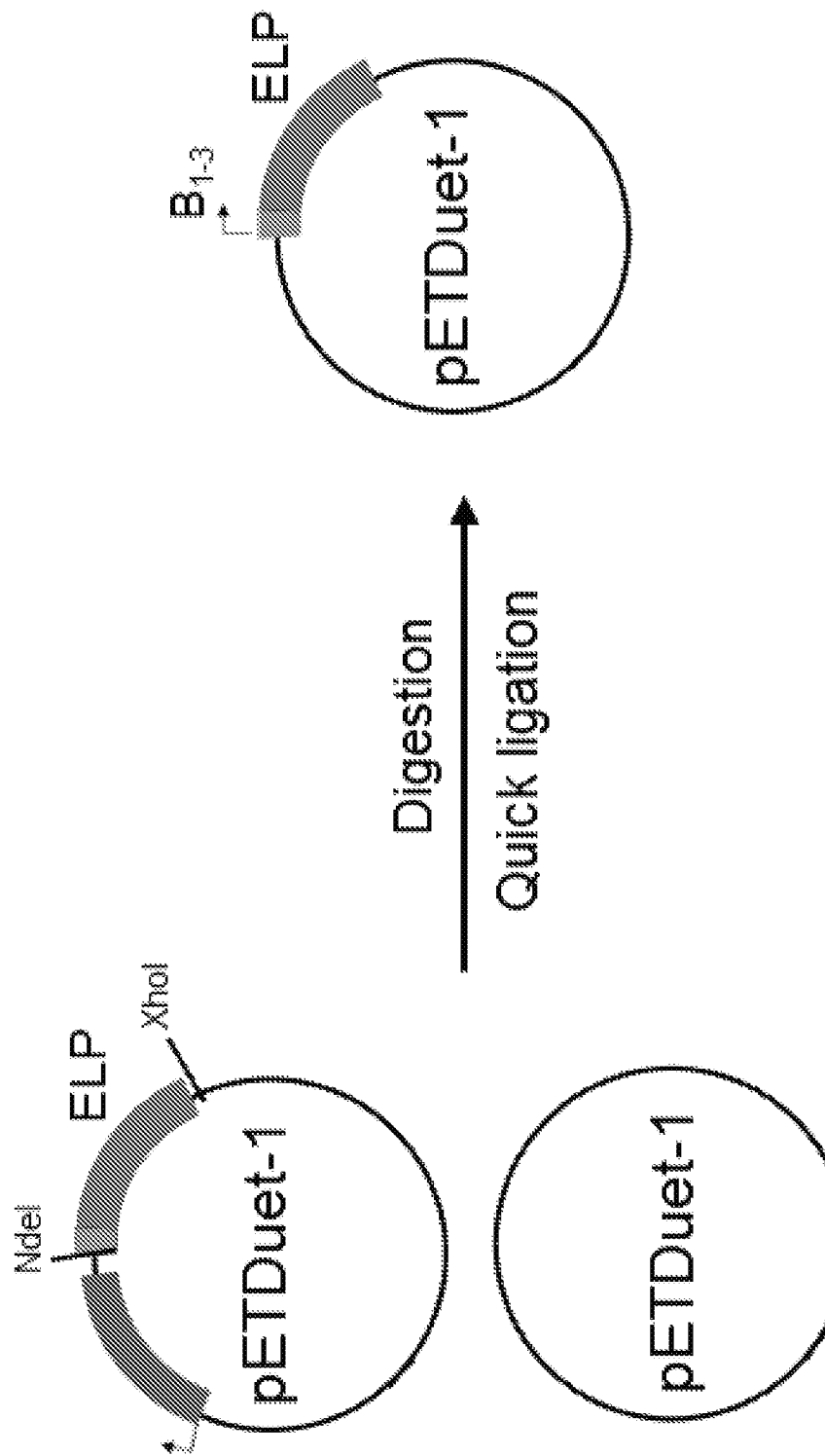
FIG. 7. Schematic of the process to prepare control plasmids.

FIG. 7. Control plasmids without NMT were prepared for the synthesis of non-myristoylated proteins. Briefly, empty pET-Duet-1 and plasmids containing the NMT and $B_{1-3}$ELP genes were digested with NdeI and XhoI and gel purified. $B_{1-3}$ELP was ligated into MCS-2 of the empty pET-Duet-1 vector and transformed into EB5alpha cells. After confirming positive clones with T7 Terminator sequencing, the DNA was transformed into BL21(DE3) competent cells for expression.

Amino Acid Sequence of Proteins.

The amino acid sequences of the proteins used in this study are reported below. N-terminal methionine is shown in italics and was removed co-translationally by methionine aminopeptidase before modification with the myristoyl group. A lysine residue was included for fluorophore conjugation as shown (underlined). A single tryrosine residue was encoded at the C-terminal to assist with UV-Vis detection of the proteins.

ELP
(SEQ ID NO: 41)
*M*GVGVPGVGVPGVGVPGVGVPGVGVPGVGVPGVGVPGVGVPGVGVPGVGV
PGVGVPGVGVPGVGVPGVGVPGVGVPGVGVPGVGVPGVGVPGVGVPGVGV

-continued

PGVGVPGVGVPGVGVPGVGVPGVGVPGVGVPGVGVPGVGVPGVGVPGVGV

PGVGVPGVGVPGVGVPGVGVPGVGVPGVGVPGVGVPGVGVPGVGVPGVGV

PGY

B₁-ELP (SEQ ID NO: 42)
MGAGASRGGSGGSGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGY

B₂-ELP (SEQ ID NO: 43)
MGAGAGAYRGGSGGSGGSGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGY

B₃-ELP (SEQ ID NO: 44)
MGLSLSRGGSGGSGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGY

B₁-ELP-GKG (SEQ ID NO: 45)
MGAGASRGGSGGSGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGGKGY

B₂-ELP-GKG (SEQ ID NO: 46)
MGAGAGAYRGGSGGSGGSGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGGKGY

B₃-ELP-GKG (SEQ ID NO: 47)
MGLSLSRGGSGGSGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGVGVPGVGVPGVGVPGVGVPGVGVPGVGVPGVGVPGV

GVPGVGVPGVGVPGGKGY

Expression Protocol

A single bacterial colony was selected to inoculate 50 mL of autoclaved TB medium containing 100 μg/mL ampicillin at 37° C. on an orbital shaker at 200 rpm. After 12 h, the seed culture was centrifuged at 3500 rpm and 4° C. for 15 min to harvest the cells. The *E. coli* pellet was re-suspended in 6 mL of phosphate buffer saline (PBS) solution. 1 mL of this suspension was used to inoculate 1 L of autoclaved TB media containing 100 μg/mL ampicillin. The bacteria were cultivated in an orbital shaker incubator at 37° C. at 180 rpm. After 6 h, the temperature of the incubator was reduced to 28° C. Myristic acid was added to each flask to a final concentration of 100 μM (i.e., 1 mL of 100 mM myristic acid that had been dissolved in molecular biology grade DMSO was added to each flask). After 15 min, expression was induced by the addition of IPTG to a final concentration of 0.5 mM.

Protein Purification Protocol

After 18 h post-induction, the cells were harvested by centrifugation at 3500 rpm and 4° C. for 15 min. The bacterial pellet was re-suspended in PBS (5 mL PBS for each 1 L of expression culture). The cells were then lysed by two cycles of sonication at 4° C. using sequential pulses of 10 s at 85 W followed by 40 s resting-time for a total sonication period of 90 s. The lysed bacterial solution was transferred to polycarbonate centrifuge tubes and 10% w/v polyethylenimine (2 mL per every 1 L of expression culture) was added to remove the nucleic acid fragments. Each tube was vortexed several times to ensure complete mixing until a white homogenous precipitate appeared in the entire volume of the solution. After which, the solution was centrifuged at 14 krpm and 4° C. for 15 min to separate the protein from insoluble cell debris. The clear supernatant layer was transferred to clear polycarbonate tubes and was then subjected to two rounds of inverse transition cycling (ITC). First, we triggered the phase-transition of the Fatty Acid Modified ELPs (FAMEs) or ELPs isothermally by the addition of solid NaCl. The polymer coacervates were then collected by a "hot spin" centrifugation step at 15 krpm and 35° C. for 15 min, after which the supernatant was discarded. The pellet was then re-suspended in 4 mL of deionized $H_2O$, and the tubes were placed in a tube rotisserie within a 4° C. refrigerator. After 1 h, the pellets were scraped with a metallic spatula to help the solubilization process. After 6 h, the mixture was centrifuged at 15 krpm and 4° C. for 15 min for a "cold spin" step, and then the pellet was discarded. The supernatant was delivered to a clean tube and was subjected to another round of ITC. For the second round of ITC, a 5 M NaCl aqueous solution was used to trigger the phase-transition of FAMEs or ELPs isothermally. After the second 'cold spin' cycle, the supernatant was collected and purified by preparative HPLC as described below to ensure purity (>95%) for the self-assembly studies.

Reverse phase HPLC (RP-HPLC) was performed on a Waters 600 HPLC system (Phenomenex Jupiter® 10 μm C18 300 Å, LC Column 250×21.2 mm, solvent A: $H_2O$+ 0.1% TFA, solvent B: acetonitrile+0.1% TFA). A sample of the protein (0.5 mL, 5 mg/mL) was injected into the HPLC system using these conditions (TABLE 3) and the absorbance was monitored at 230 nm.

TABLE 3

| Gradient program used for preparative RP-HPLC | |
| --- | --- |
| Time (min) | Solvent B % |
| 0 | 30% |
| 5 | 30% |
| 25 | 90% |

Fractions corresponding to each peak were collected and analyzed using matrix-assisted laser desorption/ionization time-of-flight mass spectrometry (MALDI-TOF-MS) using an Applied Biosystems Voyager-DE™ PRO instrument according to the procedure below.

Fractions containing the desired proteins were combined and dialyzed extensively against deionized water at 4° C. using a snake skin dialysis tube with a MWCO of 3.5 kDa for 12 h. After dialysis, each sample was lyophilized and kept at −20° C. for long-term storage. The purity and identity of the constructs were assessed by sodium dodecyl sulfate polyacrylamide gel electrophoresis (SDS-PAGE), analytical HPLC, and MALDI-TOF. The N-terminal myristoylation was further confirmed by digesting the FAME constructs with trypsin and analyzing the N-terminal peptide fragment using MALDI-TOF-MS.

Synthesis of Control Peptide Amphiphiles

Control peptide amphiphiles (PAs) were synthesized using standard Fmoc (9-fluorenylmethoxy-carbonyl)-based chemistry on rink amide resin using Protein Technologies PS3 automated peptide synthesizer (Coin, et al., *Nat. Protoc.* 2007, 2, 3247). We coupled standard Fmoc-protected amino acids using 4 equivalents of HBTU-activated amino acids in the presence of N-methylmorpholine in DMF for 20 min. Fmoc deprotection was achieved using 20% piperidine in DMF. Myristic acid was coupled as the last residue using a similar protocol used for coupling the canonical amino acids. After the last coupling reaction, the resin was washed twice with DMF, twice with dichloromethane, and then air-dried.

Peptide cleavage and deprotection was accomplished by re-suspending the resin in 5 mL of a cleavage cocktail (95% TFA, 2.5% $H_2O$, and 2.5% triisopropylsilane) for 3 h. The resin was filtered and the cleavage cocktail was concentrated in vacuo. Peptides were precipitated in cold diethyl ether and were collected by centrifugation at 3500 rpm and 4° C. for 15 min. The pellet was washed with cold diethyl ether and air dried before storage at −20° C. The purity and the identity of each peptide was confirmed by liquid chromatography-mass spectrometry and MALDI-TOF-MS.

Alternatively, the control PAs could be synthesized by trypsin digestion of the corresponding FAME, similar to a method described below (see "Trypsin Digestion of Proteins"). Briefly, to biosynthetically produce the PAs, 10 mg of the corresponding FAME (dissolved in 1 mL of digest buffer) and 1 µg of trypsin were incubated at 37° C. overnight. The PAs were collected by centrifugation and further purified by utilizing the thermally-triggered phase transition of the ELP domains and the low-solubility of PAs in water.

Chemical Synthesis of M-ELP

Figure 8:
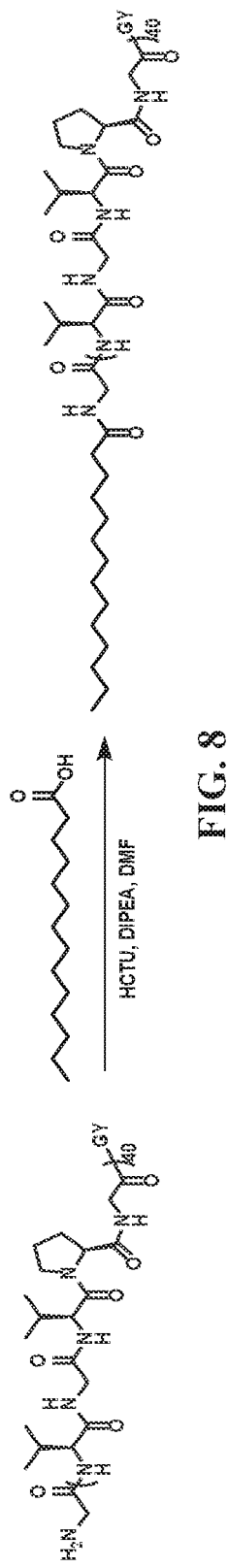
FIG. 8. Semisynthetic preparation of M-ELP.
Figure 9:
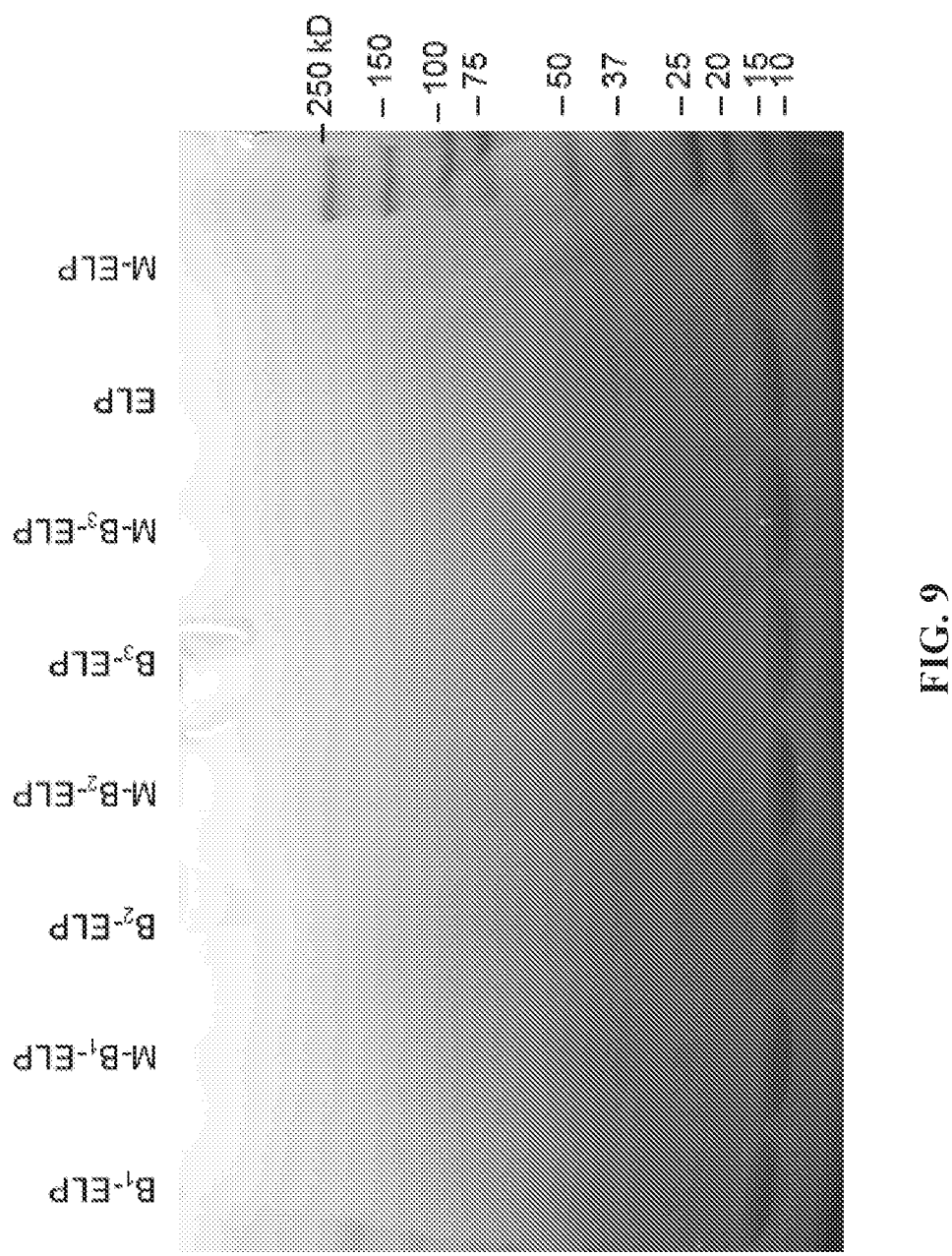
FIG. 9. Negatively stained SDS-PAGE gel of purified constructs in this study.
Figure 10:
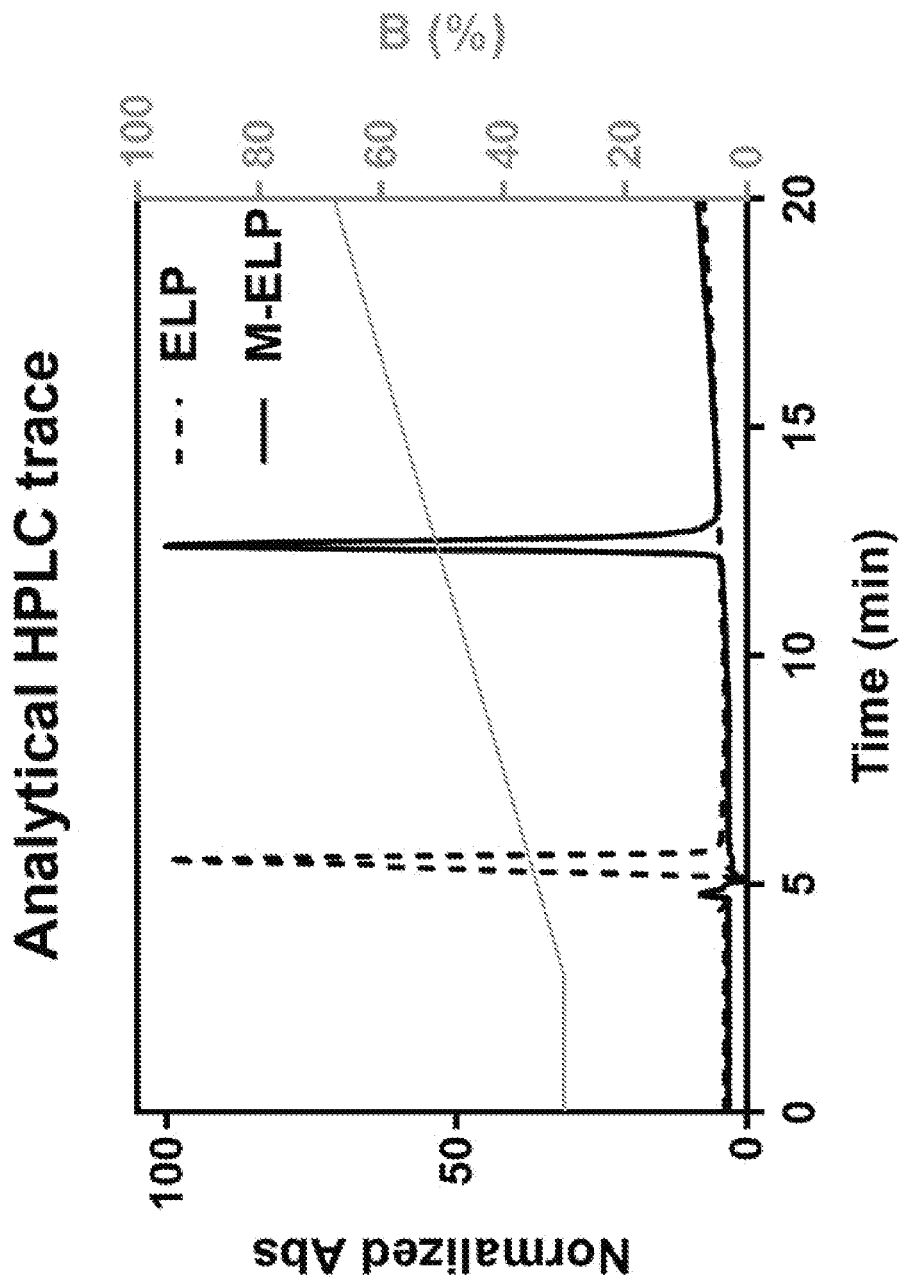
FIG. 10. Analytical reverse phase-high performance liquid chromatography (RP-HPLC) trace for ELP (dashed black line) and M-ELP (solid black line).
Figure 11:
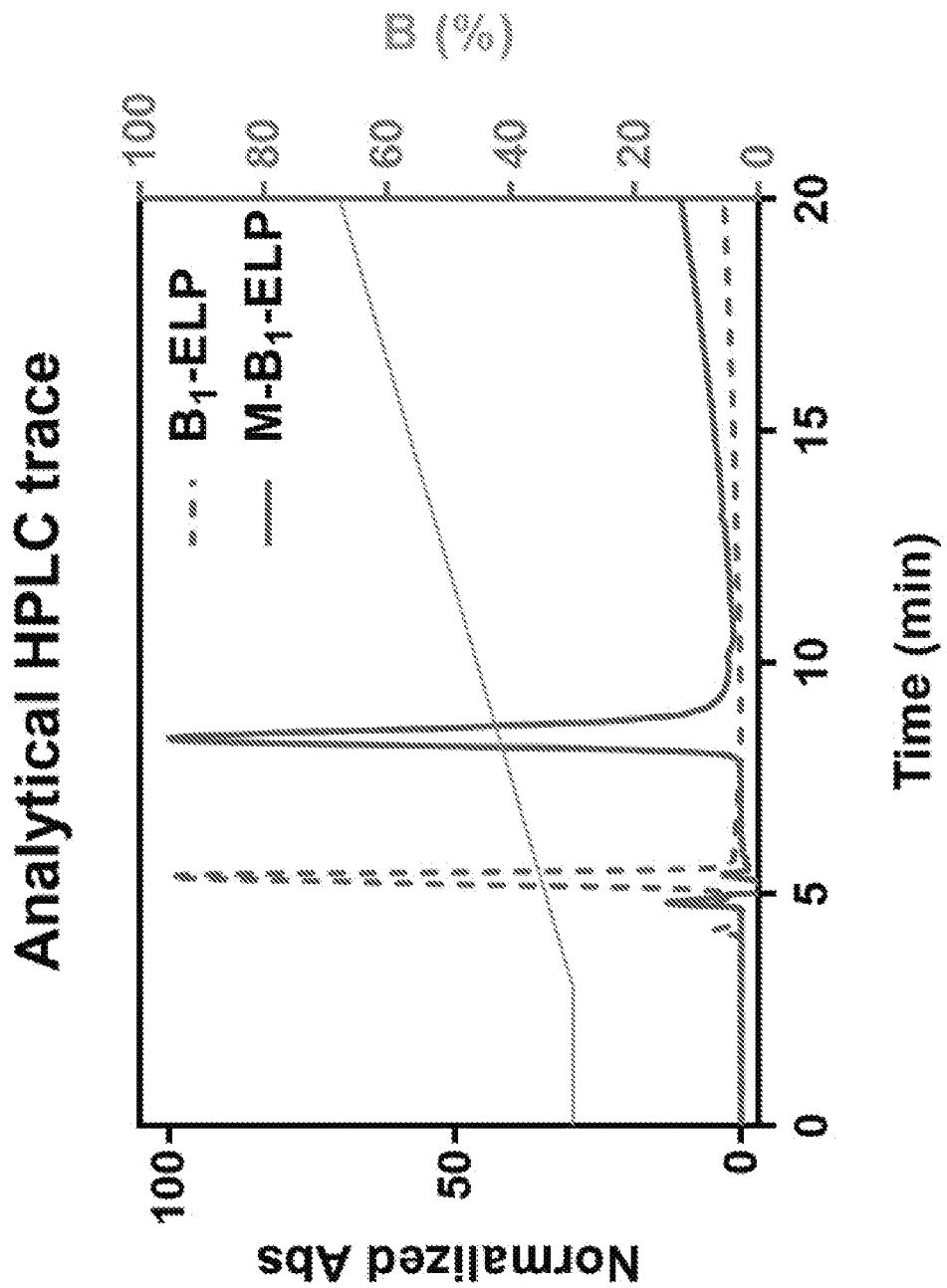
FIG. 11. Analytical RP-HPLC trace for B$_1$-ELP (dashed green line) and M-B$_1$-ELP (solid green line).
Figure 12:
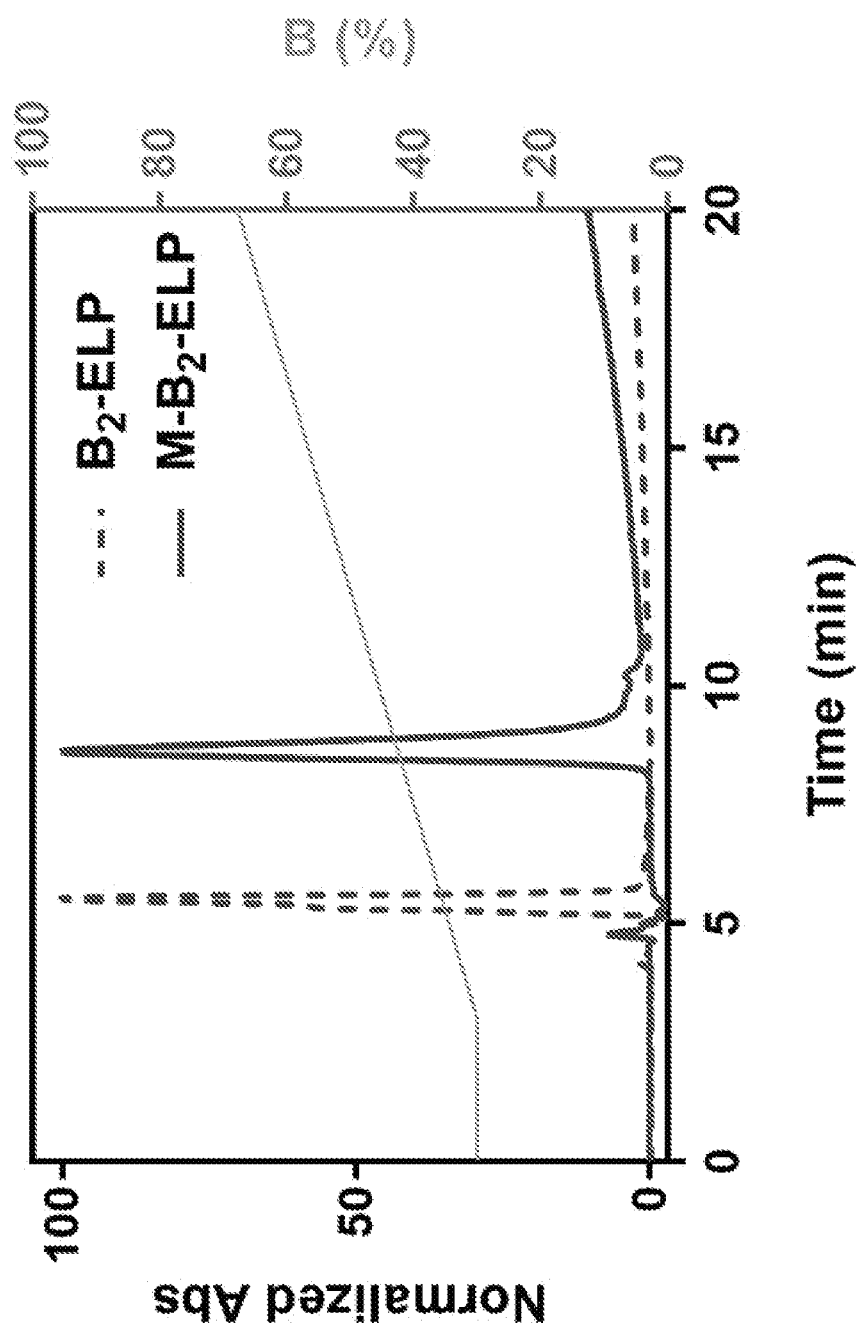
FIG. 12. Analytical RP-HPLC trace for B$_2$ELP (dashed blue line) and M-B$_2$-ELP (solid blue line).
Figure 13:
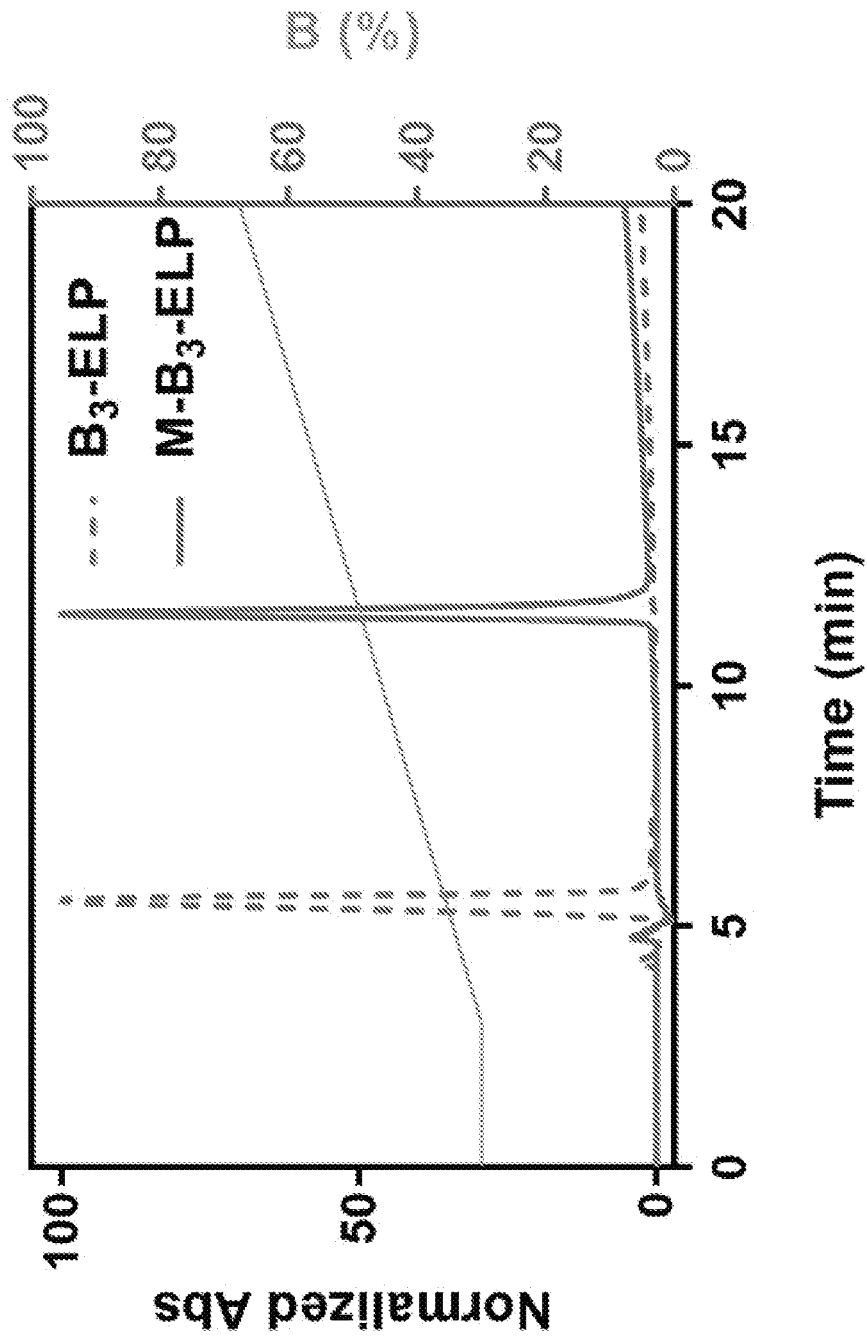
FIG. 13. Analytical RP-HPLC trace for B$_3$-ELP (dashed red line) and M-B$_3$-ELP (solid red line).
Figure 14:
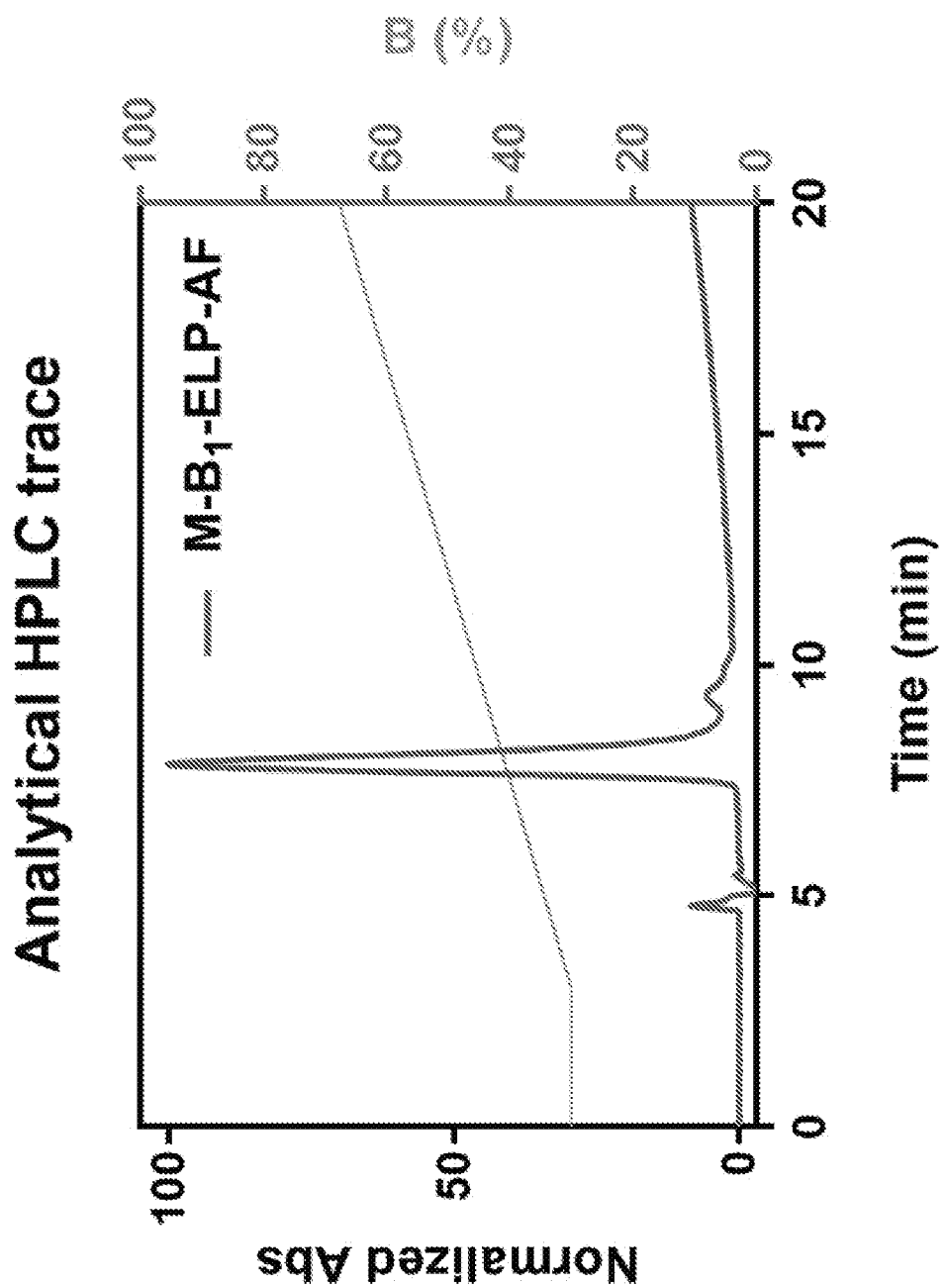
FIG. 14. Analytical RP-HPLC trace for M-B$_1$-ELP-GKG labeled with Alexa Fluor® 488 dye (AF).
Figure 15:
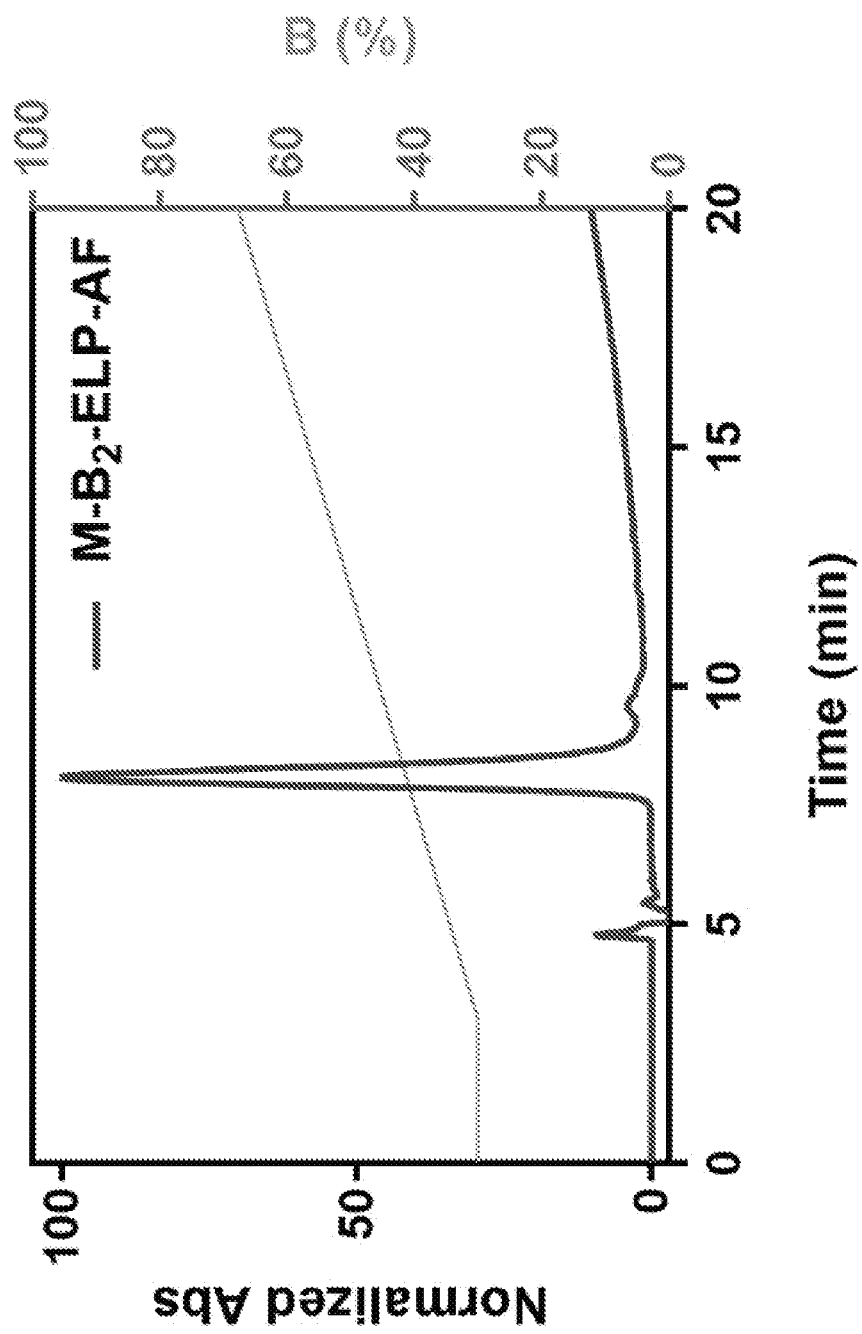
FIG. 15. Analytical RP-HPLC trace for M-B$_2$-ELP-GKG labeled with Alexa Fluor® 488 dye (AF).
Figure 16:
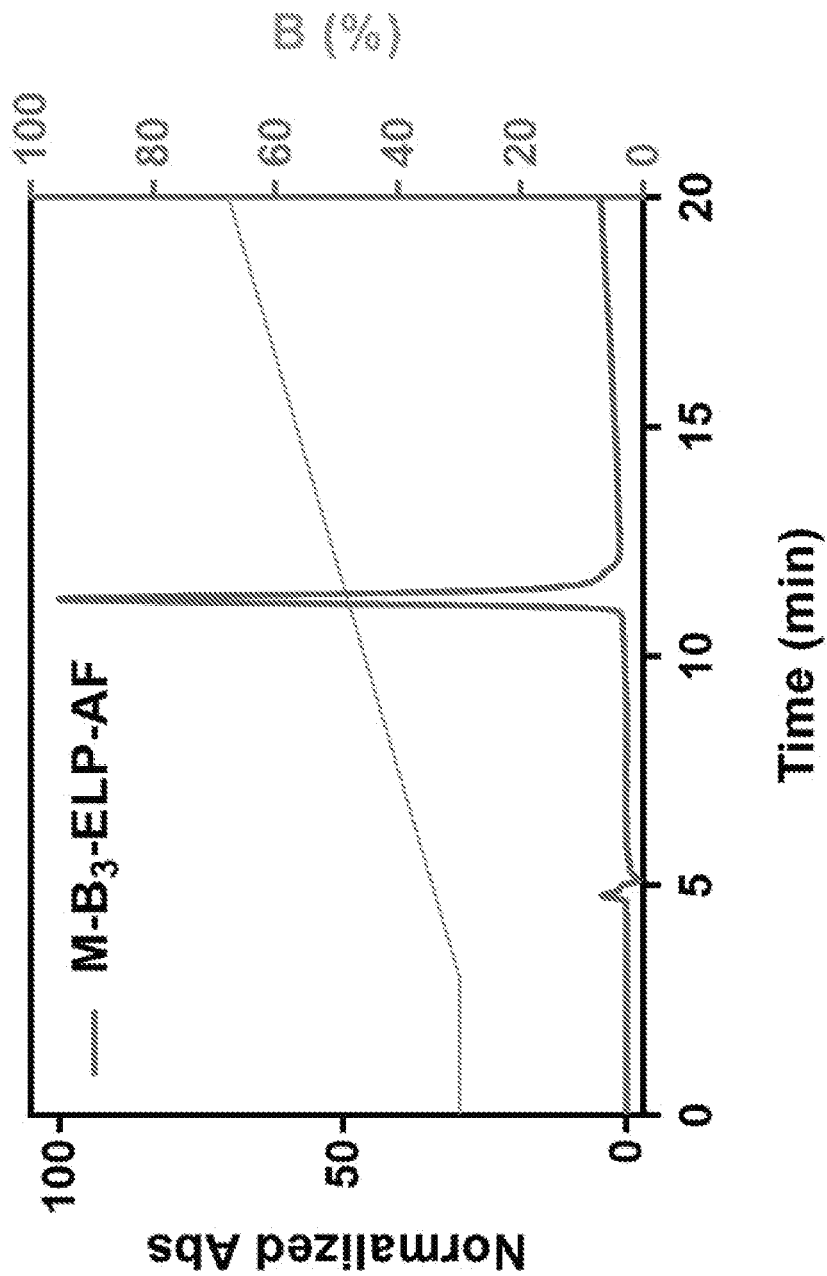
FIG. 16. Analytical RP-HPLC trace for M-B$_3$-ELP-GKG labelled with Alexa Fluor® 488 dye (AF).
Figure 17:
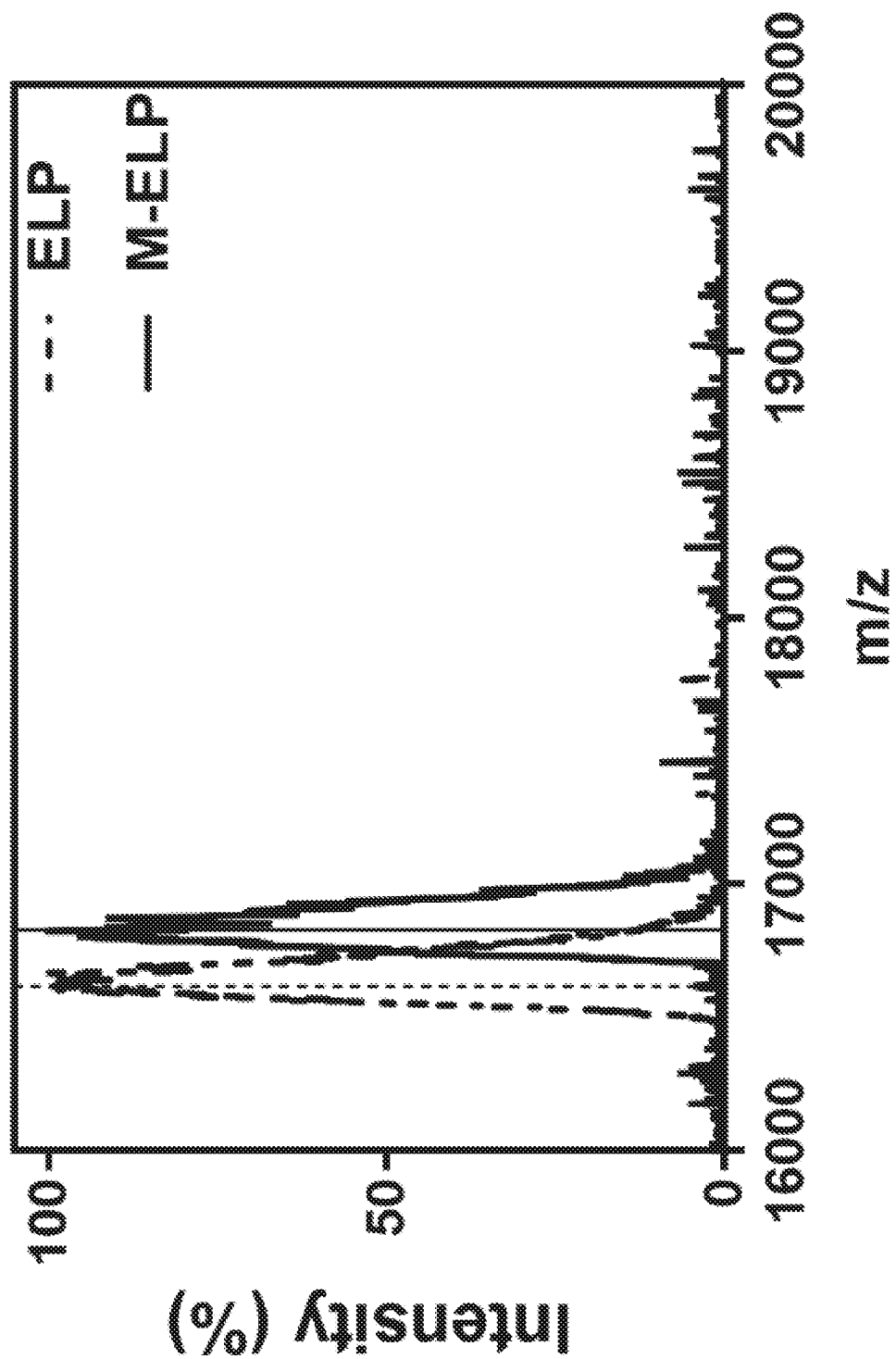
FIG. 17. Matrix-assisted laser desorption/ionization-time of flight-mass spectrometry (MALDI-TOF-MS) spectra of ELP (dashed black curve) and M-ELP (solid black curve). Vertical lines represent the theoretical $M_w$ of each construct.
Figure 18:
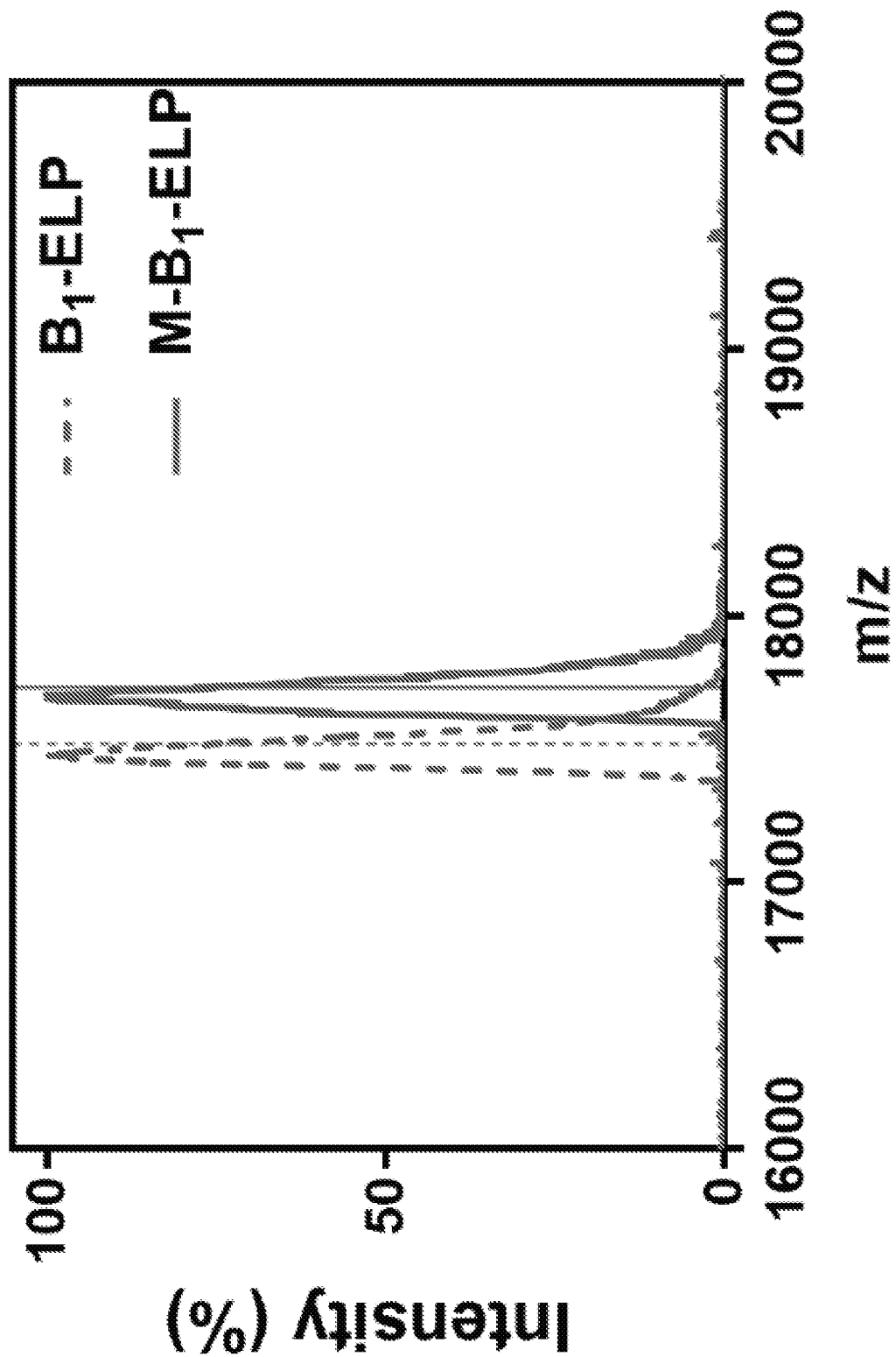
FIG. 18. MALDI-TOF-MS spectra of B$_1$-ELP (dashed green curve) and M-B$_1$-ELP (solid green curve). Vertical lines represent the theoretical $M_w$ of each construct.
Figure 19:
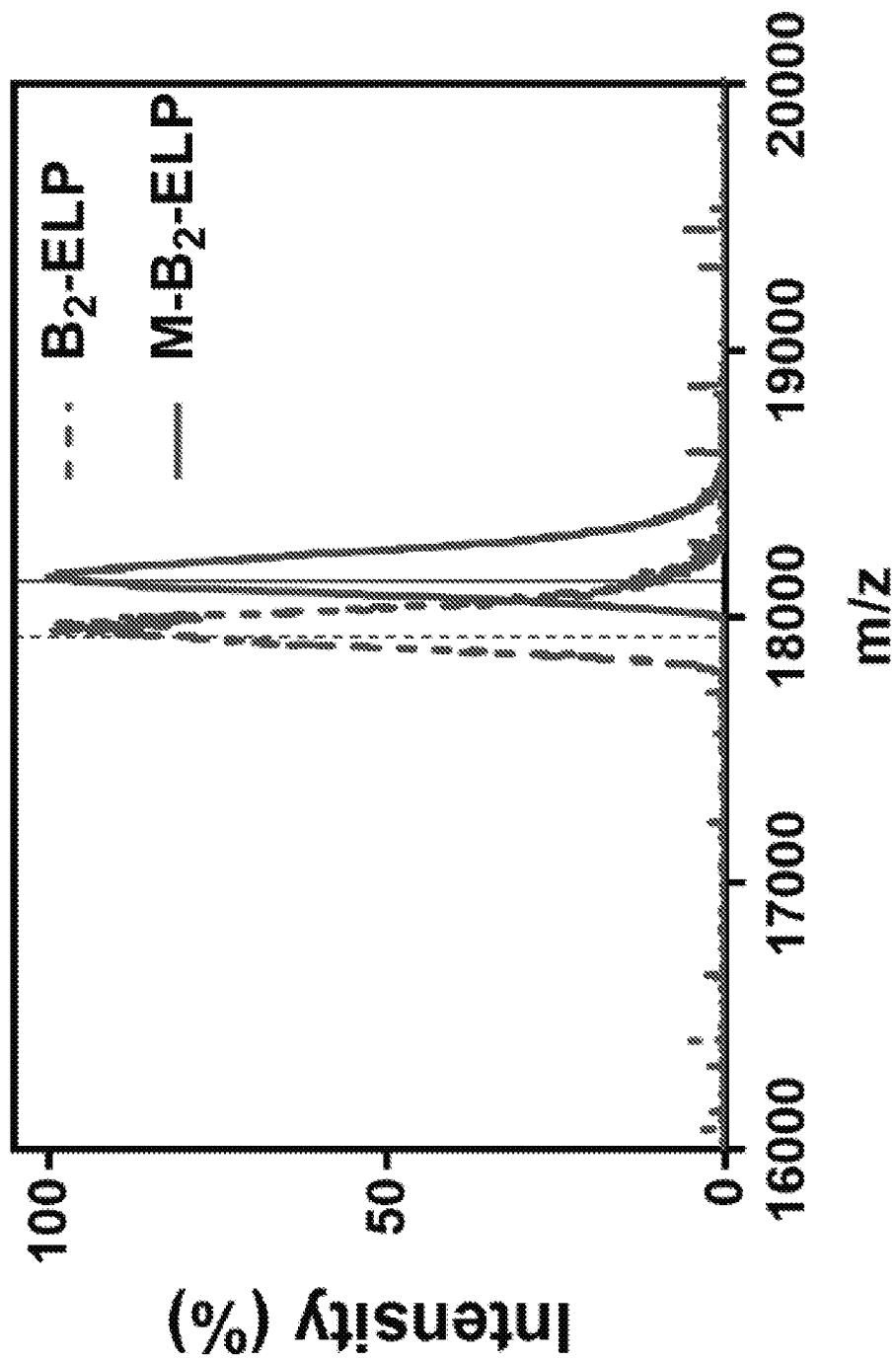
FIG. 19. MALDI-TOF-MS spectra of $B_2$-ELP (dashed blue curve) and M-$B_2$ELP (solid blue curve). Vertical lines represent the theoretical $M_w$ of each construct.
Figure 20:
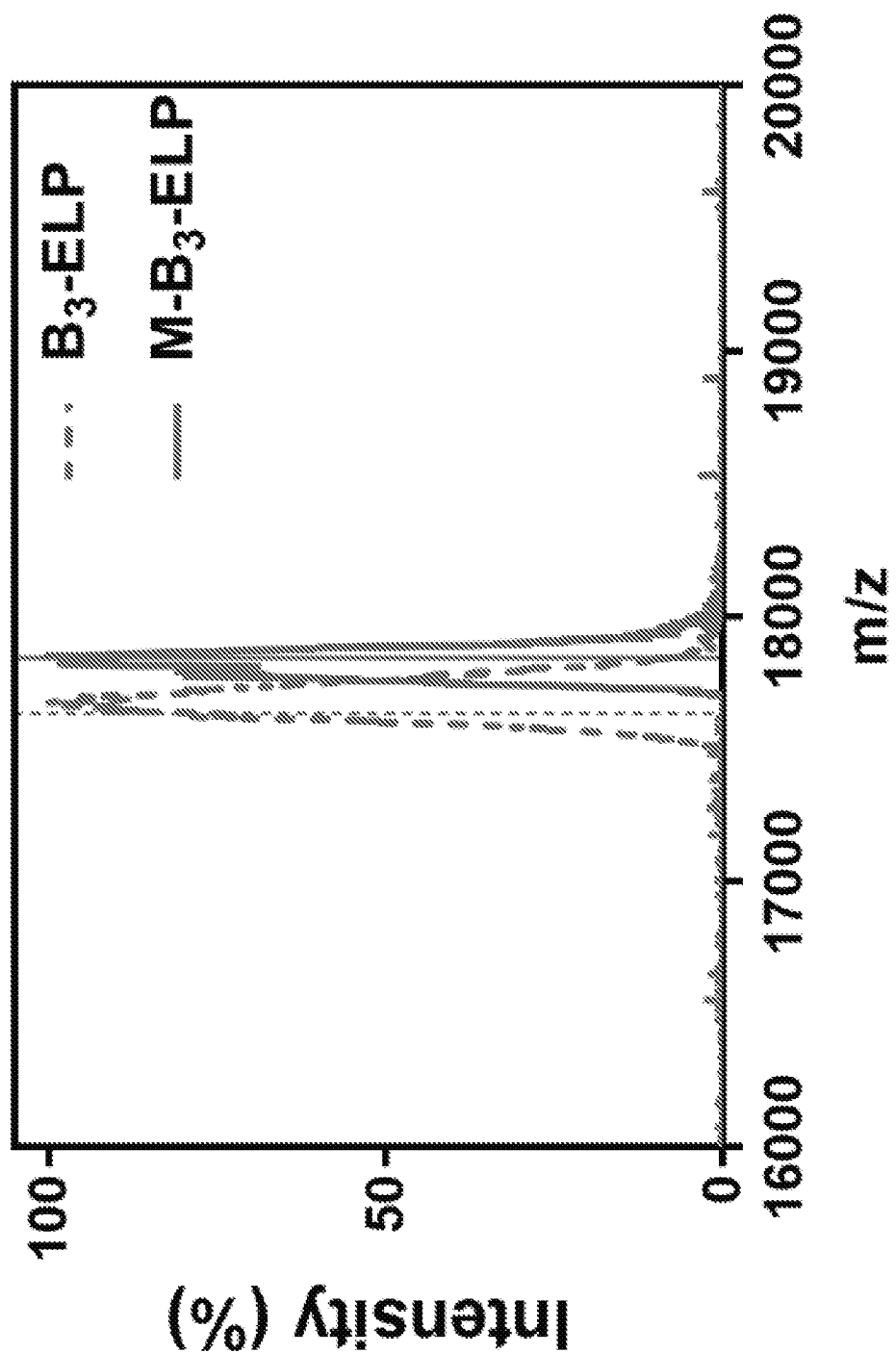
FIG. 20. MALDI-TOF-MS spectra of Br-ELP (dashed red curve) and M-$B_3$-ELP (solid red curve). Vertical lines represent the theoretical $M_w$ of each construct.
Figure 21:
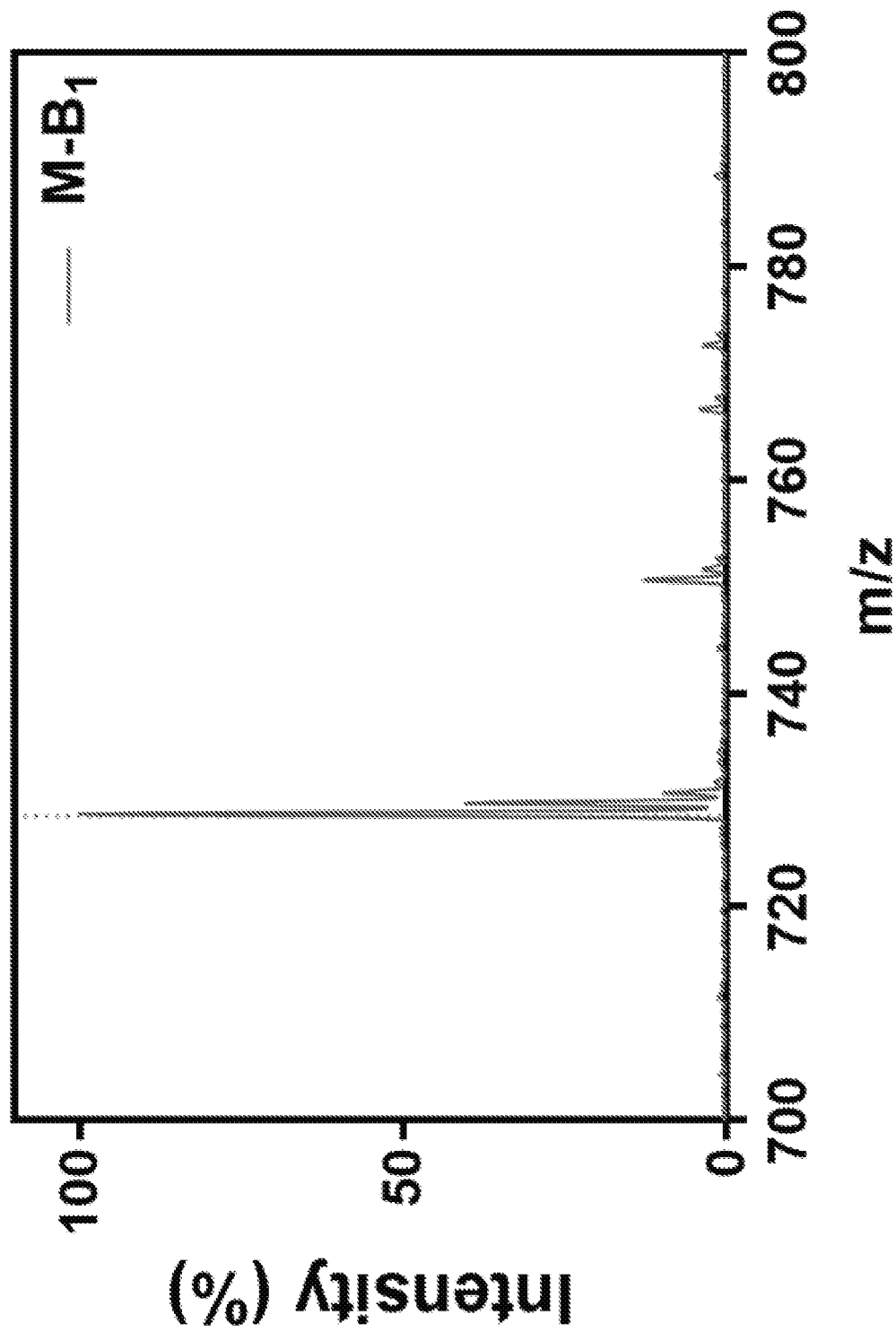
FIG. 21. MALDI-TOF-MS spectra of M-$B_1$ peptide (green) confirms N-terminal myristoylation. Vertical line represents the theoretical $M_w$.
Figure 22:
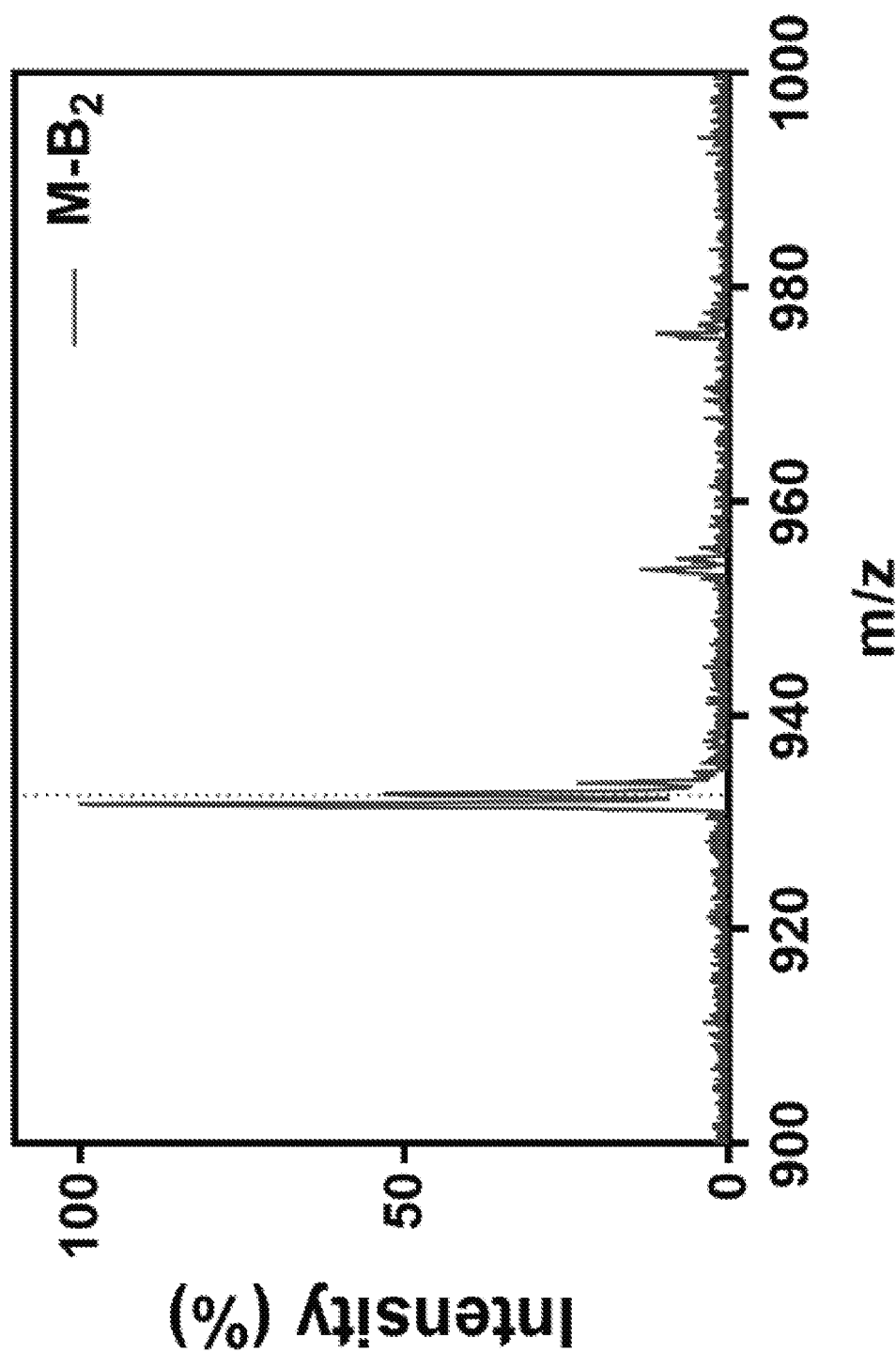
FIG. 22. MALDI-TOF-MS spectra of M-$B_2$ peptide (blue) confirms N-terminal myristoylation. Vertical line represents the theoretical $M_w$.
Figure 23:
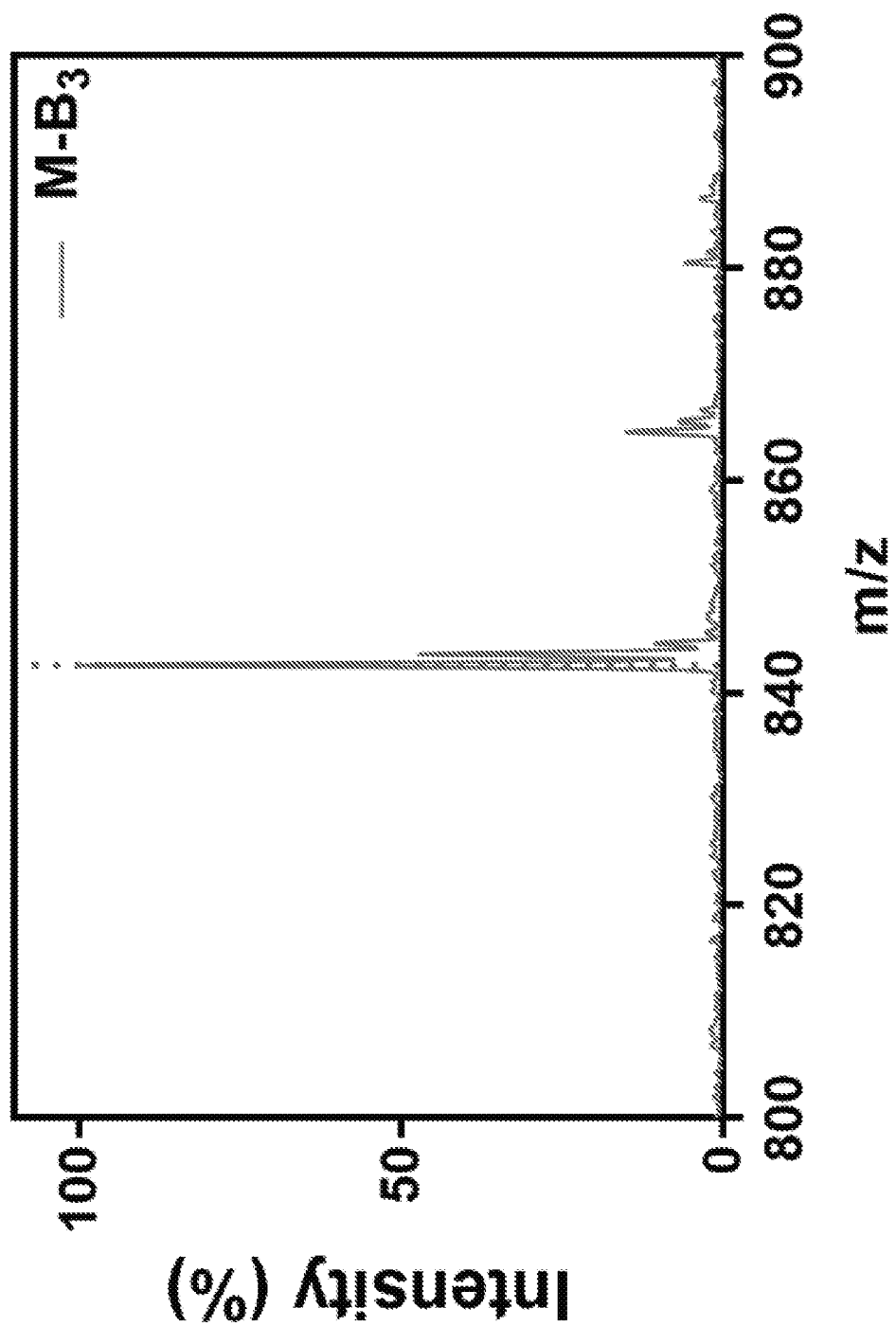
FIG. 23. MALDI-TOF-MS spectra of M-$B_3$ peptide (red) confirms N-terminal myristoylation. Vertical line represents the theoretical $M_w$.
Figure 24A:
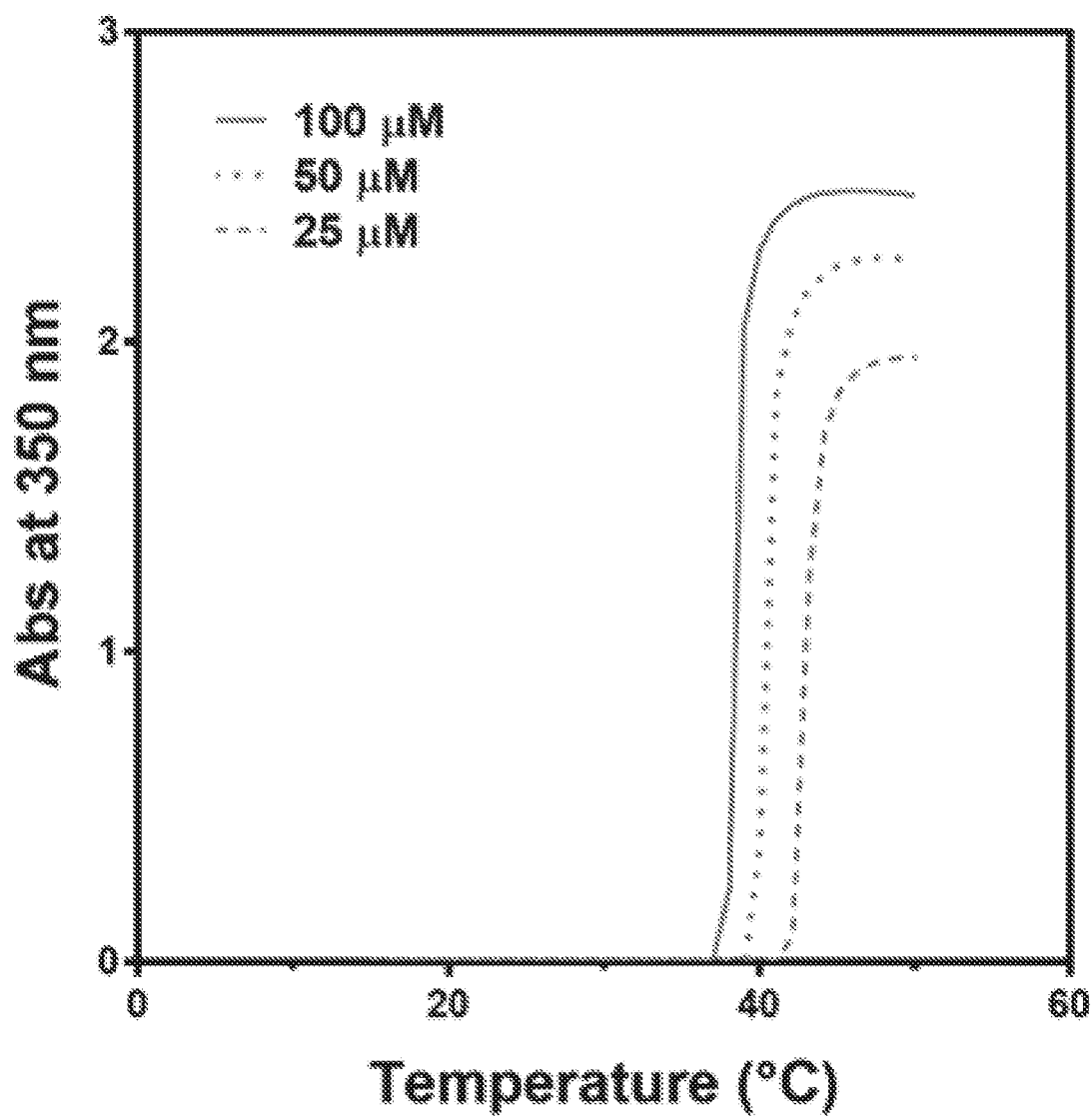
FIG. 24A-B.
Figure 24B:
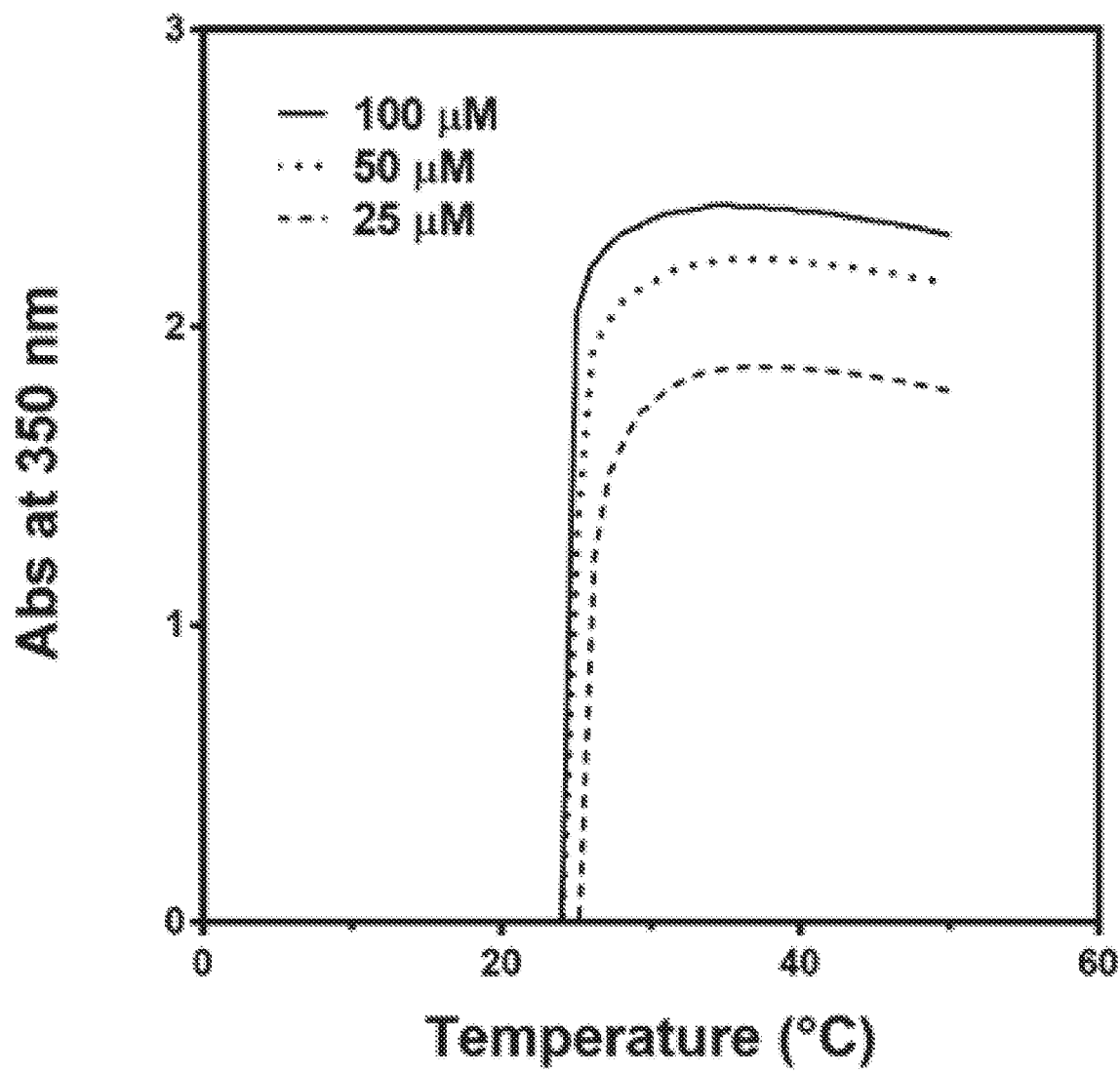
Figure 25A:
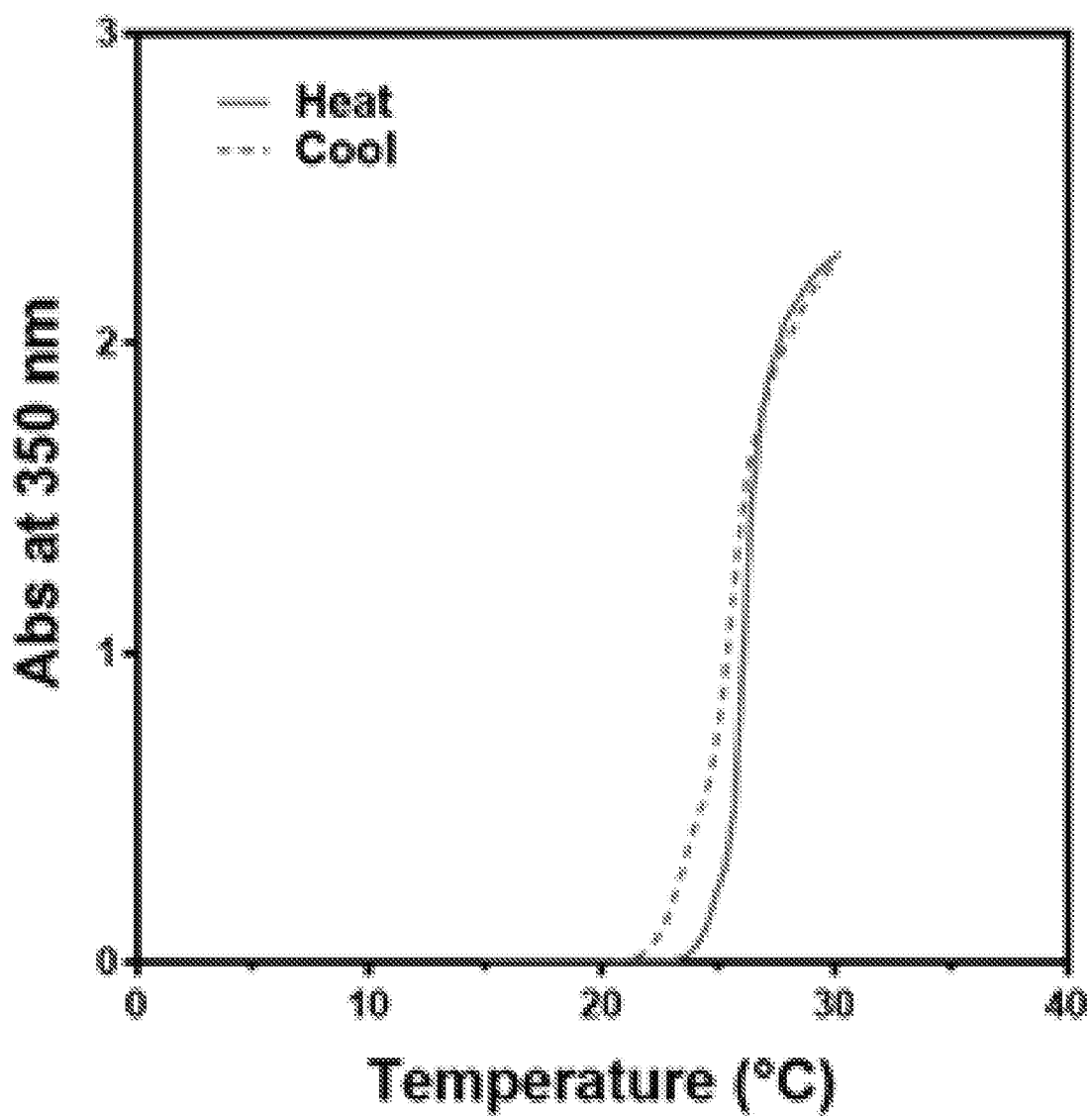
FIG. 25A-C. Temperature-programmed turbidimetry assay demonstrates that the phase transition of FAMEs is reversible at lower temperature.
Figure 25B:
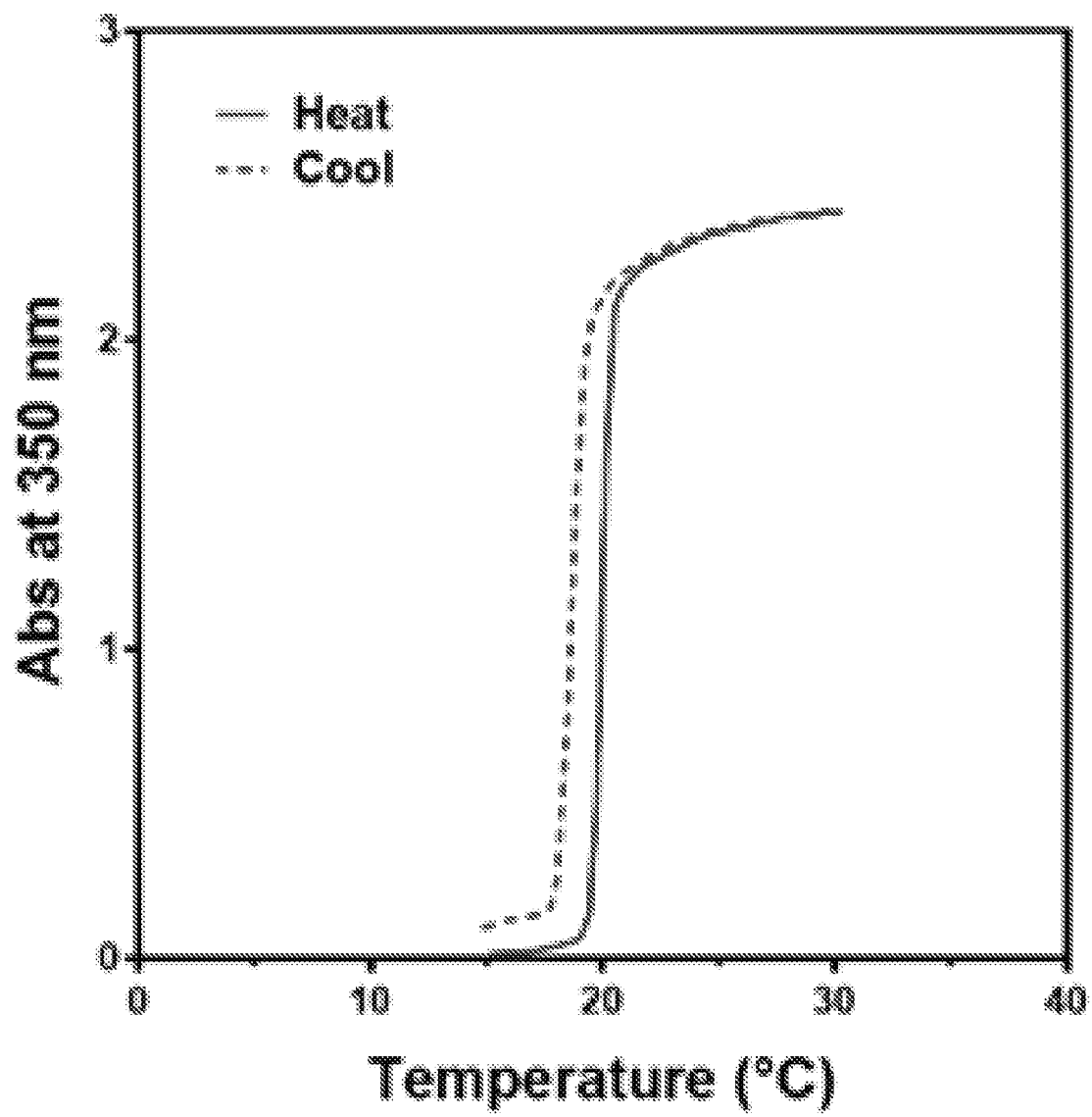
Figure 25C:
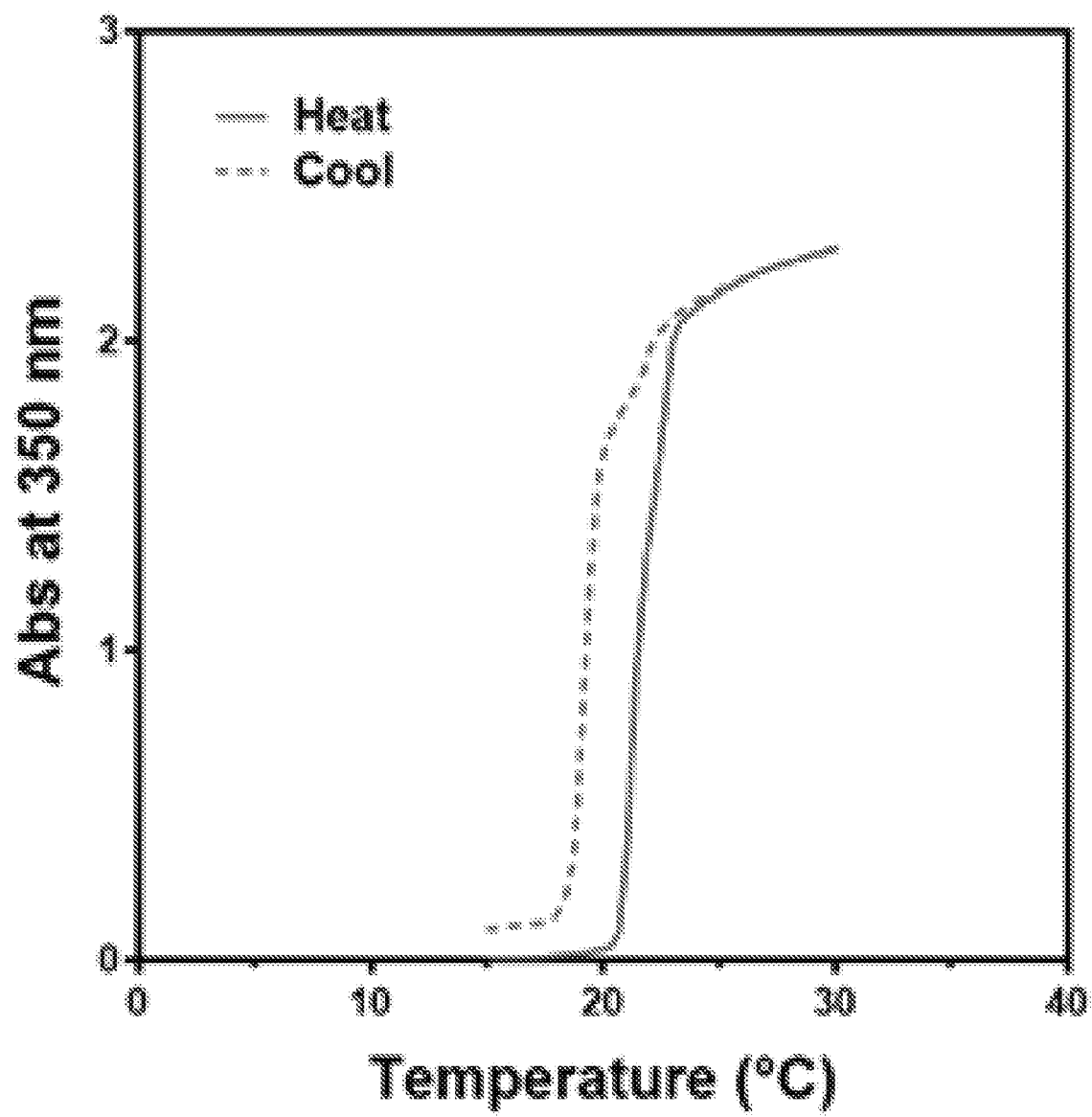
Figure 26A:
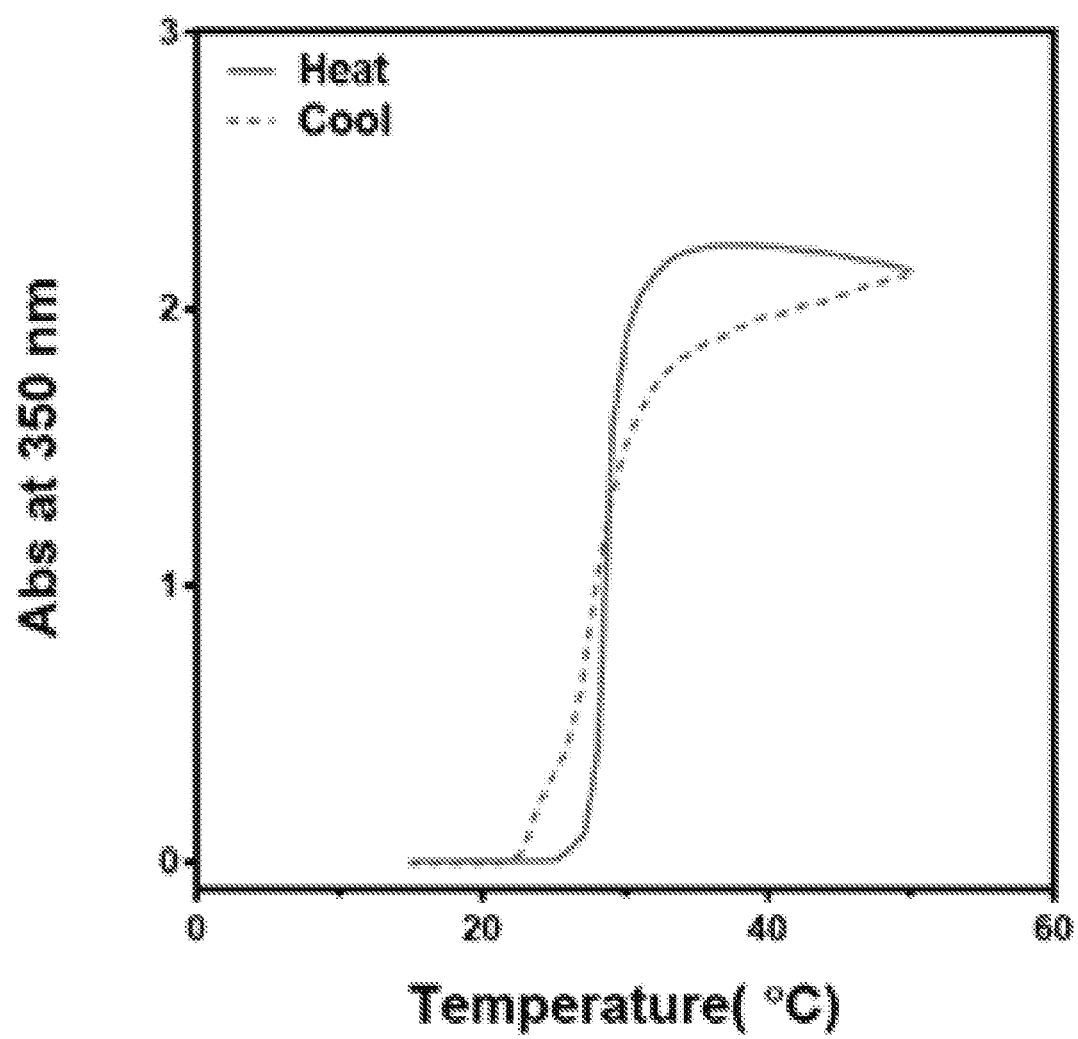
FIG. 26A-C. Temperature-programmed turbidimetry assay demonstrates the phase-transition of M-$B_1$-ELP is reversible up to 50° C. but the phase transition of M-$B_2$-ELP and M-$B_3$-ELP is not reversible.
Figure 26B:
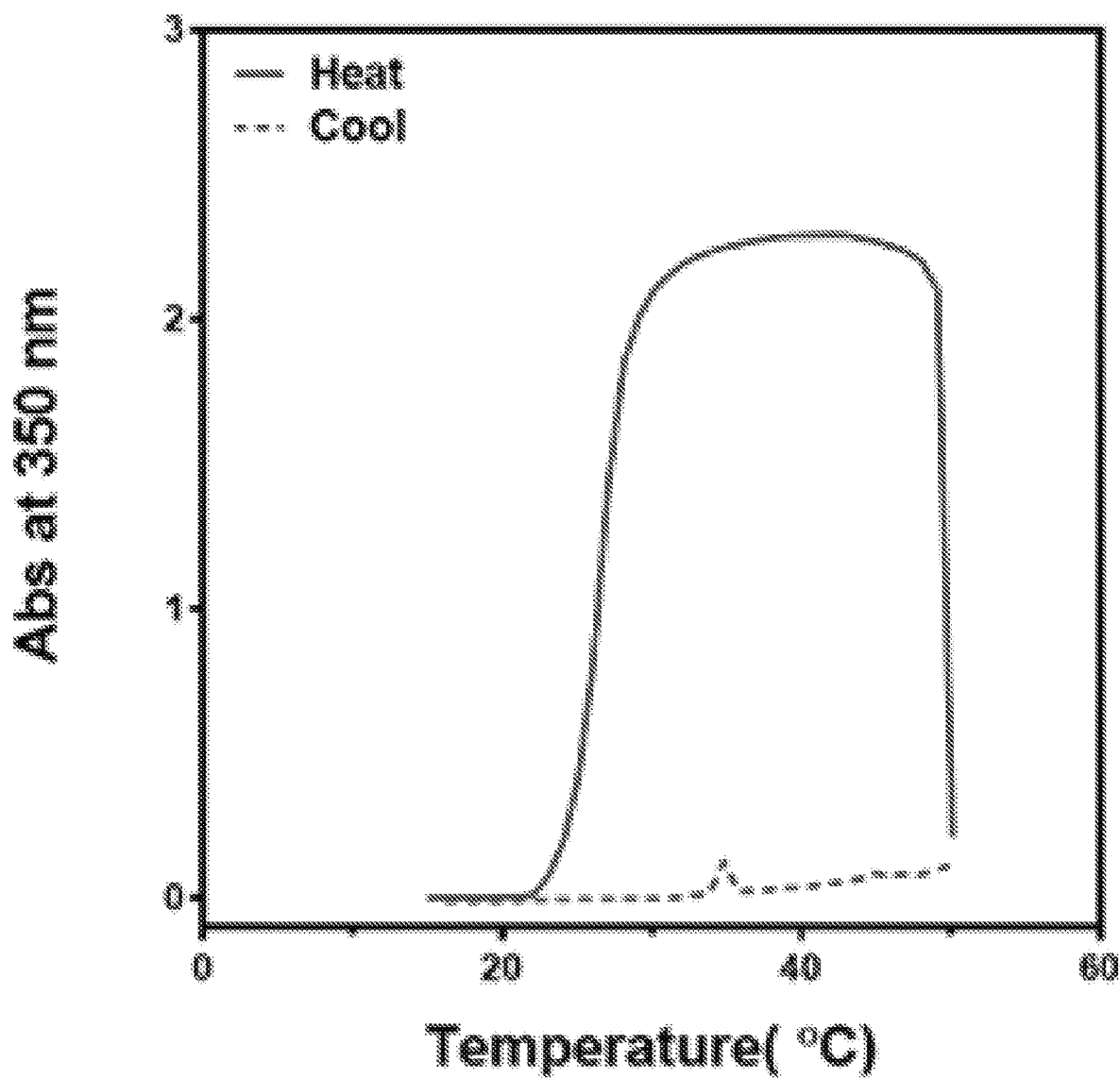
Figure 26C:
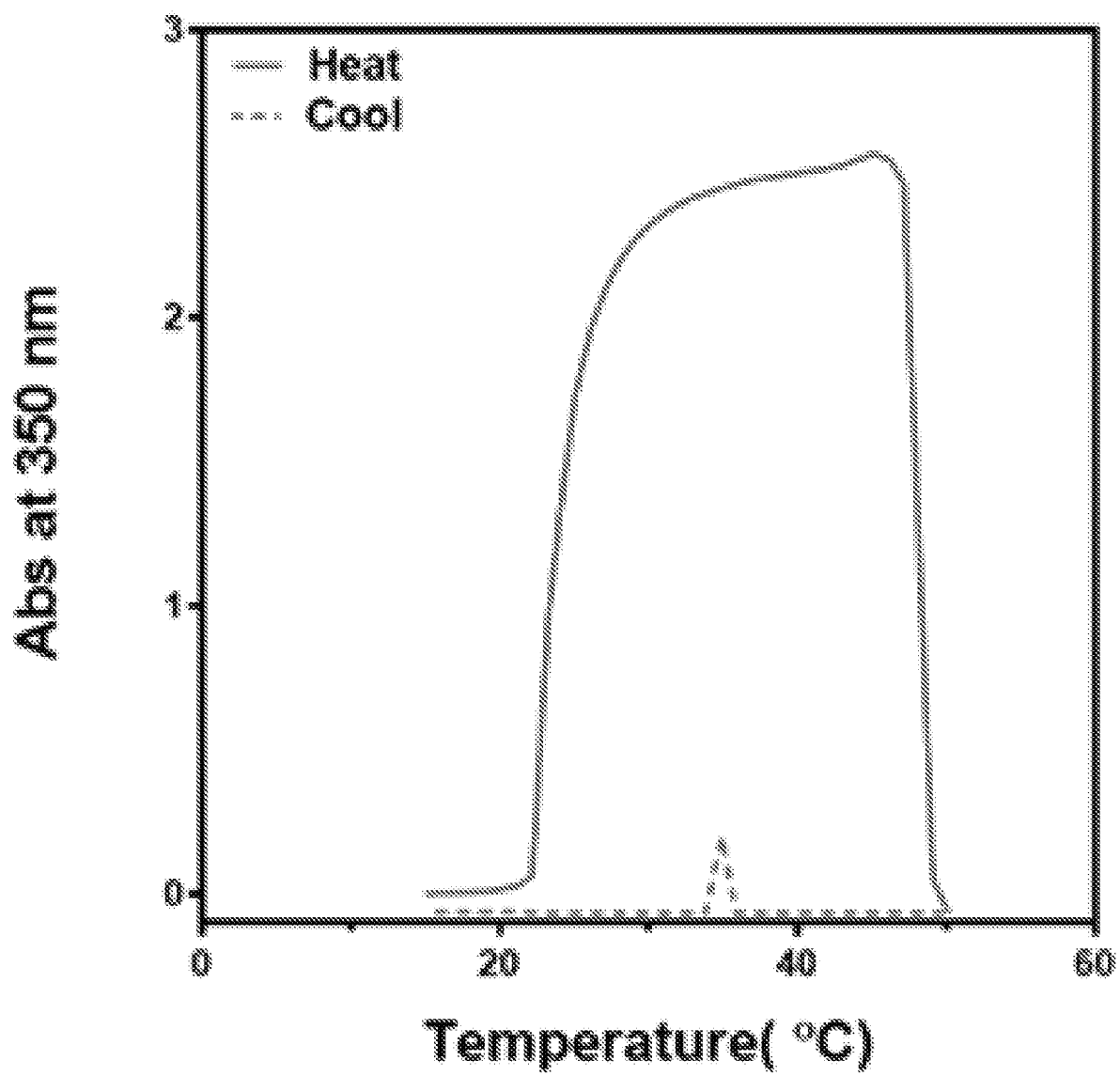
Figure 27:
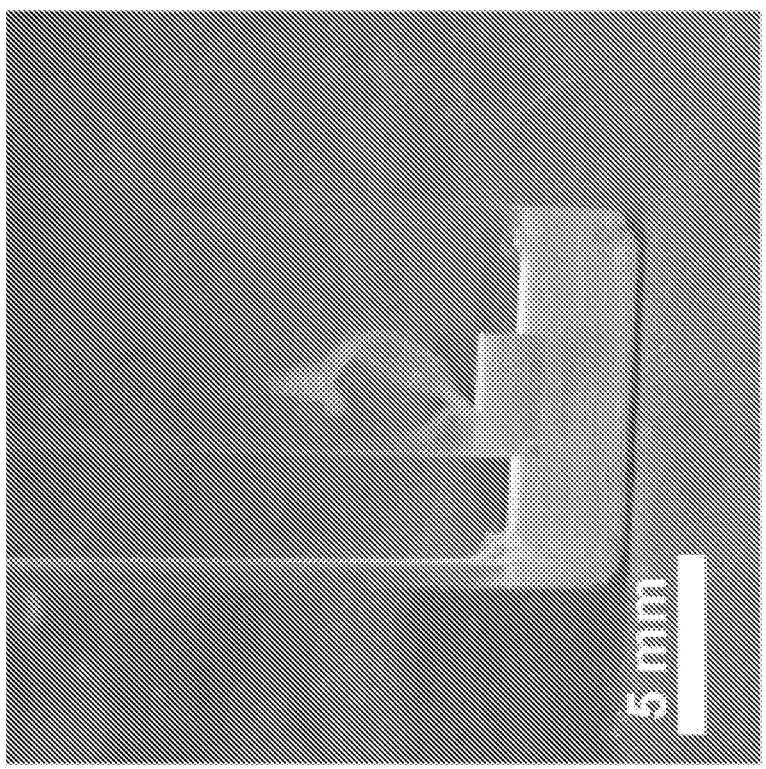
FIG. 27. Optical images of the structures formed by the M-$B_2$-ELP constructs.
Figure 27:
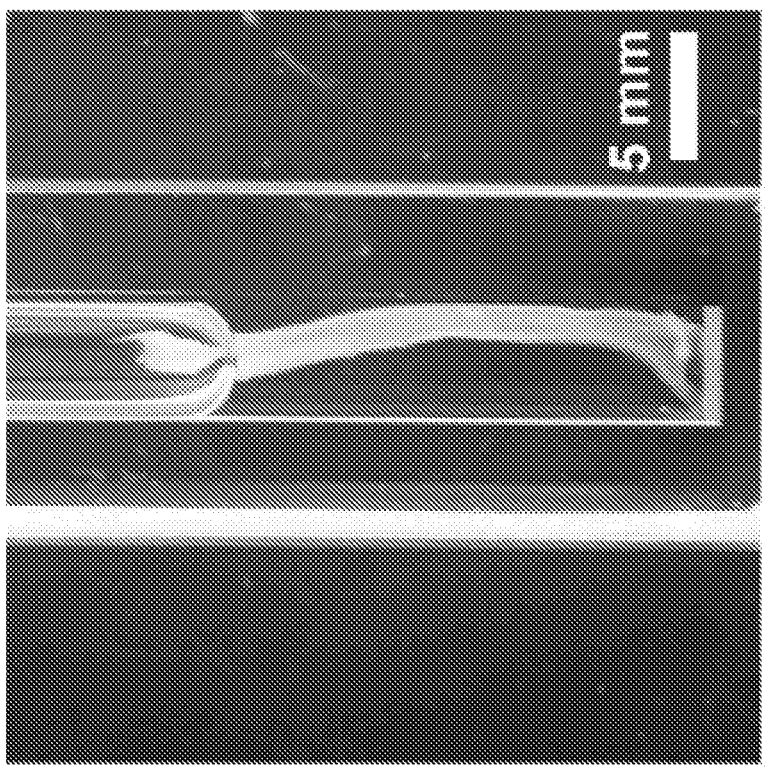

M-ELP was prepared as a control to investigate the contribution of PA-like domains to the self-assembly and phase-transition of FAMEs. Due to the lack of a recognition sequence in this construct, it was not possible to prepare M-ELP through co-expression with NMT. Instead, we devised an alternative semisynthetic method to prepare this construct as shown in FIG. 8. ELP and M-ELP were studied using CD (FIG. 27), FT-IR (FIG. 28), DLS (FIG. 30), and ThT fluoresce assays (FIG. 31 and FIG. 32) to dissect the effect of the self-assembly domain. The combination of this data proves that the PA-lie domain is necessary for the control of self-assembly and macroscale morphogenesis.

FIG. 8. In this procedure, myristic acid (1.0 mg, 4.4 µmol, 4.4 equiv) was dissolved in 1.0 mL DMF in a glass scintillation vial. HCTU (1.8 mg, 4.4 µmol, 4.4 equiv) and DIPEA (1.0 µL, 6.0 µmol, 6.0 equiv) were added to the vial to activate the fatty acid. After 15 min, the ELP (47 mg, 2.8 µmol, 1.0 equiv) was added to the vial and the reaction was stirred overnight. The reaction was quenched by the addition of 9 mL deionized water. The mixture was then transferred to a dialysis bag, and water soluble impurities were dialyzed against 4 L of deionized water. The M-ELP construct was then purified by RP-HPLC and lyophilized (33.1 mg, 70% yield).

Fluorescent Labelling of Proteins

A lysine residue was encoded near the C-terminal of the protein to ensure that the fluorophore conjugation site was distant from the PA-like domain. Labelling genetically encoded lysine was achieved using NHS-activated Alexa Fluor® 488 dye. The M-$B_{1-3}$ELP-GKG construct (25 mg, 1.4 µmol) was dissolved in anhydrous DMF (1 mL), and the labelling dye (~1 mg, 1.6 µmol, 1.1 equiv) was dissolved in anhydrous DMSO (1 mL) before use. The dye and the protein solution were mixed, followed by the addition of DIPEA (3 µL, 18 µmol, 16 equiv). After 12 h, the reaction was quenched by the addition of water (8 mL), and water soluble impurities were subsequently removed by dialysis against 4 L of deionized water. The fluorescently labeled protein was separated from the unreacted dye using RP-HPLC by monitoring the absorbance at 230 nm and 350 nm. The labelling efficiency was determined by dissolving a known amount of labeled protein in water and measuring the absorbance at 494 nm (according to the manufacturer protocol, the $\varepsilon_{494}$ of Alexa Fluor® 488 dye is 71000 $cm^{-1}\,M^{-1}$). Based on this measurement, we determined that the labelling efficiency was 42% for M-$B_1$-ELP-GKG, 37% for M-$B_2$-ELP-GKS, and 32% for M-$B_3$-ELP-GKG. For the encapsulation experiments, the molar ratio of the fluorescently-labeled to unlabeled FAMEs was kept at 25% by adding unlabeled FAME constructs as needed. The N-terminal amine of control ELP was labeled using a similar procedure.

Characterization

SDS-PAGE. FIG. 9.

The purity and molecular weight of the purified proteins was characterized using a 10-20% gradient Tris-glycerol SDS-PAGE gel (Thermo Scientific, CA). The gels were negatively stained by incubation with 0.5 M $CuCl_2$ for 20 min before imaging using a BioRad Universal imager.

Analytical HPLC.

Analytical RP-HPLC was performed on a Shimadzu instrument using a Phenomenex Jupiter® 5 µm C18 300 Å, LC Column 250×4.6 mm, solvent A: $H_2O$+0.1% TFA, solvent B: acetonitrile+0.1% TFA), as shown in TABLE 4.

TABLE 4

| Gradient program used for analytical RP-HPLC | |
|---|---|
| Time (min) | Solvent B (%) |
| 0 | 30 |
| 3 | 30 |
| 30 | 90 |

Constructs were dissolved in deionized water at a concentration of 70 µM. 35 µL of this solution was injected and analyzed using a photo-diode array detector to measure the absorbance at wavelengths between 190 nm and 800 nm. Representative chromatograms (at 230 nm) for each protein is displayed in FIG. 10, FIG. 11, FIG. 12, FIG. 13, FIG. 14, FIG. 15, and FIG. 16. In all the figures, the percentage of acetonitrile (right Y axis, solvent B %) in the eluent is shown with a solid grey line. Small peaks that are visible before 5 min correspond to system peaks arising from the difference between the sample diluent (i.e., deionized water) and the mobile phase.

Trypsin Digestion of Proteins.

Trypsin digestion was conducted according to the manufacturer's protocol. Briefly, 10 μL of 50 mM ammonium bicarbonate buffer (pH=7.8) was added to an Eppendorf tube. 9 μL of each construct was added to this reaction tube for a final concentration of 100 μM. To this mixture, 1 μL trypsin (reconstituted as 1 μg/μL trypsin in 50 mM acetic acid) was added and the reaction mixture was incubated at 37° C. After 2 h, the N-terminal fragment peptide was analyzed by MALDI-TOF-MS.

MALDI-TOF-MS.

Samples for MALDI-TOF-MS analysis were prepared by mixing 10 μL of each HPLC fraction with 10 μL of the sinapinic acid (SA) matrix (a saturated solution was prepared by suspending 10 mg of SA in 700 μL $H_2O$+0.1% TFA and 300 μL acetonitrile+0.1% TFA). Afterward, 3 μL of this mixture was deposited onto a sample plate and dried in air at room temperature. All spectra with an acceptable signal-to-noise (S/N) ratio (>10) were calibrated against an aldolase standard (Sigma Aldrich, $M_w$=39,211.28 Da). The following instrument parameters were optimized empirically to maximize the S/N ratio: accelerating voltage=25 kv; grid voltage=90%; guide wire=0.15%; extraction delay time=750 ns; acquisition range: 10,000-60,000 Da; low mass gate=5000 Da; number of laser shots=75/spectrum; laser intensity=3000; bin size=4 ns.

We used α-cyano-4-hydroxycinnamic acid as a matrix for analysis of the N-terminal peptide fragments and canonical peptide amphiphiles. All spectra were calibrated against adrenocorticotropic hormone fragment 18-39 (Sigma Aldrich, $M_w$=2,464.1989). The following instrument parameters were optimized empirically to maximize the S/N ratio: accelerating voltage=20 kv; grid voltage=73.5%; guide wire=0.005%; extraction delay time=90 ns; acquisition range: 500-400 Da; low mass gate=500 Da; number of laser shots=40/spectrum; laser intensity=2000; bin size=0.5 ns. Results are shown in TABLE 5 and FIG. 17, FIG. 18, FIG. 19, FIG. 20, FIG. 21, FIG. 22, and FIG. 23.

TABLE 5

Summary of MALDI-TOF-MS experiments

| | Construct | $M_W$ (Da, calculated) | m/z [M + H]$^+$ (observed) |
|---|---|---|---|
| Proteins | ELP | 16617.7 | 16616.2 |
| | M-ELP | 16828.0 | 16822.9 |
| | $B_1$-ELP | 17519.6 | 17476.3 |
| | M-$B_1$-ELP | 17729.9 | 17702.6 |
| | $B_2$-ELP | 17924.9 | 17948.1 |
| | M-$B_2$-ELP | 18135.3 | 18147.2 |
| | $B_3$-ELP | 17633.7 | 17674.4 |
| | M-$B_3$-ELP | 17844.1 | 17849.0 |
| Peptides | M-$B_1$ | 727.4 | 728.7 |
| | M-$B_2$ | 931.6 | 931.6 |
| | M-$B_3$ | 841.6 | 842.6 |

UV-Visible Spectroscopy

We investigated the temperature-triggered phase-transition of each construct by recording the optical density of the protein solution at 350 nm as a function of temperature, from 15° C. to 50° C. (ramping at a rate of 1° C./min) on a temperature controlled UV-Vis spectrophotometer (Cary 300 Bio, Varian Instruments, Palo Alto, Calif.). The transition temperature ($T_t$) is defined as the inflection point of the turbidity profile. Turbidity profiles for each sample were measured in PBS at three different solution concentrations between 25-100 μM. See FIG. 24, FIG. 25, FIG. 26, FIG. 27, FIG. 28, FIG. 29, and FIG. 30.

Dynamic Light Scattering

Dynamic light scattering (DLS) studies were conducted to investigate the self-assembly of various constructs in solution. Prior to analysis, samples were freshly prepared in PBS to a concentration of 50 μM and filtered through a 0.22 μm polyvinylidene fluoride membrane (Durapore) directly into the quartz cell. DLS experiments were conducted in a temperature-controlled DynaPro Microsampler (Wyatt Technologies). Measurements were obtained over a temperature range of 4° C. to 10° C. using 0.5° C. steps and 18 acquisitions of 5 s each for every temperature point. Autocorrelation intensities across the range of temperatures were averaged and plotted as a function of decay time with error bars representing the standard deviation of measurements (shown as a shaded band around the line). See FIG. 31.

We note that it is not possible to extract reliable size data (Rh) from the DLS autocorrelation function of myristoylated constructs, as most DLS models are developed by assuming a spherical object as the source of scattering. The electron microscopy (FIG. 5) shows that all the constructs have a structure that significantly deviates from a spherical state, thus undermining the validity of the underlying assumptions in the DLS analysis models.

Circular Dichroism

We probed the secondary structure of all the constructs using circular dichroism (CD) to study whether the incorporation of the short recognition sequences or myristoylation significantly altered the secondary structure of the constructs. CD spectroscopy was performed using an Aviv Model 202 instrument and a 1 mm quartz cell (Hellma). Each sample was freshly prepared by dissolving the lyophilized product in a salt-free phosphate buffer solution (pH 7.2, Sigma Aldrich) to a concentration of 10 μM. This solution was stored on ice prior to analysis. The CD spectra were obtained at 15° C. from 350 nm to 180 nm in 1 nm steps and 0.5 s averaging time. The CD spectra were corrected for the buffer signal at 15° C. Each experiment was repeated in triplicate, and the average of the three measurements was represented as a mean residue ellipticity ([θ], deg cm$^2$ dmol$^{-1}$). Data featuring dynode voltages above 500 V was not considered for analysis. The CD data for different constructs were then normalized at 220 nm for comparison. See FIG. 32.

We investigated the effect of myristoylation on the secondary structure of the ELPs using CD. In accordance with the turbidity profile, non-myristoylated ELPs exhibited CD signatures characteristic of canonical ELPs (FIG. 32), featuring a primary negative peak at 195 nm and a secondary negative peak at 220 nm (dashed lines, FIG. 3B). The primary negative peak is commonly attributed to random coils, while the secondary peak is assigned to transient β-turn and β-spiral structures, resulting from the periodic placement of Pro-Gly units along the ELP backbone (Nuhn, et al. *Biomacromolecules* 2008, 9, 2755). Myristoylated ELPs (solid line, FIG. 3B) exhibited a similar CD signature; however, the intensity of the negative peak at 195 nm was slightly reduced for M-$B_3$-ELP (solid red line, FIG. 3B bottom panel).

Due to the limited solubility of synthetic PAs in water and PBS, it was not possible to compare their CD spectra with ELPs as a control. However, based on previous reports of PAs, it is likely that the first 4-6 amino acids in the recognition sequence adopts a β-sheet conformation after the conjugation of the myristoyl group, characterized by two peaks at 195 nm and 220 nm (Paramonov, et al. *J. Am. Chem. Soc.* 2006, 128, 7291). The positive peak at 195 nm, indicative of β-sheet structures, overlaps with the much stronger negative peak from the ELPs. Due to similarities between the CD signature of ELPs and FAMEs, we can conclude that myristoylation did not significantly increase the beta-turn population, nor did it result in a global change in the conformational preference of the ELPs. We also point out that the CD signature of FAMEs (particularly M-B$_3$-ELP) may be less reliable due to the self-assembly and aggregation of these constructs in solution (Kelly, et al. *Biochim. Biophys. Acta—Proteins Proteomics* 2005, 1751, 119).

FT-IR

We collected Fourier transform infrared spectroscopy (FT-IR) spectra on a Nicolet 8700 FT-IR spectrometer that was equipped with an attenuated total reflectance attachment. A Ge crystal was used for collecting spectra of the proteins and peptides. In bench mode operation, the lyophilized powder was clamped tightly over the Ge crystal, and the spectra were collected from 4000 to 400 cm$^{-1}$ with 1 cm$^{-1}$ resolution. There were 128 scans accumulated per spectrum.

Figure 3A:
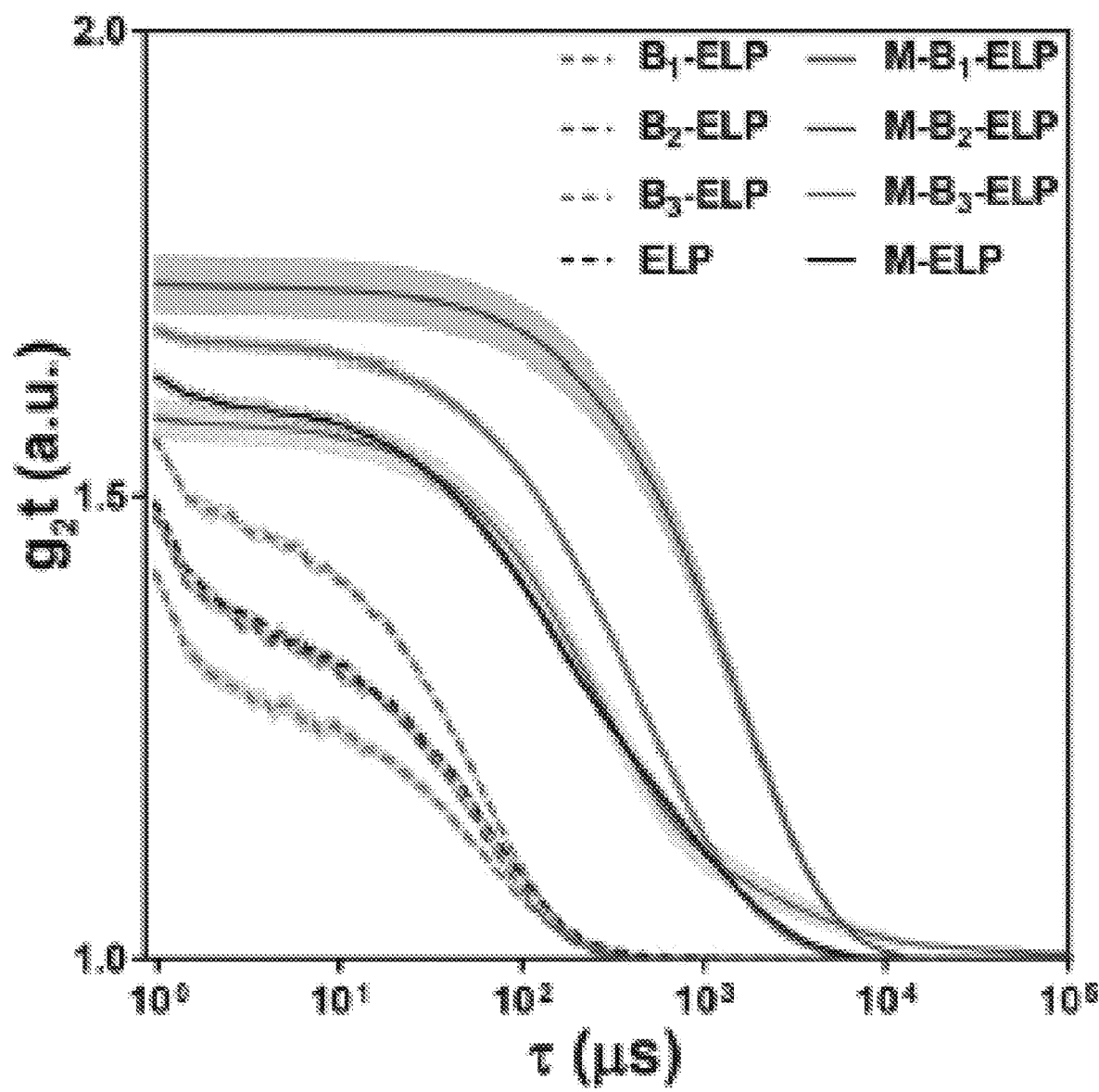
FIG. 3A-F. Spectroscopic and light-scattering characterization of the effect of fatty acid modification on the structure and the self-assembly of the FAMEs.
Figure 3B:
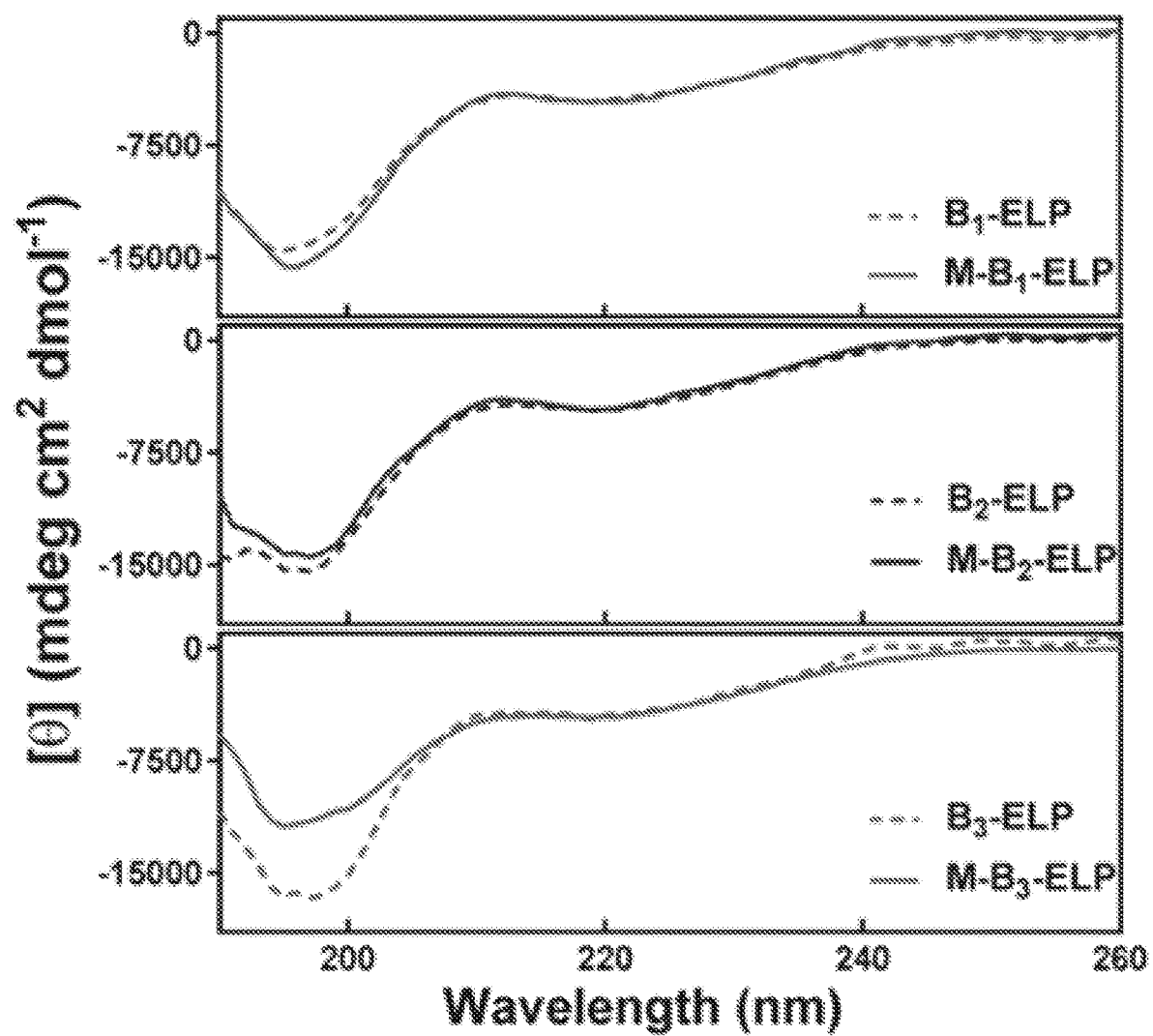
Figure 3C:
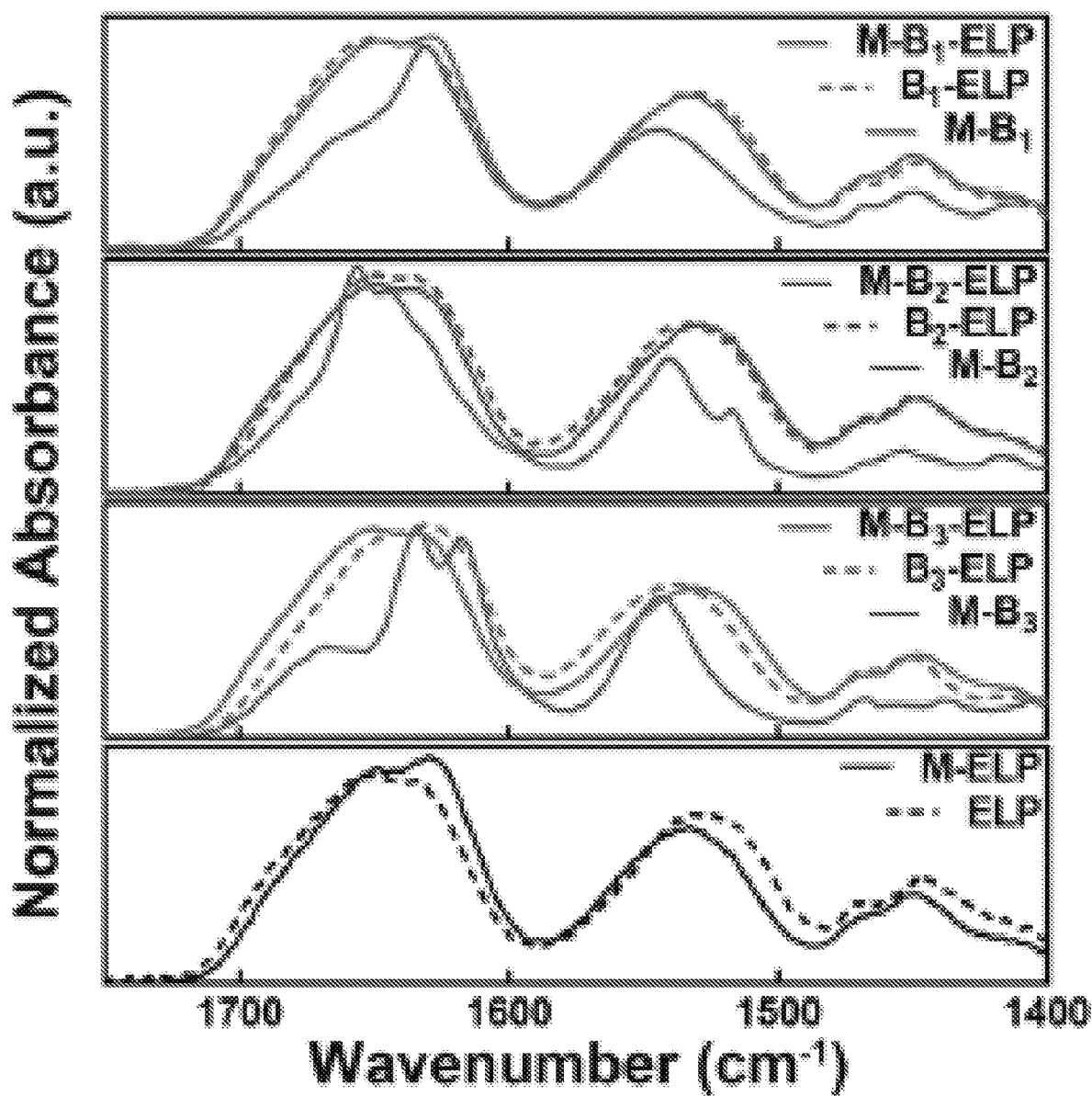
Figure 33:
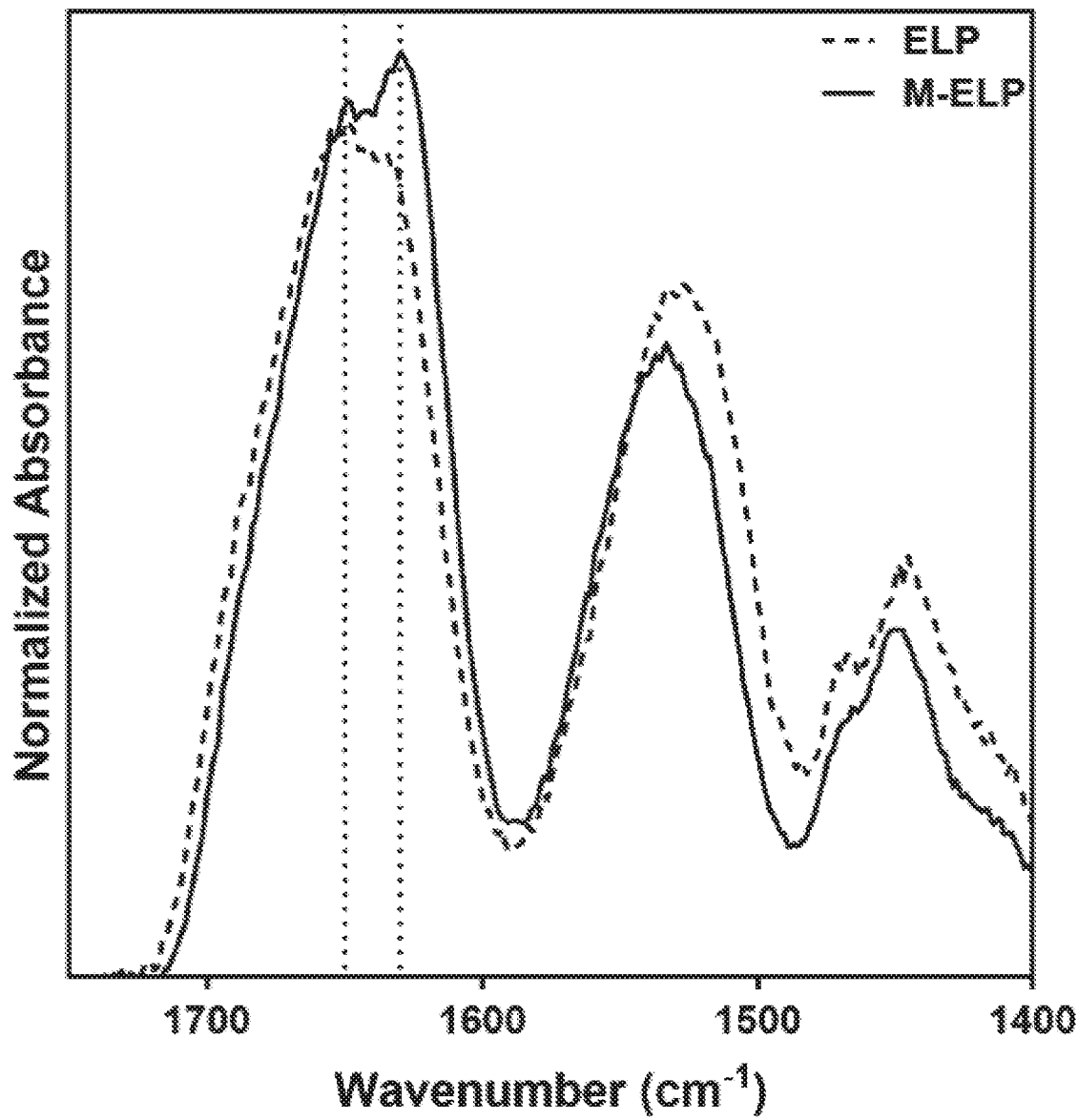
FIG. 33. FT-IR spectra of ELP (dashed black line) and M-ELP (solid black line). The vertical lines at 1630 cm$^{-1}$ and 1650 cm$^{-1}$ are drawn as a guide for the location of the major peaks of the ELP.

We utilized FT-IR spectroscopy to probe the effects of myristoylation on the conformation and hydrogen bonding of the amide carbonyls (FIG. 3B). Consistent with our interpretation of the CD spectra, both non-myristoylated and myristoylated ELPs exhibited similar FT-IR spectra. In both cases, the amide I bond displayed a characteristic low-frequency component around 1615 cm$^{-1}$ and a high frequency component near 1650 cm$^{-1}$, consistent with previous reports for ELPs (FIG. 33). However, the control PA spectra (FIG. 3B, solid grey line in each panel) exhibited a much more complex absorption pattern consistent with the presence of β-sheet structures in the lyophilized powder while demonstrating that the internal dynamics of each PA is dictated by the sequences preceding the hydrophobic tail (FIG. 34)(Jiang, et al. *Soft Matter* 2007, 3, 454; Cui, et al. *J. Am. Chem. Soc.* 2014, 136, 12461).

Variable Temperature ATR-IR

Each sample was prepared to the final concentration of 100 μM solution by dissolving lyophilized powder in cold (~4° C.) Dulbecco's Phosphate Buffered Saline (PBS, Thermo Fisher Scientific). After the addition of cold PBS, the solution was immediately mixed by vortex and left in a thermomixer (Eppendorf) at 4° C. while shaking for 30 min. From this point onward, the prepared solutions were kept in an ice bath between the ATR-IR measurements.

Experiment: ATR-IR measurements samples were performed with FT-IR Bruker TENSOR II spectroscopy (Bruker, Germany) with a diamond crystal. The samples were loaded into a metallic sample holder with an inner volume of ~0.5 mL, which was pressed on the top of the ATR crystal. A refrigerated/heated circulator (Julabo, Seelbach, Germany) combined with a custom-built copper tube was used to heat or cool the metallic sample holder by fitting the copper tube around the metallic holder. As the solution was in contact with the metallic holder, this device cooled or heated the sample solution on the ATR crystal. The metallic holder design allowed us to measure the temperature of the solution during measurement with a thermocouple and digital multimeter (Voltcraft VC 140). Before each ATR measurement of protein samples, a solution of PBS was used to verify the temperature settings on the circulator. After verification, the proper temperature was set in the circulator, the neat PBS was taken out from the sample holder, and the container was filled with the measured sample—while still monitoring the temperature. ATR-IR spectra were collected at 10° C., 30° C., and 50° C. from 400-4000 cm$^{-1}$ with an accumulation of 128 scans and using a spectral resolution of 4 cm$^{-1}$.

Data Processing: At least three different ATR-IR spectra from each sample were collected at each temperature. Data analysis of the ATR-IR spectra was done by using IgorPro (Wavemetrics, Lake Oswego, Oreg.). First, the baseline of spectra was corrected by subtracting the average absorbance value which was calculated from the absorbance values between 3877 cm$^{-1}$ and 3997 cm$^{-1}$ from each ATR-IR spectrum. All spectra of each sample at a certain temperature were averaged and the ATR-IR spectra of PBS at the same temperature was subtracted to produce difference spectra. Exemplary peaks assignments are shown in Table 6.

Figure 3D:
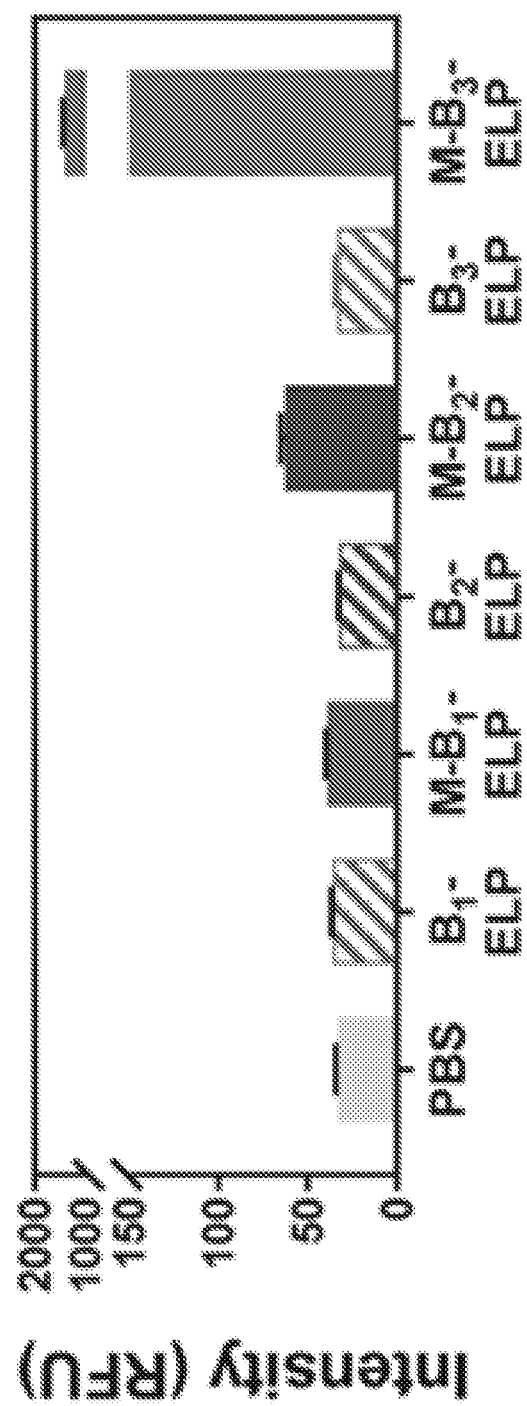
Figure 3E:
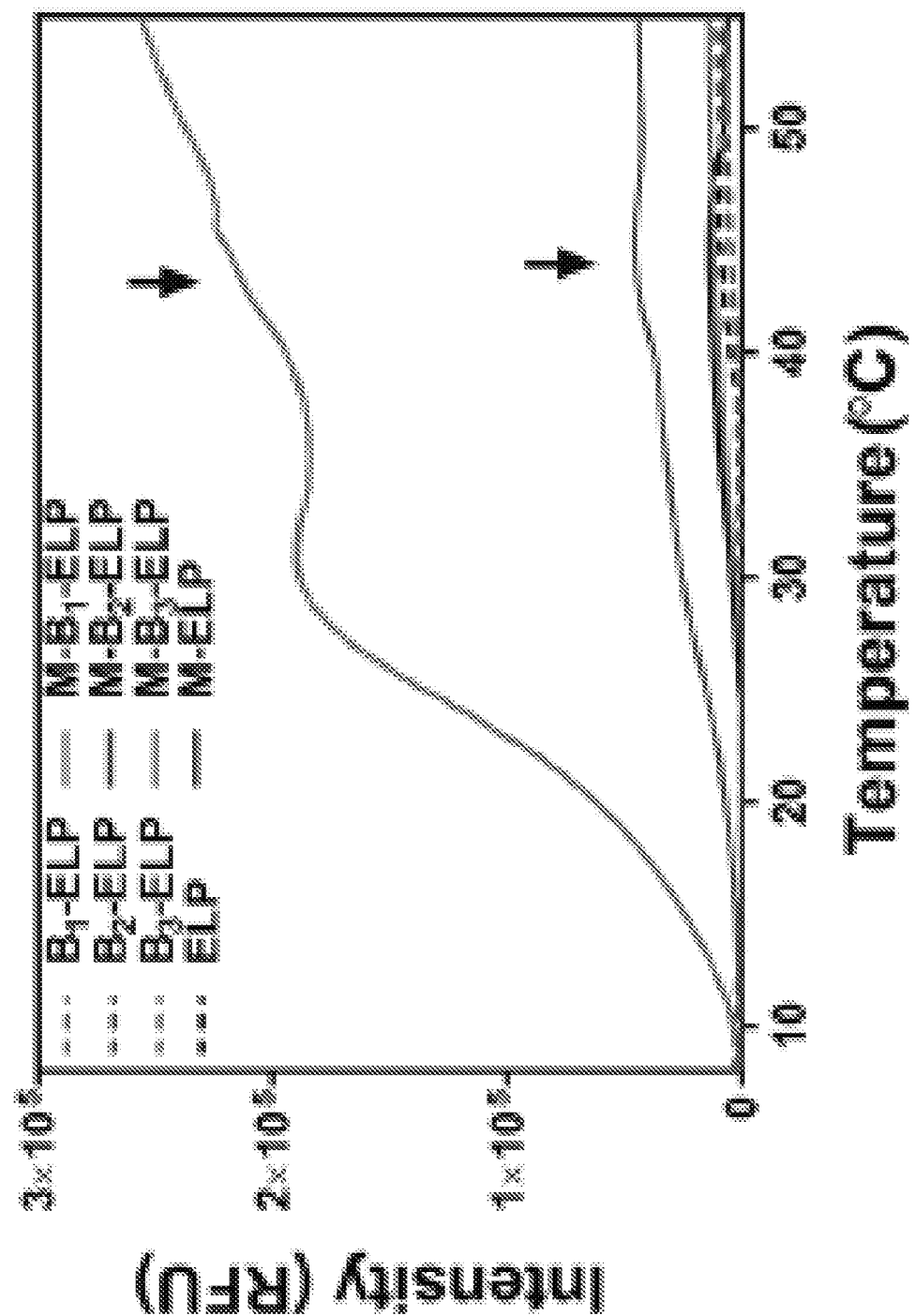
Figure 3F:
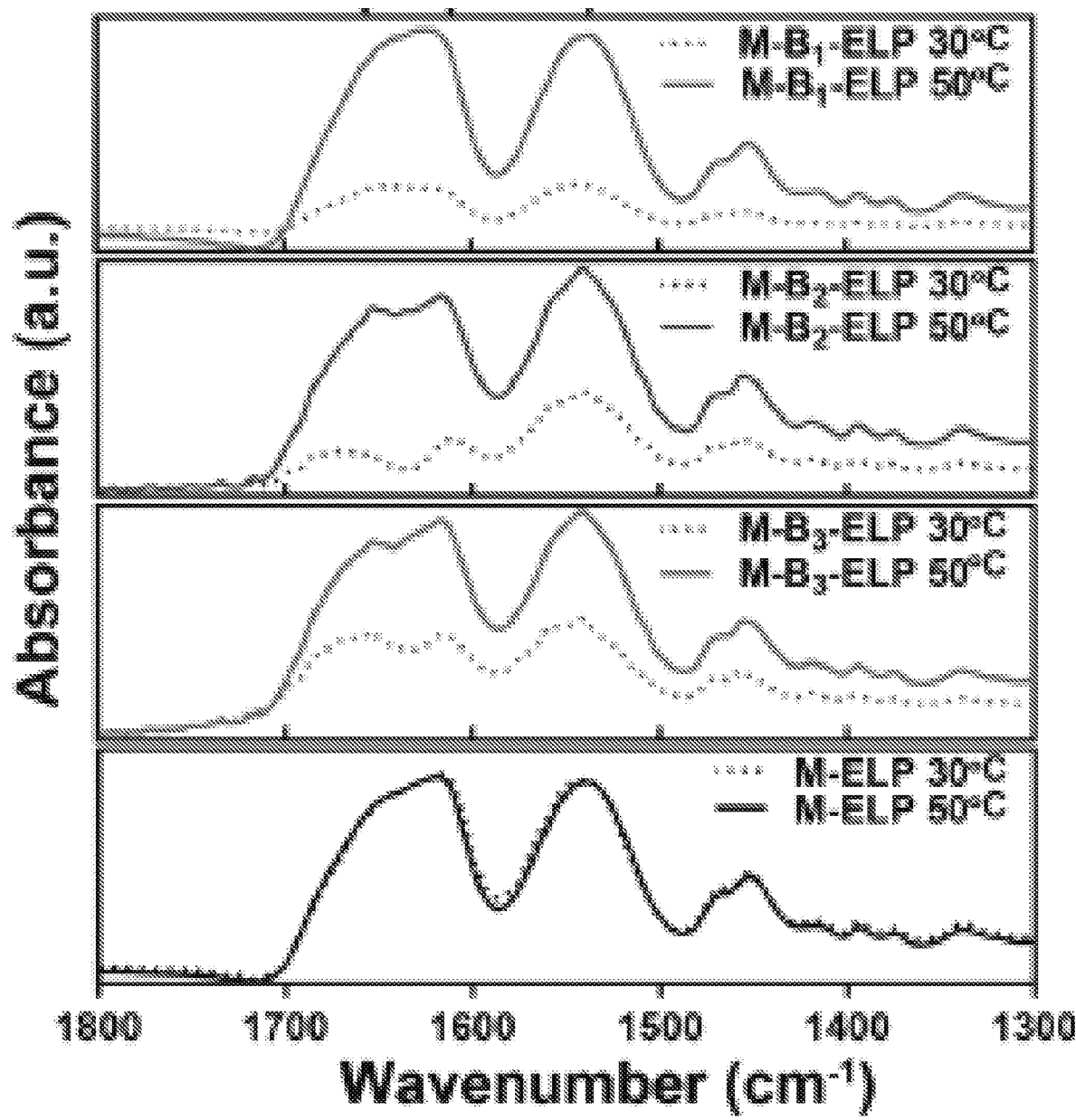

Little, if any, signal was seen at 10° C. for any of the proteins at this concentration. Notably, M-ELP showed an almost identical spectrum at 30° C. and 50° C. (FIG. 3F). However, the raw signal intensity for M-ELP was lower than M-B$_1$-ELP at 50° C. This suggests that M-ELP coacervates are not significantly dehydrated at higher temperatures. This observation is consistent with the relative constant size of coacervates observed in the wide-field microscopy at 30° C. and 50° C.

TABLE 6

ATR-IR peak assignments

| peak assignment | wavenumber |
| --- | --- |
| CH$_3$ asymmetric | 1450 ± 20 cm$^{-1}$ |
| Amide II band | 1500 cm$^{-1}$-1600 cm$^{-1}$ |
|  | (Max absorbance at 1540 cm$^{-1}$) |
| β-spiral signature in Amide I band | 1615 cm$^{-1}$ and 1656 cm$^{-1}$ |

Thioflavin T (ThT) Assay

Single Time-Point Static ThT Assay.

The static ThT assay was conducted on a SpectraMax M series microplate reader. ThT stock solution (50×) was freshly prepared by dissolving 8 mg of ThT in 10 mL of PBS, which was then kept in the dark. This solution was furthered diluted by a factor of 5 to obtain the working stock solution (10×). A freshly prepared sample of each construct (144 μL) was mixed with the ThT (16 μL). Each sample contained 100 μM of protein in addition to 50 μM of ThT and was kept on ice prior to the experiment. The mixture (130 μL) was then transferred to a black Corning® 96 well half area plate with a clear flat bottom and was incubated for 5 minutes at 20° C. The ThT fluoresce (excitation wavelength=440 nm, emission wavelength=482 nm) for each sample was recorded. See FIG. 35.

Dynamic ThT Assay.

Figure 36:
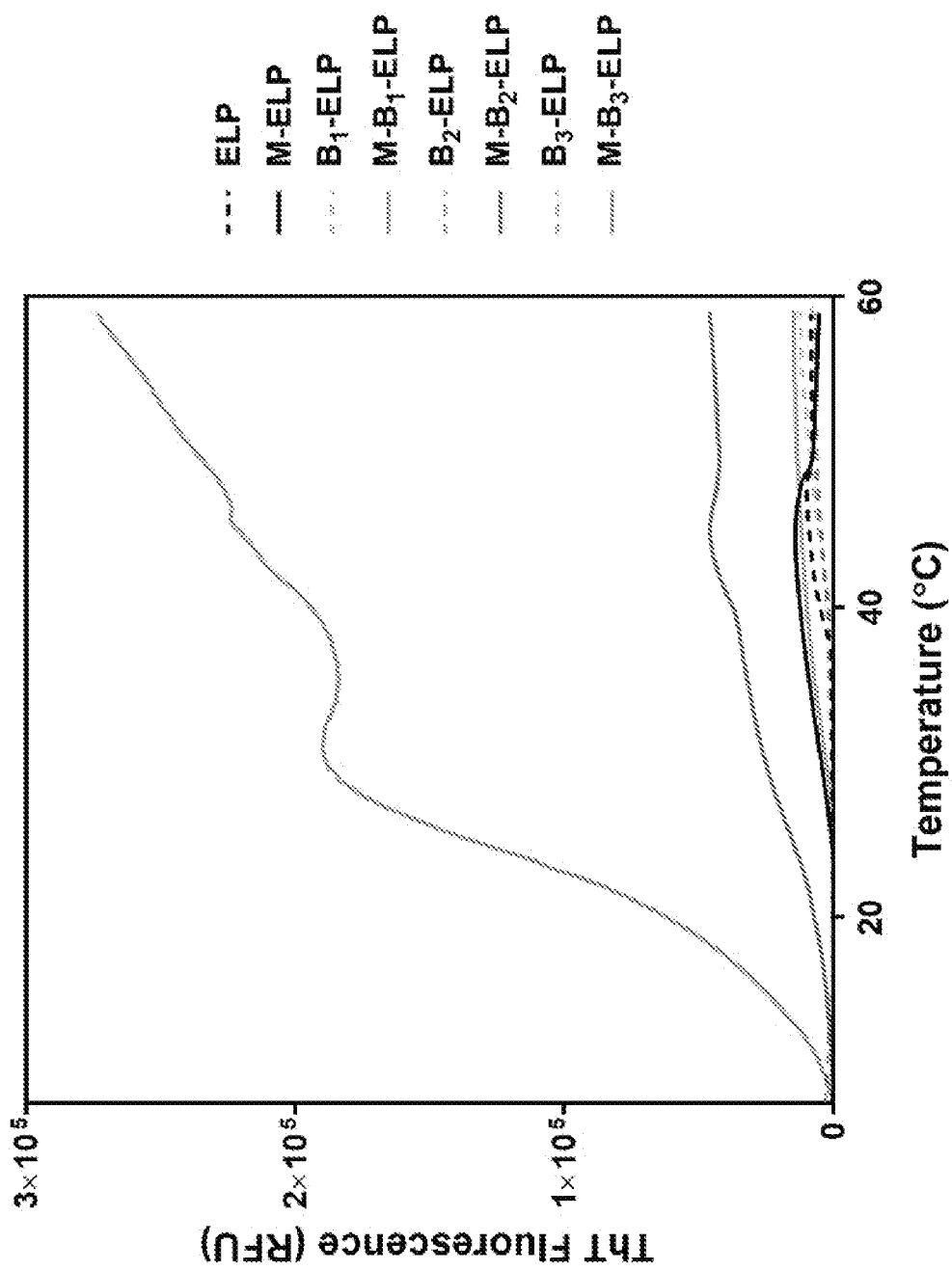
FIG. 36. Dynamic ThT assay to probe the temperature dependence of each construct interaction with ThT including ELP (black dashed) and M-ELP (black solid line). Other constructs are discussed in the paper and are only shown here for comparison. The M-ELP interaction with ThT did not significantly increase at higher temperatures.

We conducted a ThT assay on a StepOnePlus Real-Time PCR System by adapting a procedure commonly used for protein thermal shift assays. ThT stock solution (50×) was freshly prepared by dissolving 8 mg of ThT in 10 mL of PBS, which was then kept in the dark. This solution was furthered diluted by a factor of 5 to obtain the working stock solution (10×). A freshly prepared sample of each construct (18 μL) was mixed with the ThT (2 μL). Each sample contained 100 μM of protein in addition to 50 μM of ThT and was kept on ice prior to the experiment. We used the FAM™ filter in the instrument for measuring the ThT signal. Control experiments without protein and/or ThT were conducted in tandem to ensure that the fluorescent signal was due to the interaction of the proteins with the ThT. Samples were incubated at 4° C. for 10 min before the start of the experiment. Fluorescence was measured as the temperature was increased to 60° C. at a rate of 1% according to the instrument setting (i.e., approximately 1° C./min). A baseline correction was conducted using the TN020 procedure package in Igor Pro 6.37 software. See FIG. 36.

We suggest that the differences in ThT fluorescence between M-ELP and ELP in static assay can be explained by considering the peptide sequences after myristoyl group. The M-ELP sequence consists of Myristoyl-GVGVP and valine residues have a relatively high β-sheet propensity. It is likely that this short peptide sequence adopts an amyloid cross-section and thus interacts strongly with the ThT dye at low temperature.

However, presence of proline as the fifth residue in the M-ELP sequence (Myr-GVGVP) is likely to break the formation of secondary content after this position. Thus, despite having two residues with high β-sheet propensity, an extended β-sheet cannot be formed with this sequence. This hypothesis can explain the lower interaction of M-ELP with ThT at higher temperature.

We are also mindful that ThT fluorescence depends on parameters such as the solvent viscosity (which is expected to change at least in the ELP coacervates). Considering these factors, we suggest that the interaction of FAMEs with ThT can be enhanced through any of the following pathways at higher temperatures. 1) It is possible that a segment of the ELP domain, close to the PA-domain, is restricted to a conformation with favorable interactions with the ThT dye. Our variable temperature ATR-IR experiments provides a support for this hypothesis as the broad amide peaks in the ELP and M-ELP are replaced with more well-defined sharper peaks. 2) Above $T_t$, the core of the FAME aggregates (PA-domain) can grow as the aggregates are no longer stabilized by the dehydrated ELP corona. This extended core can interact with more ThT molecules. In particular, this pathway is consistent with microscopy results obtained for M-$B_2$-ELP. 3) The increased viscosity of the ELP coacervates can also increase the ThT fluorescence above $T_t$.

Our current mechanism does not explain the small decrease in ThT fluorescent signals for ELP and M-ELP at high temperatures (with an inflection point ~50° C.). It may be that presence of charged amino acid (in this case, Arg which is found in all recognition sequences but not in ELP or M-ELP) can also affect the kinetics of coacervate coalescence.

Spinning Disk Confocal Laser Microscopy (SDCLM)

SDCLM was conducted on an Olympus SD-OSR System based on a IX83 inverted microscope equipped with Yokogowa W1 Spinning disk confocal with 50 nm disk and Tokai Hit WSKM environmental control module. The spatial distribution of the fluorophore-labeled FAMEs was characterized via fluorescence microscopy using a 100X Si oil objective with correction collar and the appropriate filter set (excitation BP 470/40, emission BP 525/50). Fluorescence intensities of the acquired images were analyzed using Metamorph acquisition software.

SDCLM has the sensitivity and the resolution of traditional confocal microscopy but offers the advantage of faster data acquisition over a larger area of the sample. We leveraged these capabilities to visualize the fine details of the self-assembly process. SDCLM was conducted by depositing 20 µL of the fluorescently labelled protein samples below $T_t$ onto a glass bottom MatTek dish (Ashland, Mass.) and transferring the slide to microscope stage and heating it to 30° C. We monitored the assembly by taking consecutive images from a focal plane above the cover slips to avoid surface induced artifacts. The temperature was then raised to 50° C. to monitor the final stage of the self-assembly. Following the stabilization of the network, we also used the super resolution mode of the microscope and recorded multiple images at different focal planes and collapsed these z-stack images using ImageJ to visualize finer details of the final entangled network.

Encapsulation and Imaging

We also visualized the phase transition of FAMEs and ELPs in monodisperse, well-defined droplets at micron-level resolution during the second and third stages of self-assembly. We chose this system because it prevents the coalescence of aggregates beyond the well-defined boundaries of each micron-scale droplet, which is ideal for studying the morphogenesis of structures at the micro-scale. To visualize the self-assembled structures, we genetically encoded a Lys residue at the C-terminus of the M-$B_{1-3}$-ELP constructs to enable labeling with Alexa Fluor® 488 dye. The turbidity profile of these labeled FAMEs was identical to their parent sequences, indicating that the addition of a Lys and a fluorophore at a position distant from the PA domain does not perturb the self-assembly process. We then used a microfluidic device to form water-in-oil emulsions containing each FAME at 100 µM. The structural evolution of each construct was then visualized using wide-field fluorescence microscopy while increasing the temperature from 10° C. to 50° C. at a rate of 1° C./min.

Droplet Formation.

Microfluidic water-in-oil droplet generators were purchased from Dolomite Microfluidics. To create aqueous droplets, we injected two liquid phases—a dispersed aqueous phase of the FAME sample, and an organic continuous phase comprised of TEGOSOFT® DEC/ABIL® EM 90/mineral oil (75/5/20 v/v %)—into the drop generators at constant flow rates using precision syringe pumps. We tuned the flow rates of the dispersed and continuous fluids to ensure droplet formation in the dripping regime and used a constant flow rate of 250 µL·hr$^{-1}$ for the organic continuous phase and 75-100 µL·hr$^{-1}$ for the aqueous, dispersed phase. We monitored the production of droplets within the microfluidic device using a 5× objective on an inverted microscope (Leica) equipped with a digital microscopy camera (Lumenera Infinity 3-1 CCD).

The organic phase contains commercially available surfactants to stabilize aqueous droplets. It was noticed that this mixture does not affect the cloud point ($T_t$) of ELPs. However, we performed the following control experiment to ensure that the surfactants do not perturb the self-assembly of FAMEs. We have mixed PBS (1 mL) with the organic phase (containing the same three components described above) by vigorous agitation on a vortex. After waiting for 1 hour, the cloudy mixture separated into three layers, oil phase at top, narrow emulsion layer at the middle, and a PBS phase at the bottom. We carefully removed the top layer and dissolved the M-$B_2$-ELP in this mixture to the final concentration of 50 µM. As a control, M-$B_2$-ELP was dissolved in PBS to the similar concentration. The phase behavior and self-assembly of both samples were analyzed by a turbidimetry assay. Both samples exhibited almost identical $T_t$, $T_c$, and overall macroscopic morphology.

Visualization of the FAME Constructs' Thermally Triggered Phase-Transition.

The FAME emulsion samples were collected on a glass microscope slide and heated using a precision Peltier heating and cooling stage (Linkam LTS120) equipped with a Linkam PE95 digital temperature control unit. The spatial distribution of the fluorophore-labeled FAMEs was characterized via fluorescence microscopy using an upright Zeiss Axio Imager A2 microscope with a 20× objective and the appropriate filter set (excitation BP 470/40, emission BP 525/50). Fluorescence intensities of the acquired images were analyzed using Zeiss ZEN imaging software. M-B$_2$-ELP and M-B$_3$-ELP fluorophores were artificially colored blue and red in the images in FIG. 4 for distinction and clarity. See FIG. 37.

Cryo-TEM

Figure 38:
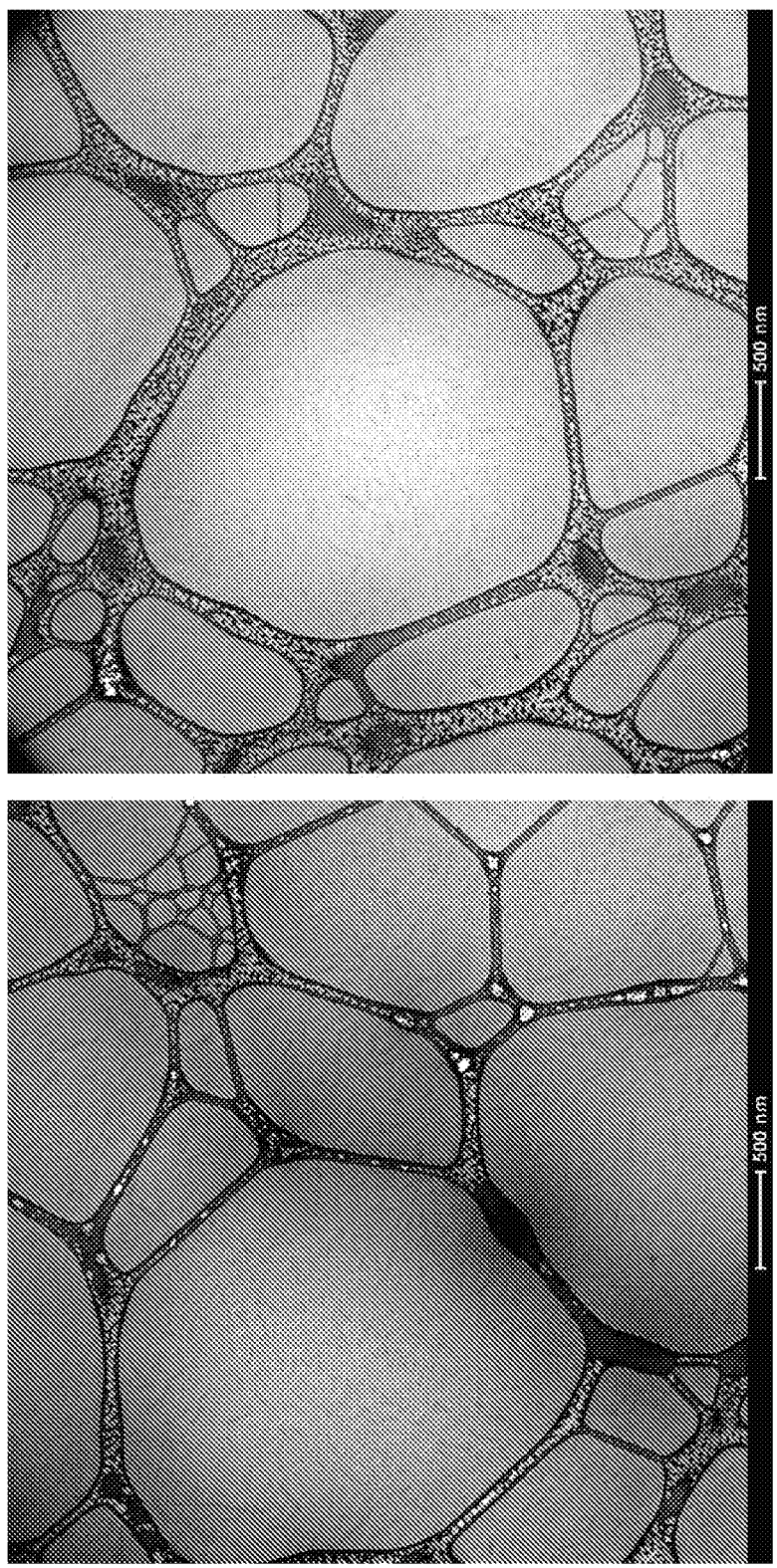
FIG. 38. Cryo-TEM images of self-assembled M-$B_1$-ELP.

Cryo-transmission electron microscopy (TEM) experiments were performed at Duke University's Shared Materials Instrumentation Facility. Lacey holey carbon grids (Ted Pella, Redding, Calif.) were glow discharged in a PELCO EasiGlow Cleaning System (Ted Pella, Redding, Calif.). A 3 μL drop of the sample (100 μM of each construct) at 25° C. or 30° C. (above the T$_t$ for FAME constructs) was deposited onto the grid, blotted for 3 s with an offset of −3 mm, and vitrified in liquid ethane using the Vitrobot Mark III (FEI, Eindhoven, Netherlands). The sample chamber was maintained at 100% relative humidity to prevent sample evaporation. Grids were transferred to a Gatan 626 cryoholder (Gatan, Pleasanton, Calif.) and imaged with an FEI Tecnai G$^2$ Twin TEM (FEI, Eindhoven, Netherlands), which was operated at 80 keV (Mcdaniel, et al. *Nano Left.* 2014, 14, 6590). Control PA (M-B$_{1-3}$) were resuspended in 20% aqueous acetic acid solution (v/v %) due to their low solubility in PBS or water. See FIG. 38, FIG. 39, and FIG. 40.

Scanning Force Microscopy

We prepared a 100 μM solution of FAMEs in cold PBS buffer. Then 1.5 μl of the solution was put in an Eppendorf tube and heated to 30° C. for typically 1-2 min in a water bath. Then the entire solution was pipetted onto a freshly cleaved mica substrate and then carefully dried in an air stream. Subsequently the surface was rinsed with pure water provided by a Sartorius Arium 611 VF purification system (Milli-Q, specific resistivity of 18.2 MΩ·cm). Then the sample was dried again in an air stream and installed on the xy-stage of a Dimension ICON SFM instrument (Bruker, Karlsruhe, Germany). For the SFM investigation we used Olympus AC240TS-R3 cantilevers having a nominal spring constant of 2 N/m. The SFM was operated in the peak force tapping mode at 1 kHz. For all studies, we recorded the surface topography, the adhesion and the DMT modulus map simultaneously.

Cryo-Scanning Electron Microscopy (SEM)

Cryo-SEM analyses were conducted using a JEOL JSM-7600 FE SEM (JEOL USA, Peabody, Mass.) outfitted with an Alto-2500 preparation chamber Gatan, Warrendale, Pa.). The macroscopic object formed by M-B$_2$-ELP was carefully placed on the SEM stage using a tweezer and was plunge frozen in liquid nitrogen slush, then transferred under vacuum to the preparation chamber and cryo-fractured. The fractured sample was etched for 5 min at −95° C. and 4×10$^{-6}$ mbar to reveal the underlying microstructure. Subsequently, the samples were allowed to cool down to −120° C. An in situ cold magnetron coater was used to make a 5 nm thick Au/Pd coating on the etched samples. The SEM images were then taken using 15 keV accelerating voltage energy and a working distance of 5 mm under cryo-temperature. The observed microstructure is consistent with the morphology observed by SEM following fixation and dehydration. M-B$_3$-ELP structure did not survive the direct freezing and cryo-fracturing and were instead analyzed by regular SEM as described below.

SEM

SEM was performed using a FEI XL30 SEM-FEG instrument with an accelerating voltage of 5 kv. We used the FAMEs with a genetically encoded lysine at the C-terminal to include a chemical handle for fixation with gluteraldehyde. The assembly of M-B$_2$-ELP-GKG and M-B$_3$-ELP-GKG was triggered by heating the 750 μL of the solution of each one of the protein at the concentration of 100 μM in a UV cuvette. The solution temperature was increased at the rate of 1° C./min from 15° C. to 50° C. while monitoring the turbidity of the solution by measuring the absorbance at 350 nm. Once the temperature reached 50° C., which coincided with the sudden decrease in turbidity, the cuvettes were removed from the instrument and the solution and the white solid structure was transferred by inversion to a 20-mL scintillation vial containing 750 μL of 8% glutaraldehyde aqueous solution (Electron Microscopy Sciences, Hatfield, Pa.) to achieve final glutaraldehyde concentration of 4%). After fixing the structures at room temperature for 4 hours, the structures were washed 2× with PBS before being dehydrated using increasing concentration of ethanol (30, 50, 70, 90, and 100). We prepared two replicas of each sample and dried them either using a critical point drier (CPD, Ladd Research Industries, Williston, Vt.) or washed twice with hexamethyldisilazane (HMDS, Electron Microscopy Sciences). The method of drying did not seem to affect the overall morphology of the fibers for M-B$_2$-ELP-GKG. M-B$_3$-ELP-GKG did not survive CPD treatment and the SEM images were taken from the HDMS dried sample. Each sample was then fixed on the SEM stage with carbon tape and sputter coated with gold before imagining.

Aggregation above T$_c$

For M-B$_2$-ELP, the onset of T$_c$ (defined as the critical temperature corresponding to sudden decrease in the turbidity) depends on the nominal concentration of the protein in solution. For example, at 100 μM, T$_c$ is approximately 45° C.; at 50 μM, T$_c$ is approximately 50° C. We do not observe T$_c$ in solution containing 25 μM below 50° C. (The upper limit in our experiments). In the case of M-B$_3$-ELP, T$_c$ does not show the same dependence on the initial concentration (i.e. at all concentrations T$_c$ appears to be ~50° C.).

We hypothesize that ELP chains are responsible for the stabilization of aggregates during stage 1 and to some extent in stage 2. The last stage of self-assembly manifested at higher temperatures (T>T$_c$), where the repulsion between the ELP coronas is reduced due to further dehydration, which results in a decrease in the core-core (PA-domain) distances inside the coacervates. At some point, it is possible that the cores are connected (non-covalently cross-linked) through a dynamic rearrangement (e.g., the formation of bundle fibers in M-Br ELP). If the cores are held together by very strong forces, as appears to be the case in M-B$_3$-ELP, this dynamic rearrangement may not occur in the window of opportunity before non-specific aggregation of the ELP chains, resulting in the formation of ill-defined aggregates.

Dynamic of core-core supramolecular cross-linking can depend on the strength of interactions holding these cores together, and the concentration of self-assembly intermediates. In the case of M-B$_2$-ELP with weaker core interaction (lower propensity to form β-sheets), increasing the concentration of aggregates in solution may be expected to decrease T$_c$.

Additionally, increasing the size of the ELP length (e.g., protective corona) may increase T$_c$. We have conducted this simple experiment, using M-B$_2$-ELP$_{20}$ and M-B$_2$-ELP$_{60}$ (subscript denotes the number of pentapeptide repeats). T$_c$ for M-B$_2$-ELP$_{20}$ at 100 μM is lowered to ~40° C. and no critical aggregation is observed for M-B$_2$ELP$_{60}$ at the same concentration up to 50° C. M-B$_2$-ELP$_{20}$ aggregates remained stable below T$_t$ while M-B$_2$-ELP$_{60}$ solution turned clear below T$_t$.

Statistics

Characterization techniques were used to collect data with technical replicates. The error bars (shown as shaded band) in FIG. 3A represent mean±standard error of the mean, n=12. The error bars in FIG. 3D represent mean±standard deviation, n=3 for 3d. The CD signal is depicted as the average of three measurements. Structural properties of the constructs from cryo-TEM images were quantified using ImageJ. Real value measurements were made by setting the size with the scale bar. A representative image was selected for each sample and 25 measurements were made to calculate width and, when relevant, length. Values are reported as the mean and standard error of the mean.

Example 2

As a proof-of-concept to demonstrate the feasibility of creating a genetically encoded biohybrid material via PTM, we chose to create a recombinant lipid-modified polypeptide that we call Fatty Acid-Modified Elastin-like polypeptide (FAME). FAME includes three components. The first component is myristic acid (C14:0), chosen because it can be genetically incorporated at the N-terminus of proteins in a single reaction catalyzed by the enzyme N-myristoyl transferase (NMT). The second component of FAME is a short, structure-directing peptide sequence of ~5-10 amino acids that, when conjugated to an alkyl tail such as the myristoyl group, creates a peptide amphiphile (PA) that introduces a pre-programmed secondary structure (e.g., beta sheet, FIG. 1A). PAs have been shown to self-assemble into diverse morphologies depending on the peptide and lipid combination and they have been used in a number of biomedical applications, including scaffolds for tissue engineering.

The third segment of the FAME is an elastin-like polypeptide (ELP), which is incorporated at the C-terminus of the FAME at the gene level. ELPs are a class of peptide polymers that includes repeat units of the tropoelastin-derived pentapeptide, [Val-Pro-Gly-Xaa-Gly]$_n$, in which Xaa can be any amino acid, except Pro (Urry. *J. Phys. Chem. B* 1997, 101, 11007-11028; Roberts, et al. *FEBS Lett.* 2015, 589, 2477-2486). We chose ELPs as the third segment of FAME for several reasons. First, they can be conveniently synthesized with high yield by recombinant expression in *E. coli*. Second, they exhibit a lower critical solution temperature (LCST) phase transition, which enables them to transition from a soluble state to an insoluble coacervate by: 1) increasing the solution temperature or, 2) isothermally depressing their T$_t$ below the operating temperature by the addition of kosmotropic salts in the Hofmeister series (Cho, et al. *J. Phys. Chem. B.* 2008, 112, 13765-13771). The T$_t$ can be precisely tuned to within a narrow temperature range at the molecular level by manipulating two genetically encoded and orthogonal variables—the composition of Xaa and the chain length (McDaniel, et al. *Biomacromolecules* 2013, 14, 2866-2872). Their stimulus-responsive behavior, we hypothesized, could be used as a convenient trigger to control the hierarchical self-assembly embedded in the PA, as well as to purify the FAME. Third, because ELPs are genetically encoded, they are monodisperse, non-toxic, and biodegradable, and may be used for many biomedical applications, including injectable controlled release depots, tissue-engineering scaffolds, and thermally triggered targeting of tumors.

Figure 1B:
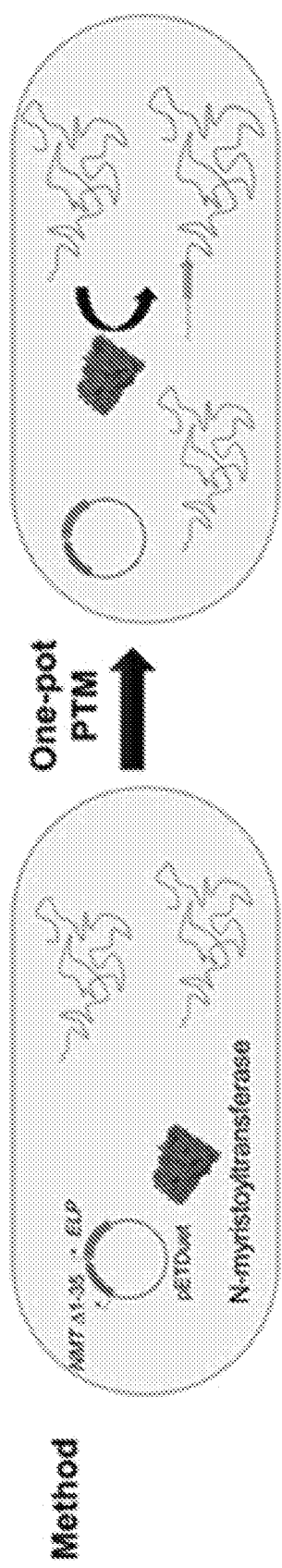

To create a recombinant expression system that is capable of lipidation in *E. coli*, we used a bicistronic expression vector (pETDuet-1) that simultaneously expresses two proteins of interest: (1) an ELP containing a substrate peptide at its N-terminus that is recognized by NMT; and (2) NMT from *S. cerevisiae*, the enzyme that catalyzes the covalent attachment of a myristoyl group to the N-terminus of the peptide substrate. In principle, NMT should covalently append a single copy of myristic acid to the N-terminal residue of the ELP through the formation of an amide bond. We hypothesized that the simultaneous expression of NMT and the substrate-containing ELP in *E. coli* should enable the in vivo, one-pot synthesis of FAME (FIG. 1B). We also hypothesized that these hybrid materials would retain defining characteristics of both ELP and PA, namely thermal responsiveness and hierarchical self-assembly, yielding unique programmable behavior.

The first major challenge that we had to address was the identification of structure-directing peptides that could also function as an in vivo myristoylation substrate. Previous studies have shown that it is possible to modify heterologous proteins in *E. coli* lysate by fusing an 11-amino acid signal peptide from the natively myristoylated yeast protein, ADP-ribosylation factor, in the presence of co-expressed NMT, but, to date, the ability of NMT to myristoylate other sequences, and in particular structure-directing peptides has not been investigated.

Analysis of the N-terminal sequence of myristoylated proteins reveals no universal consensus sequence except the presence of an N-terminal Gly residue (Eisenhaber, et al. *Nucleic Acids Res.* 2003, 31, 3631-3634). This lack of consensus, we speculated, should enable diverse sequences to serve as suitable substrates without the need for site-directed mutagenesis or evolution of NMT. We hence used software predictors of the myristoylation recognition sequence to guide the de novo design of PAs that have a dual functionality—they function as a signal sequence for recognition and myristoylation by NMT and they also act as a structure-directing self-assembly domain. To satisfy the first requirement, we utilized an online predictor (Maurer-Stroh, et al. *J. Mol Biol.* 2002, 317, 523-540; Maurer-Stroh, et al. *J. Mol. Biol.* 2002, 317, 541-557), which employs a machine learning algorithm from verified NMT substrates, to predict the possibility of N-terminal myristoylation.

Our de novo design was also informed by previous studies on PAs that have established the critical role of interactions among the first 4-6 residues after the alkyl tail in controlling self-assembly through the formation of β-sheets. PAs that could also serve as NMT substrates (TABLE 7) were designed based on the following considerations. First, we ensured that all sequences had a Gly residue at the N-terminus because an N-terminal Gly is critical for myristoylation. Next, we designed three sequences that, upon myristoylation, could function as PAs. (i) Sequence B$_1$ consists of Gly-Ala-Gly-Ala-Ser, whose alternating repeats of Gly/Ala residues were inspired by a repeat unit commonly found in spider silk and represent the minimum structural motif necessary for the formation of a β-sheet. (ii) The second sequence, B$_2$, with the sequence Gly-Ala-Gly-Ala-Gly-Ala-Tyr, was designed to enhance inter-strand interactions by increasing the number of Gly-Ala repeat units to three, as well as introducing an aromatic residue, Tyr. (iii) Sequence B$_3$ consisting of Gly-Leu-Ser-Leu-Ser, combines the bulky hydrophobic amino acid, Leu, with the hydrogen-bonding residue, Ser, which increases the peptide's overall propensity to form β-sheets. In order to characterize these materials and verify recombinant myristoylation by mass spectrometry, we also included an Arg residue to enable selective cleavage of the N-terminal peptide by trypsin. Finally, a short and flexible (Gly-Gly-Ser)$_n$ linker was included between the self-assembly domain and the ELP to ensure that access to the enzyme's active site was not sterically hindered by the ELP. The software predictor categorized our de novo designed recognition sequences as reliable potential sites for modification.

tures. The phase transition of unmodified ELPs and FAMEs was quantified for each polypeptide by measuring the optical density at 350 nm while gradually increasing the temperature from 10° C. to 50° C. for solutions with varying concentrations of polypeptide (FIG. 2). In the absence of myristoylation, all the constructs ($B_{1-3}$-ELP) exhibited a similar LCST transition, demonstrating that the short NMT recognition sequences at the N-terminus of the ELP did not

TABLE 7

A summary of the ELPs, FAMES, and control PAs used in this study.

|  | Identifier | N-terminal Modification | NMT Recognition sequences[a] | ELP |
|---|---|---|---|---|
| ELPs | $B_1$-ELP | N/A | GAGAS<u>R</u>*GGSGGS* (SEQ ID NO: 38) | (GVGVP)$_{40}$GY (SEQ ID NO: 54) |
|  | $B_2$-ELP | N/A | GAGAGAY<u>R</u>*GGSGGSGGS* (SEQ ID NO: 40) |  |
|  | $B_3$-ELP | N/A | GLSLS<u>R</u>*GGSGGS* (SEQ ID NO: 42) |  |
| FAMEs | M-$B_1$-ELP | Myristoyl | GAGAS<u>R</u>*GGSGGS* (SEQ ID NO: 38) |  |
|  | M-$B_2$-ELP | Myristoyl | GAGAGAY<u>R</u>*GGSGGSGGS* (SEQ ID NO: 40) |  |
|  | M-$B_3$-ELP | Myristoyl | GLSLS<u>R</u>*GGSGGS* (SEQ ID NO: 42) |  |

|  | Identifier | N-terminal Modification | Sequence |  |
|---|---|---|---|---|
| Control PAs | M-$B_1$ | Myristoyl | GAGASR (SEQ ID NO: 48) | N/A |
|  | M-$B_2$ | Myristoyl | GAGAGAYR (SEQ ID NO: 49) |  |
|  | M-$B_3$ | Myristoyl | GLSLSR (SEQ ID NO: 50) |  |

[a] De novo designed recognition sequences have three components: self-assembly domain (bold), trypsin cleavage site (Arg, underlined), and a flexible linker (italics).

We chose an ELP with the sequence [Gly-Val-Gly-Val-Pro]$_{40}$ (SEQ ID NO:52) and call it "ELP" for simplicity. It should be noted, however, that this design framework can be easily applied to other ELPs, featuring different lengths and guest residue compositions to tune the LCST of the desired FAME. In principle, this approach is also applicable to a wide range of protein polymers that could be substituted for the ELP, such as resilin-like polypeptides (RLP; Quiroz, et al. *Nat. Mater.* 2015, 14, 1164-1171) and collagens.

The NMT and the polypeptide gene were cloned into tandem expression cassettes of the pETDuet-1 vector. The pETDuet-1 plasmid—containing the NMT gene and the ELP substrate—was transformed into *E. coli* BL21(DE3) cells, cultured in the presence of myristic acid, and then chemically induced to express both genes by the addition of isopropyl-J-D-thiogalactopyranoside. The FAMEs were purified by taking advantage of their temperature-triggered phase transition using inverse transition cycling, a non-chromatographic method for purification of ELPs and ELP fusion proteins (ITC; Hassouneh, et al. *Curr. Protoc. Protein Sci.* 2010, 6.11.1-6.11.16).

Example 3

We first sought to investigate whether FAMEs exhibited temperature-triggered LCST phase behavior, which is an important feature, as it would enable extrinsic control of their hierarchical self-assembly. The LCST phase transition of ELPs and their fusions can be conveniently monitored by measuring the turbidity of the solution at different temperasignificantly alter its phase transition behavior (FIG. 2A, FIG. 2D, FIG. 2G, and FIG. 24A). Additionally, the $T_t$ of all three constructs exhibited an identical inverse dependence on the concentration of the ELP in solution. For example, reducing the concentration of ELP from 100 μM to 25 μM increased the $T_t$ by 10° C. Finally, the phase transition of non-myristoylated ELPs was completely reversible within the experimental temperature range.

In contrast, all three FAMEs exhibited a lower $T_t$ compared to their non-myristoylated counterparts (i.e., ELPs). For example, the $T_t$ of all FAMEs was ~20-25° C. at 100 μM (FIG. 2B, FIG. 2E, and FIG. 2H), which is 15° C. lower than that of the non-myristoylated parent polypeptides. This behavior can be explained by the fact that the $T_t$ inversely scales with hydrophobicity, and myristoylation increases the chain hydrophobicity and removes the charged N-terminal amine. Interestingly, subtle differences in the NMT recognition sequence significantly altered the concentration dependence and reversibility of the LCST phase behavior. The $T_t$ of M-$B_1$-ELP and M-$B_2$-ELP exhibited a steep concentration dependence (FIG. 2B, FIG. 2E), while the $T_t$ of M-$B_3$-ELP did not change when its concentration was reduced from 100 μM to 25 μM (FIG. 2H). All FAMEs exhibited reversible phase transition behavior up to 30° C. (FIG. 25), but only M-$B_1$-ELP's phase transition was completely reversible across the entire experimental temperature range of 15-50° C. M-$B_2$-ELP and M-$B_3$-ELP displayed hysteretic phase transition behavior (FIG. 26) after the temperature had reached a critical point (~45° C.). The onset of this hysteretic behavior was marked by a sudden decrease in the turbidity of the solution (indicated by arrows in FIG. 2E, and FIG. 2H), which is due to M-$B_2$-ELP and M-$B_3$-ELP self-assembling into macroscopic objects (mm to cm length scale) that drifted out of the light path.

Figure 2A:
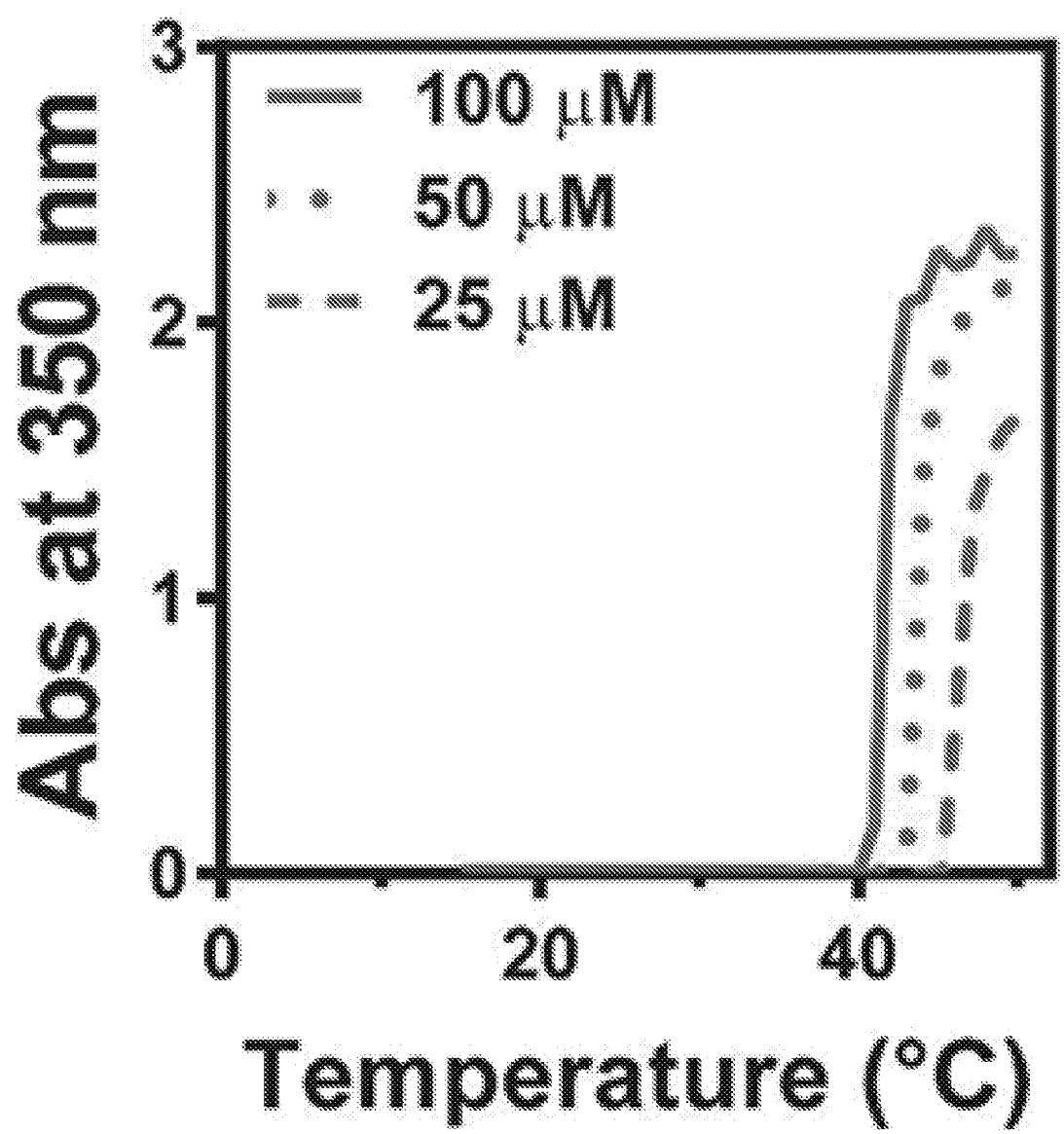
FIG. 2A-I. Temperature triggers the macroscale self-assembly of un-modified ELPs and FAMEs, as measured by a temperature-programmed turbidimetry assay.
Figure 2B:
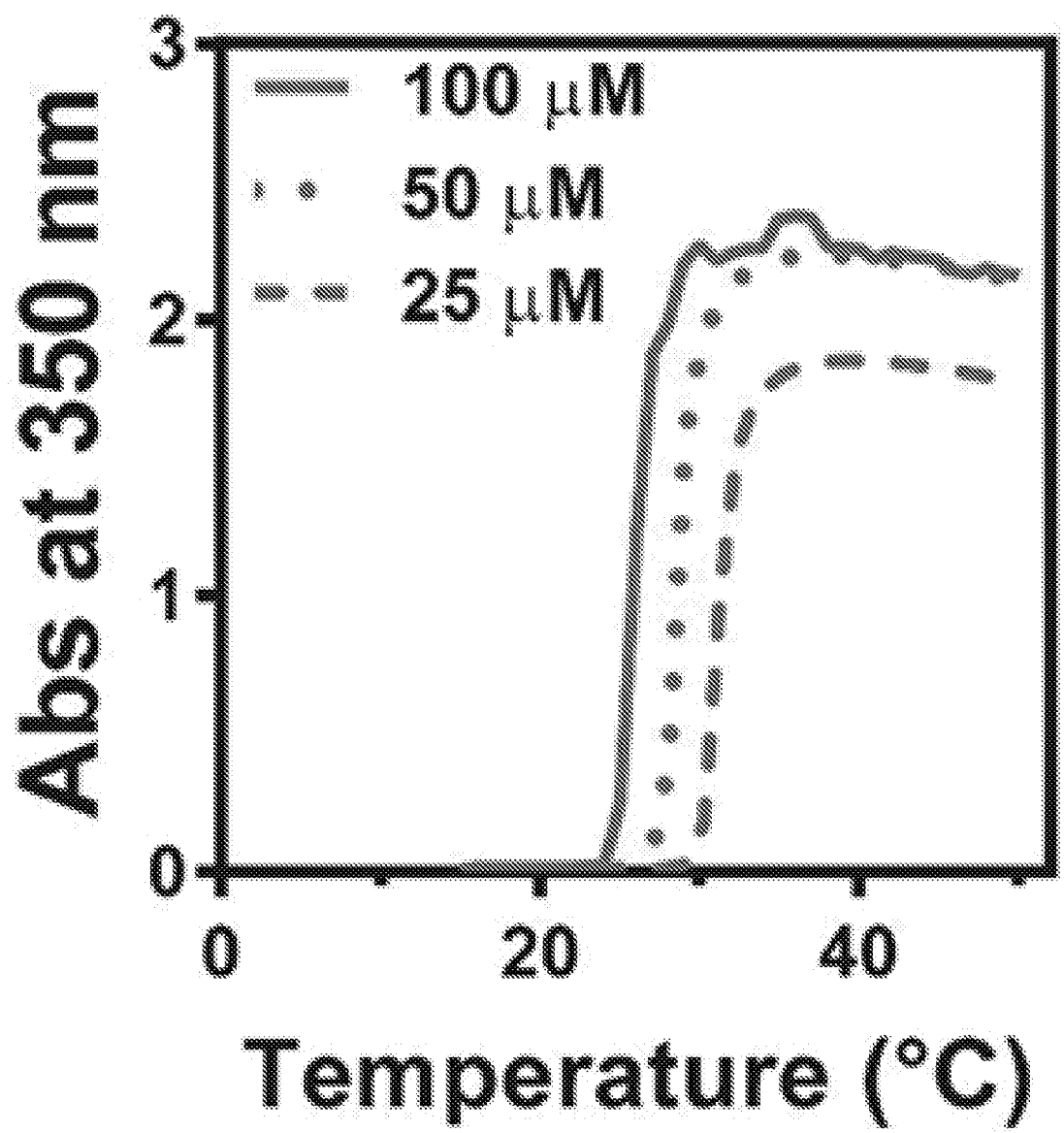
Figure 2C:
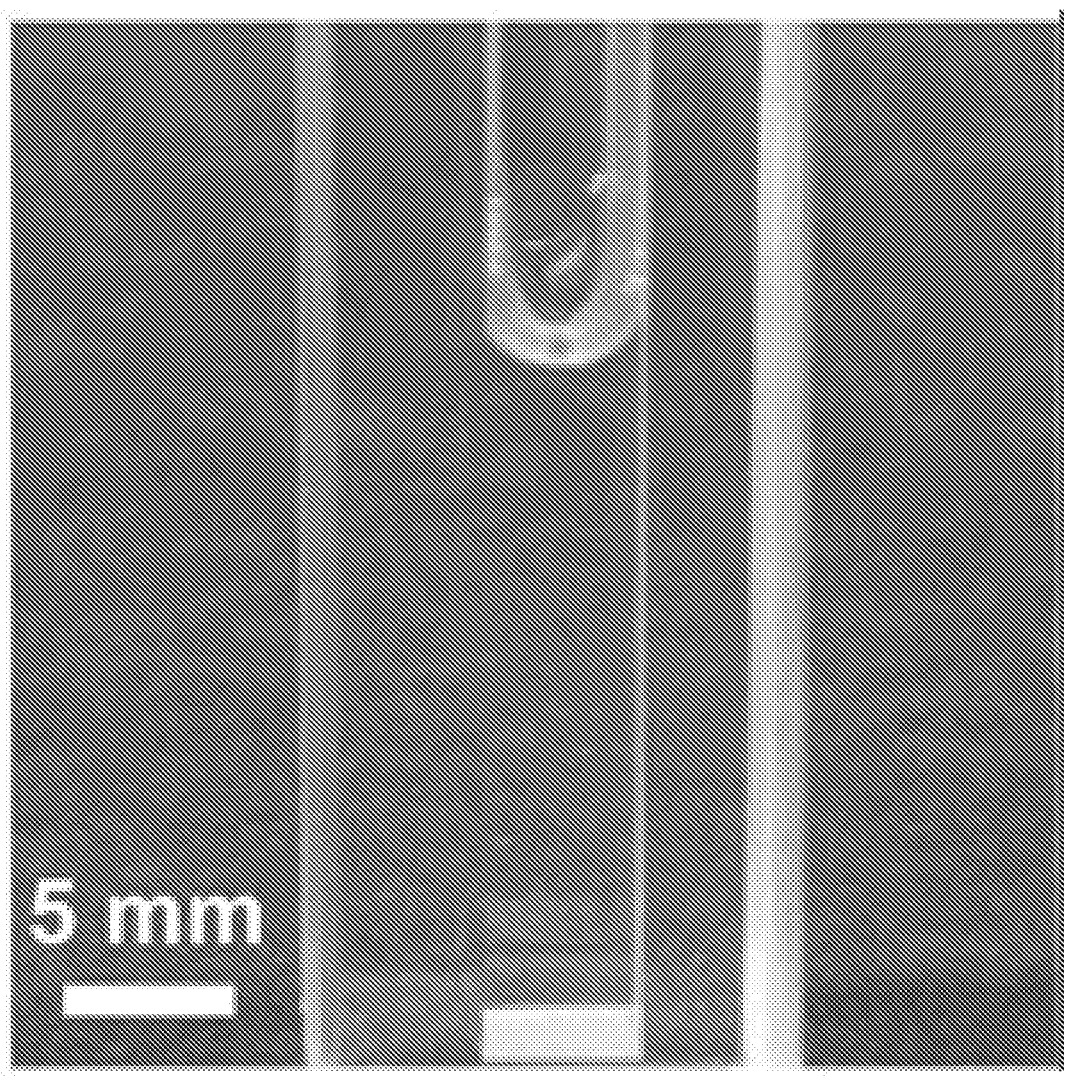
Figure 2D:
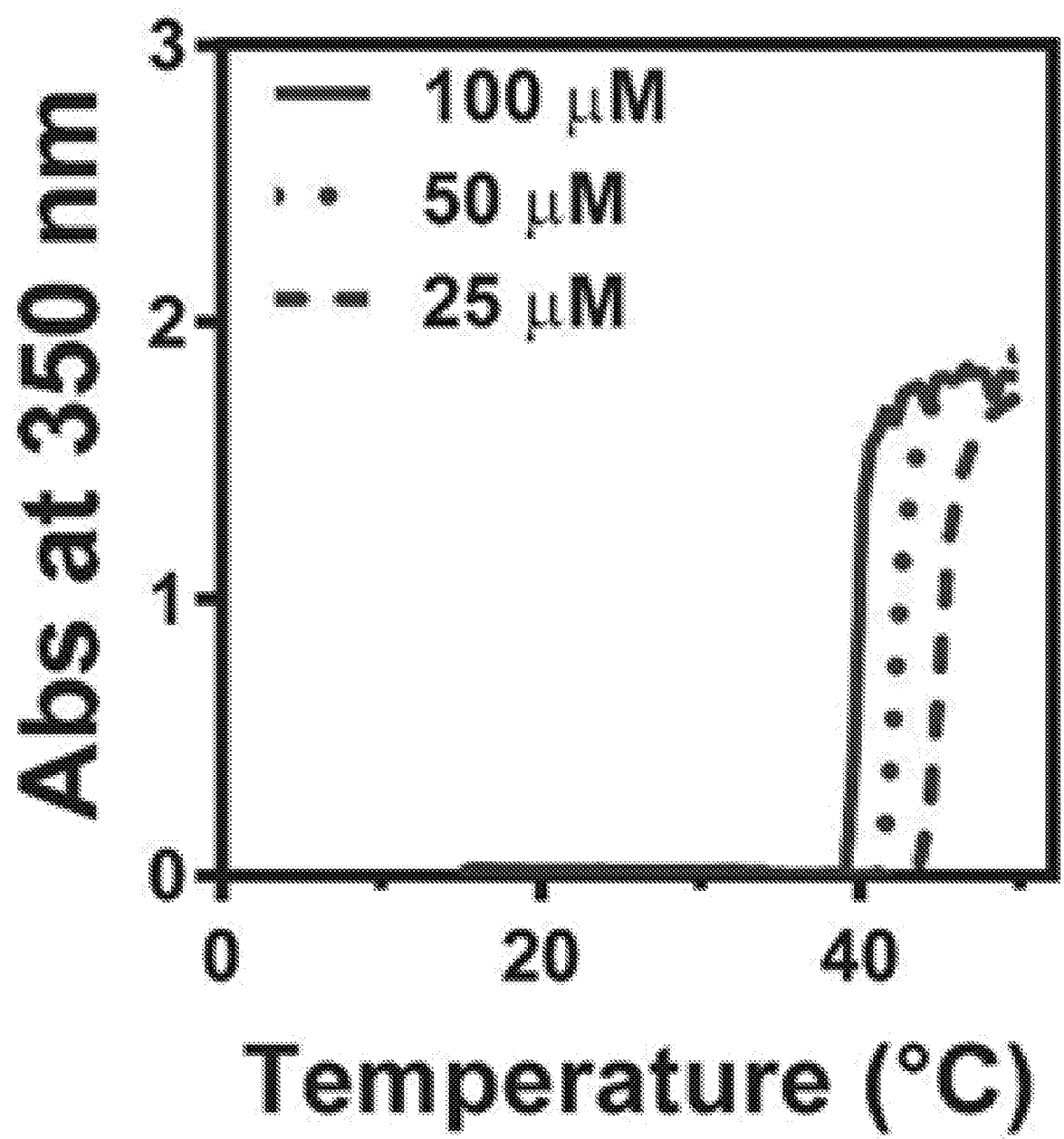
Figure 2E:
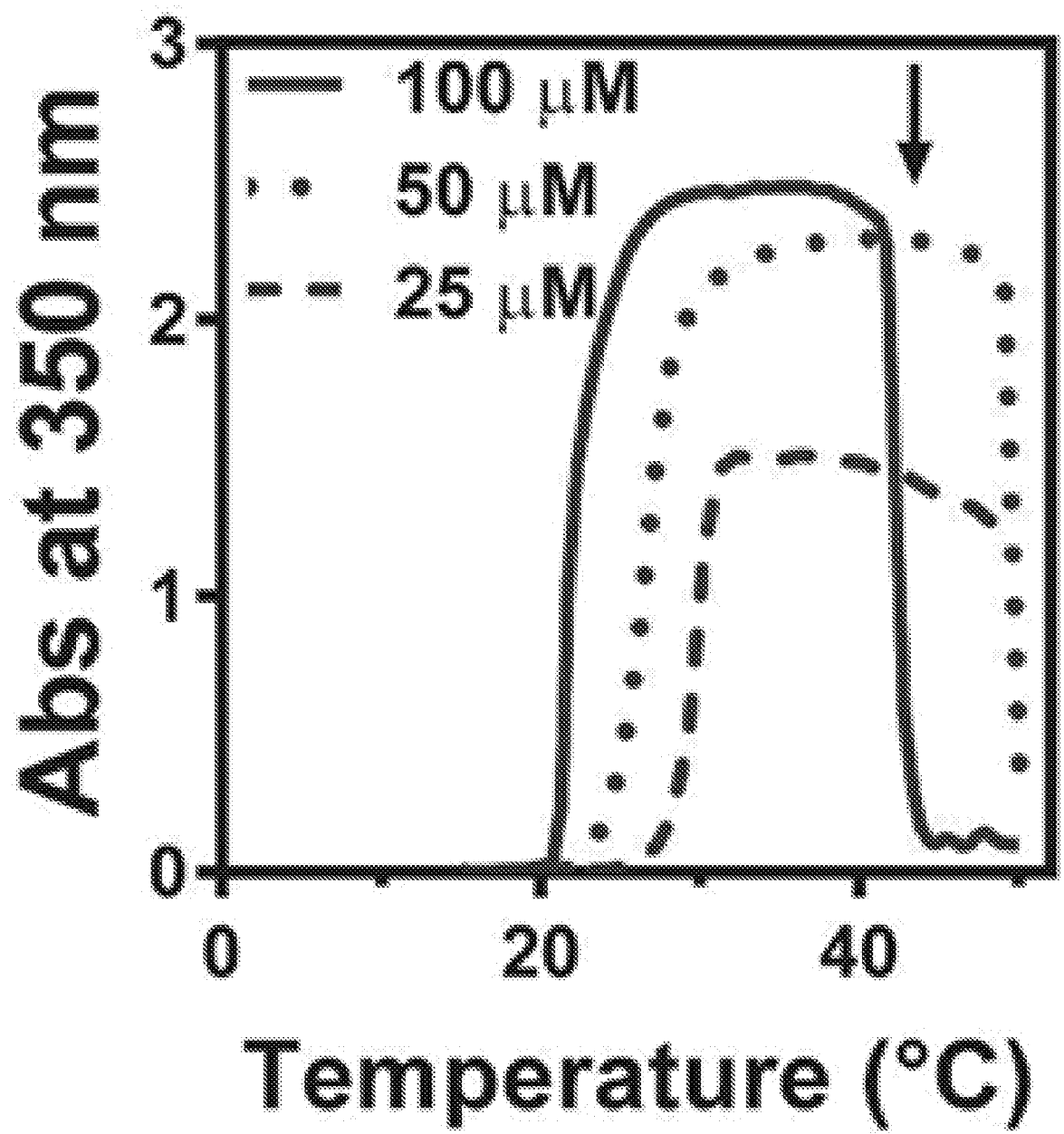
Figure 2F:
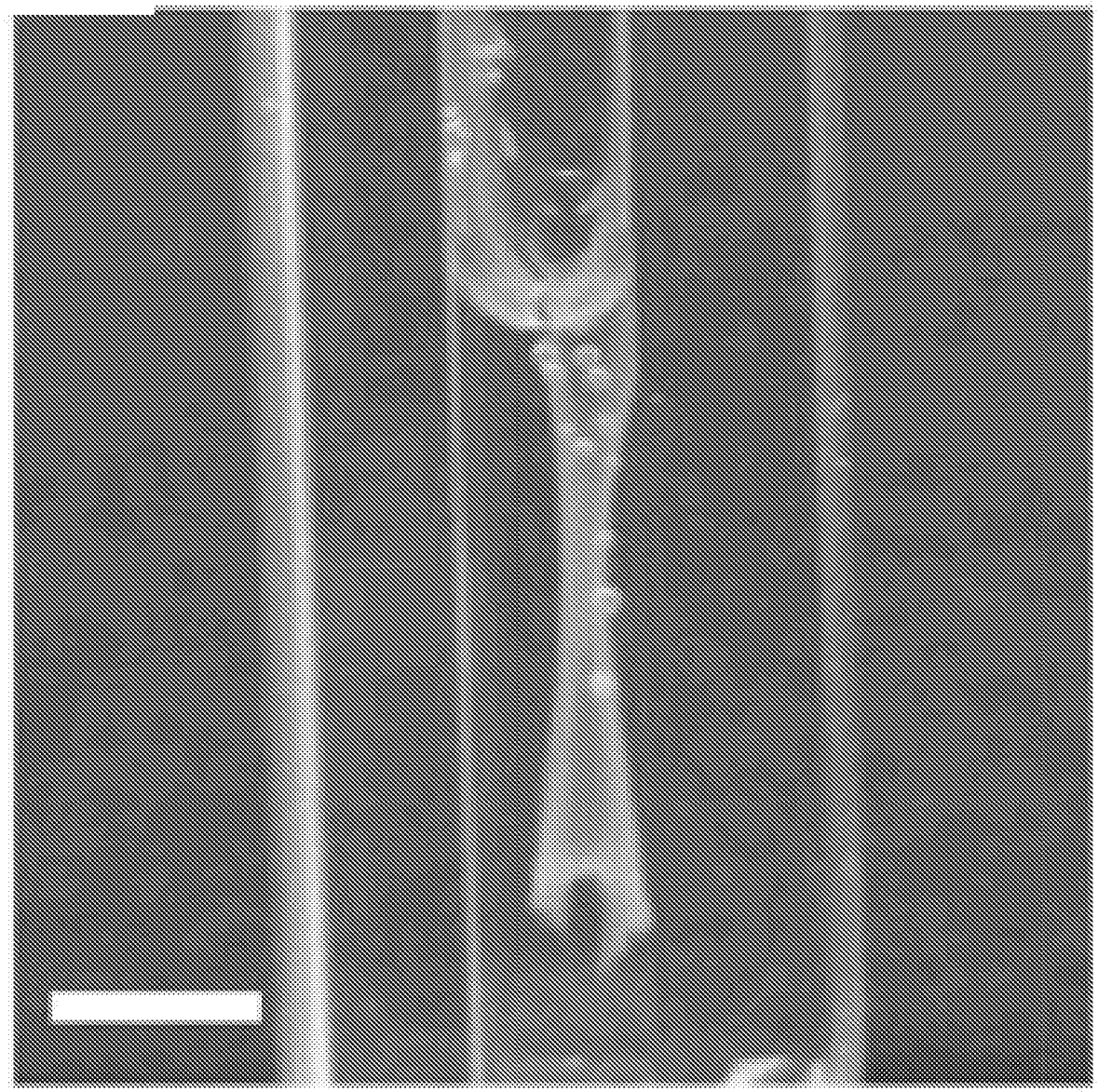
Figure 2G:
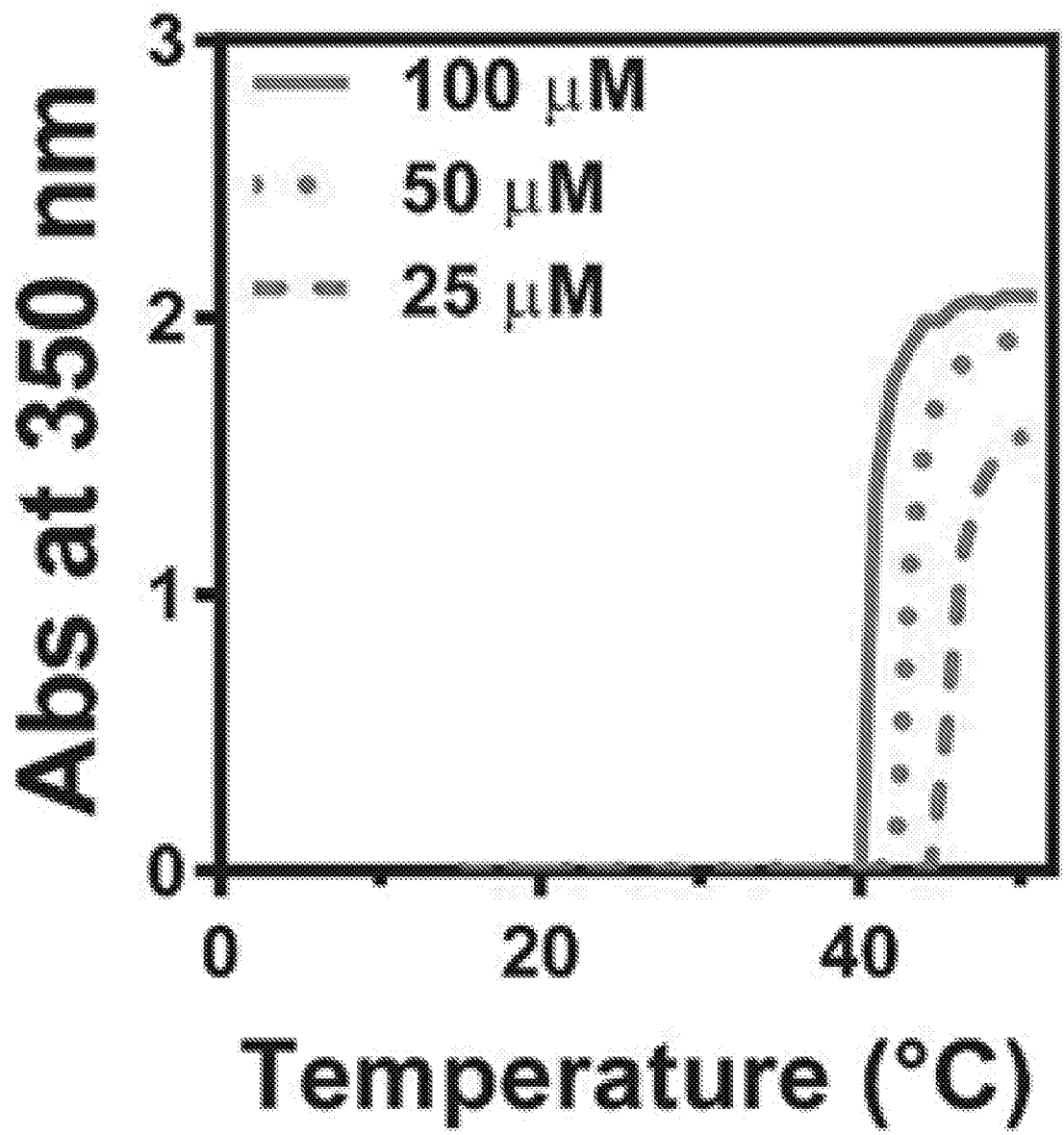
Figure 2H:
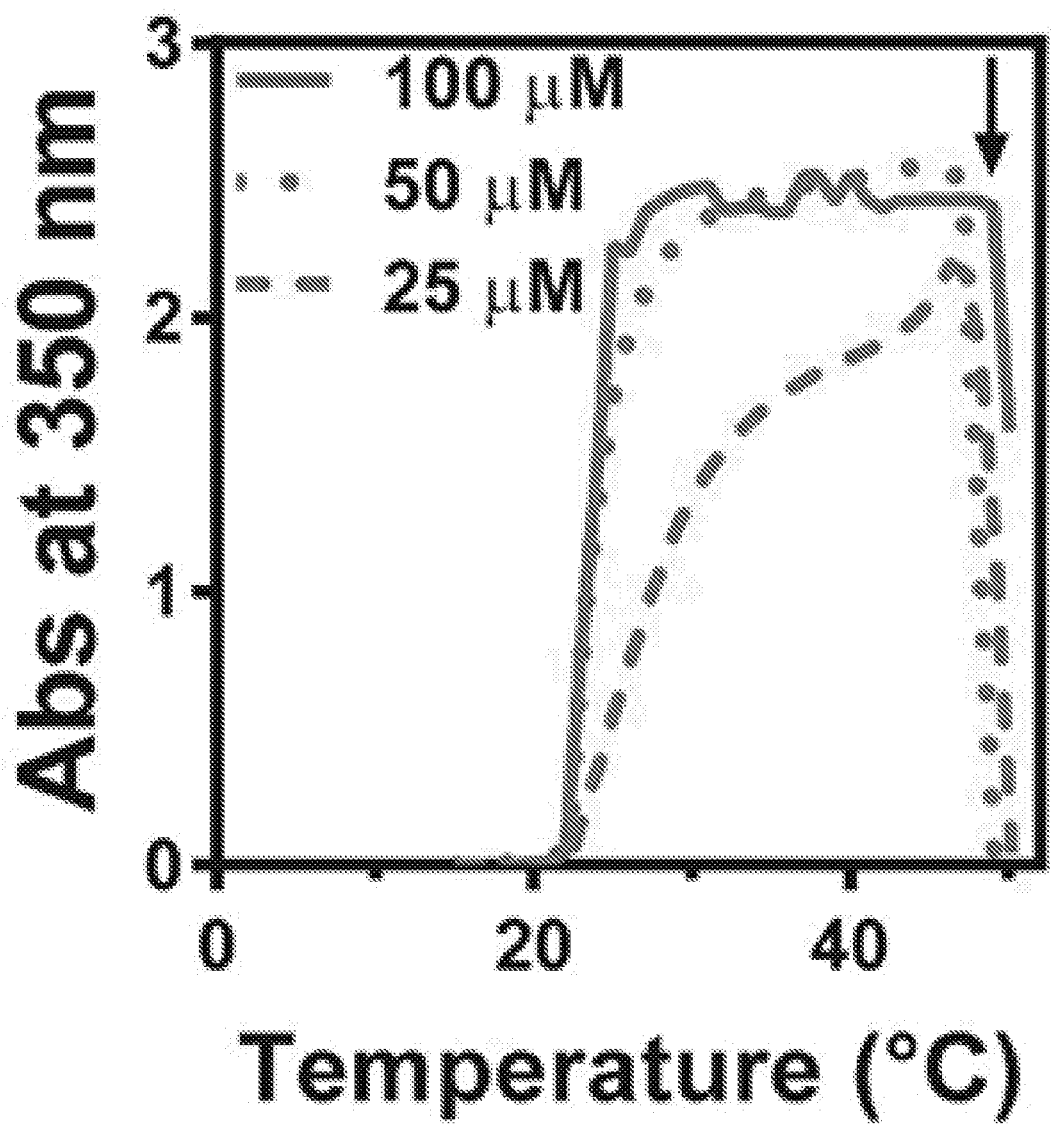
Figure 2I:
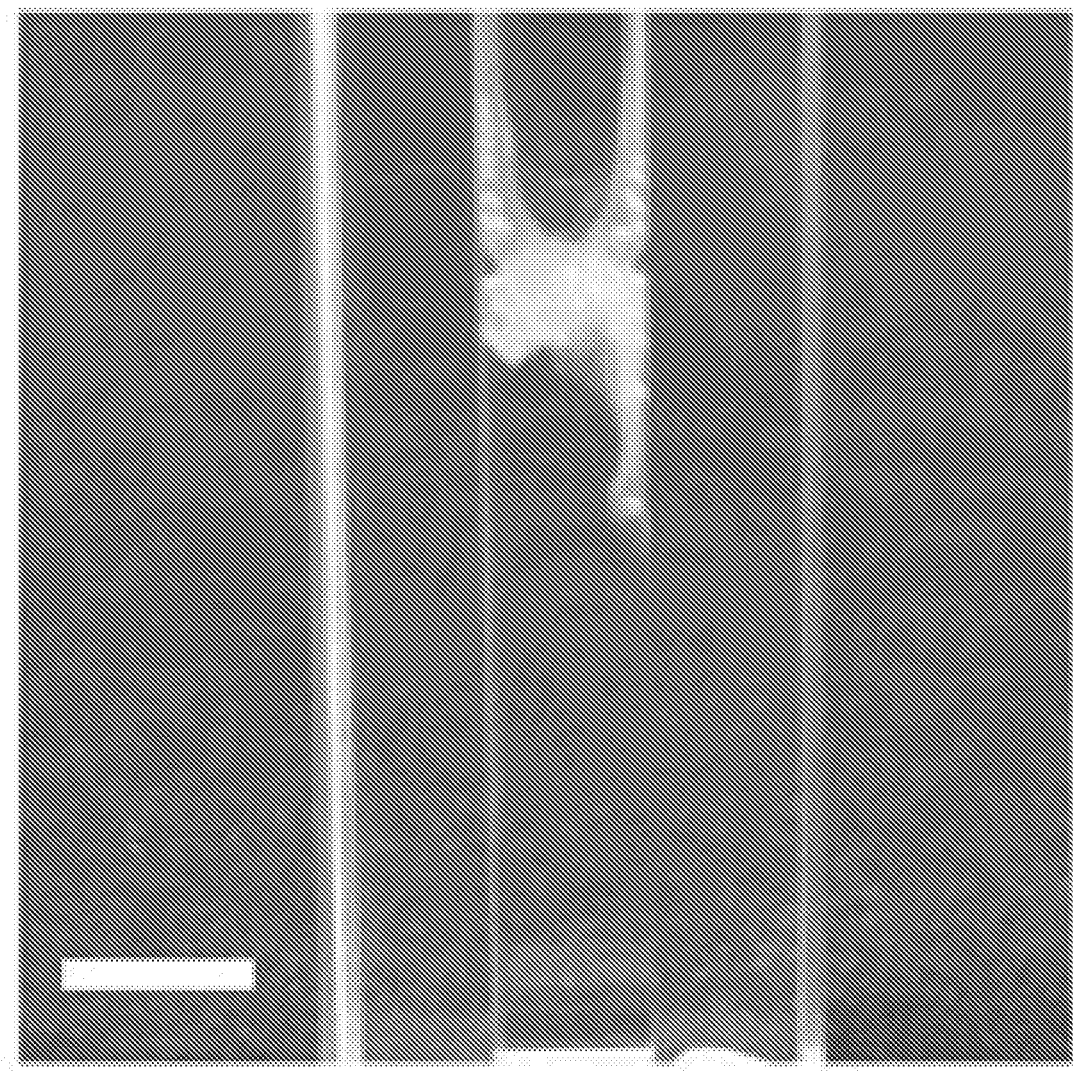
Figure 28:
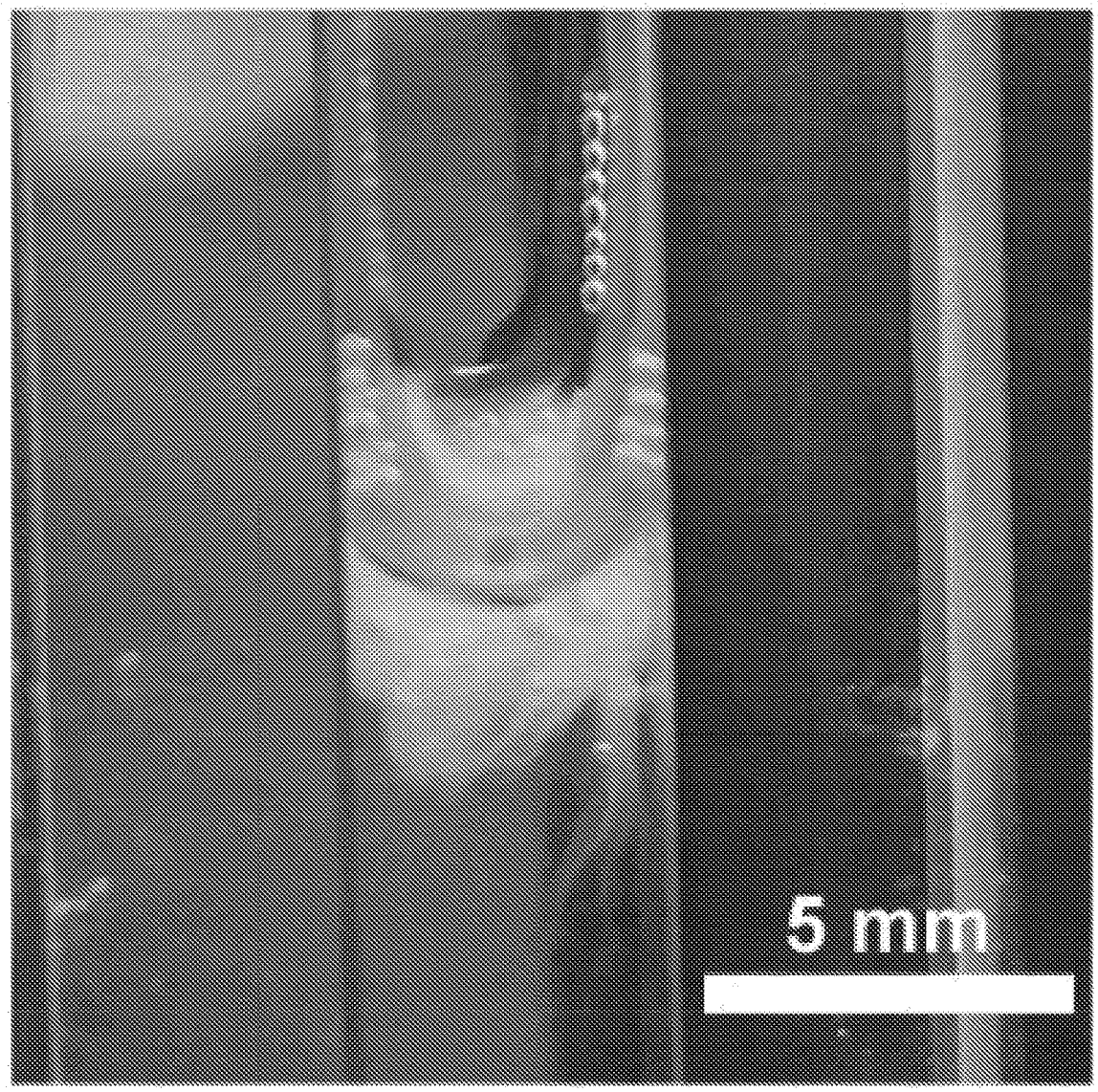
FIG. 28. Optical image of the structures formed by the M-$B_2$-ELP constructs.
Figure 29A:
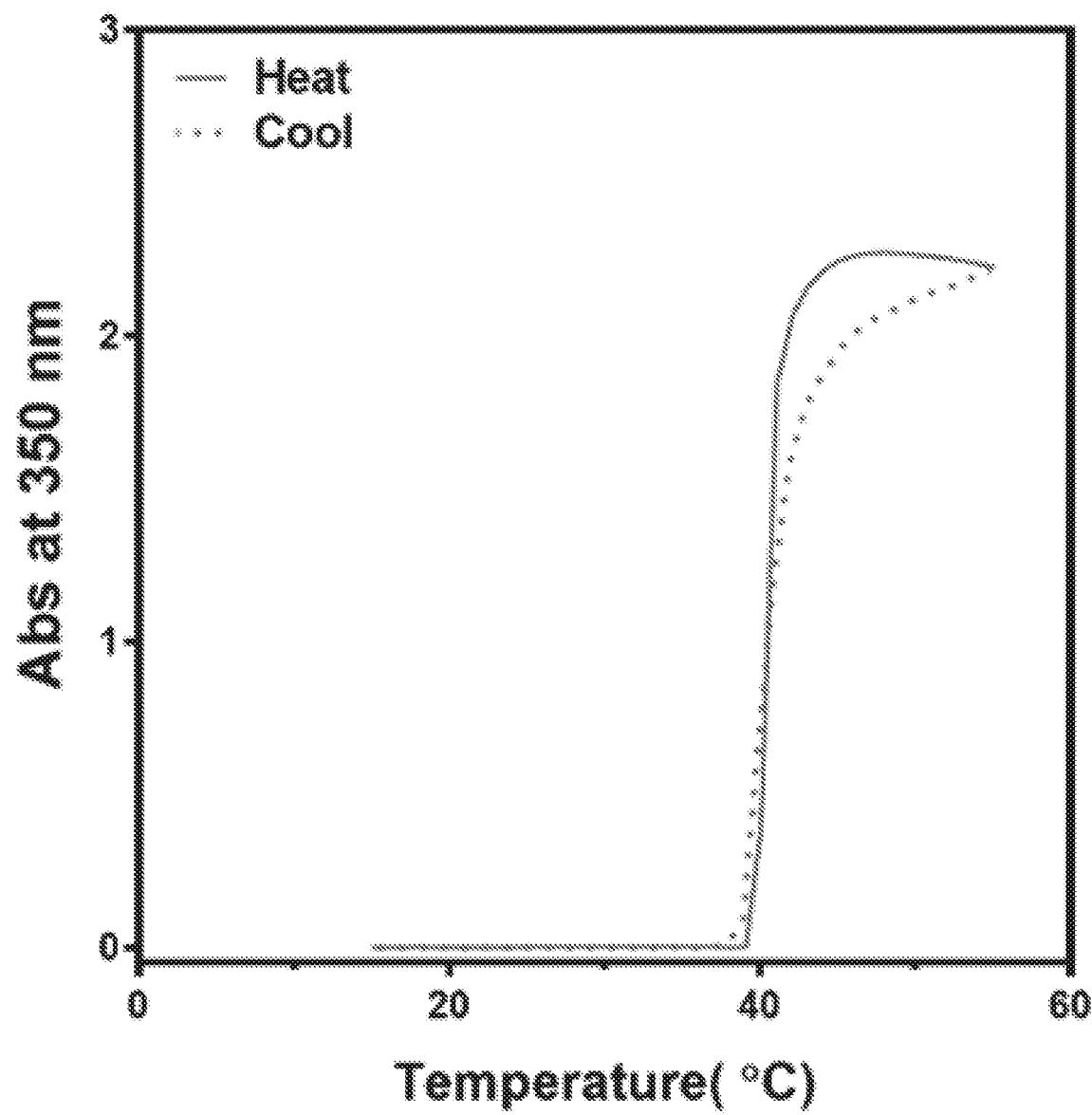
FIG. 29A-B. Temperature-programmed turbidimetry assay demonstrates that the phase transition of FIG. 29A: ELP
Figure 29B:
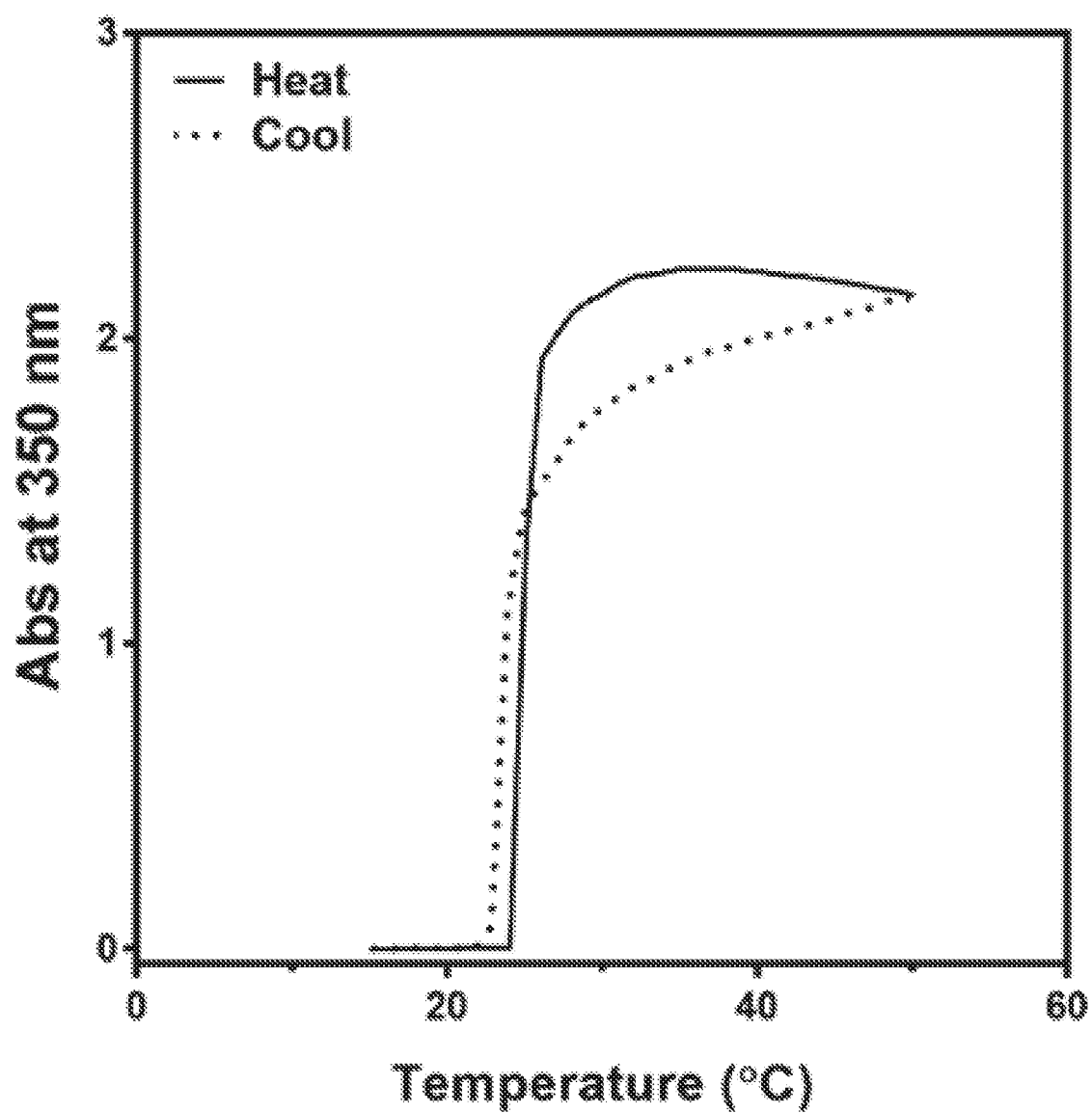

While M-$B_1$-ELP resolubilized completely upon cooling (FIG. 2C), we observed that M-$B_2$-ELP self-assembled into long, flat sheets above its $T_t$ (FIG. 2F, and FIG. 27), while M-$B_3$-ELP formed weaker amorphous aggregates, which stemmed from the association of smaller "needle-like" structures (FIG. 2I, and FIG. 28). These results demonstrate that the temperature can be used as an external cue to trigger the hierarchical self-assembly of FAMEs. It is also intriguing that the differences in these self-assembled macroscopic structures were the result of minor sequence variations in the short N-terminal recognition sequences appended to a much longer ELP, highlighting the potent ability of PAs to direct hierarchical self-assembly.

Example 4

Figure 31:
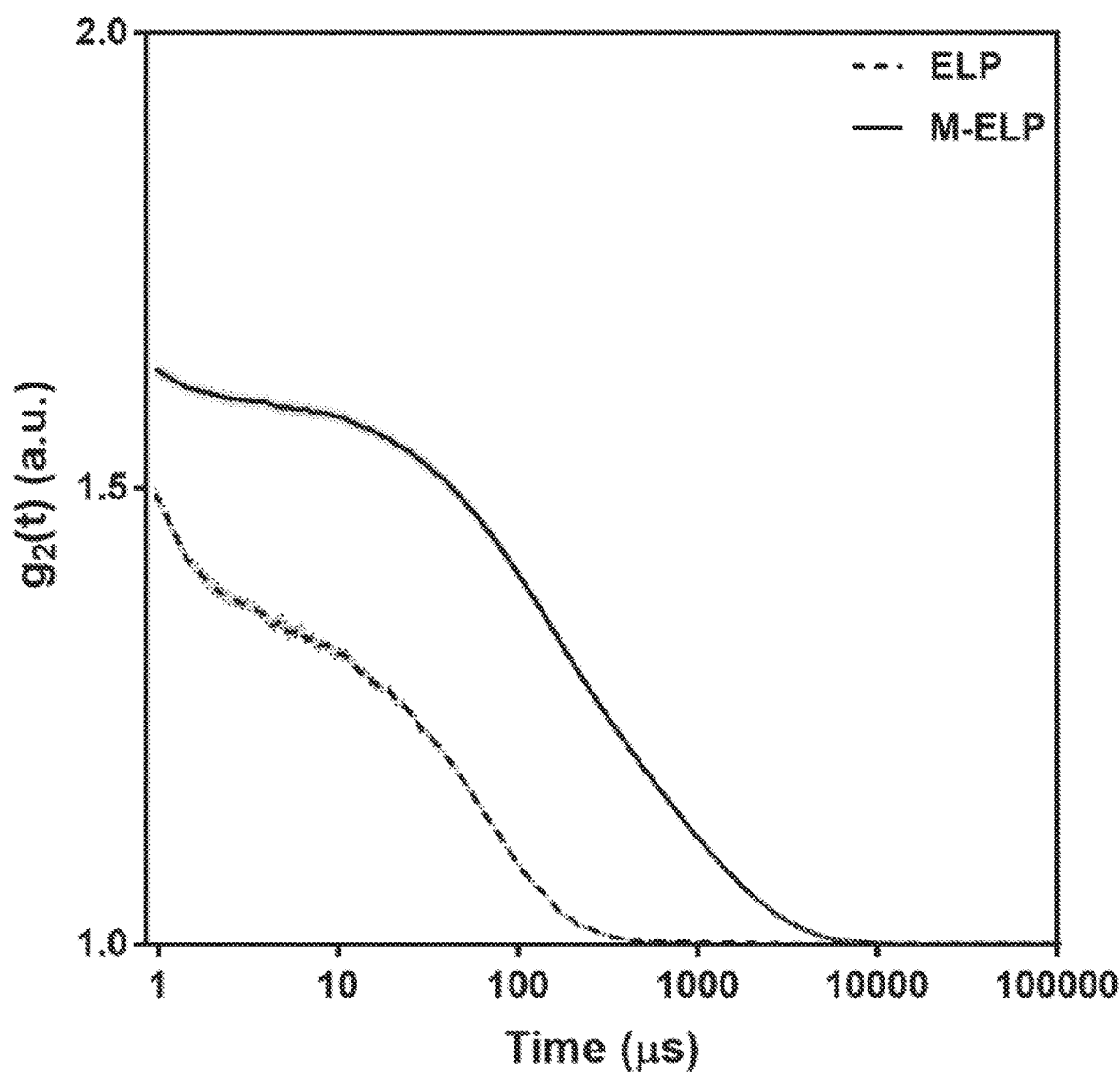
FIG. 31. DLS autocorrelation function for ELP (dashed black line) and M-ELP (solid black line).

To understand the self-assembly mechanism at the molecular level, we utilized various spectroscopic techniques to study the effect of myristoylation on the structure and self-assembly of FAMEs below their $T_t$. We used dynamic light scattering (DLS) to probe the self-assembly of each construct below its ELP-driven phase transition. As shown in FIG. 3A, in the absence of myristoylation (dashed lines), $B_{1-3}$ELP exist as unimers in solution, as evidenced by the autocorrelation decay at short time scales that is consistent with the random coil structure of canonical ELP of comparable length (FIG. 31). In contrast, DLS conclusively showed that all three FAMEs, M-$B_{1-3}$-ELP, self-assembled to form significantly larger aggregates, as shown by the shift in their autocorrelation decay function to longer time scales. There are two important conclusions from the DLS data. First DLS clearly shows that the incorporation of a single myristoyl group is enough to trigger the association of FAMEs even below the $T_t$. It is plausible that the formation of these nanoscale assemblies in solution further decreases the entropy of inter-chain association and contributes to their lower $T_t$ (particularly in the case of M-$B_3$-ELP) compared to their non-myristoylated counterparts. Second, since the ELP domains are identical in all the FAMEs studied in this paper, the differences observed in nanoscale assemblies below $T_t$, are a result of the subtle differences in the sequence of the PA-like domain.

Example 5

Figure 32:
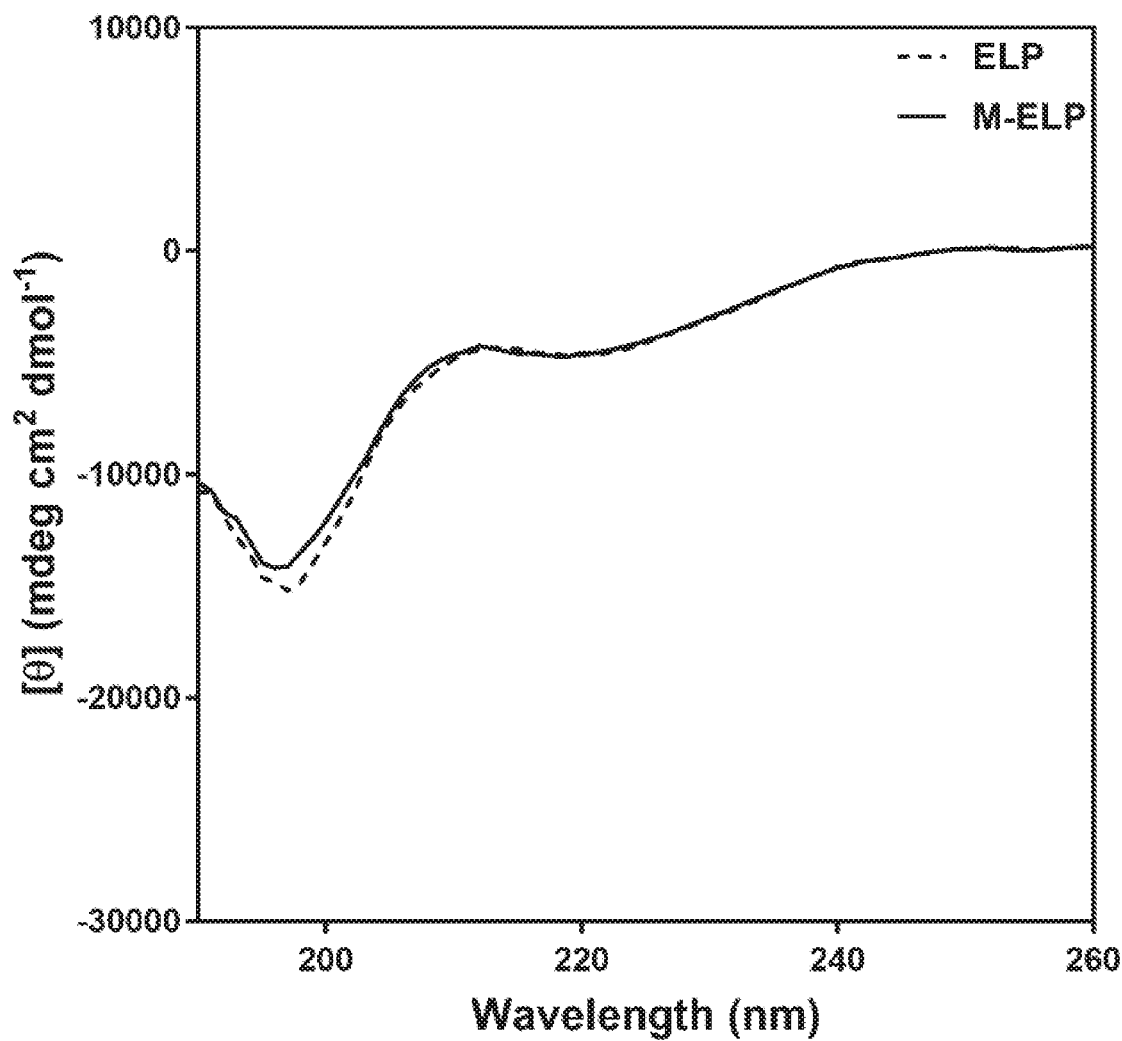
FIG. 32. The CD spectra for the ELP (dashed black line) and M-ELP (solid black line) constructs.

We next investigated the effect of myristoylation on the secondary structure of the ELPs using circular dichroism (CD). Non-myristoylated ELPs exhibited CD signatures (FIG. 3B, dashed line in each panel) with a major peak at 195 nm, indicative of a random coil, and a smaller peak at 220 nm indicative of a β-turns from the Pro-Gly dipeptides in the pentapeptide repeat, that is characteristic of the ELP (FIG. 32). Myristoylated ELPs (FIG. 3B, solid line in each panel) exhibited a similar CD signature, suggesting that myristoylation did not result in a global change in the secondary structure of the ELP in its solvated state below its $T_t$.

Figure 34:
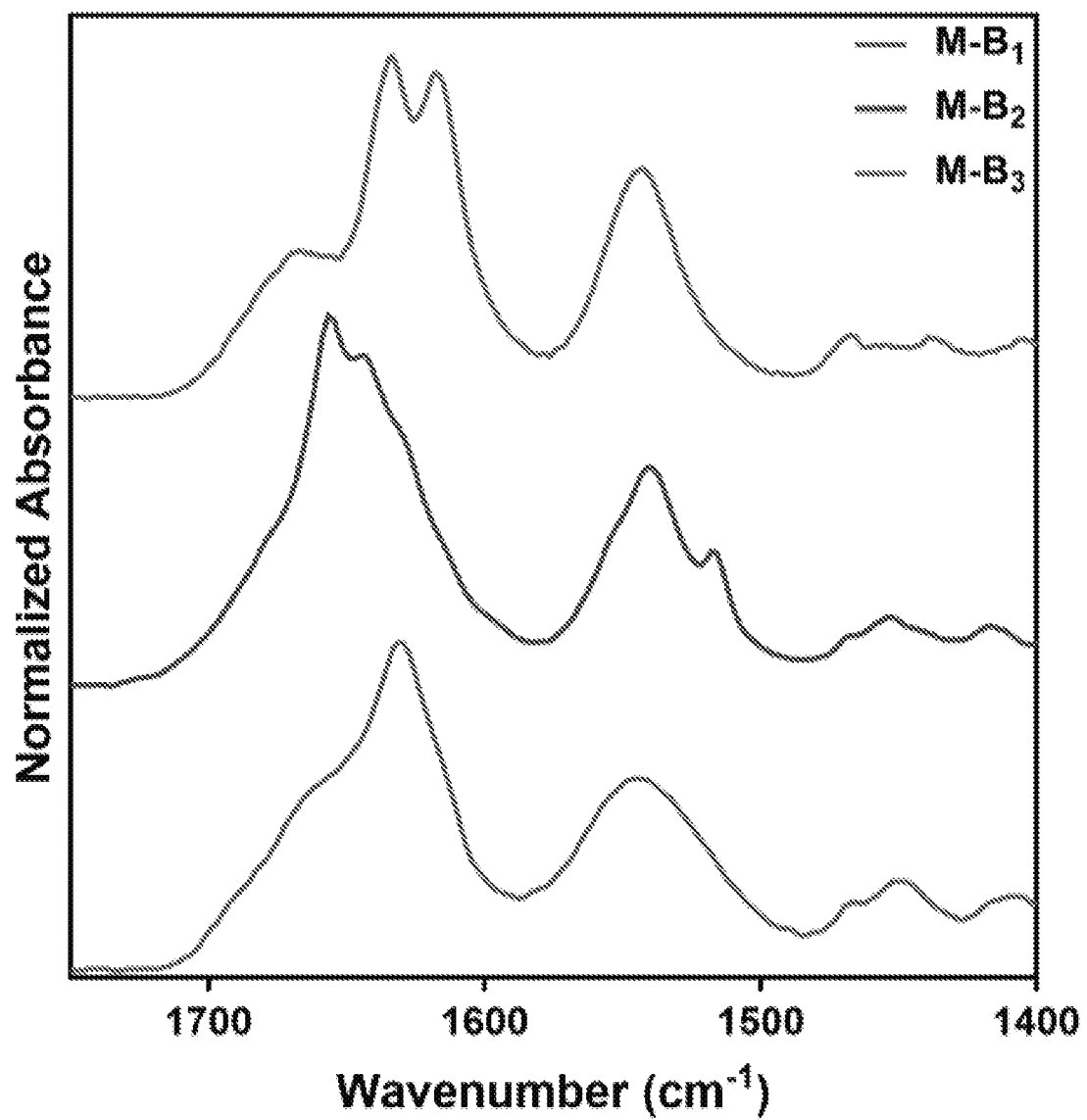
FIG. 34. Stacked FT-IR spectra of M-$B_1$ (green), M-$B_2$ (blue), and M-$B_3$ (red) demonstrates the different internal dynamics of these PAs.

Consistent with the CD spectra, both FAMEs and their non-myristoylated controls exhibited similar FT-IR spectra, consistent with previous reports for ELPs (FIG. 33). While we could not collect CD spectra for the control PAs (i.e. synthetic M-$B_{1-3}$ containing the structure-directing peptide without the ELP) due to their limited solubility, their FT-IR spectra were noticeably different from the ELPs and FAMEs (FIG. 3B, solid grey line in each panel). The complex absorption pattern of amide carbonyls observed for PAs is consistent with the presence of β-sheet structures in the lyophilized powder while demonstrating that the internal dynamics of each PA is dictated by the sequences preceding the hydrophobic tail (FIG. 34).

Figure 35:
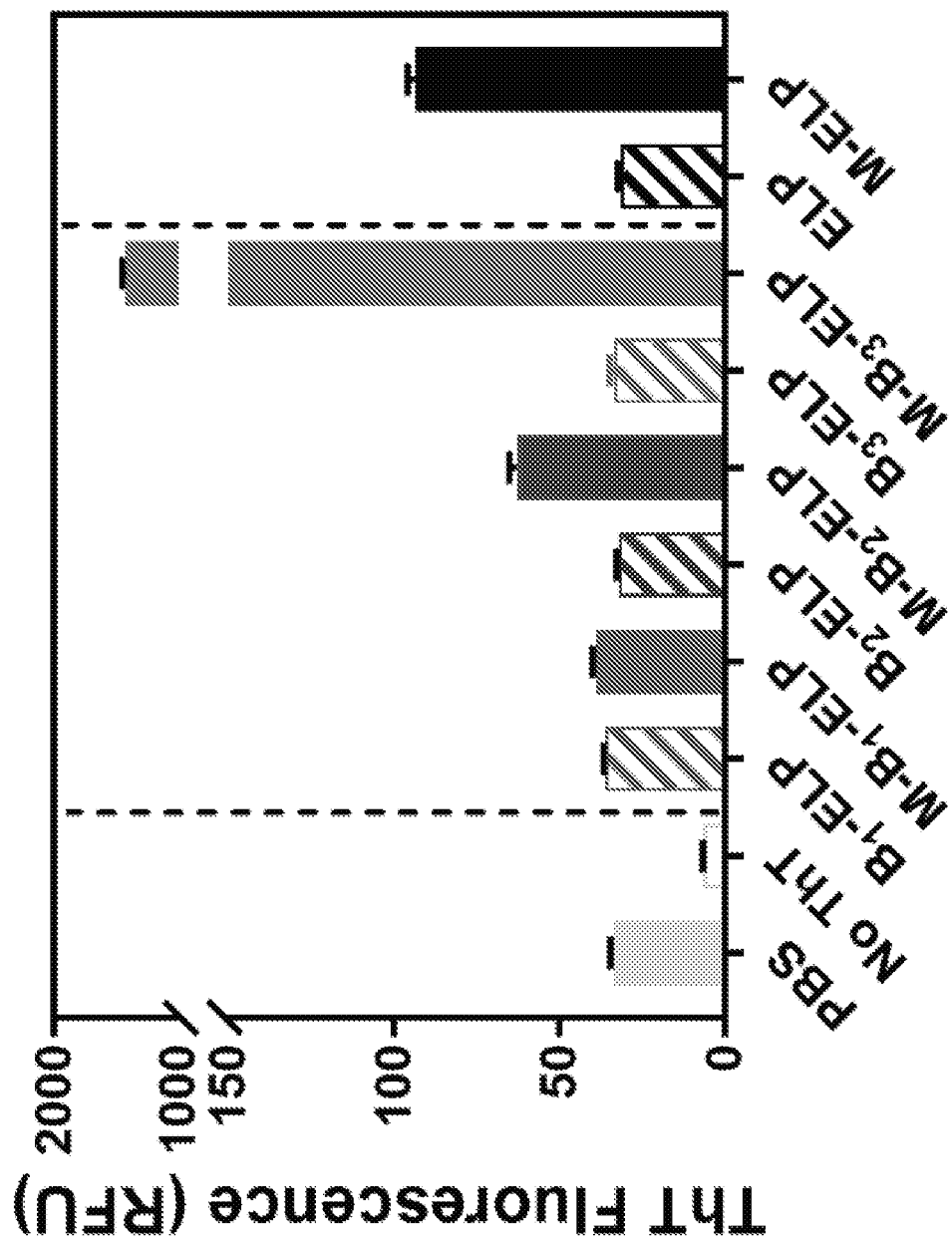
FIG. 35. Single time-point static ThT assay at 20° C. Interaction of the ThT with different constructs is dependent on the myristoylation and the recognition sequence preceding the alkyl group. Error bars represent standard deviations calculated from three measurements.

Because the FT-IR spectroscopy of the PAs suggests that they have a propensity to adopt a β-sheet secondary structure, we reasoned that a thioflavin T (ThT) fluorescence assay could be used to investigate the role of the PA in directing hierarchical self-assembly of the FAMEs. ThT is a benzothioazole salt that is commonly used to visualize and quantify the presence of fibrillar- or amyloid-like aggregates. The fluorescence of free ThT in solution is strongly quenched by water but, upon binding to aggregates rich in β-sheets, the fluorescence is significantly enhanced by up to a 1000-fold. We began with a single time-point "static" ThT assay at 15° C., a temperature below the $T_t$ of each FAME (FIG. 3D and FIG. 35). The static ThT assay is a spectroscopic probe of the initial nanoscale self-assembled structures that is directed by the PA component of each FAME. The results from the static ThT assay clearly show that myristoylation is necessary for uptake of the ThT dye, because in the absence of myristoylation, the fluorescence of ThT is strongly quenched in all constructs. The comparison of ThT uptake between the FAMEs demonstrates that the recognition sequence following the myristoyl group also strongly influences the interaction of the FAME with ThT. Below the $T_t$, ThT did not interact strongly with the structures formed by M-$B_1$-ELP, which features flexible and small amino acids in the recognition sequence (Gly-Ala-Gly-Ala-Ser). In comparison, M-$B_2$-ELP exhibited a 2-fold increase in ThT uptake and fluorescence, likely due to an increase in the number Gly-Ala repeats, and through the added effect of π-π stacking via the Tyr residue inter-chain interactions in its recognition sequence. Strikingly, ThT fluorescence increased 43-fold in the presence of the M-$B_3$-ELP construct which contains amino acids with larger hydrophobic side chains (Leu) and can form additional hydrogen bonds via the side chain of the Ser residues.

Example 6

Next, to understand the hierarchical self-assembly of the nanoscale structures into larger macroscopic objects that is directed by the LCST phase transition of the ELP component of each FAME, we carried out a dynamic ThT assay by monitoring the evolution of ThT fluorescence as a function of temperature by a temperature ramp experiment. As shown in FIG. 3E, the differences between these constructs were more pronounced, though many of the observations from the static assay were also corroborated by the dynamic ThT assay. Uptake of ThT did not increase significantly as non-myristoylated ELPs were heated above their $T_t$; we observed only a minor increase in the fluorescence after 40° C., corresponding to their $T_t$ at 100 μM (FIG. 3E). This is presumably due to non-specific sequestration of ThT into the hydrophobic polypeptide-rich coacervate phase. In contrast, at 30° C. (5° C. above $T_t$), even M-$B_1$-ELP, the FAME that did not exhibit macroscopic assembly, exhibited a six-fold increase in ThT fluorescence compared to its non-myristoylated control ($B_1$-ELP). This increase in the ThT fluorescence of FAMEs above their $T_t$, was significantly greater for the other two FAMEs that form macroscopic objects above their $T_t$. At 30° C., a temperature just above the $T_t$ of both FAMEs, M-$B_2$-ELP showed a 150-fold and M-$B_3$-ELP showed a 270-fold increase in the ThT fluorescence compared to non-myristoylated controls, supporting our original hypothesis that the temperature-triggered phase-transition of ELP domain can be used as a convenient trigger of a second, LCST driven stage of hierarchical self-assembly of the FAMEs. Both M-$B_2$-ELP and M-$B_3$-ELP displayed another transition in the ThT fluorescence close to 45° C. (marked by an arrow in FIG. 3E). This second transition coincided with the onset of hysteretic behavior and the formation of the macroscopic objects shown in FIG. 2.

Based on these results, we conclude that the self-assembly of FAMEs is initially triggered below the $T_t$ and is driven by the hydrophobic collapse of the myristoyl group. DLS and the static ThT assay confirm that the higher order self-assembly of these nanoaggregates below the $T_t$ is influenced by the programmed secondary interactions (propensity to form β-sheets) encoded in the myristoylation sequence. Above the $T_t$, we propose that the phase transition and the desolvation of ELP chains drive a second stage in the self-assembly of all FAMEs, and raising the temperature further drives a third stage for M-$B_2$-ELP and M-$B_2$ELP that is marked by the appearance of macroscopic self-assembled objects.

Example 7

Figure 30:
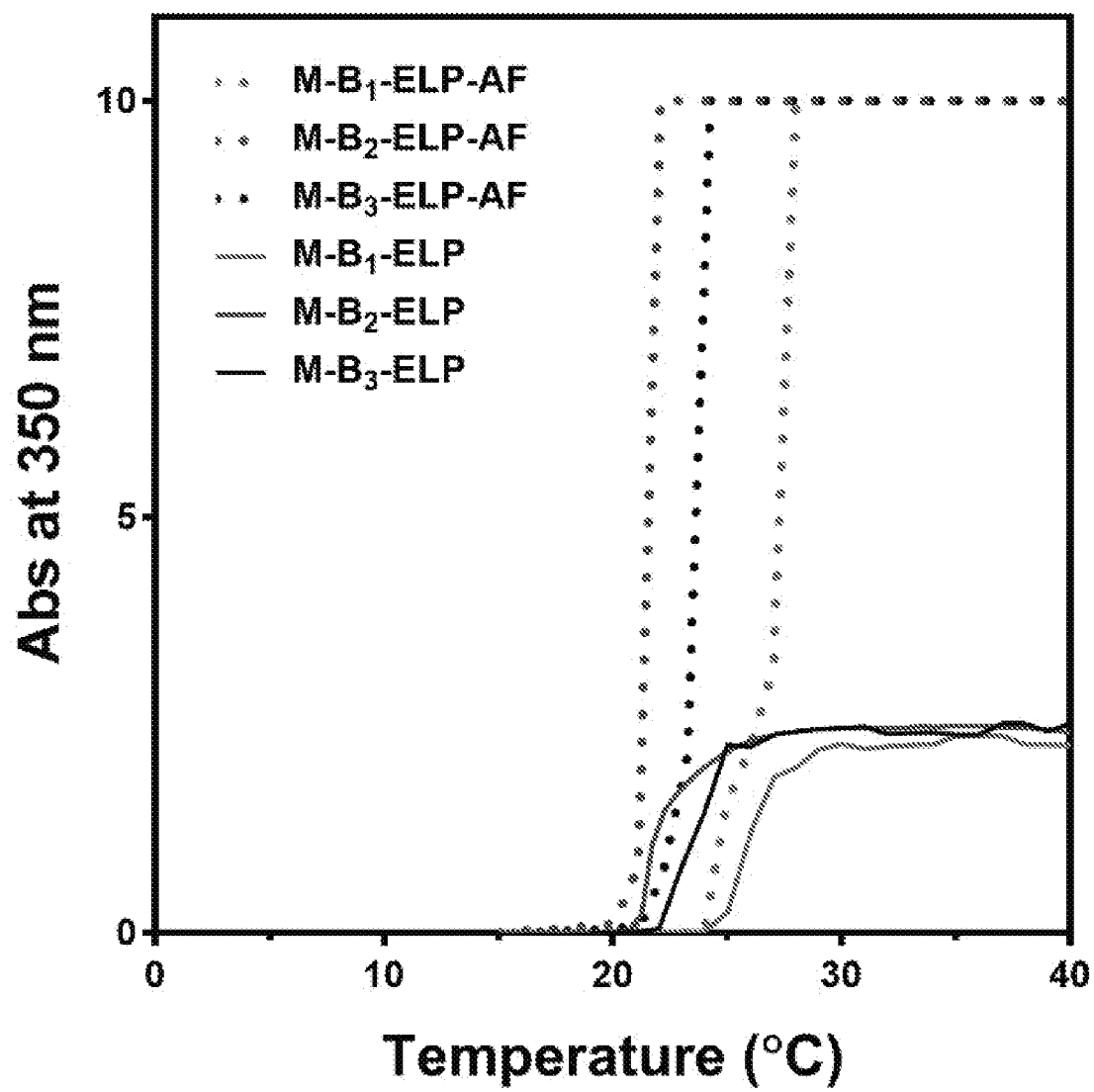
FIG. 30. Temperature-programmed turbidimetry assay demonstrates that labeling with Alexa Fluor 488 does not change the phase transition of ELPs. The higher absorbance of the labeled samples (M-$B_{1-3}$-ELP-AF) is due to the smaller size of the chamber window in the microcuvettes used. Each construct was prepared at 100 μM.

We next turned our attention to structural characterization of these self-assembled FAMEs at increasing levels of spatial resolution to elucidate their morphology. We began with fluorescence microscopy to visualize the phase transition and self-assembly of the FAMEs in monodisperse, well-defined droplets at micron-level resolution. We chose this system because it prevents the coalescence of aggregates beyond the well-defined boundaries of each micron-scale droplet, which is ideal for studying the morphogenesis of structures at the micro-scale. To visualize the self-assembled structures, we genetically encoded a Lys residue at the C-terminus of the M-$B_{1-3}$-ELP constructs to enable labeling with Alexa Fluor® 488 dye. The turbidity profile of each labeled FAME was identical to their parent sequences, indicating that the addition of a Lys and a fluorophore at a position distant from the recognition sequence does not perturb the self-assembly process (FIG. 30). We then used a microfluidic device to form water-in-oil emulsions containing each FAME at a concentration of 100 μM (FIG. 4). The structural evolution of each construct was then visualized using fluorescence microscopy while increasing the temperature from 10° C. to 50° C. at the rate of 1° C./min.

Figure 4A:
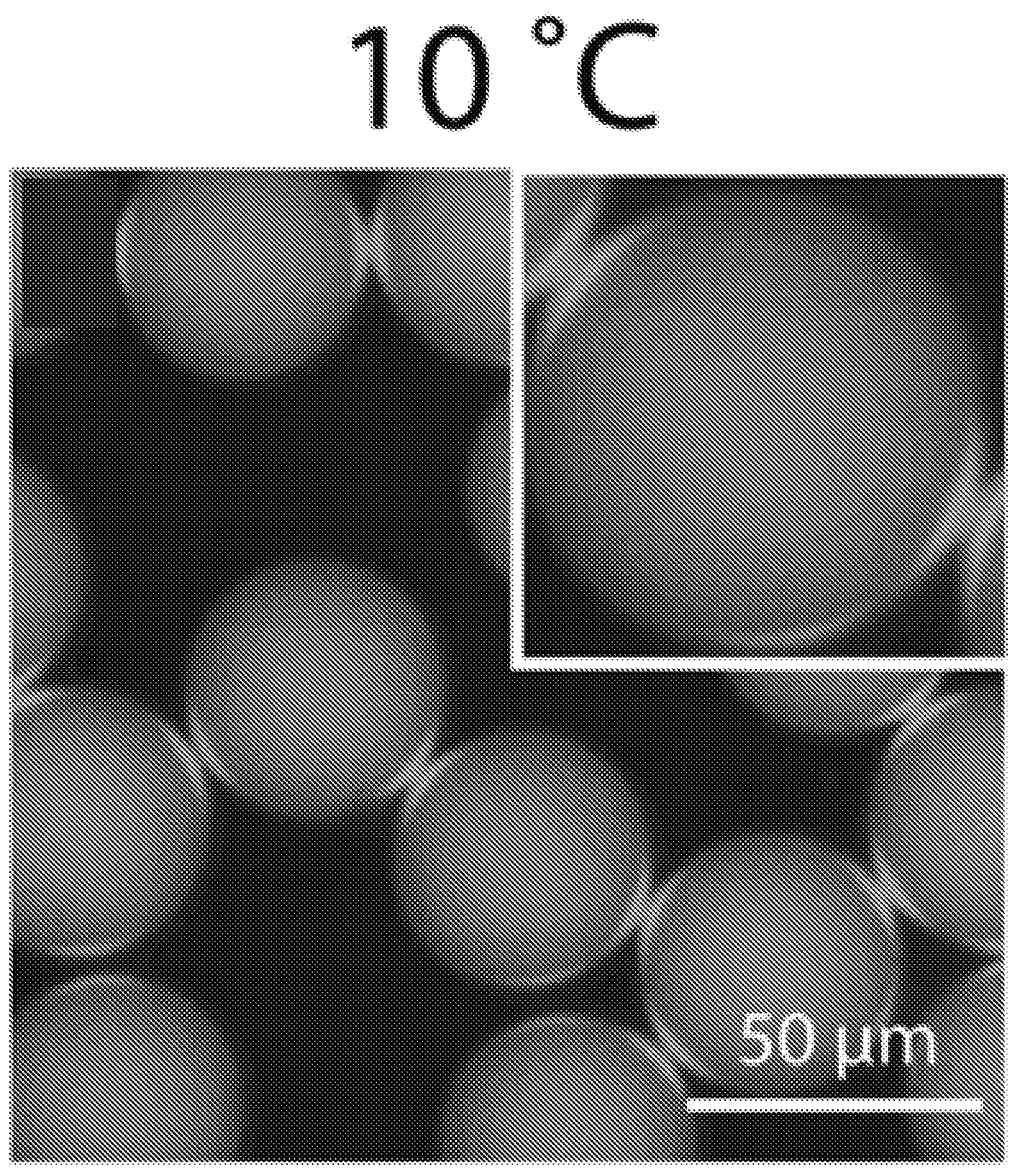
FIG. 4A-I. Visualization of temperature-triggered phase transition and self-assembly of FAMEs using fluorescence microscopy.
Figure 4B:
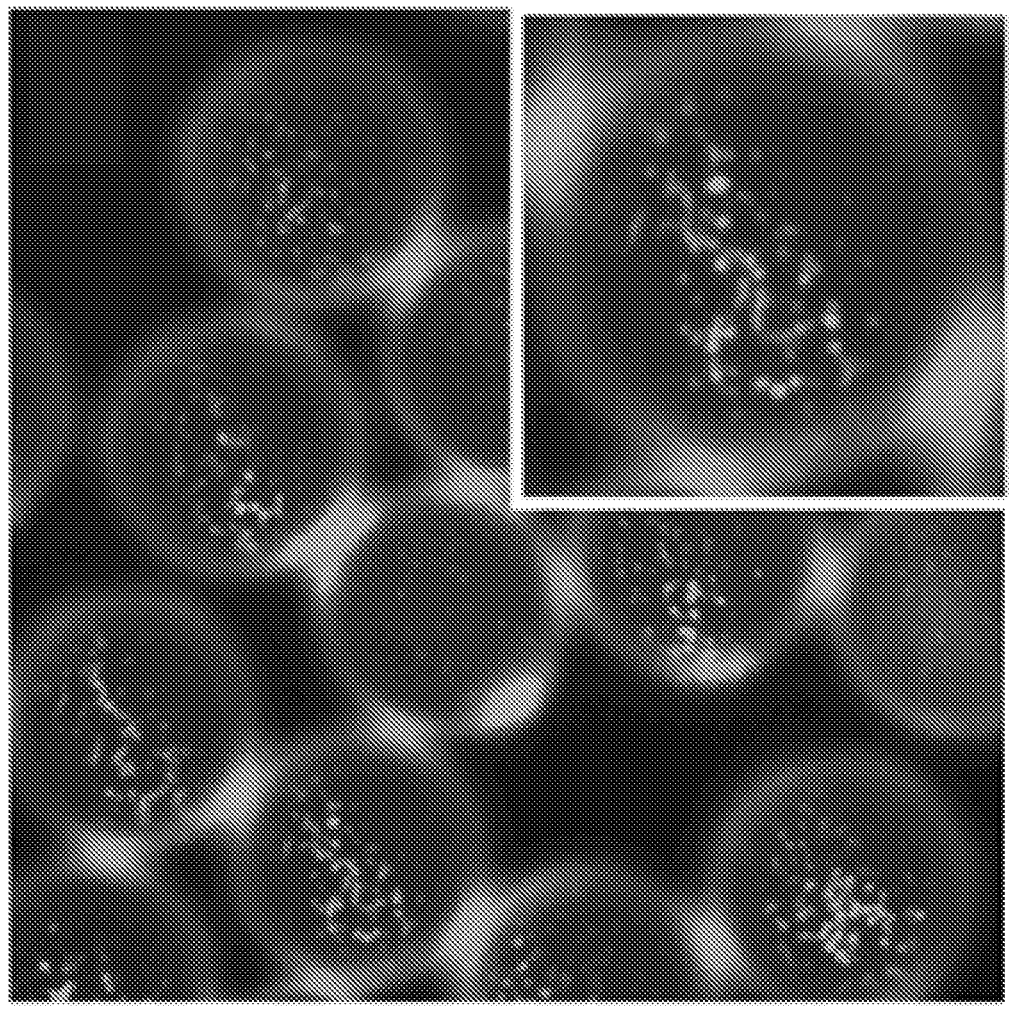
Figure 4C:
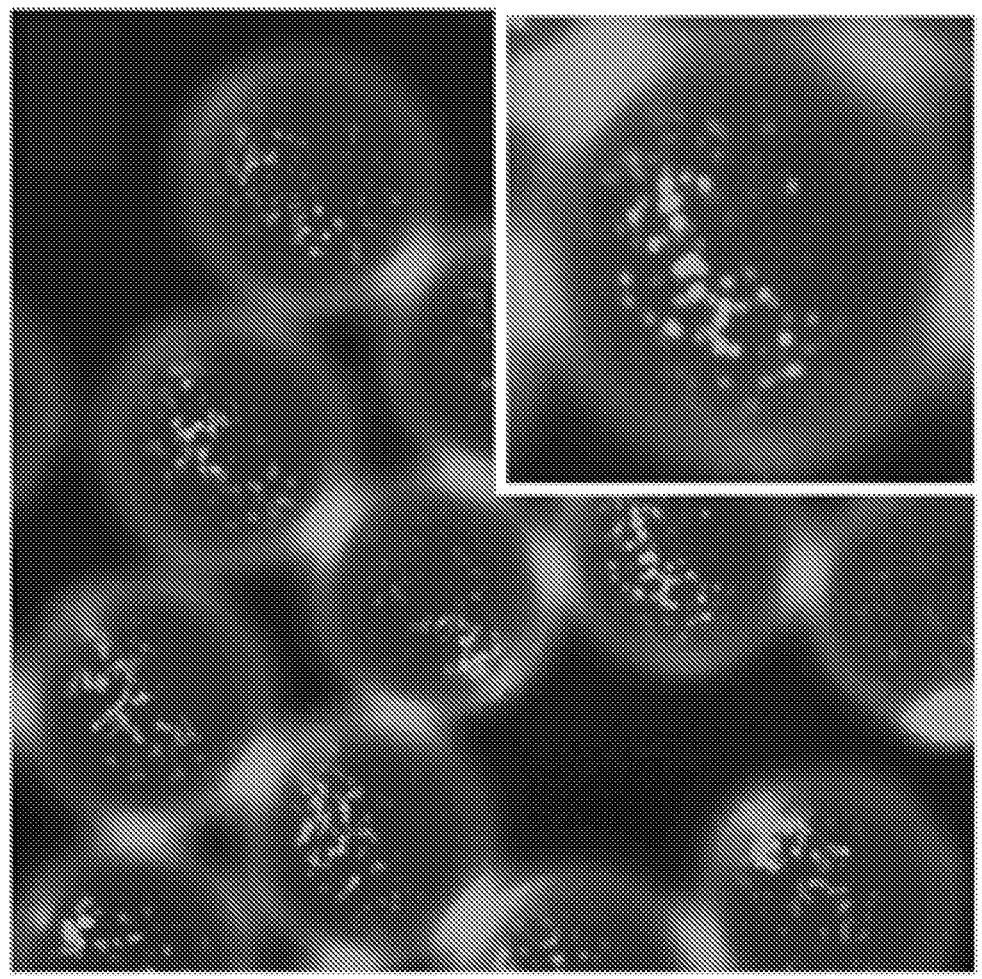
Figure 4D:
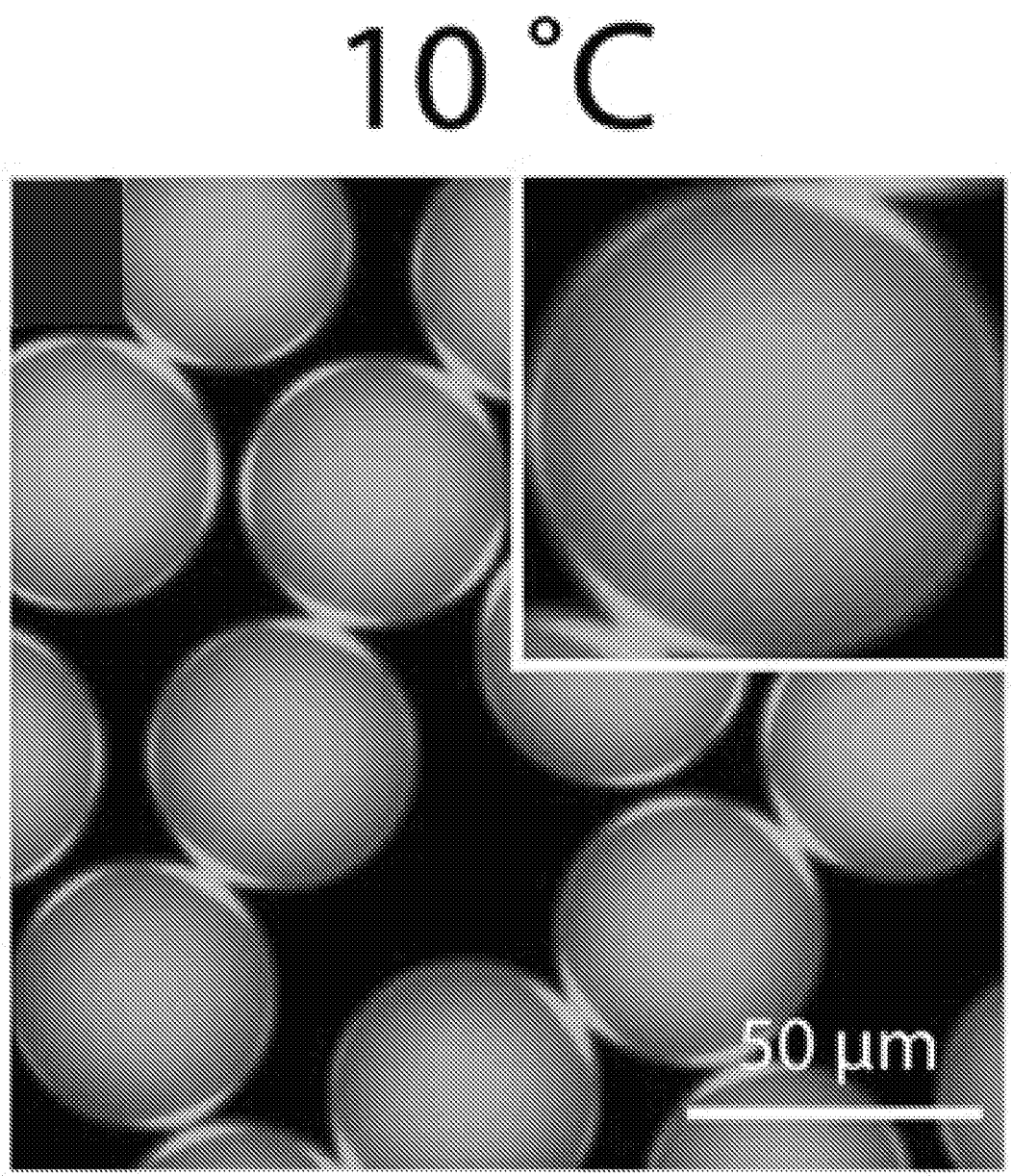
Figure 4E:
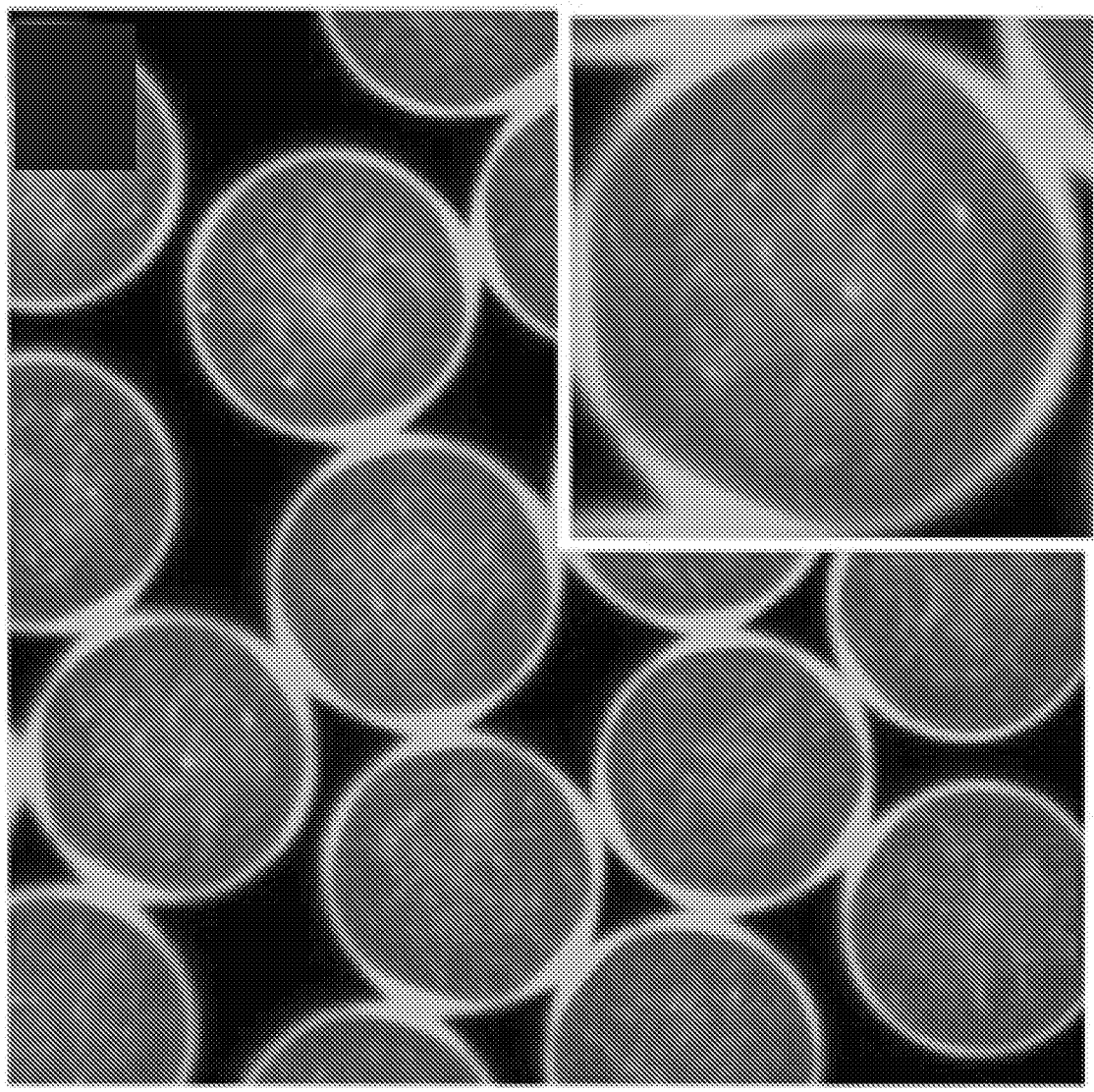
Figure 4F:
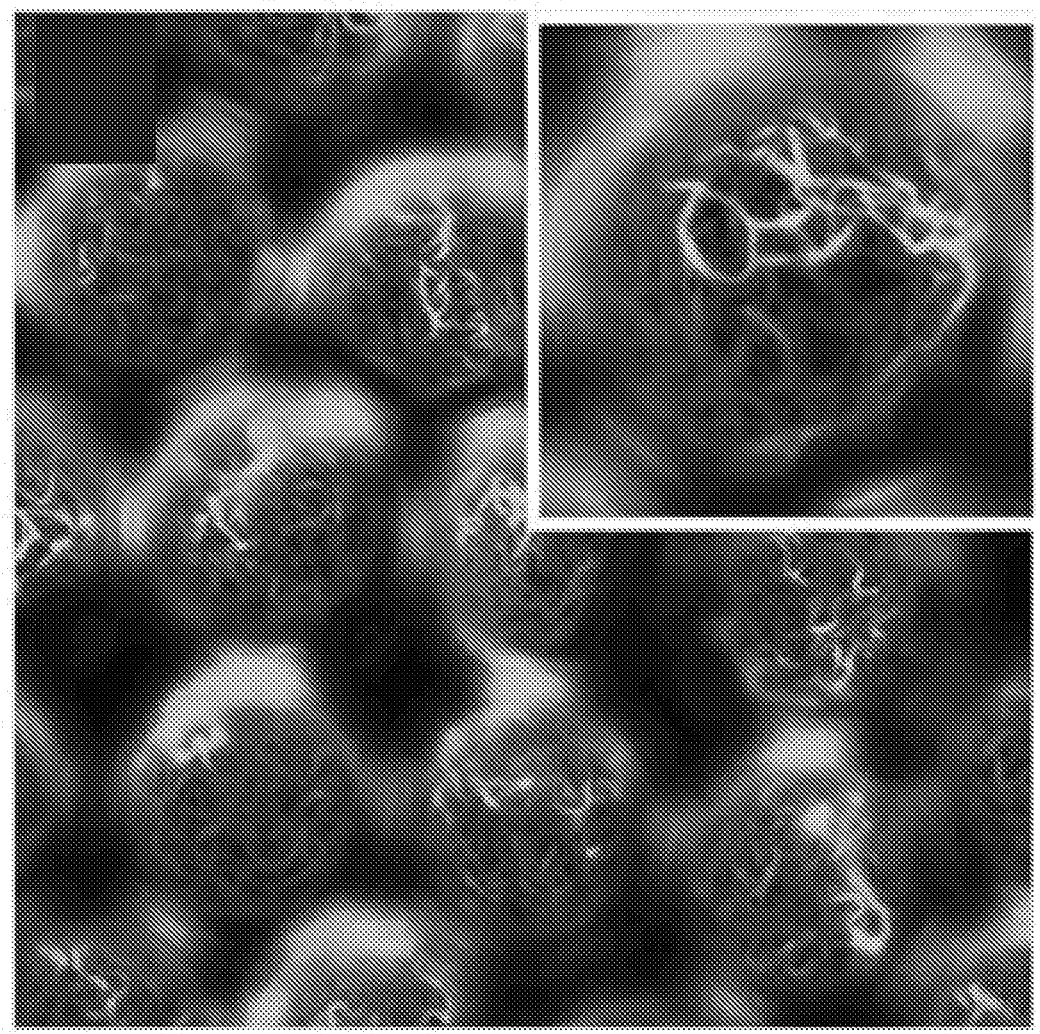
Figure 4G:
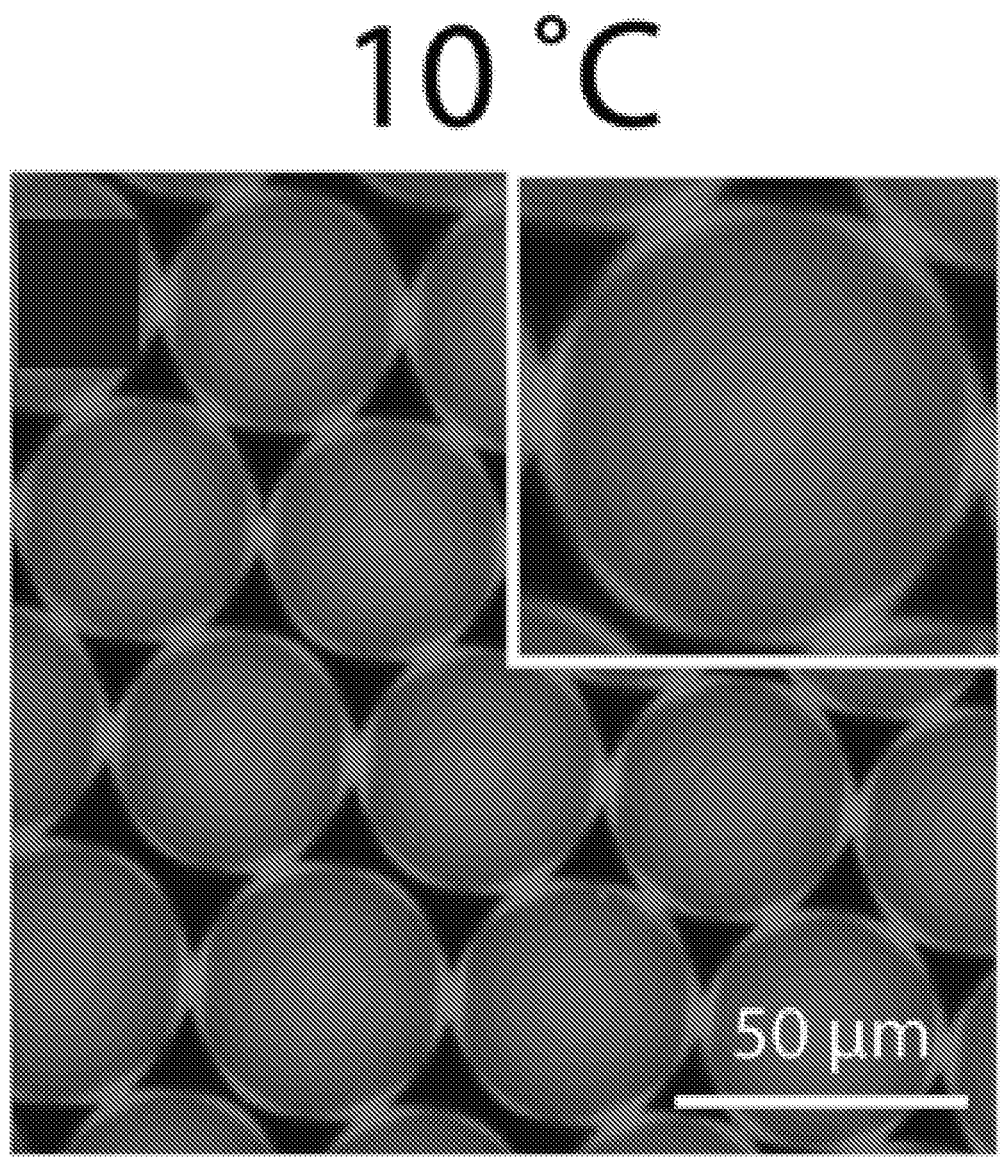
Figure 4H:
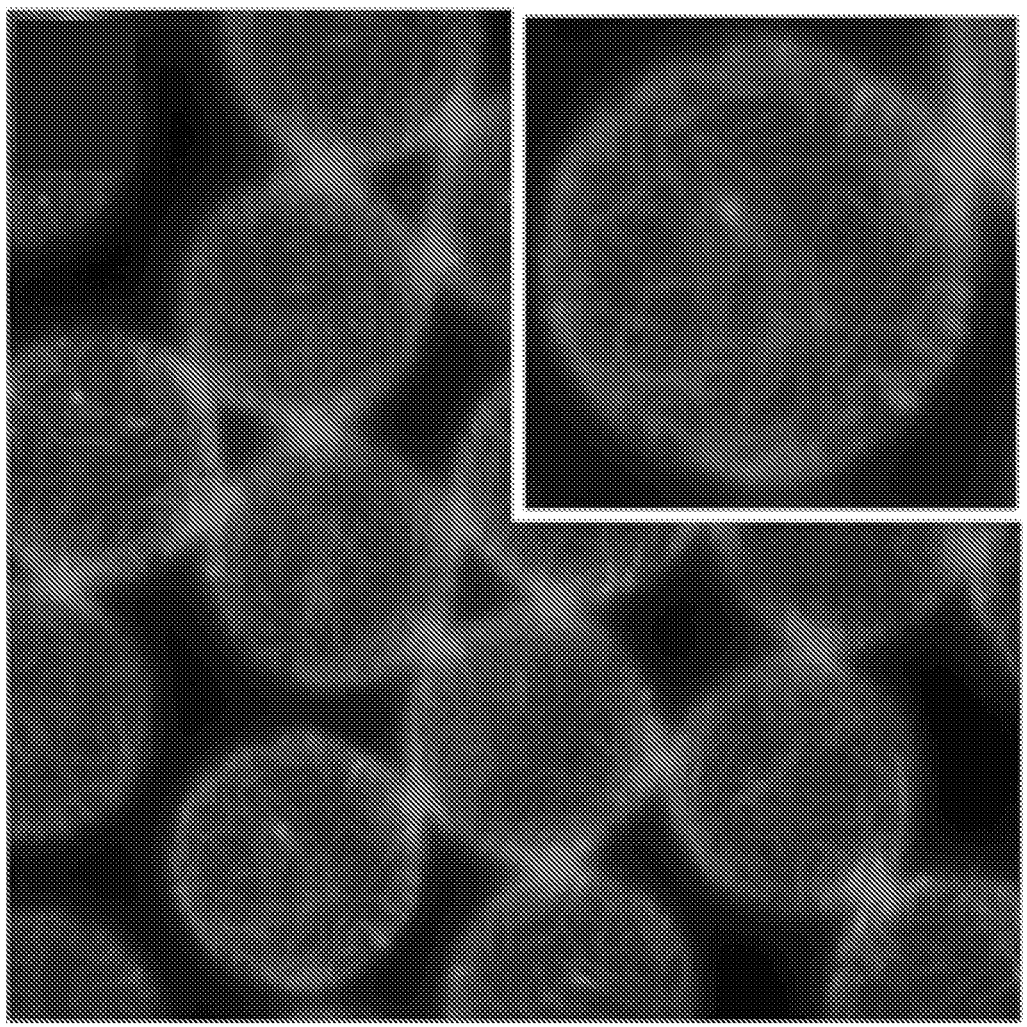
Figure 4I:
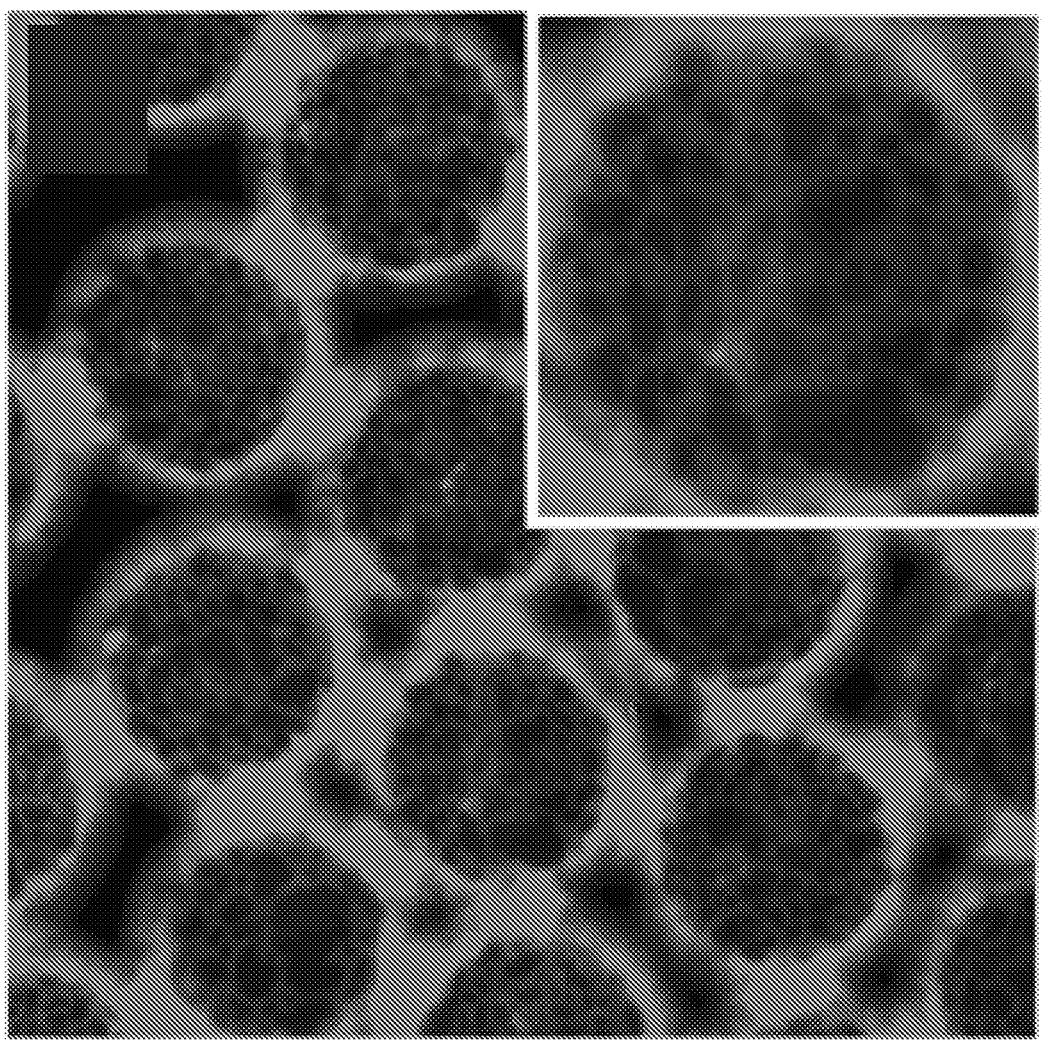
Figure 37A:
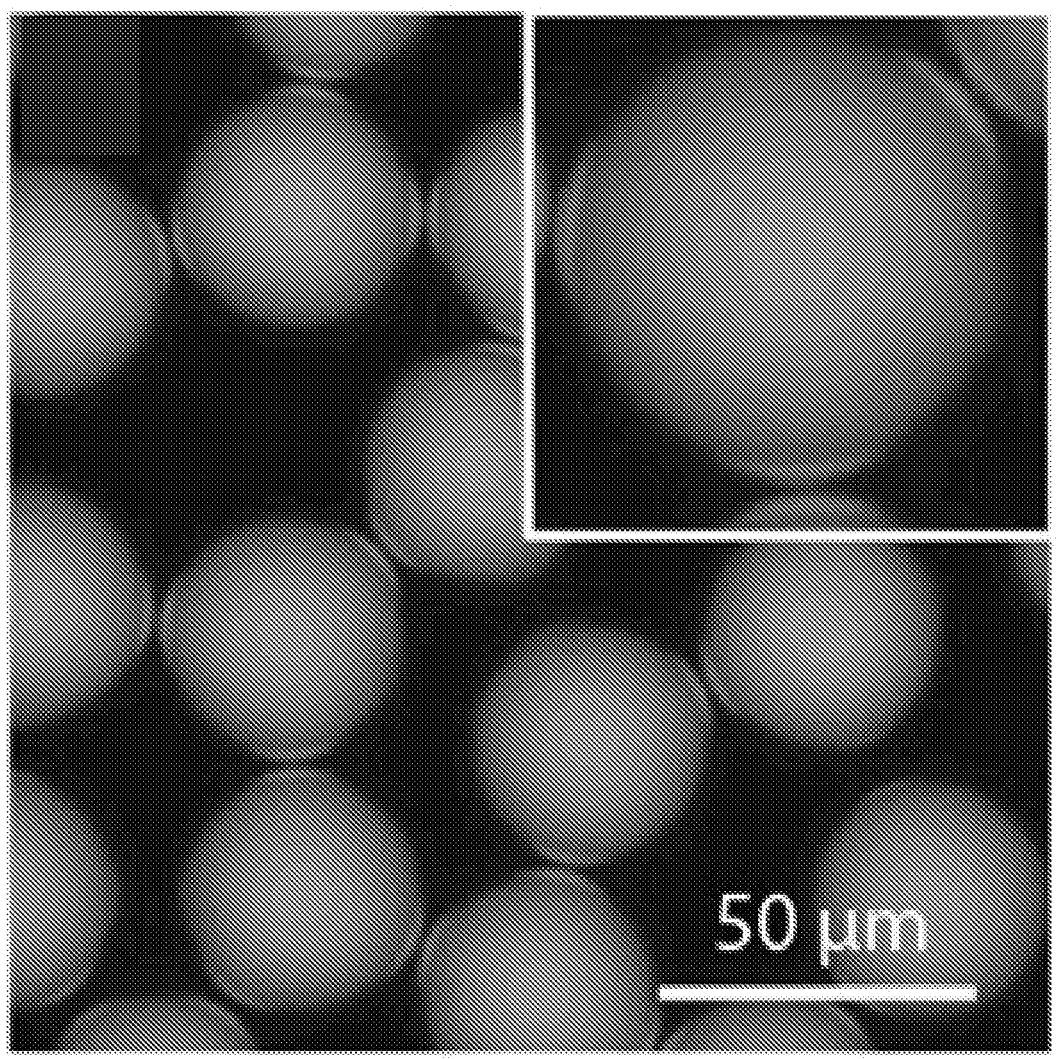
FIG. 37A-C. Visualization of temperature-triggered phase transition and self-assembly of canonical ELP using fluorescence microscopy.
Figure 37B:
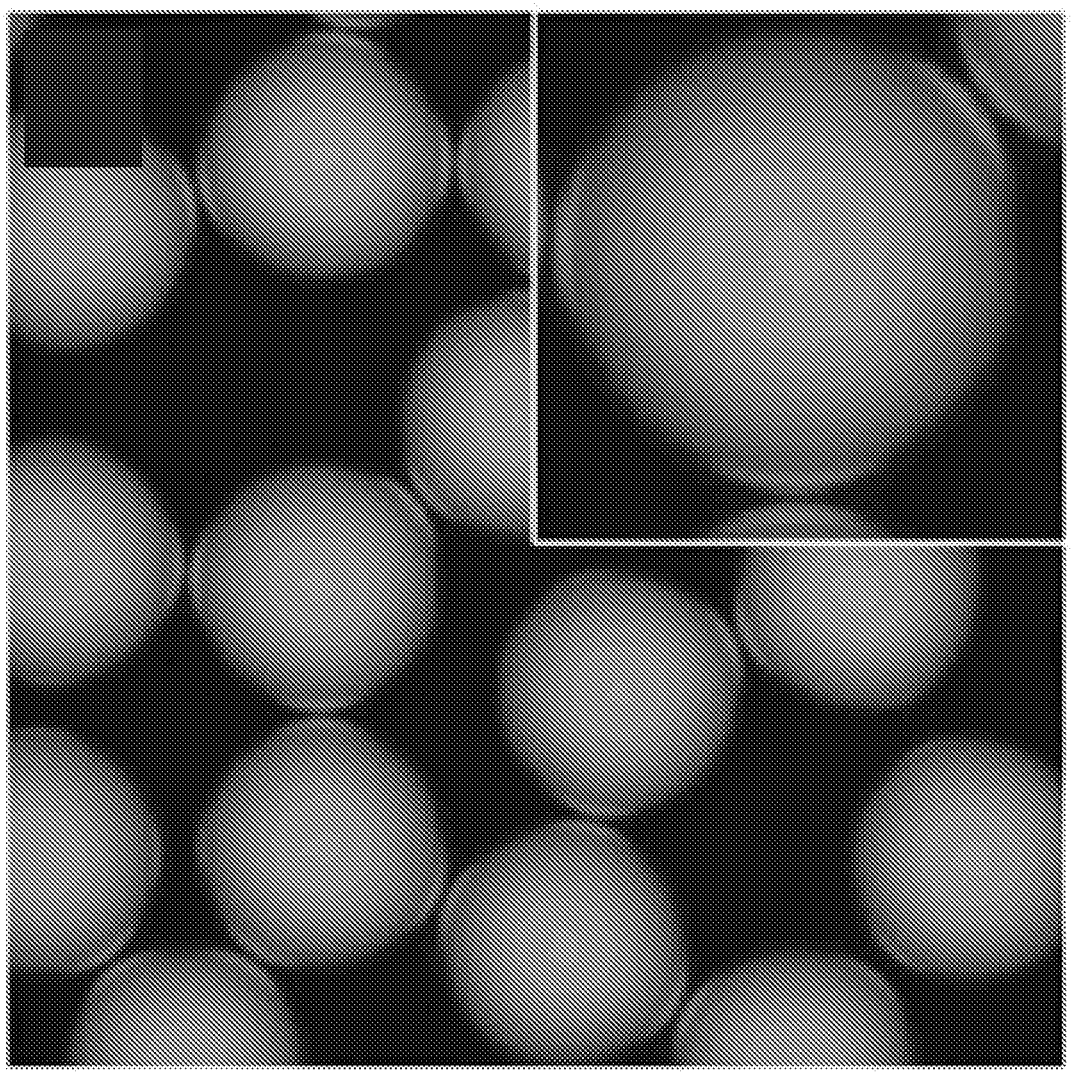
Figure 37C:
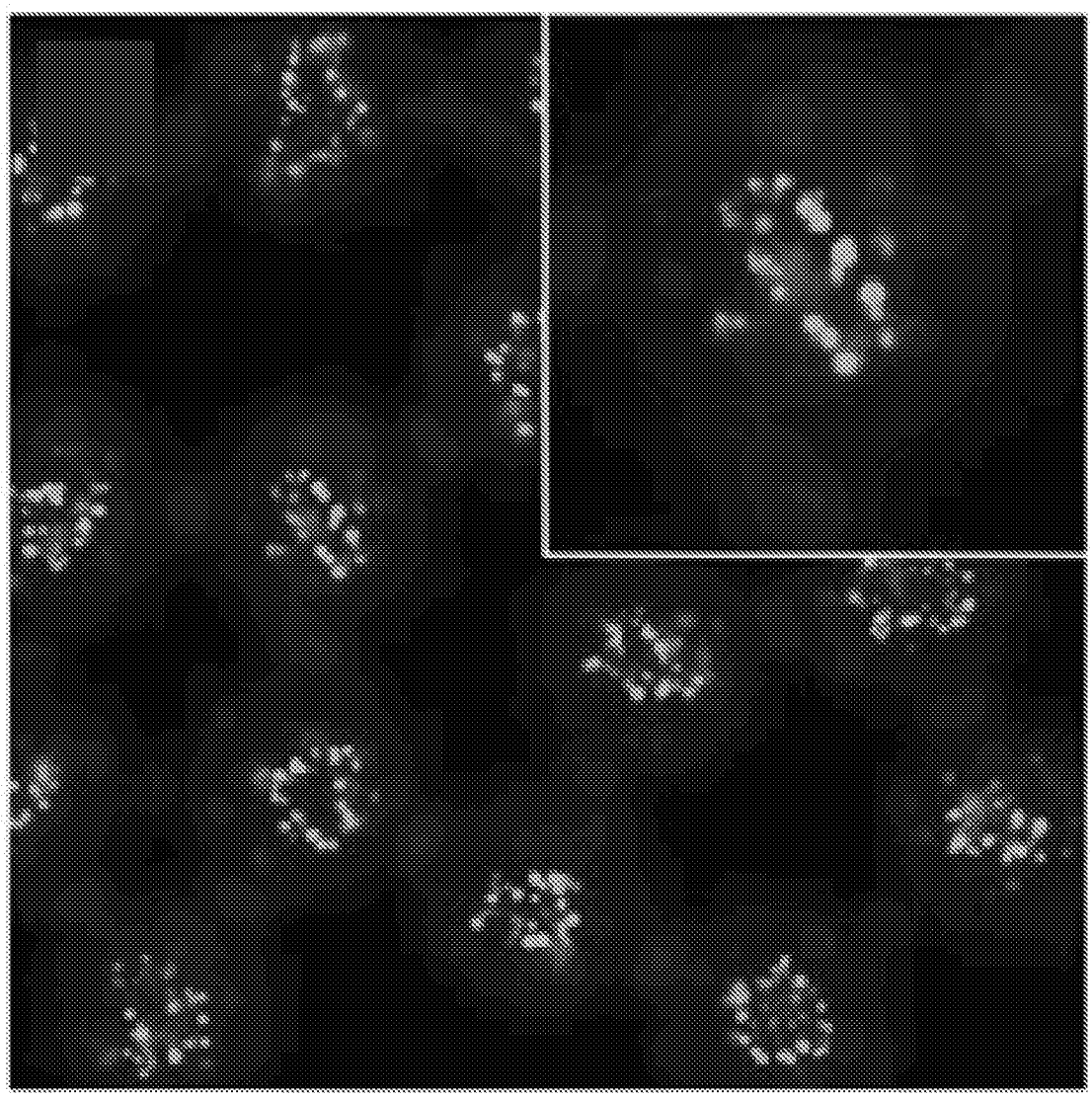

At lower temperatures (10° C.), a homogenous fluorescent signal was detected across each droplet (FIG. 4A, FIG. 4D, and FIG. 4G), suggesting that each population of FAMEs exists as a nanoscale assembly below the diffraction limit, which is consistent with DLS data (FIG. 2A). However, the N-terminal PA-like domain significantly altered the morphogenesis of aggregates at higher temperatures. Above the $T_t$, M-$B_1$-ELP, which features the recognition sequence with the lowest propensity to form β-sheets, formed spherical liquid coacervates (FIG. 4B) that resemble canonical ELPs (FIG. 37). These liquid coacervates remained stable at higher temperatures (up to 50° C., FIG. 4C) and were reversibly dissolved as the temperature was reduced below the $T_t$, further demonstrating their similarity to canonical ELPs. At intermediate temperatures (30° C.), M-$B_2$-ELP transitioned into an entangled network of small fibers (FIG. 4E), with no obvious long-range order. However, as the temperature was increased to 50° C., these shorter fibers coalesced to form longer fibers that stack together and exhibit order at the microscale (FIG. 4F). The resulting fibrillar network underwent compaction at higher temperature (50° C.), but fiber stacking and microscale assembly was not observed (FIG. 4I), which we postulate could be due to the kinetic entrapment of such long fibers. These results confirm that M-$B_2$ELP and M-$B_3$-ELP undergo three distinct stages in their hierarchical-self-assembly that drive the formation of large macroscopic objects, consistent with the results of the ThT assays, while M-$B_1$-ELP does not undergo a final maturation step above its $T_t$, resulting in structures that remain trapped in the nanoscale size regime.

Example 8

To dissect the morphology of these hierarchical self-assembled structures on a smaller length scale than fluorescence microscopy, we next turned to cryogenic transmission electron microscopy (cryo-TEM). Cryo-TEM enables imaging of these materials in their near-native hydrated state with nanometer spatial resolution (FIG. 5).

Figure 5A:
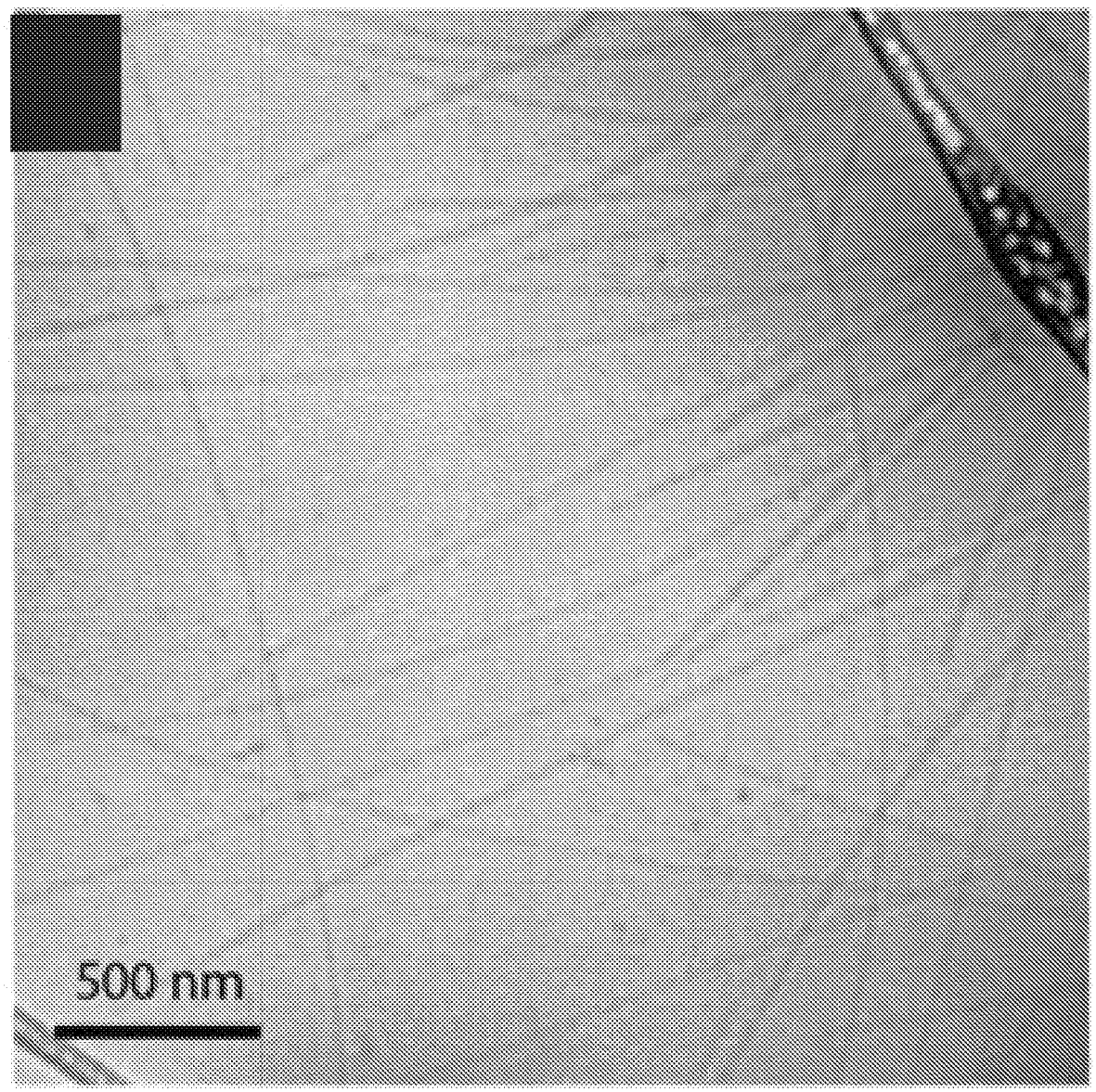
FIG. 5A-F. Cryogenic transmission electron microscopy (cryo-TEM) of the self-assembled constructs above $T_t$ of FAMEs. Cryo-TEM of control PAs, including
Figure 5B:
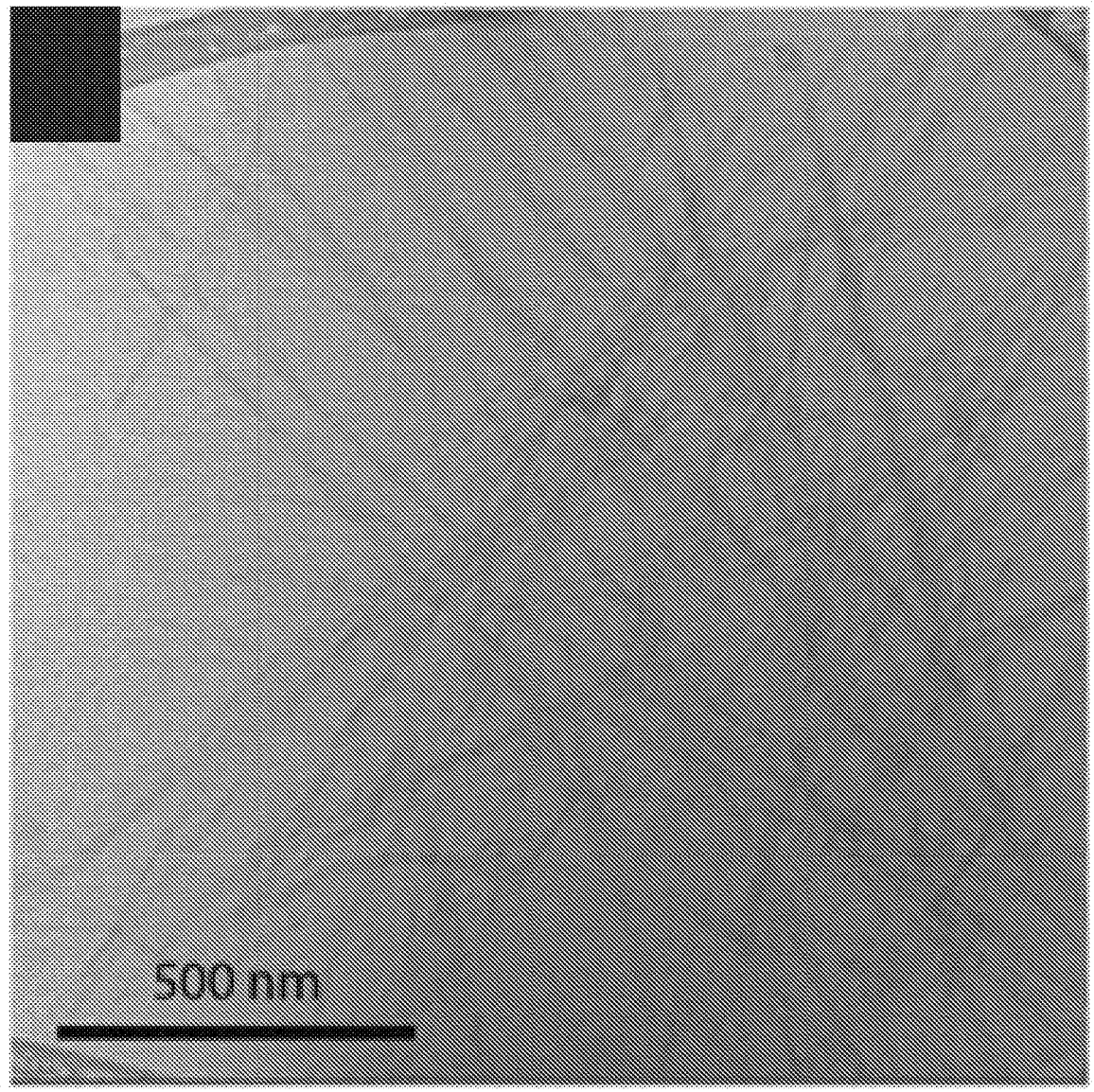
Figure 5C:
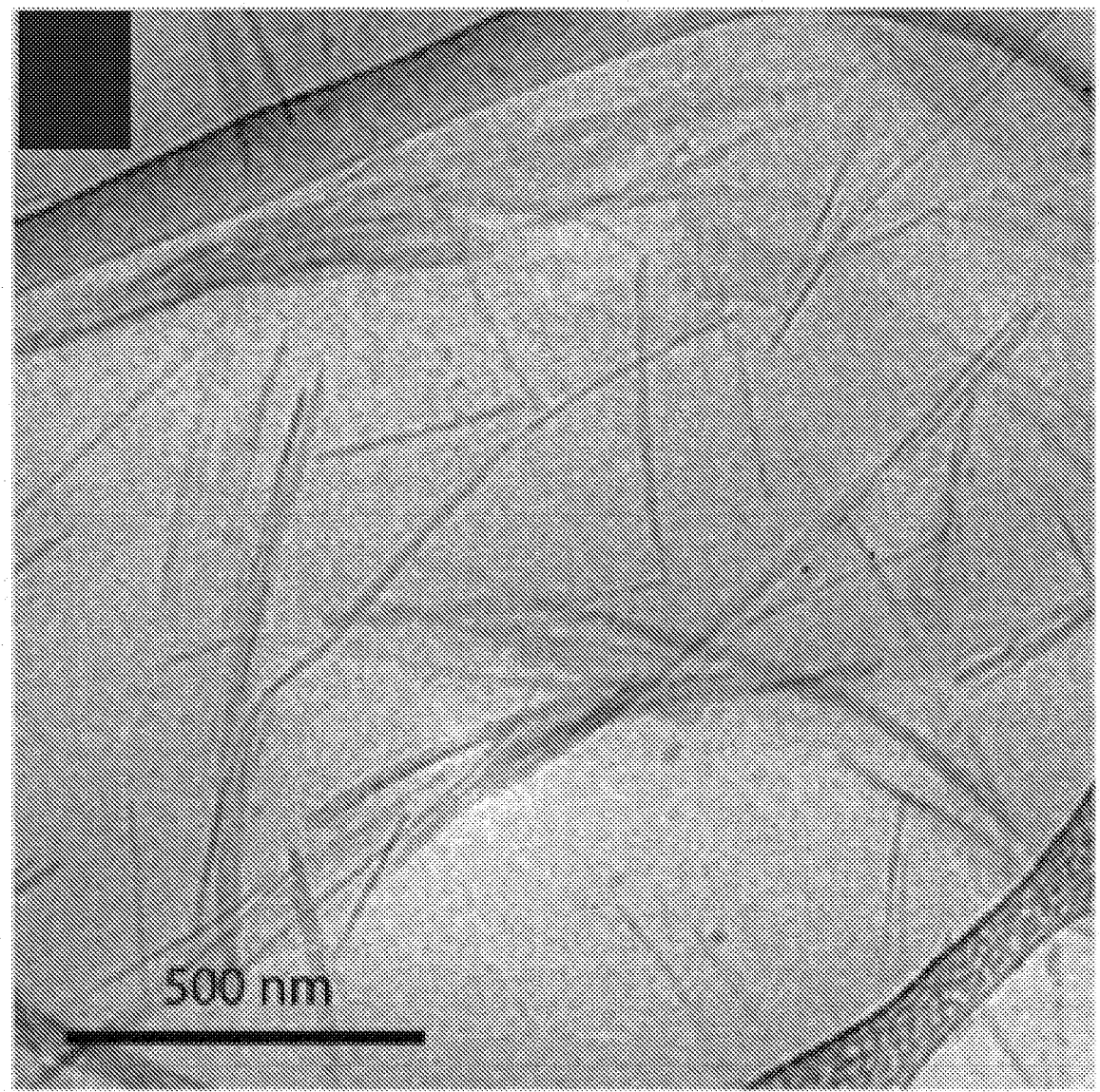
Figure 5D:
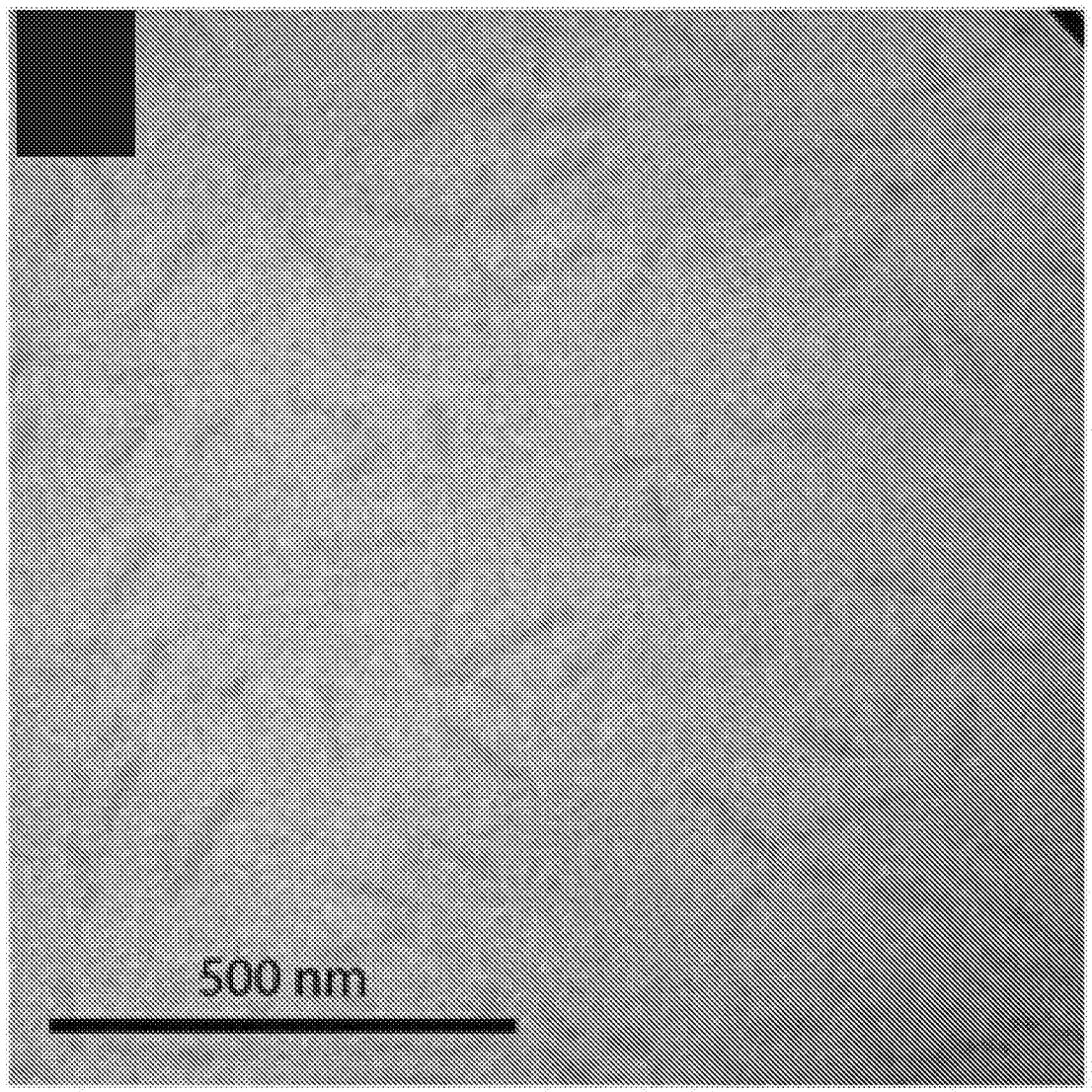
Figure 5E:
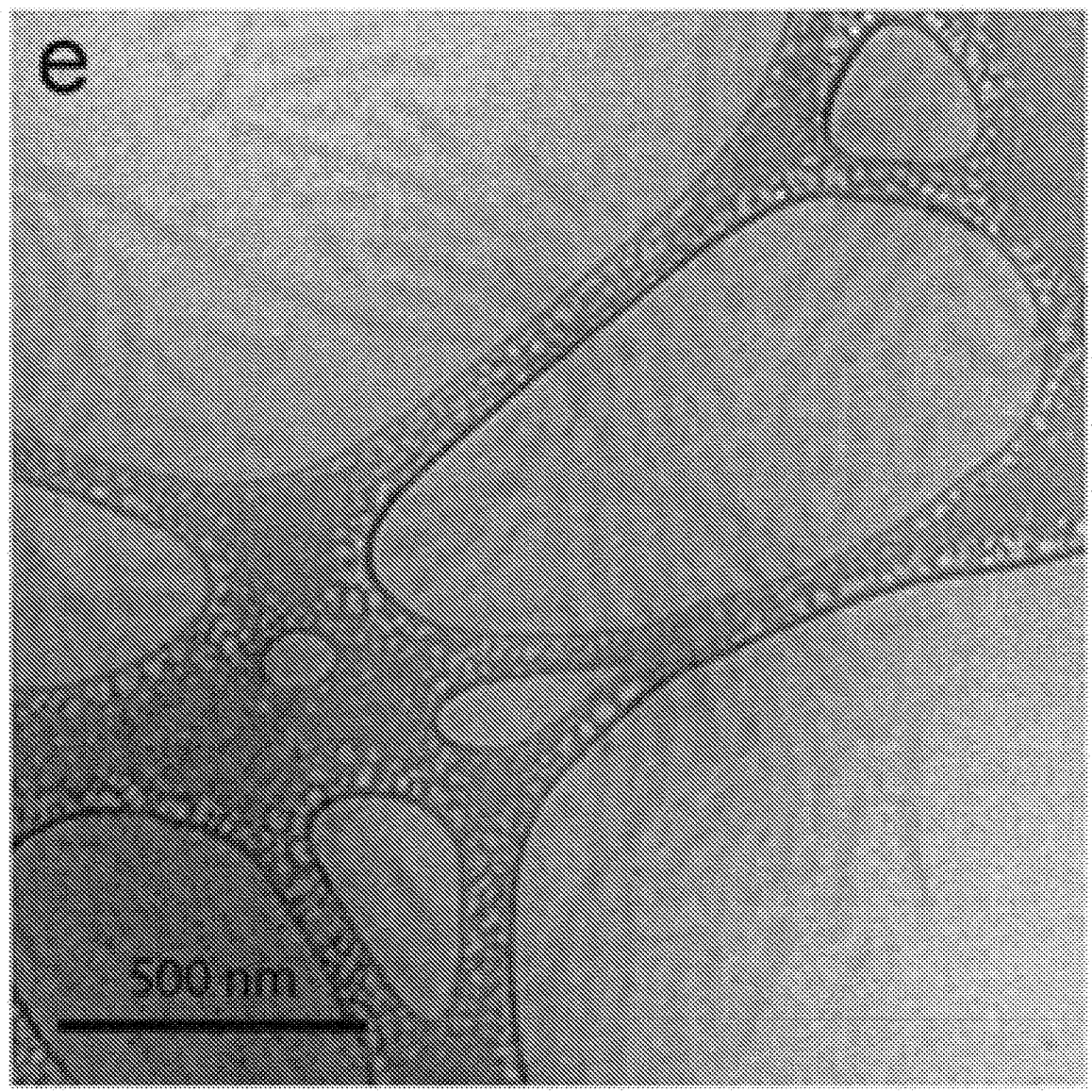
Figure 5F:
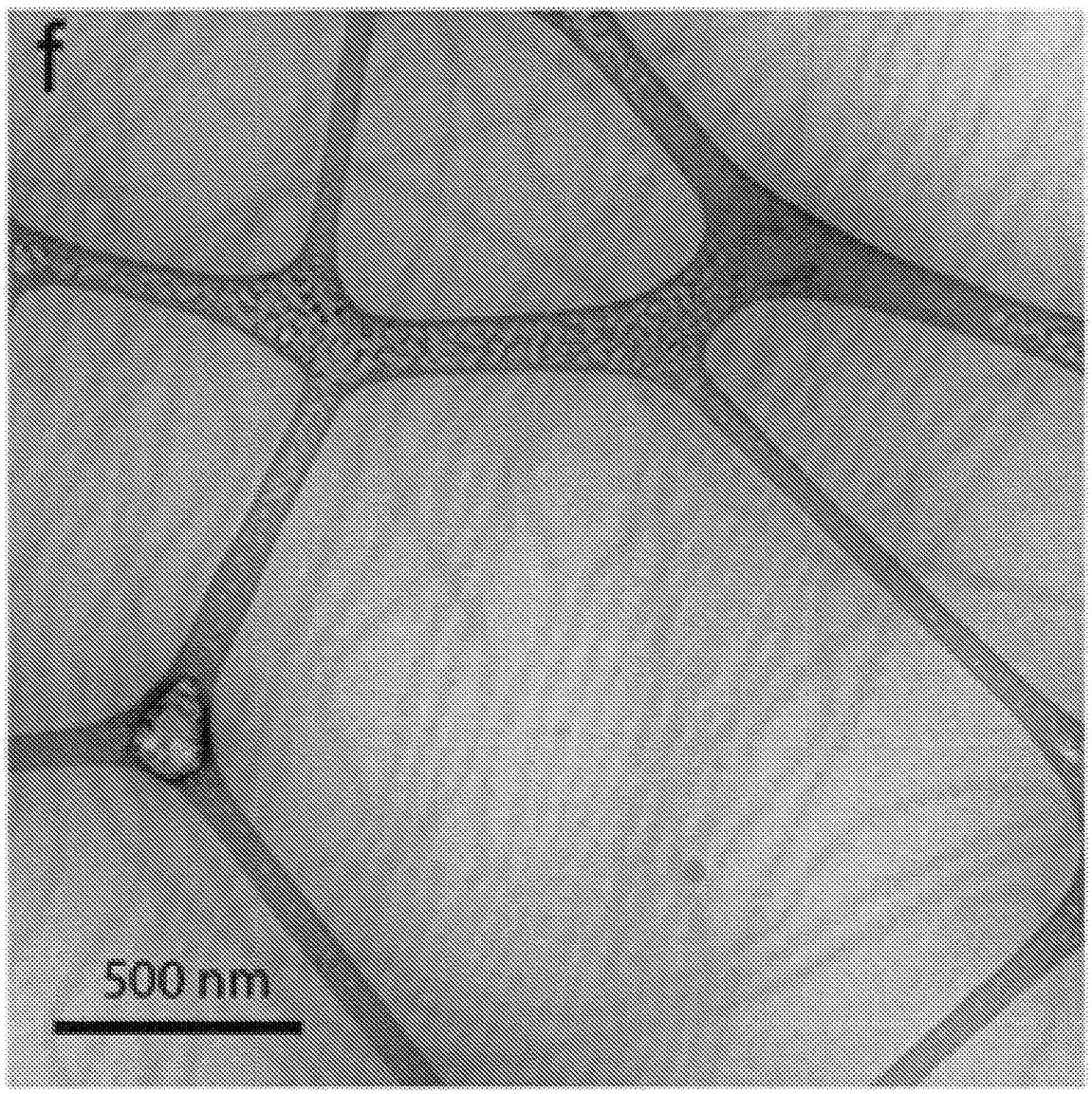
Figure 39:
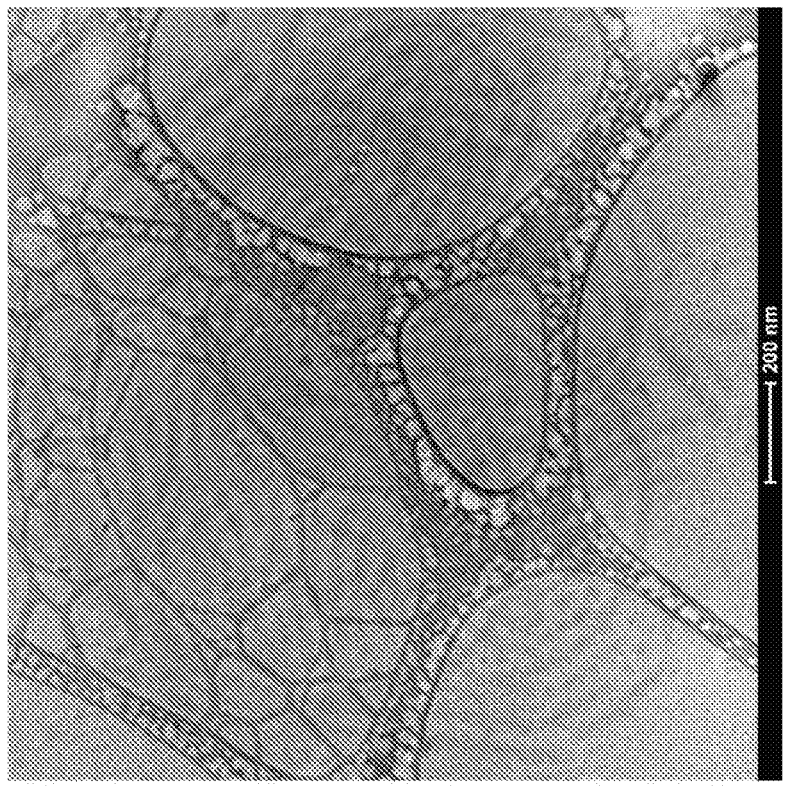
FIG. 39. Cryo-TEM images of self-assembled M-$B_2$-ELP.
Figure 39:
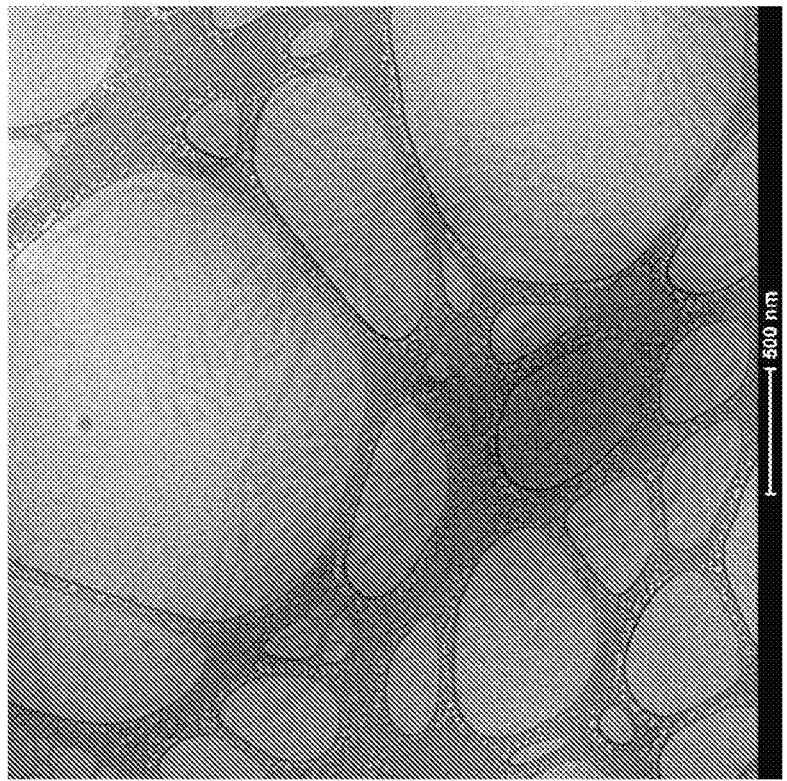
Figure 40:
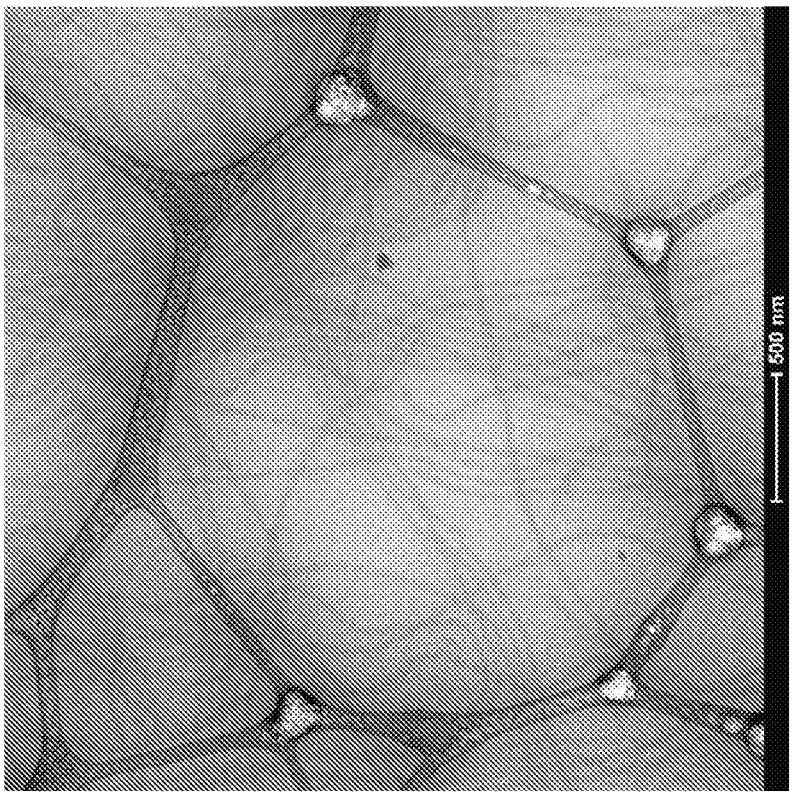
FIG. 40. Cryo-TEM images of self-assembled M-$B_3$-ELP.
Figure 40:
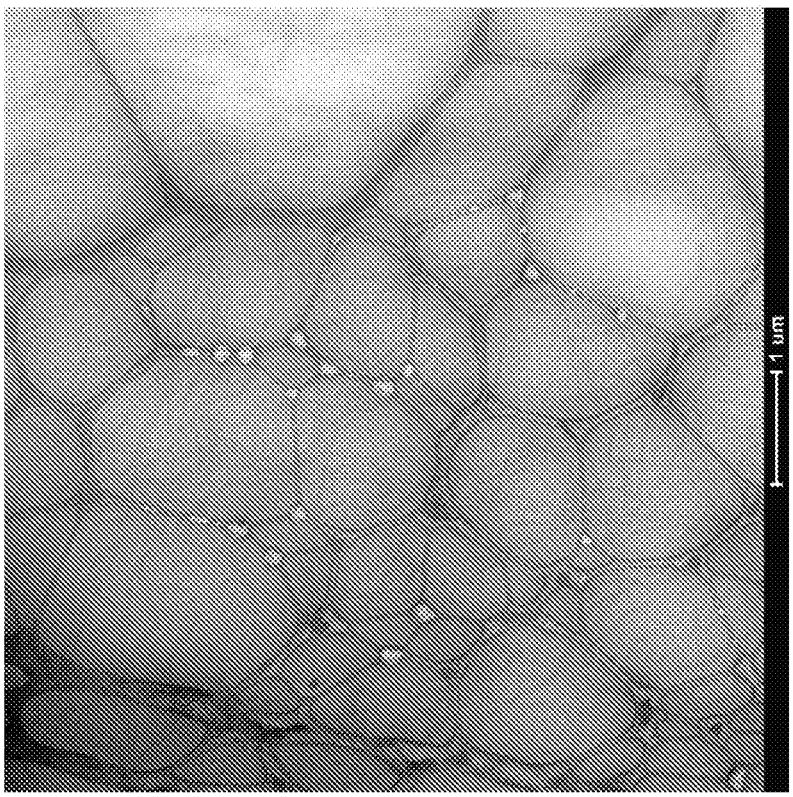

Cryo-TEM imaging confirmed that control PAs (M-$B_{1-3}$) primarily formed thin fibers (diameters equal to 11.8±2.9 nm, 9.7±2.7 nm, and 13.9±0.89 nm, mean±s.e.m., respectively) with large aspect ratios, (FIG. 5A, FIG. 5B, FIG. 5C), consistent with the behavior of previously reported canonical PAs. However, the FAMEs exhibited a diverse range of nanoscale morphologies above the $T_t$ of ELP, which were dependent on the recognition sequence. M-$B_1$-ELP formed cylindrical worm-like aggregates (FIG. 5D, and FIG. 38, width of 11.43±0.53 nm, length of 88.09±5.22 nm). Alternatively, M-$B_2$-ELP showed evidence of an aligned network of fibers (average diameter of 21.00±0.73 nm), comprised of structures approximately twice the width of M-$B_1$-ELP, but with lengths ranging from about 10 nm to 1500 nm (FIG. 5E and FIG. 39). Cryo-TEM of M-$B_3$-ELP shows that incorporation of Leu and Ser residues in the recognition sequence resulted in the formation of an extended network of long fibers (>10 μm, diameter of 22.89±0.68 nm), with alignment evident in some regions (FIG. 5F and FIG. 40). The nanostructures of both M-$B_2$ELP and M-$B_3$-ELP are consistent with the appearance of macroscale aggregates upon heating in the turbidity and droplet experiments (FIG. 2 and FIG. 4).

ELPs are difficult to visualize in cryo-TEM due to poor electron contrast resulting from their high water content. Therefore, the observed structures are likely reflective of the dehydrated core of the FAME assemblies, which consists of the PA-domain. The hydrated ELP corona (not seen in cryo-TEM) surrounds the M-$B_{1-3}$ core and prevents further assembly at lower temperatures (T<$T_t$). We did not observe major differences in the nanoscale morphology of the aggregates below versus above the T using cryo-TEM (structures with similar widths were observed at $T_c$>T>$T_t$), although the cross-section of larger scale M-$B_2$-ELP and M-$B_3$-ELP assemblies was visible as a shadow of dehydrated PA-domains on the TEM grid.

Example 9

Figure 41A:
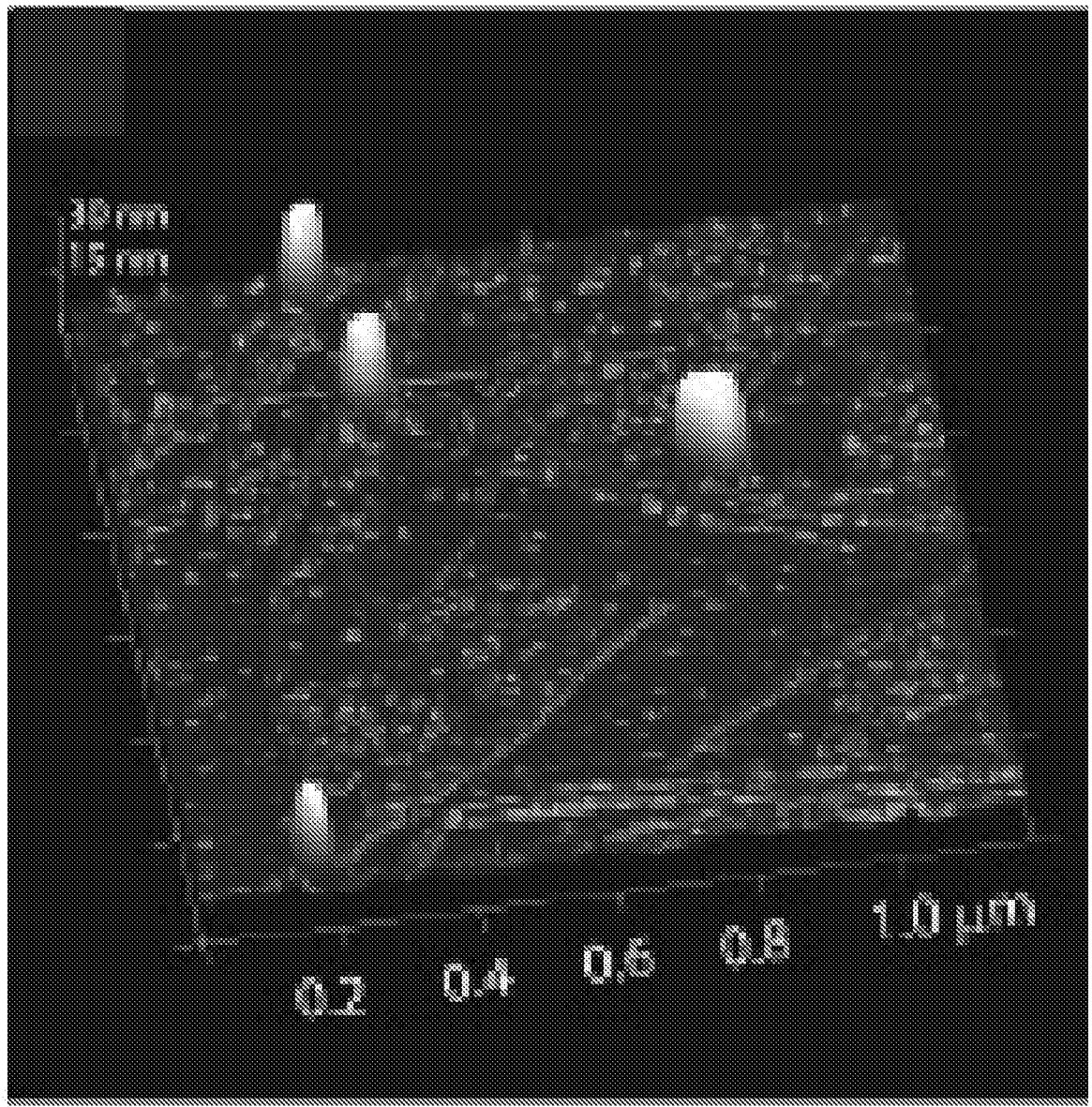
FIG. 41A-I. Scanning force microscopy (SFM) characterization of the topography of constructs.
Figure 41B:
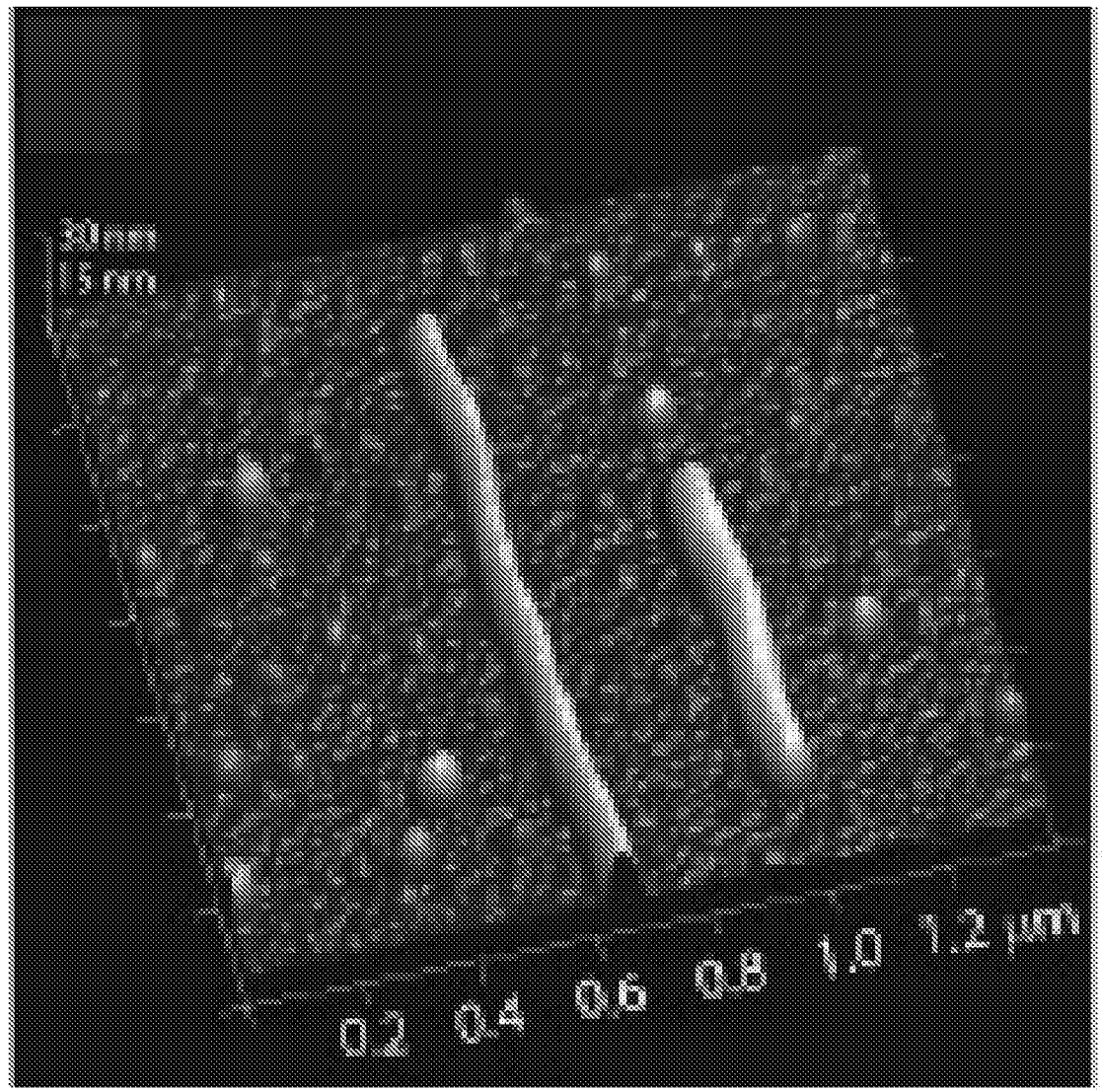
Figure 41C:
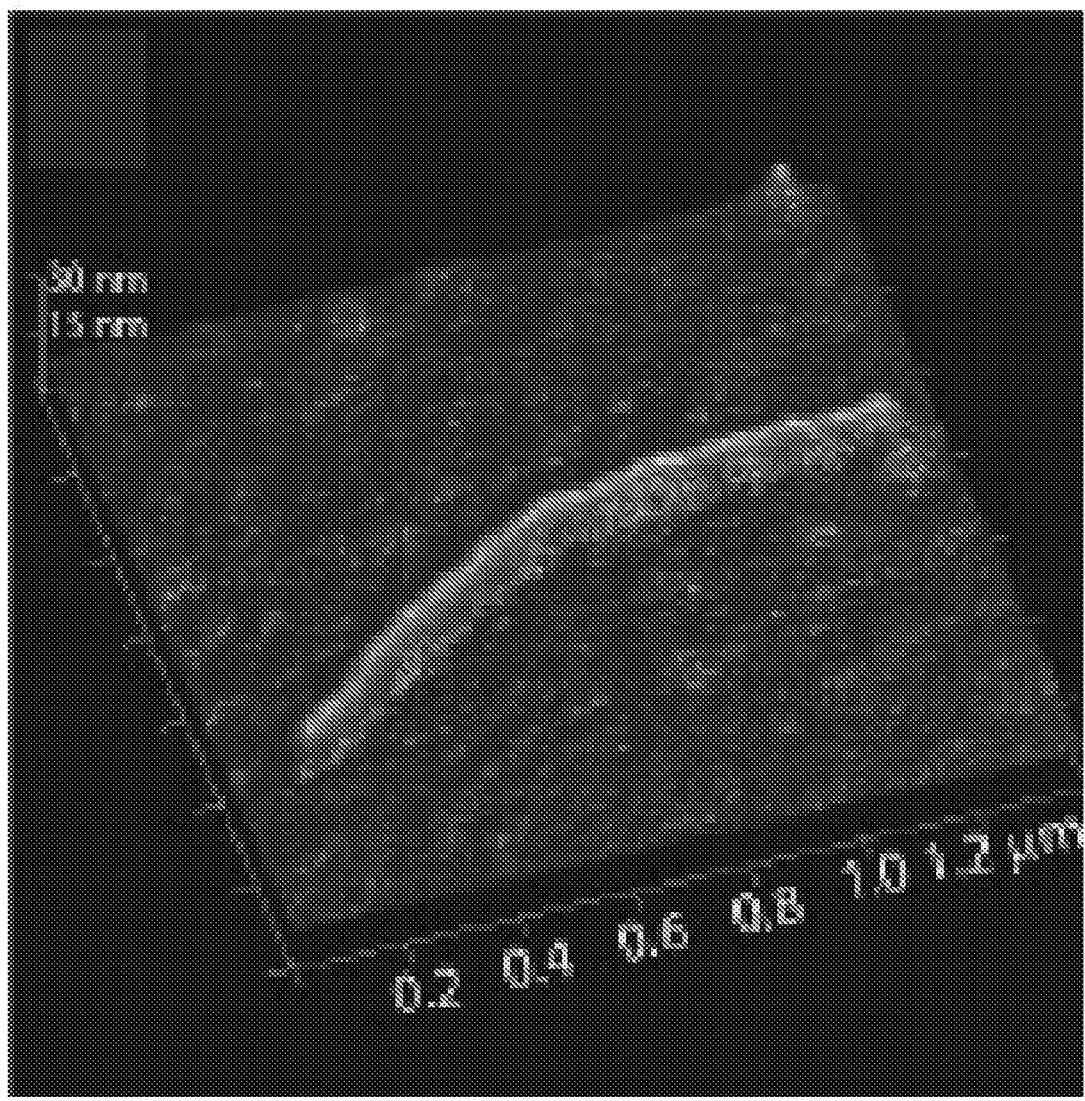

Next, scanning force microscopy (SFM) was used to visualize the nanoscale morphology of the aggregates at 30° C. ($T_c$>T>$T_t$, stage 2). The topography showed rod-like structures for M-$B_2$-ELP and M-$B_3$-ELP that consist of a PA-core and an ELP-corona (FIG. 41A-C). Mapping the mechanical response of all three FAMEs by SFM confirmed a structure composed of a stiffer core surrounded by a softer corona. On the mica surface, M-$B_1$-ELP (FIG. 41A) formed small spherical aggregates and no rods were observed, although it is possible that these smaller structures are caused by surface-induced aggregation. In contrast, M-B$_2$-ELP (FIG. 41B) primarily formed elongated fibers (10-20 nm in height, length >1 μm), although a sub-population of spherical aggregates were also visible. M-B$_3$-ELP (FIG. 41C) formed elongated fibers (6-10 nm in height, length >1 μm).

Figure 41D:
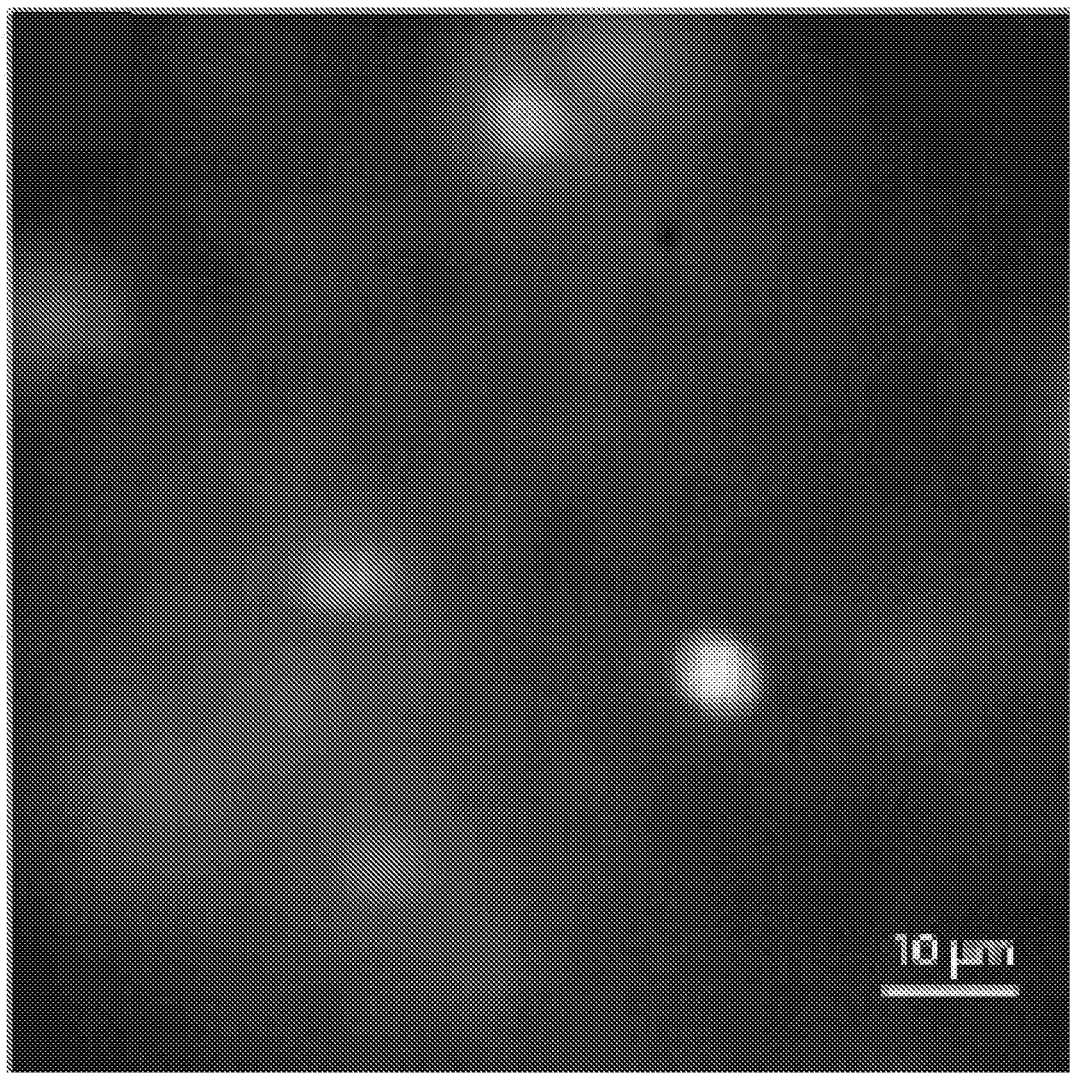
Figure 41E:
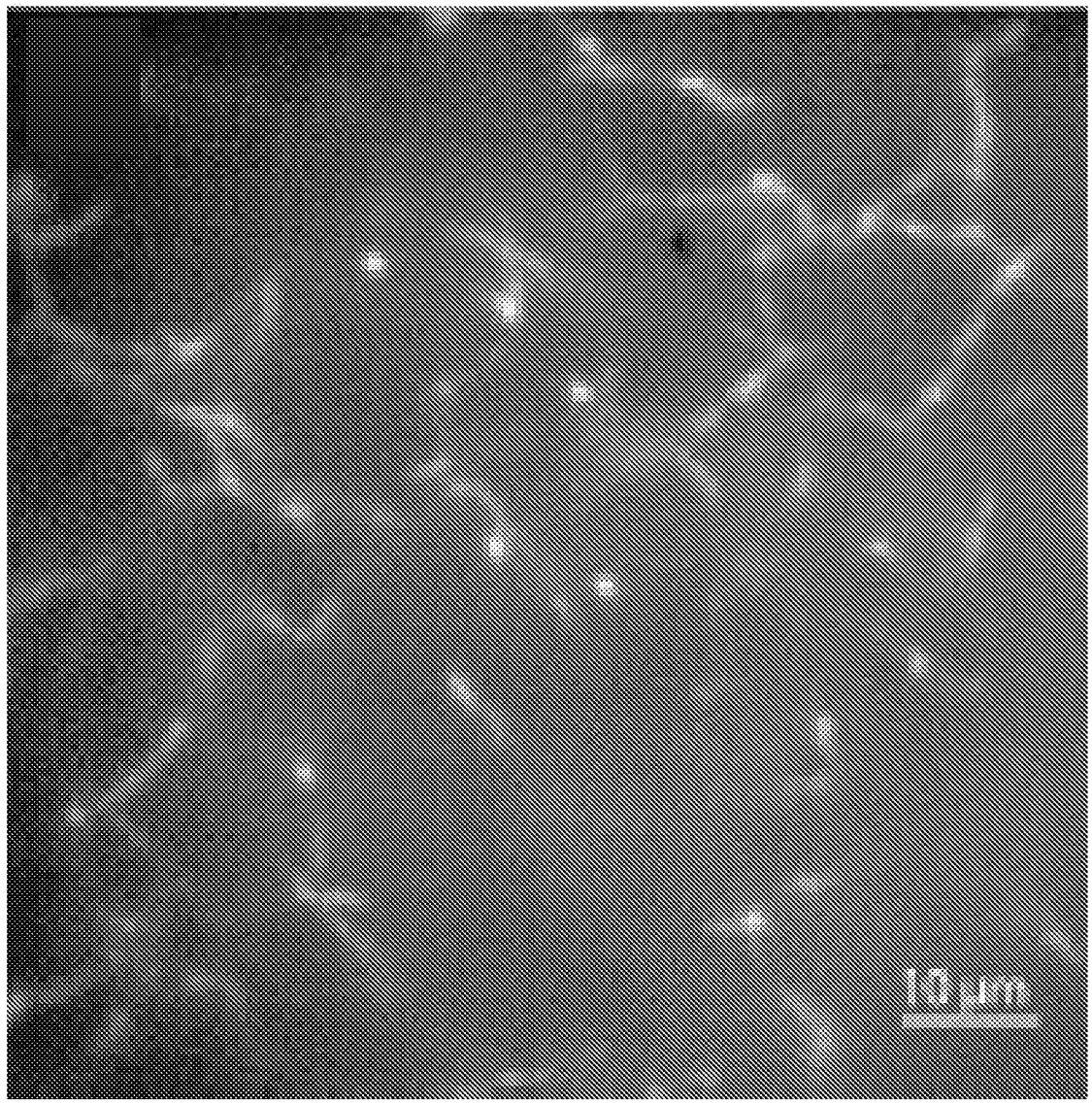
Figure 41F:
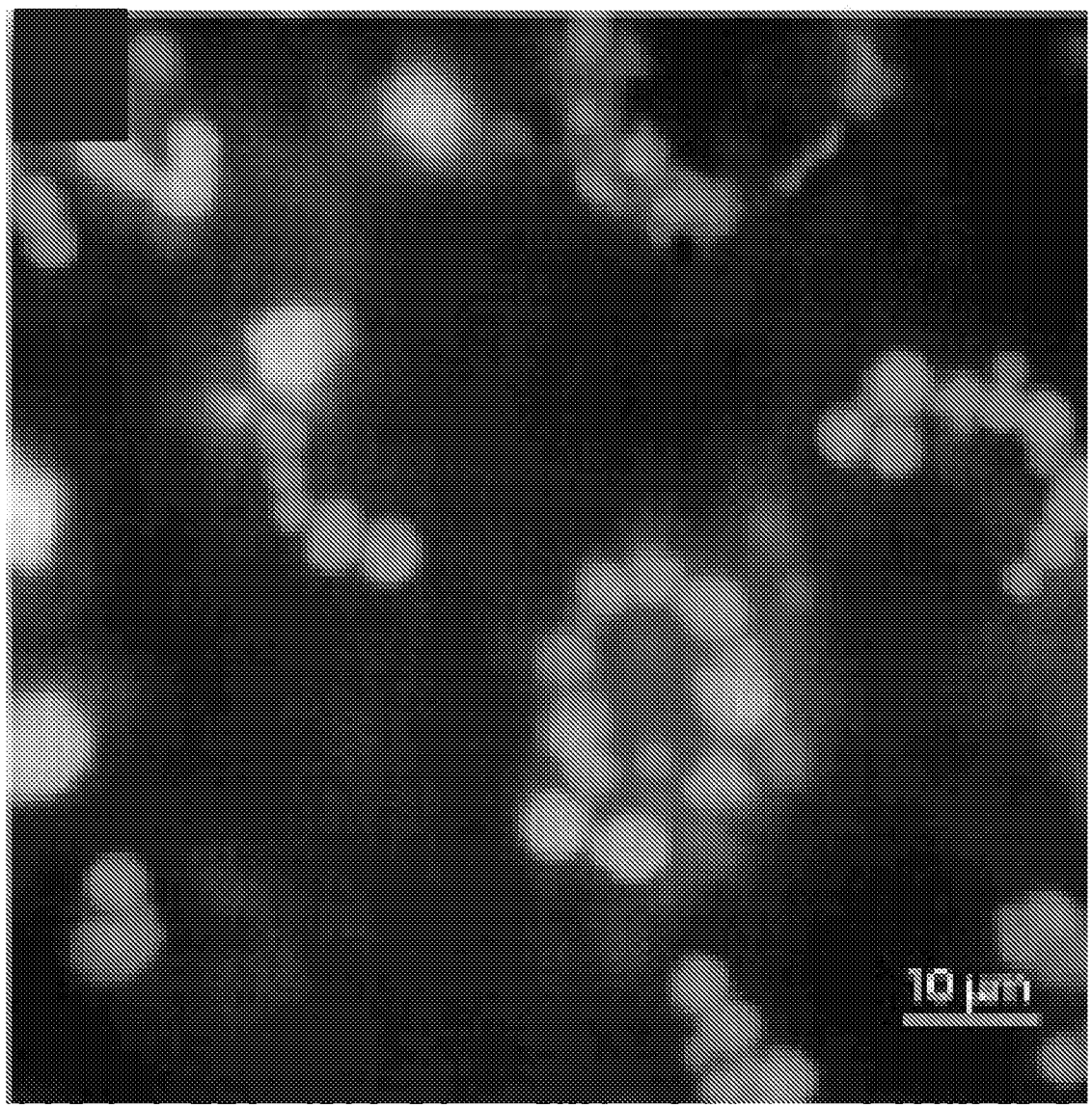

The temperature-triggered assembly process of FAMEs in the hydrated state was visualized in real time at longer length scale by spinning disk confocal laser microscopy (SDCLM). We genetically encoded a Lys residue at the C-terminus of the M-B$_{1-3}$-ELP constructs to enable labeling with Alexa Fluor® 488 dye. While heating fluorescently labeled protein samples from ~4° C. (T<T$_t$) to 30° C. (T$_c$>T>T$_t$), we monitored the second stage of self-assembly by taking consecutive images from a focal plane distant from the cover slip to avoid surface-induced artifacts (FIG. 41D-F). The temperature was then raised to 50° C. to monitor the third and final stage of self-assembly (T>T$_c$, FIG. 41G-I).

Figure 41G:
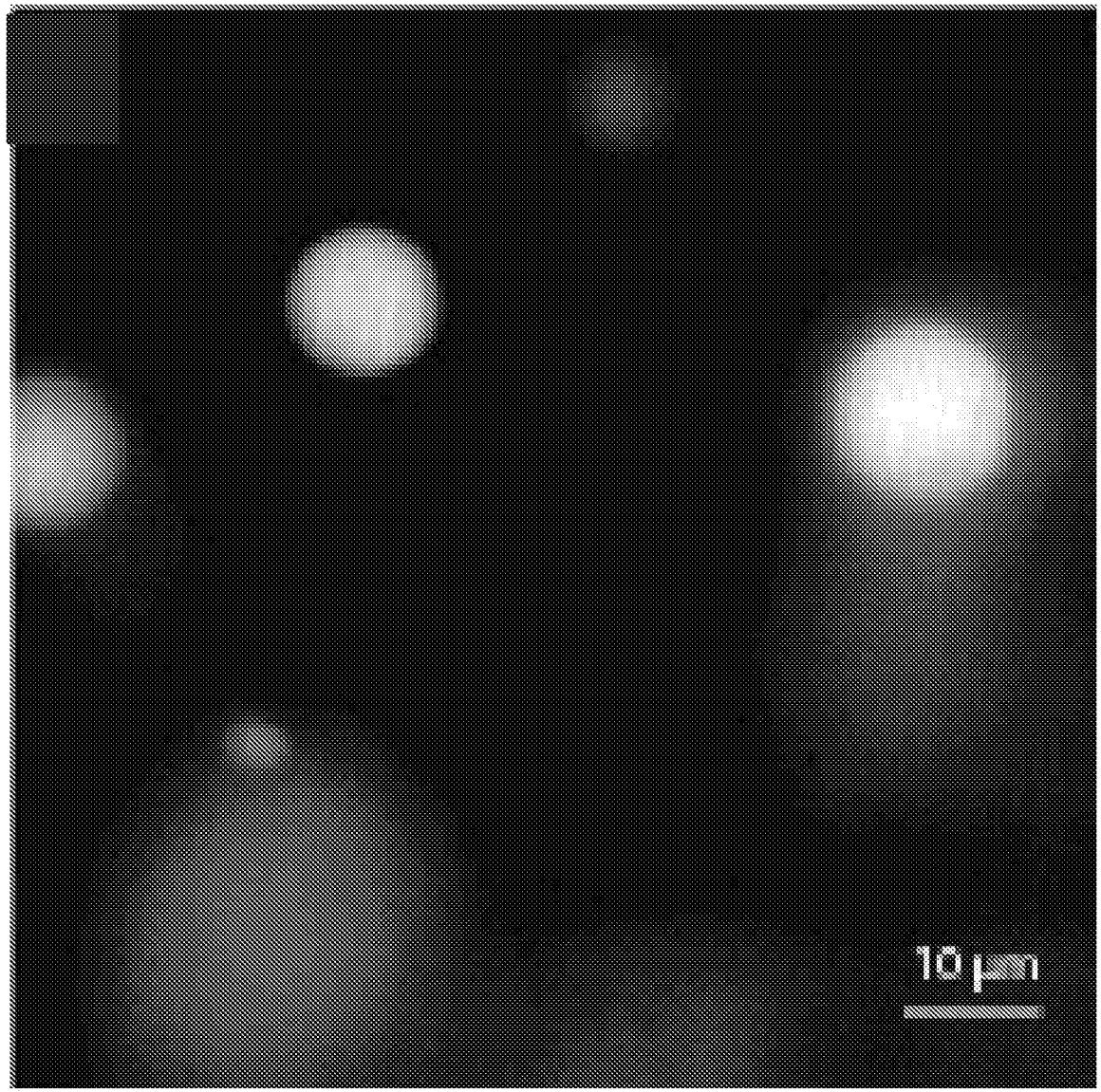
Figure 41H:
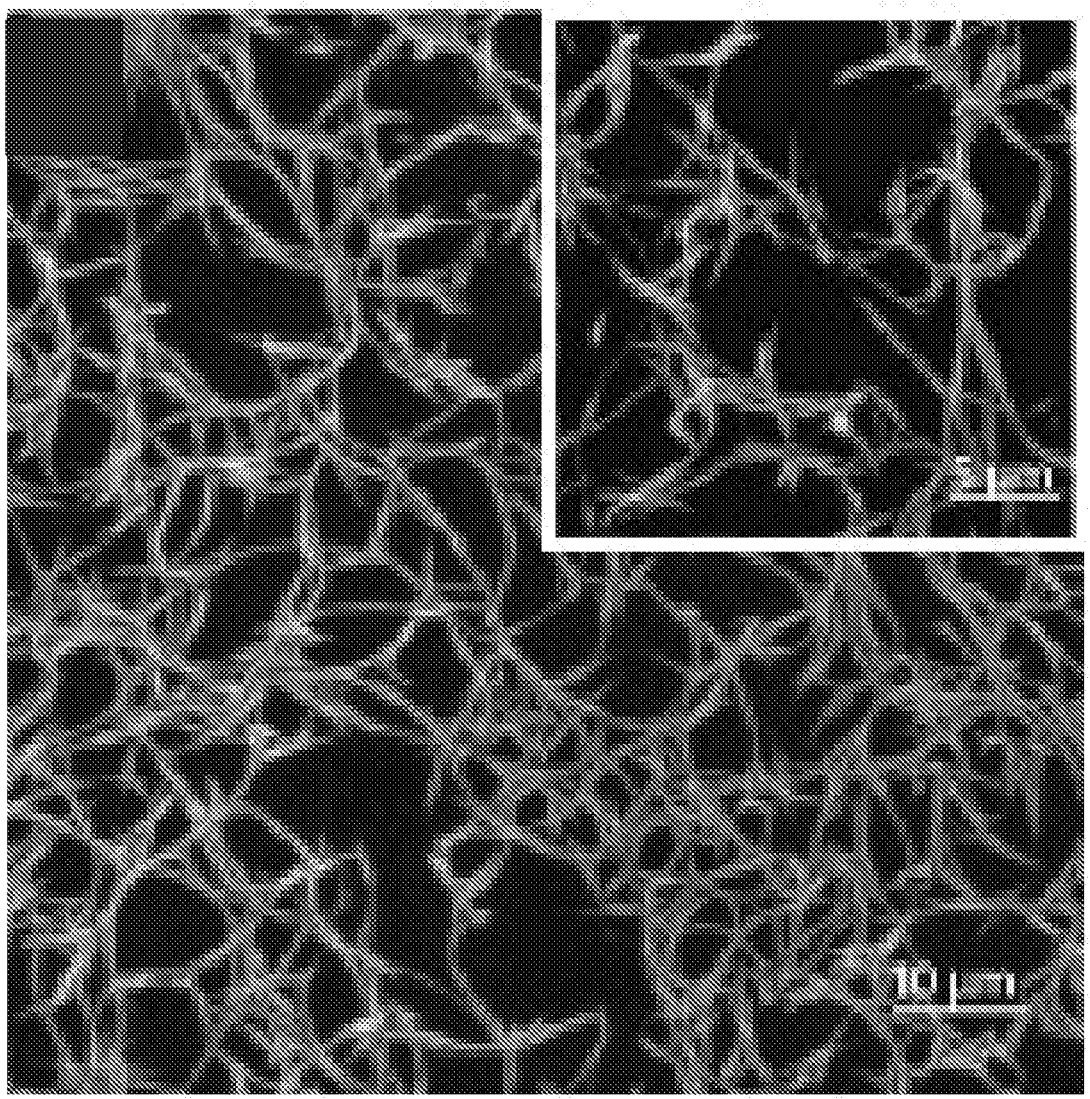

Before reaching thermal equilibrium a homogeneous fluorescent signal was observed across the viewing field, suggesting that at stage 1 (T<T$_t$) each population of the FAMEs exists as a nanoscale assembly below the diffraction limit, consistent with DLS and cryo-TEM data. However, the PA domain significantly altered the morphogenesis of aggregates at higher temperatures. During stage 2, at 30° C. (T$_c$>T>T$_t$), M-B$_1$-ELP, whose PA domain has the lowest propensity to form β-sheets, transitioned into liquid-like droplets similar to canonical ELPs. These droplets moved quickly in and out of the focal plane, which rendered the accurate measurement of their diameter difficult. However, as expected, these liquid-like smaller coacervates coalesced with each other over time and equilibrated to a larger coacervate ~4-5 μm in diameter (FIG. 41 D). At 50° C. (T>T$_c$), these liquid-like coacervates further coalesced to form slightly larger droplets ~8-12 μm in diameter (FIG. 41G).

In the case of M-B$_2$ELP at 30° C., we did not observe liquid droplets but instead observed the anisotropic growth of small fibers with a width of 0.1-0.2 μm (FIG. 41 E). These fibrous structures exhibited high mobility, but at 50° C. formed a stable interconnected network of fibers (FIG. 41H). To visualize the finer details of the entangled network, we used the microscope's super-resolution mode, recording multiple images at different focal planes and then merging these z-stack images (FIG. 41H inset). This higher resolution image demonstrates the stacking of narrow fibers into a bundle of fibers exhibiting a larger width and some polydispersity. The smallest fiber width observed was ~130 nm, which is close to the resolution limit of the instrument.

Figure 41I:
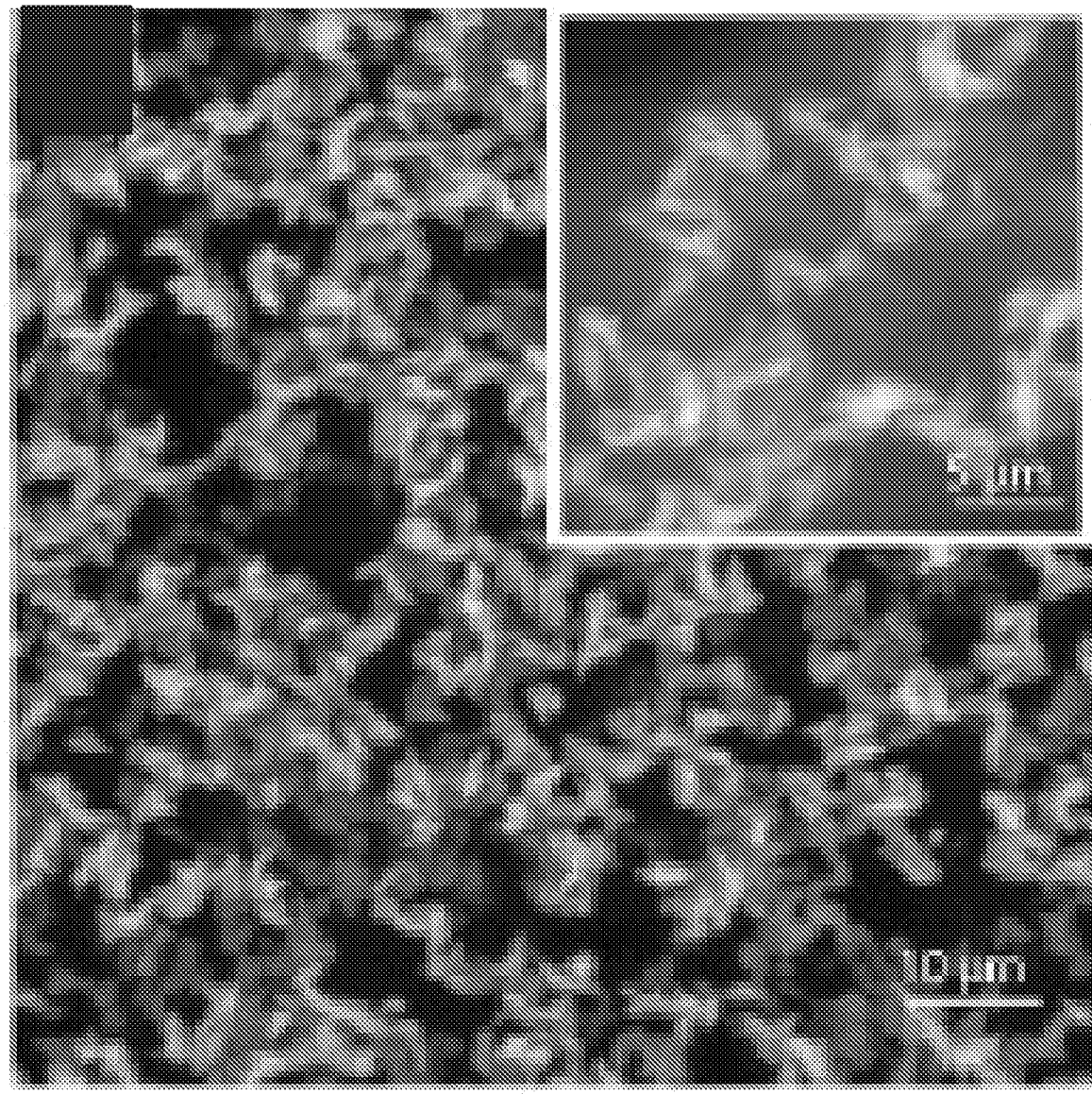

Interestingly, M-B$_3$-ELP initially transitioned into liquid-like droplets at 30° C. (FIG. 41F), but these droplets had distinct features compared to M-B$_1$-ELP (FIG. 41D) and canonical ELP coacervates. We observed many polydisperse droplets that form a "beads-on-a-string" morphology (FIG. 41F). Upon increasing the temperature to 50° C., these arrested coacervates formed aggregates with a "fractal-like" morphology that we propose is a consequence of increased desolvation of the ELP chains within the coacervates, leading to network formation through aggregated ELP chains (FIG. 41I).

We are mindful that slight differences in the heating profile used in the spectroscopic characterization and SDCLM may impact the final structure of the aggregates. Nevertheless, these results confirm the hierarchical self-assembly process of M-B$_2$ELP and M-B$_3$-ELP that drives the formation of macroscopic objects through three distinct stages, consistent with the results of the turbidimetry and spectroscopic characterization. These experiments confirm the influence of the PA domain on the interactions between the coacervates and the dynamics of their coalescence.

In our system, we propose that the nanoscale structure of the PA domain drives the morphological differences observed in the later stages of FAME coacervation, since the spectroscopic data suggest that temperature has very little effect on the protein secondary structure in all constructs.

Example 10

Figure 42A:
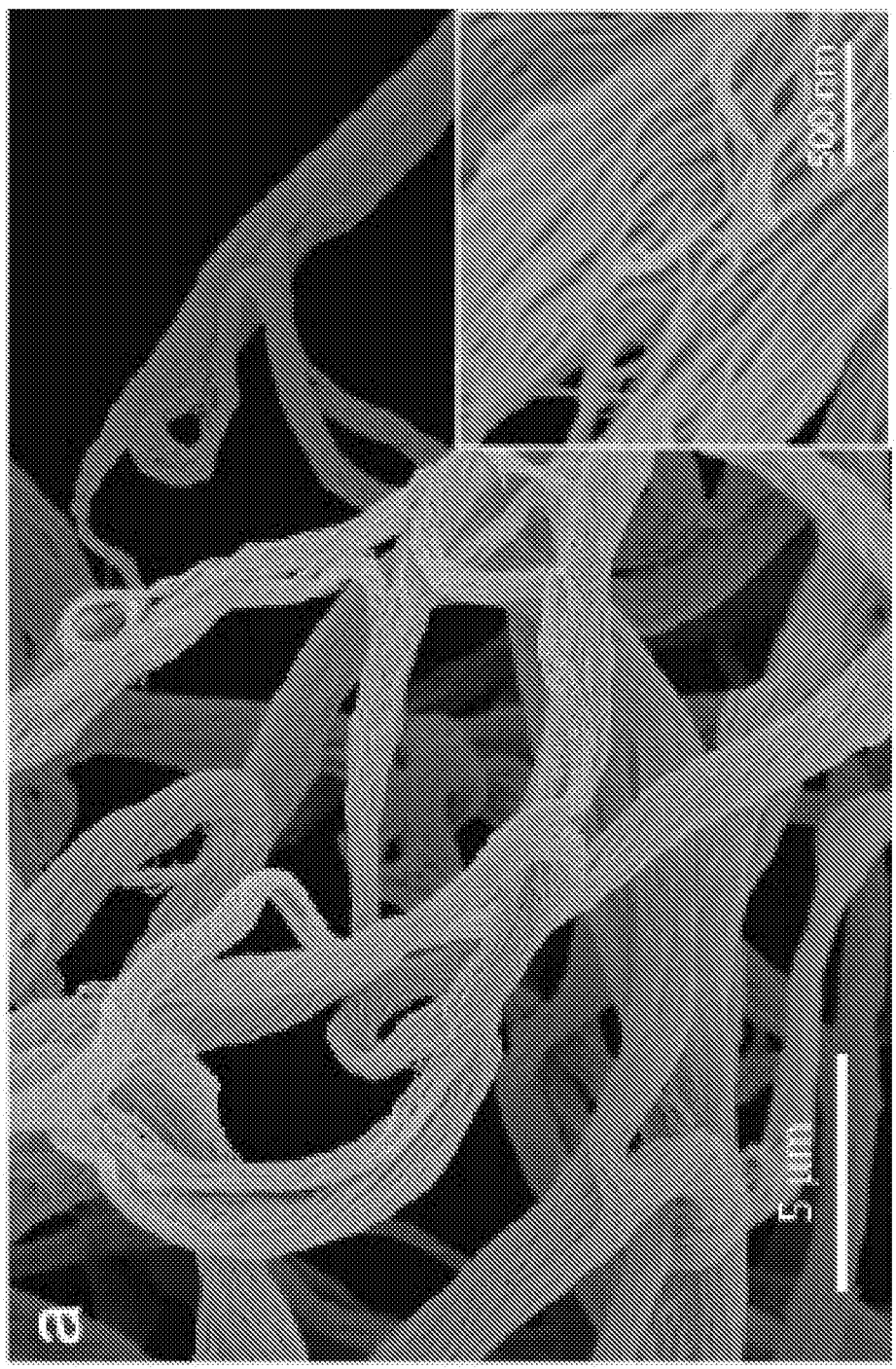
FIG. 42A-B. Scanning electron microscopy characterization of constructs above their $T_c$.
Figure 42B:
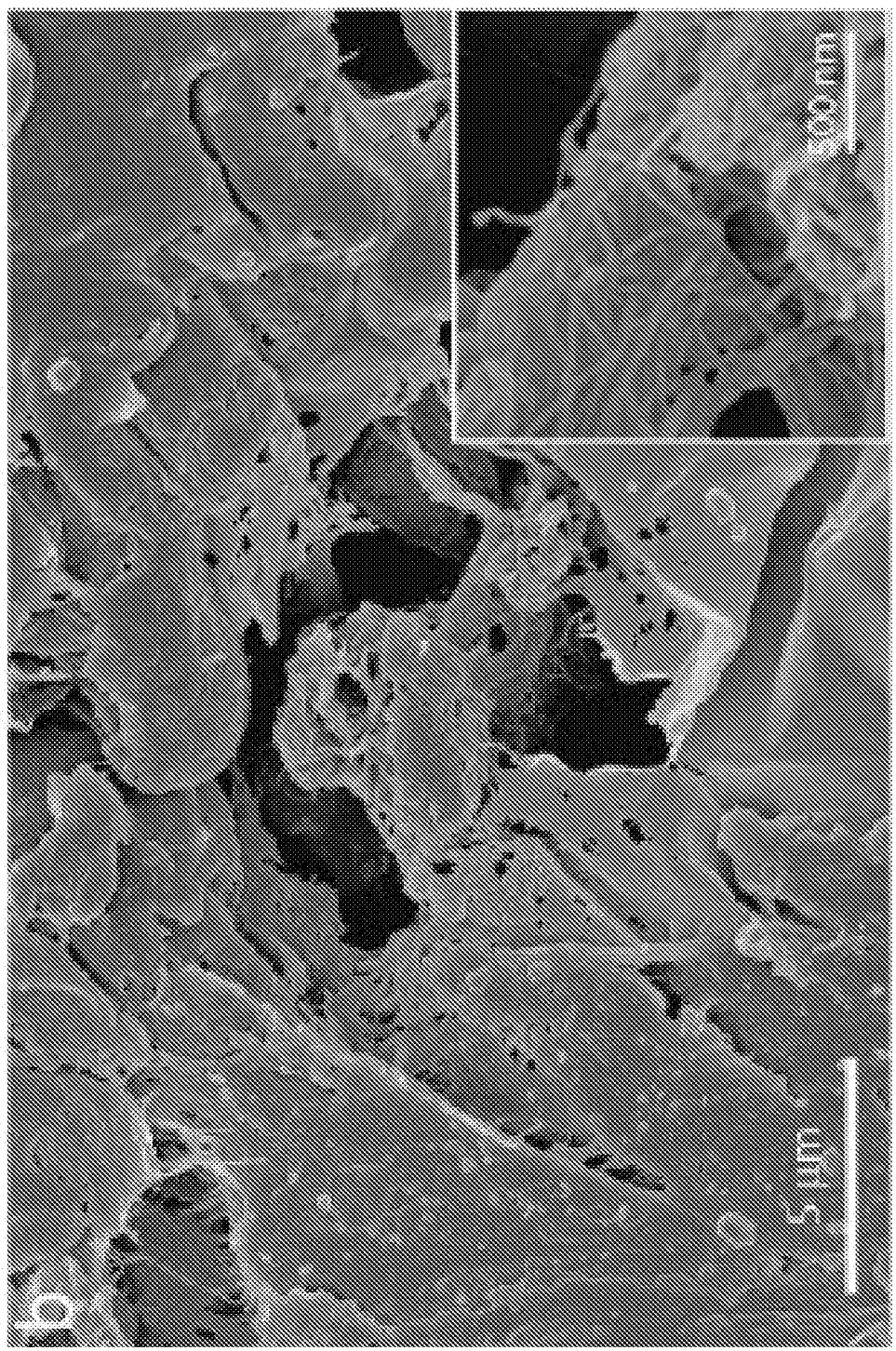

To gain a better understanding of the third stage of the self-assembly process, we fixed the macroscopic objects formed by M-B$_2$-ELP and M-B$_3$-ELP above their T$_c$ and investigated their structure with scanning electron microscopy (SEM). M-Br-ELP showed a network of narrow interwoven fibers (~50 nm) that extended in the fiber axis direction to form long bundles with much larger overall diameters (1 μm, FIG. 42A). We observed a similar bundle of fibers using cryo-SEM, demonstrating that the sample preparation process, cross-linking and dehydration, did not perturb the overall morphology. In contrast, the M-B$_2$-ELP structure was composed of amorphous aggregates, which were made of entangled fibers that were visible upon closer inspection (FIG. 42B).

As discussed above, unlike canonical ELP coacervates, structures formed by M-Br ELP and M-B$_3$-ELP above T$_c$ do not dissolve upon re-cooling, and in the case of M-B$_2$-ELP they were able to withstand moderate mechanical agitation (inversion and brief mixing by vortex). These observations, coupled with SEM, point to the PA domains undergoing an irreversible transition during the self-assembly process, perhaps forming a network of connected PA domains that is further reinforced by the interaction among the ELP chains. This hypothesis may explain the observed thermal hysteresis, as structures held together by just the ELP chains are expected to dissolve back into solution once the temperature is lowered below the T$_t$.

Figure 43:
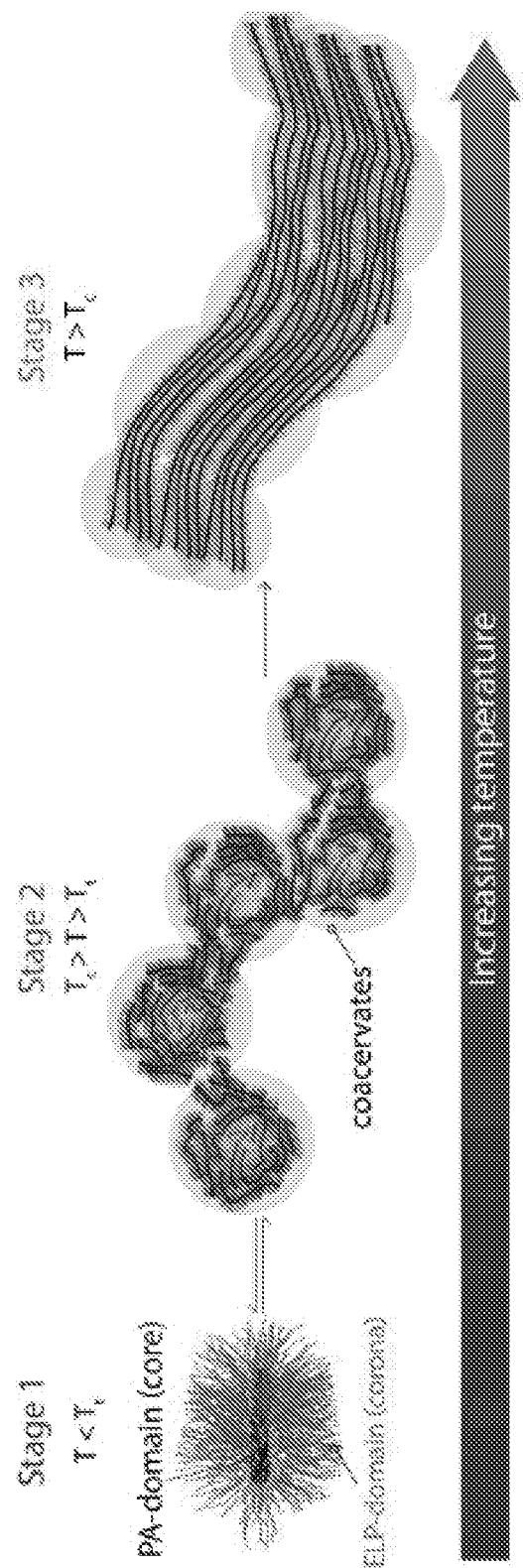
FIG. 43. Hypothesized three-stage self-assembly mechanism of constructs as a function of temperature in relation to the construct's $T_t$.

Combining the insights gained from the spectroscopic and structural studies, we propose the following three-stage self-assembly mechanism (FIG. 43). At temperatures below their T$_t$, the nanostructure formed by each FAME is determined by the fine balance between the attractive forces of the PA-domain at the core (hydrophobic interactions, β-sheet propensity, and secondary interactions such as hydrogen bonds) and the repulsive steric force of the hydrated ELP domain at the corona. This notion is consistent with the mechanism proposed for the self-assembly of canonical PAs, which is traditionally controlled by fine-tuning similar attractive interactions against ionic repulsive forces that can be turned off using triggers such as pH or ionic strength. At this stage, the ELP chains in the nanostructures of the FAMEs are hydrated and responsible for stabilizing the nanostructures in aqueous solution.

In stage 2 (T$_c$>T>T$_t$), the ELP domain in the nanostructure dehydrates and undergoes an LCST phase-transition into a liquid-like coacervate with a preference to form spherical droplets to minimize the surface tension of the polymer-rich colloidal particle suspended in the solvent. This dehydration step has several consequences. (1) Above their T$_t$, the ELP domains are more desolvated, rendering the corona more hydrophobic and thus increasing the interactions between the FAME nanostructures. (2) The self-assembly of the ELP chains into polymer-rich coacervates concentrates the PA domain in a polymer rich medium, thereby reducing the water content and increasing the strength of the core-core interactions. (3) The nano-aggregation of the cores inside the coacervates consequently controls the kinetics of coacervate maturation and coalescence. If the cores are held together by weak interactions, as in the case of M-B$_1$-ELP, the overall assembly behavior is similar to canonical ELPs. For FAMEs with stronger core interactions, the equilibrium size and coalescence of the coacervates is significantly affected by the PA-domain self-assembly at stage 1 as seen by the anisotropic growth of M-B$_2$-ELP fibers and the disrupted coalescence of M-B$_3$-ELP stemming from a large coacervate size and slow coalescence dynamics.

The third and final stage of self-assembly occurs at temperatures T>T$_c$, where the repulsion between the ELP coronas is reduced due to further dehydration, which results in a decrease in the core-core distances inside the coacervates. In M-B$_2$-ELP, we hypothesize that the cores are connected (non-covalently cross-linked) in this stage through a thermally-driven dynamic rearrangement leading to the formation of bundled fibers. In contrast, if the cores are held together by very strong forces as for M-B$_3$-ELP, this dynamic rearrangement may not be competitive with non-specific aggregation of the ELP chains, resulting in the formation of ill-defined macroscopic aggregates.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A conjugate comprising: a fatty acid; a self-assembly domain comprising a sequence of 5 to 10 amino acids that is a substrate of a lipid enzyme transferase and that adopts a secondary structure at about 25° C., a pH of about 7, and a salt concentration of about 150 mM; and a polypeptide, wherein the fatty acid is N-terminal to the self-assembly domain, the polypeptide is C-terminal to the self-assembly domain, and the conjugate has a first phase transition at a transition temperature (T$_t$) and a second phase transition at a critical temperature (T$_c$), the T$_c$ being higher than the T$_t$.

Clause 2. The conjugate of clause 1, wherein the fatty acid is selected from myristic acid, palmitic acid, lauric acid, arachidic acid, strearic acid, erucic acid, oleic acid, arachidonic acid, linoleic acid, and linolenic acid.

Clause 3. The conjugate of clause 2, wherein the fatty acid is myristic acid.

Clause 4. The conjugate of any one of the preceding clauses, wherein the self-assembly domain comprises a glycine at the N-terminus.

Clause 5. The conjugate of any one of the preceding clauses, wherein the self-assembly domain comprises an amino acid sequence of (G[XZ]$_n$) (SEQ ID NO:1) wherein X is an amino acid, Z is an amino acid more polar than X, and n is an integer from 2 to 5.

Clause 6. The conjugate of any one of clauses 1-4, wherein the self-assembly domain comprises an amino acid sequence of (GAGA), (GAGAS) (SEQ ID NO:2), (GAGAGAY) (SEQ ID NO:3), or (GLSLS) (SEQ ID NO:4).

Clause 7. The conjugate of any one of the preceding clauses, wherein the self-assembly domain adopts a beta-sheet secondary structure at about 25° C., a pH of about 7, and a salt concentration of about 150 mM.

Clause 8. The conjugate of any one of the preceding clauses, wherein the conjugate further comprises a linker in between the self-assembly domain and the polypeptide.

Clause 9. The conjugate of clause 8, wherein the linker comprises an amino acid sequence selected from (GGC), ([GGC]$_8$) (SEQ ID NO:5), ([G$_4$S]$_3$) (SEQ ID NO:6), and [GGS]$_n$ (SEQ ID NO:7), wherein n is an integer from 1 to 10.

Clause 10. The conjugate of any one of clauses 1-9, wherein the polypeptide comprises a repeated unstructured polypeptide or a non-repeated unstructured polypeptide.

Clause 11. The conjugate of any one of clauses 1-9, wherein the polypeptide comprises a zwitterionic polypeptide.

Clause 12. The conjugate of any one of clauses 1-9, wherein the polypeptide comprises an amino acid sequence of [GVGVP]$_n$ (SEQ ID NO:8), wherein n is an integer from 10 to 120.

Clause 13. The conjugate of any one of the preceding clauses, wherein the conjugate self-assembles into aggregates above the T$_t$ of the conjugate.

Clause 14. The conjugate of clause 13, wherein the conjugate self-assembles into aggregates in three phases relative to the T$_t$ and the T$_c$ of the conjugate, wherein the three phases comprise: (1) a first phase at a temperature below the T$_t$, wherein the conjugate is soluble and self-assembles into nanoscale aggregates; (2) a second phase at a temperature above the T$_t$ and below the T$_c$, wherein the conjugate forms micron-sized aggregates; and (3) a third phase at a temperature greater than the T$_c$, wherein the conjugate forms macroscale aggregates that are visible to the naked eye.

Clause 15. The conjugate of clause 14, wherein the aggregate comprises a micelle.

Clause 16. The conjugate of clause 14 or 15, wherein the aggregate comprises a rod-like structure.

Clause 17. The conjugate of clause 14 or 15, wherein the aggregate comprises a sheet.

Clause 18. A drug delivery composition comprising: a plurality of conjugates as detailed in any of clauses 1-17 self-assembled into a micelle; and an agent encapsulated within the micelle.

Clause 19. A method of treating a disease in a subject in need thereof, the method comprising administering the drug delivery composition of clause 18 to the subject.

Clause 20. A method of delivering an agent to a subject, the method comprising: encapsulating the agent in a micelle, the micelle comprising a plurality of conjugates as detailed in any of clauses 1-17; and administering the micelle to the subject.

Clause 21. The method of clause 20, wherein encapsulating comprises mixing the conjugates and agent and raising the temperature above the $T_t$ of the conjugates.

Clause 22. A method of increasing the maximum tolerated dose of an agent, the method comprising: encapsulating the agent in a micelle comprising a plurality of conjugates as detailed in any of clauses 1-17; and administering the agent-encapsulated micelle to a subject.

Clause 23. The method of any one of clauses 19-22, wherein the agent is hydrophobic.

Clause 24. The method of any one of clauses 19-22, wherein the agent comprises a small molecule, a polypeptide, a polynucleotide, a lipid, a carbohydrate, or a combination thereof.

Clause 25. A method of preparing a conjugate as detailed in any of clauses 1-17, the method comprising: (a) transforming a bacteria with a recombinant expression vector comprising a first polynucleotide encoding a first polypeptide and a second polynucleotide encoding a second polypeptide, wherein the first polypeptide comprises an N-myristoyl transferase (NMT), and wherein the second polypeptide comprises the self-assembly domain; and (b) culturing the transformed bacteria to express the first and second polypeptides and adding myristic acid to the N-terminus of the self-assembly domain.

Clause 26. The method of clause 25, wherein the bacteria comprise *E. coli*.

Clause 27. The method of any one of clauses 25-26, wherein the bacteria is cultured in media comprising myristic acid.

Clause 28. The method of any one of clauses 25-27, wherein the vector further comprises a single polynucleotide encoding a single antibiotic selection marker.

Clause 29. The method of clause 28, wherein the bacteria is cultured in media comprising the antibiotic.

Clause 30. The method of any one of clauses 25-29, wherein the NMT comprises NMT from *S. cerevisiae*.

Clause 31. The method of any one of clauses 25-30, wherein the NMT comprises an amino acid sequence consisting of residues 36-455 of NM_001182082.1 (*S. cerevisiae* NMTΔ36-455).

Clause 32. The method of any one of clauses 25-31, further comprising (c) isolating the conjugate.

| Sequences |
|---|
| G[XZ]$_n$) (SEQ ID NO: 1) |
| (GAGAS) (SEQ ID NO: 2) |
| (GAGAGAY) (SEQ ID NO: 3) |
| (GLSLS) (SEQ ID NO: 4) |
| ([GGC]$_8$) (SEQ ID NO: 5) |
| ([G$_4$S]$_3$) (SEQ ID NO: 6) |
| ([GGS]$_n$) (SEQ ID NO: 7) |
| [GVGVP]$_n$ (SEQ ID NO: 8) |
| P(X)$_n$G (SEQ ID NO: 9) |
| (U)$_m$P(X)$_n$G(Z)$_p$ (SEQ ID NO: 10) |
| PXXXG (SEQ ID NO: 11) |
| PXXXXG (SEQ ID NO: 12) |
| PXXXXXG (SEQ ID NO: 13) |
| PXXXXXXG (SEQ ID NO: 14) |
| PXXXXXXXG (SEQ ID NO: 15) |
| PXXXXXXXXG (SEQ ID NO: 16) |
| PXXXXXXXXXG (SEQ ID NO: 17) |
| PXXXXXXXXXXG (SEQ ID NO: 18) |
| PXXXXXXXXXXXG (SEQ ID NO: 19) |
| PXXXXXXXXXXXXG (SEQ ID NO: 20) |
| PXXXXXXXXXXXXXG (SEQ ID NO: 21) |
| PXXXXXXXXXXXXXXG (SEQ ID NO: 22) |
| PXXXXXXXXXXXXXXXG (SEQ ID NO: 23) |
| (VPGXG)$_n$ (SEQ ID NO: 24) |
| VPX$_1$X$_2$G (SEQ ID NO: 25) |
| VPGXG (SEQ ID NO: 26) |

| Sequences |
|---|
| (VPX₁X₂G)ₙ(VPGXG)ₘ (SEQ ID NO: 27) |
| (VPGXG)ₘ(VPX₁X₂G)ₙ (SEQ ID NO: 28) |
| {(VPX₁X₂G)(VPGXG)}ᵦ (SEQ ID NO: 29) |
| GAGASRGGSG GSGVGVPGVG VP (SEQ ID NO: 30) |
| GAGAGAYRGG SGGSGGSGVG VPGVGVP (SEQ ID NO: 31) |
| GLSLSRGGSG GSGVGVPGVG VP (SEQ ID NO: 32) |
| GVEVERGGSG GSGGSGVGVP GVGVP (SEQ ID NO: 33) |
| 5'-CAATGGTATATCTTCCGGGCGCTATCATGCCATACCTTTTTATACCATGGGCAGCA GCCATCACCATCATCACCACAAAGACCACAAATTTTGGCGTACCCAGCCGGTTAAAGATTT TGATGAAAAAGTTGTTGAAGAAGGTCCGATCGACAAACCGAAAACACCGGAAGATATTAGC GATAAACCGCTGCCGCTGCTGAGCAGCTTTGAATGGTGTAGCATTGATGTGGACAACAAAA AACAGCTGGAAGATGTTTTTGTGCTGCTGAACGAAAACTATGTGGAAGATCGTGATGCAGG TTTTCGCTTGAATTATAGCAAAGAGTTTTTCAACTGGGCACTGAAAAGTCCGGGTTGGAAA AAGATTGGCATATTGGTGTTCGTGTGAAAGAAACCCAGAAACTGGTTGCATTTATTAGCGC AATTCCGGTTACCCTGGGTGTGCGTGGTAAACAGGTTCCGAGCGTTGAAATTAAGTTTCTG TGTGTTCATAAACAGCTGCGTAGCAAACGTCTGACACCGGTTCTGATTAAAGAAATCACCC GTCGTGTGAACAAATGCGATATTTGGCATGCACTGTATACCGCAGGTATTGTTGTGCCTGC ACCGGTTAGCACCTGTCGTTATACCCATCGTCCGCTGAACTGGAAAAAACTGTATGAAGTT GATTTCACCGGTCTGCCGGATGGTCATACCGAAGAAGATATGATTGCAGAAAATGCACTGC CTGCAAAAACCAAAACCGCAGGTCTGCGTAAACTGAAAAAAGAGGACATCGATCAGGTCTT TGAGCTGTTTAAACGTTATCAGAGACCGCTTTGAACTGATCCAGATTTTTACCAAAGAAGAGT TCGAGCACAACTTTATTGGTGAAGAAAGCCTGCCGCTGGATAAACAGGTGATTTTTAGCTA TGTTGTTGAACAGCCGGATGGCAAAATTACCGATTTTTTCAGCTTTTATAGCCTGCCGTTTA CCATTCTGAACAACACCAAATACAAAGACCTGGGCATTGGCTATCTGTATTATTACGCAACC GATGCCGATTTCCAGTTTAAAGATCGTTTTGATCCGAAAGCAACCAAAGCCCTGAAAACCC GTCTGTGCGAACTGATTTATGATGCATGTATTCTGGCCAAAAACGCCAACATGGATGTTTTT AATGCACTGACCAGCCAGGATAATACCCTGTTTCTGGATGATCTGAAATTTGGTCCGGGTG ATGGTTTTCTGAATTTCTACCTGTTTAACTATCGTGCCAAACCGATTACCGGTGGTCTGAAT CCGGATAATAGCAATGATATTAAACGTCGCAGCAATGTTGGTGTGGTTATGGTGTGATAAT GATAATGATCTTCTGAATTCCGTCATATCCGCTGAGCAATAACTAGCATAACCCCTTATAC GTTACAT-3' (SEQ ID NO: 34) |
| (GAGASRGGSGGS) (SEQ ID NO: 35) |
| ATCTTAGTATATTAGTTAAGTATAAGAAGGAGATATACATATGGGGCGGGCGCATCTCGT GGTGGCAGTGGTGGGAGCGGcTAATGATCTCCTCTATGAGGATCCGCTCGAGTCTGGTAA AGAAACCGCTGCTGCGAAATTTGAA (SEQ ID NO: 36) |
| (GAGAGAYRGGSGGSGGS) (SEQ ID NO: 37) |
| CATCTTAGTATATTAGTTAAGTATAAGAAGGAGATATACATATGGGAGCGGGTGCAGGTGC CTATAGAGGTGGGTCGGGAGGCAGTGGAGGCTCAGGCTAATGATCTCCTCAATGAGCTCG AGTCTGGTAAAGAAACCGCTGCTGCGAAATTTGAACG (SEQ ID NO: 38) |
| (GLSLSRGGSGGS) (SEQ ID NO: 39) |
| ATCTTAGTATATTAGTTAAGTATAAGAAGGAGATATACATATGGGGCTGAGCCTGTCTCGTG GTGGCAGTGGTGGGAGCGGCTAATGATCTCCTCAATGAGCTCGAGTCTGGTAAAGAAACC GCTGCTGCGAAATTTGAA (SEQ ID NO: 40) |
| *M*GVGVPGVGVPGVGVPGVGVPGVGVPGVGVPGVGVPGVGVPGVGVPGVGVPGVGVPGVG VPGVGVPGVGVPGVGVPGVGVPGVGVPGVGVPGVGVPGVGVPGVGVPGVGVPGVGVPGV GVPGVGVPGVGVPGVGVPGVGVPGVGVPGVGVPGVGVPGVGVPGVGVPGVGVPGVGVPG VGVPGVGVPGVGVPGVGVPGVGVPGY (SEQ ID NO: 41) |
| *M*GAGASRGGSGSGVGVPGVGVPGVGVPGVGVPGVGVPGVGVPGVGVPGVGVPGVGVPG VGVPGVGVPGVGVPGVGVPGVGVPGVGVPGVGVPGVGVPGVGVPGVGVPGVGVPGVGVP GVGVPGVGVPGVGVPGVGVPGVGVPGVGVPGVGVPGVGVPGVGVPGVGVPGVGVPGVGV PGVGVPGVGVPGVGVPGVGVPGVGVPGVGVPGVGVPGVGVPGY (SEQ ID NO: 42) |
| *M*GAGAGAYRGGSGGSGGSGVGVPGVGVPGVGVPGVGVPGVGVPGVGVPGVGVPGVGVPG VGVPGVGVPGVGVPGVGVPGVGVPGVGVPGVGVPGVGVPGVGVPGVGVPGVGVPGVGVP GVGVPGVGVPGVGVPGVGVPGVGVPGVGVPGVGVPGVGVPGVGVPGVGVPGVGVPGVGV PGVGVPGVGVPGVGVPGVGVPGVGVPGVGVPGVGVPGVGVPGY (SEQ ID NO: 43) |
| *M*GLSLSRGGSGGSGVGVPGVGVPGVGVPGVGVPGVGVPGVGVPGVGVPGVGVPGVGVPG VGVPGVGVPGVGVPGVGVPGVGVPGVGVPGVGVPGVGVPGVGVPGVGVPGVGVPGVGVP GVGVPGVGVPGVGVPGVGVPGVGVPGVGVPGVGVPGVGVPGVGVPGVGVPGVGVPGVGV PGVGVPGVGVPGVGVPGVGVPGVGVPGVGVPGVGVPGVGVPGY (SEQ ID NO: 44) |

| Sequences |
|---|
| *MGAGASRGGSGGSGVGVPGVGVPGVGVPGVGVPGVGVPGVGVPGVGVPGVGVPGVGVPG*<br>*VGVPGVGVPGVGVPGVGVPGVGVPGVGVPGVGVPGVGVPGVGVPGVGVPGVGVPGVGVP*<br>*GVGVPGVGVPGVGVPGVGVPGVGVPGVGVPGVGVPGVGVPGVGVPGVGVPGVGVPGVGV*<br>*PGVGVPGVGVPGVGVPGVGVPGVGVPGVGVPGVGVPGVGVPGG*<u>K</u>*GY* (SEQ ID NO: 45) |
| *MGAGAGAYRGGSGGSGGSGVGVPGVGVPGVGVPGVGVPGVGVPGVGVPGVGVPGVGVPG*<br>*VGVPGVGVPGVGVPGVGVPGVGVPGVGVPGVGVPGVGVPGVGVPGVGVPGVGVPGVGVP*<br>*GVGVPGVGVPGVGVPGVGVPGVGVPGVGVPGVGVPGVGVPGVGVPGVGVPGVGVPGVGV*<br>*PGVGVPGVGVPGVGVPGVGVPGVGVPGVGVPGVGVPGVGVPGG*<u>K</u>*GY* (SEQ ID NO: 46) |
| *MGLSLSRGGSGGSGVGVPGVGVPGVGVPGVGVPGVGVPGVGVPGVGVPGVGVPGVGVPG*<br>*VGVPGVGVPGVGVPGVGVPGVGVPGVGVPGVGVPGVGVPGVGVPGVGVPGVGVPGVGVP*<br>*GVGVPGVGVPGVGVPGVGVPGVGVPGVGVPGVGVPGVGVPGVGVPGVGVPGVGVPGVGV*<br>*PGVGVPGVGVPGVGVPGVGVPGVGVPGVGVPGVGVPGVGVPGG*<u>K</u>*GY* (SEQ ID NO: 47) |
| GAGASR (SEQ ID NO: 48) |
| GAGAGAYR (SEQ ID NO: 49) |
| GLSLSR (SEQ ID NO: 50) |
| (GVGVP)$_{40}$GY (SEQ ID NO: 51) |
| [Gly-Val-Gly-Val-Pro]$_{40}$ (SEQ ID NO: 52) |

The invention claimed is:

1. A conjugate comprising:
   a fatty acid comprising myristic acid;
   a self-assembly domain that is a substrate of a lipid enzyme transferase and that adopts a secondary structure at about 25° C., a pH of about 7, and a salt concentration of about 150 mM, wherein the self-assembly domain comprises an amino acid sequence of (G[XZ]$_n$) (SEQ ID NO:1) wherein X is A or L, Z is G, S, or Y, and n is an integer from 2 to 5;
   a polypeptide comprising an amino acid sequence of [GVGVP]$_n$ (SEQ ID NO:8), wherein n is an integer from 10 to 120; and
   a linker between the self-assembly domain and the polypeptide, wherein the linker comprises an amino acid sequence selected from (GGC), ([GGC]$_8$) (SEQ ID NO:5), ([G$_4$S]$_3$) (SEQ ID NO:6), and [GGS]$_n$(SEQ ID NO:7), wherein n is an integer from 1 to 10,
   wherein the fatty acid is N-terminal to the self-assembly domain, the polypeptide is C-terminal to the self-assembly domain, and the conjugate has a first phase transition at a transition temperature ($T_t$) and a second phase transition at a critical temperature ($T_c$), the $T_c$ being higher than the $T_t$.

2. The conjugate of claim 1, wherein the fatty acid is myristic acid.

3. The conjugate of claim 1, wherein the self-assembly domain comprises a glycine at the N-terminus.

4. The conjugate of claim 1, wherein the self-assembly domain comprises an amino acid sequence of (GAGAS) (SEQ ID NO:2), (GAGAGAY) (SEQ ID NO:3), or (GLSLS) (SEQ ID NO:4).

5. The conjugate of claim 1, wherein the self-assembly domain adopts a beta-sheet secondary structure at about 25° C., a pH of about 7, and a salt concentration of about 150 mM.

6. The conjugate of claim 1, wherein the polypeptide comprises a repeated unstructured polypeptide or a non-repeated unstructured polypeptide.

7. The conjugate of claim 1, wherein the polypeptide comprises a zwitterionic polypeptide.

8. The conjugate of claim 1, wherein the conjugate self-assembles into aggregates above the $T_t$ of the conjugate.

9. The conjugate of claim 8, wherein the conjugate self-assembles into aggregates in three phases relative to the $T_t$ and the $T_c$ of the conjugate, wherein the three phases comprise:

(1) a first phase at a temperature below the $T_t$, wherein the conjugate is soluble and self-assembles into nanoscale aggregates;

(2) a second phase at a temperature above the $T_t$ and below the $T_c$, wherein the conjugate forms micron-sized aggregates; and (3) a third phase at a temperature greater than the $T_c$, wherein the conjugate forms macroscale aggregates that are visible to the naked eye.

10. The conjugate of claim 9, wherein the aggregate comprises a micelle.

11. The conjugate of claim 9, wherein the aggregate comprises a rod-like structure.

12. The conjugate of claim 9, wherein the aggregate comprises a sheet.

13. A drug delivery composition comprising:

a plurality of conjugates as detailed in claim 1 self-assembled into a micelle; and an agent encapsulated within the micelle.

* * * * *

SEQUENCE LISTING

```
<160> NUMBER OF SEQ ID NOS: 52

<210> SEQ ID NO 1
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(2)
<223> OTHER INFORMATION: Xaa can be any amino acid
<220> FEATURE:
<221> NAME/KEY: REPEAT
<222> LOCATION: (2)..(3)
<223> OTHER INFORMATION: Repeat unit:  repeating between 2 to 5 times
<220> FEATURE:
<221> NAME/KEY: Xaa
<222> LOCATION: (3)..(3)
<223> OTHER INFORMATION: Xaa at position 3 can be any amino acid
      independent more polar than Xaa at position 2

<400> SEQUENCE: 1

Gly Xaa Xaa
1

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Gly Ala Gly Ala Ser
1               5

<210> SEQ ID NO 3
<211> LENGTH: 7
<212> TYPE: PRT
<213> ORGANISM: Artificial sequence
```

```
<220> FEATURE:
<223> OTHER INFORMATION: Synthetic

<400> SEQUENCE: 3

Gly Ala Gly Ala Gly Ala Tyr
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic

<400> SEQUENCE: 4

Gly Leu Ser Leu Ser
1               5

<210> SEQ ID NO 5
<211> LENGTH: 24
<212> TYPE: PRT
<213> ORGANISM: Artificial sequence
<220> FEATURE:
<223> OTHER INFORMATION: Synthetic

<400> SEQUENCE: 5

Gly Gly Cys Gly Gly Cys Gly Gly Cys Gly Gly Cys Gly Gly Cys Gly
1               5                   10                  15

Gly Cys Gly Gly Cys Gly Gly Cys
            20

<210> SEQ ID NO 6
<211> LENGTH: 15
<212> TYPE: PRT
<213> ORGANISM: Artificial sequence
<220> FEATURE:
<223> OTHER INFORMATION: Synthetic

<400> SEQUENCE: 6

Gly Gly Gly Gly Ser Gly Gly Gly Ser Gly Gly Gly Gly Ser
1               5                   10                  15

<210> SEQ ID NO 7
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(3)
<223> OTHER INFORMATION: Repeat unit: repeating between 1 to 10 times

<400> SEQUENCE: 7

Gly Gly Ser
1

<210> SEQ ID NO 8
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit: repeating between 1 to 200 times
```

```
<400> SEQUENCE: 8

Gly Val Gly Val Pro
1               5

<210> SEQ ID NO 9
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(2)
<223> OTHER INFORMATION: Xaa is any amino acid
<220> FEATURE:
<221> NAME/KEY: REPEAT
<222> LOCATION: (2)..(2)
<223> OTHER INFORMATION: Repeat unit:  repeating between 1 to 15 times

<400> SEQUENCE: 9

Pro Xaa Gly
1

<210> SEQ ID NO 10
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (1)..(1)
<223> OTHER INFORMATION: Xaa at position 1 is any amino acid independent
      of Xaa at positions 3 and 5
<220> FEATURE:
<221> NAME/KEY: REPEAT
<222> LOCATION: (1)..(1)
<223> OTHER INFORMATION: Repeat unit:  repeating between 1 to 15 times
<220> FEATURE:
<221> NAME/KEY: Xaa
<222> LOCATION: (3)..(3)
<223> OTHER INFORMATION: Xaa at position 3 is any amino acid independent
      of Xaa at positions 1 and 5
<220> FEATURE:
<221> NAME/KEY: REPEAT
<222> LOCATION: (3)..(3)
<223> OTHER INFORMATION: Repeat unit:  repeating between 1 to 15 times
<220> FEATURE:
<221> NAME/KEY: Xaa
<222> LOCATION: (5)..(5)
<223> OTHER INFORMATION: Xaa at position 5 is any amino acid independent
      of Xaa at positions 1 and 3
<220> FEATURE:
<221> NAME/KEY: REPEAT
<222> LOCATION: (5)..(5)
<223> OTHER INFORMATION: Repeat unit:  repeating between 1 to 15 times

<400> SEQUENCE: 10

Xaa Pro Xaa Gly Xaa
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(4)
<223> OTHER INFORMATION: Xaa may be independently any amino acid

<400> SEQUENCE: 11
```

Pro Xaa Xaa Xaa Gly
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(5)
<223> OTHER INFORMATION: Xaa may be independently any amino acid

<400> SEQUENCE: 12

Pro Xaa Xaa Xaa Xaa Gly
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(6)
<223> OTHER INFORMATION: Xaa may be any independent amino acid

<400> SEQUENCE: 13

Pro Xaa Xaa Xaa Xaa Xaa Gly
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(7)
<223> OTHER INFORMATION: Xaa may be any independent amino acid

<400> SEQUENCE: 14

Pro Xaa Xaa Xaa Xaa Xaa Xaa Gly
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(8)
<223> OTHER INFORMATION: Xaa may be any independent amino acid

<400> SEQUENCE: 15

Pro Xaa Xaa Xaa Xaa Xaa Xaa Xaa Gly
1               5

<210> SEQ ID NO 16
<211> LENGTH: 10
<212> TYPE: PRT
<213> ORGANISM: Artificial sequence
<220> FEATURE:
<223> OTHER INFORMATION: Synthetic

```
<220> FEATURE:
<221> NAME/KEY: Xaa
<222> LOCATION: (2)..(9)
<223> OTHER INFORMATION: Xaa may be any independent amino acid

<400> SEQUENCE: 16

Pro Xaa Xaa Xaa Xaa Xaa Xaa Xaa Xaa Gly
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(10)
<223> OTHER INFORMATION: Xaa may be any independent amino acid

<400> SEQUENCE: 17

Pro Xaa Xaa Xaa Xaa Xaa Xaa Xaa Xaa Xaa Gly
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(11)
<223> OTHER INFORMATION: Xaa may be any independent amino acid

<400> SEQUENCE: 18

Pro Xaa Xaa Xaa Xaa Xaa Xaa Xaa Xaa Xaa Xaa Gly
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(12)
<223> OTHER INFORMATION: Xaa may be any independent amino acid

<400> SEQUENCE: 19

Pro Xaa Xaa Xaa Xaa Xaa Xaa Xaa Xaa Xaa Xaa Xaa Gly
1               5                   10

<210> SEQ ID NO 20
<211> LENGTH: 14
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(13)
<223> OTHER INFORMATION: Xaa may be any independent amino acid

<400> SEQUENCE: 20

Pro Xaa Xaa Xaa Xaa Xaa Xaa Xaa Xaa Xaa Xaa Xaa Xaa Gly
1               5                   10
```

```
<210> SEQ ID NO 21
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(14)
<223> OTHER INFORMATION: Xaa may be any independent amino acid

<400> SEQUENCE: 21

Pro Xaa Xaa Xaa Xaa Xaa Xaa Xaa Xaa Xaa Xaa Xaa Xaa Xaa Gly
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(15)
<223> OTHER INFORMATION: Xaa may be any independent amino acid

<400> SEQUENCE: 22

Pro Xaa Xaa Xaa Xaa Xaa Xaa Xaa Xaa Xaa Xaa Xaa Xaa Xaa Xaa Gly
1               5                   10                  15

<210> SEQ ID NO 23
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(16)
<223> OTHER INFORMATION: Xaa may be any independent amino acid

<400> SEQUENCE: 23

Pro Xaa Xaa Xaa Xaa Xaa Xaa Xaa Xaa Xaa Xaa Xaa Xaa Xaa Xaa Xaa
1               5                   10                  15

Gly

<210> SEQ ID NO 24
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit:  repeating 1 or more times
<220> FEATURE:
<221> NAME/KEY: Xaa
<222> LOCATION: (4)..(4)
<223> OTHER INFORMATION: Xaa is any amino acid except proline

<400> SEQUENCE: 24

Val Pro Gly Xaa Gly
1               5

<210> SEQ ID NO 25
<211> LENGTH: 5
<212> TYPE: PRT
<213> ORGANISM: Artificial sequence
<220> FEATURE:
```

```
<223> OTHER INFORMATION: Synthetic
<220> FEATURE:
<221> NAME/KEY: REPEAT
<222> LOCATION: (1)..(5)
<223> OTHER INFORMATION: Repeat unit:  repeating 1 or more times
<220> FEATURE:
<221> NAME/KEY: Xaa
<222> LOCATION: (2)..(2)
<223> OTHER INFORMATION: Xaa is a negatively or positively charged amino
      acid
<220> FEATURE:
<221> NAME/KEY: Xaa
<222> LOCATION: (3)..(3)
<223> OTHER INFORMATION: Xaa is the other of a negatively or positively
      charged amino acid

<400> SEQUENCE: 25

Val Pro Xaa Xaa Gly
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (4)..(4)
<223> OTHER INFORMATION: Xaa is any amino acid except proline

<400> SEQUENCE: 26

Val Pro Gly Xaa Gly
1               5

<210> SEQ ID NO 27
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit:  repeating 1 or more times and may
      be referred to as a diblock polymer independent from the repeat
      unit at positions 6 to 10
<220> FEATURE:
<221> NAME/KEY: Xaa
<222> LOCATION: (3)..(3)
<223> OTHER INFORMATION: Xaa is a negatively or positively charged amino
      acid
<220> FEATURE:
<221> NAME/KEY: Xaa
<222> LOCATION: (4)..(4)
<223> OTHER INFORMATION: Xaa is the other of a negatively or positively
      charged amino acid
<220> FEATURE:
<221> NAME/KEY: REPEAT
<222> LOCATION: (6)..(10)
<223> OTHER INFORMATION: Repeat unit:  repeating 1 or more times and may
      be referred to as a diblock polymer independent from the repeat
      unit at positions 1 to 5
<220> FEATURE:
<221> NAME/KEY: Xaa
<222> LOCATION: (9)..(9)
<223> OTHER INFORMATION: Xaa is any amino acid except proline

<400> SEQUENCE: 27

Val Pro Xaa Xaa Gly Val Pro Gly Xaa Gly
1               5                   10

<210> SEQ ID NO 28
```

```
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit:  repeating 1 or more times and
      independent from repeat unit at positions 6 to 10
<220> FEATURE:
<221> NAME/KEY: Xaa
<222> LOCATION: (4)..(4)
<223> OTHER INFORMATION: Xaa is any amino acid except proline
<220> FEATURE:
<221> NAME/KEY: REPEAT
<222> LOCATION: (6)..(10)
<223> OTHER INFORMATION: Repeat unit:  repeating 1 or more times and
      independent from repeat unit at positions 1 to 5
<220> FEATURE:
<221> NAME/KEY: Xaa
<222> LOCATION: (8)..(8)
<223> OTHER INFORMATION: Xaa is a negatively or positively charged amino
      acid
<220> FEATURE:
<221> NAME/KEY: Xaa
<222> LOCATION: (9)..(9)
<223> OTHER INFORMATION: Xaa is the other of a negatively or positively
      charged amino acid

<400> SEQUENCE: 28

Val Pro Gly Xaa Gly Val Pro Xaa Xaa Gly
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: REPEAT
<222> LOCATION: (1)..(10)
<223> OTHER INFORMATION: Repeat unit:  repeating 1 or more times
<220> FEATURE:
<221> NAME/KEY: Xaa
<222> LOCATION: (3)..(3)
<223> OTHER INFORMATION: Xaa is a negatively or positively charged amino
      acid
<220> FEATURE:
<221> NAME/KEY: Xaa
<222> LOCATION: (4)..(4)
<223> OTHER INFORMATION: Xaa is the other of a negatively or positively
      charged amino acid
<220> FEATURE:
<221> NAME/KEY: Xaa
<222> LOCATION: (9)..(9)
<223> OTHER INFORMATION: Xaa is any amino acid except proline

<400> SEQUENCE: 29

Val Pro Xaa Xaa Gly Val Pro Gly Xaa Gly
1               5                   10

<210> SEQ ID NO 30
<211> LENGTH: 22
<212> TYPE: PRT
<213> ORGANISM: Artificial sequence
<220> FEATURE:
<223> OTHER INFORMATION: Synthetic

<400> SEQUENCE: 30

Gly Ala Gly Ala Ser Arg Gly Gly Ser Gly Gly Ser Gly Val Gly Val
1               5                   10                  15
```

Pro Gly Val Gly Val Pro
            20

<210> SEQ ID NO 31
<211> LENGTH: 27
<212> TYPE: PRT
<213> ORGANISM: Artificial sequence
<220> FEATURE:
<223> OTHER INFORMATION: Synthetic

<400> SEQUENCE: 31

Gly Ala Gly Ala Gly Ala Tyr Arg Gly Gly Ser Gly Gly Ser Gly Gly
1               5                   10                  15

Ser Gly Val Gly Val Pro Gly Val Gly Val Pro
            20                  25

<210> SEQ ID NO 32
<211> LENGTH: 22
<212> TYPE: PRT
<213> ORGANISM: Artificial sequence
<220> FEATURE:
<223> OTHER INFORMATION: Synthetic

<400> SEQUENCE: 32

Gly Leu Ser Leu Ser Arg Gly Gly Ser Gly Gly Ser Gly Val Gly Val
1               5                   10                  15

Pro Gly Val Gly Val Pro
            20

<210> SEQ ID NO 33
<211> LENGTH: 25
<212> TYPE: PRT
<213> ORGANISM: Artificial sequence
<220> FEATURE:
<223> OTHER INFORMATION: Synthetic

<400> SEQUENCE: 33

Gly Val Glu Val Glu Arg Gly Gly Ser Gly Gly Ser Gly Gly Ser Gly
1               5                   10                  15

Val Gly Val Pro Gly Val Gly Val Pro
            20                  25

<210> SEQ ID NO 34
<211> LENGTH: 1412
<212> TYPE: DNA
<213> ORGANISM: Artificial sequence
<220> FEATURE:
<223> OTHER INFORMATION: Synthetic

<400> SEQUENCE: 34
caatggtata tcttccgggc gctatcatgc catacctttt tataccatgg gcagcagcca      60
tcaccatcat caccacaaag accacaaatt ttggcgtacc cagccggtta agattttga     120 tgaaaaagtt gttgaagaag gtccgatcga caaaccgaaa acaccggaag atattagcga    180
taaaccgctg ccgctgctga gcagctttga atggtgtagc attgatgtgg acaacaaaaa    240
acagctggaa gatgtttttg tgctgctgaa cgaaaactat gtggaagatc gtgatgcagg    300
ttttcgcttc aattatacca aagagttttt caactgggca ctgaaaagtc cgggttggaa    360
aaaagattgg catattggtg ttcgtgtgaa agaaacccag aaactggttg catttattag    420
cgcaattccg gttaccctgg gtgtgcgtgg taaacaggtt ccgagcgttg aaattaactt    480
tctgtgtgtt cataaacagc tgcgtagcaa acgtctgaca ccggttctga ttaaagaaat    540

| | |
|---|---|
| cacccgtcgt gtgaacaaat gcgatatttg gcatgcactg tataccgcag gtattgttct | 600 |
| gcctgcaccg gttagcacct gtcgttatac ccatcgtccg ctgaactgga aaaaactgta | 660 |
| tgaagttgat tcaccggtc tgccggatgg tcataccgaa gaagatatga ttgcagaaaa | 720 |
| tgcactgcct gcaaaaacca aaaccgcagg tctgcgtaaa ctgaaaaaag aggacatcga | 780 |
| tcaggtcttt gagctgttta acgttatca gagccgcttt gaactgatcc agatttttac | 840 |
| caaagaagag ttcgagcaca actttattgg tgaagaaagc ctgccgctgg ataaacaggt | 900 |
| gattttagc tatgttgttg aacagccgga tgcaaaatt accgatttt tcagcttta | 960 |
| tagcctgccg tttaccattc tgaacaacac caaatacaaa gacctgggca ttggctatct | 1020 |
| gtattattac gcaaccgatg ccgatttcca gtttaaagat cgttttgatc cgaaagcaac | 1080 |
| caaagccctg aaaacccgtc tgtgcgaact gatttatgat gcatgtattc tggccaaaaa | 1140 |
| cgccaacatg gatgttttta atgcactgac cagccaggat aatacccctgt ttctggatga | 1200 |
| tctgaaattt ggtccgggtg atggttttct gaatttctac ctgtttaact atcgtgccaa | 1260 |
| accgattacc ggtggtctga atccggataa tagcaatgat attaaacgtc gcagcaatgt | 1320 |
| tggtgtggtt atgctgtgat aatgataatg atcttctgaa ttcccgtcat atccgctgag | 1380 |
| caataactag cataacccct tatacgttac at | 1412 |

<210> SEQ ID NO 35
<211> LENGTH: 12
<212> TYPE: PRT
<213> ORGANISM: Artificial sequence
<220> FEATURE:
<223> OTHER INFORMATION: Synthetic

<400> SEQUENCE: 35

Gly Ala Gly Ala Ser Arg Gly Gly Ser Gly Gly Ser
1               5                   10

<210> SEQ ID NO 36
<211> LENGTH: 146
<212> TYPE: DNA
<213> ORGANISM: Artificial sequence
<220> FEATURE:
<223> OTHER INFORMATION: Synthetic

<400> SEQUENCE: 36

| | |
|---|---|
| atcttagtat attagttaag tataagaagg agatatacat atgggggcgg gcgcatctcg | 60 |
| tggtggcagt ggtgggagcg gctaatgatc tcctctatga ggatccgctc gagtctggta | 120 |
| aagaaaccgc tgctgcgaaa tttgaa | 146 |

<210> SEQ ID NO 37
<211> LENGTH: 17
<212> TYPE: PRT
<213> ORGANISM: Artificial sequence
<220> FEATURE:
<223> OTHER INFORMATION: Synthetic

<400> SEQUENCE: 37

Gly Ala Gly Ala Gly Ala Tyr Arg Gly Gly Ser Gly Gly Ser Gly Gly
1               5                   10                  15

Ser

<210> SEQ ID NO 38
<211> LENGTH: 158
<212> TYPE: DNA
<213> ORGANISM: Artificial sequence

```
<220> FEATURE:
<223> OTHER INFORMATION: Synthetic

<400> SEQUENCE: 38
catcttagta tattagttaa gtataagaag gagatataca tatgggagcg ggtgcaggtg      60
cctatagagg tgggtcggga ggcagtggag gctcaggcta atgatctcct caatgagctc     120
gagtctggta aagaaaccgc tgctgcgaaa tttgaacg                             158

<210> SEQ ID NO 39
<211> LENGTH: 12
<212> TYPE: PRT
<213> ORGANISM: Artificial sequence
<220> FEATURE:
<223> OTHER INFORMATION: Synthetic

<400> SEQUENCE: 39

Gly Leu Ser Leu Ser Arg Gly Gly Ser Gly Gly Ser
1               5                   10

<210> SEQ ID NO 40
<211> LENGTH: 140
<212> TYPE: DNA
<213> ORGANISM: Artificial sequence
<220> FEATURE:
<223> OTHER INFORMATION: Synthetic

<400> SEQUENCE: 40
atcttagtat attagttaag tataagaagg agatatacat atggggctga gcctgtctcg      60
tggtggcagt ggtgggagcg gctaatgatc tcctcaatga gctcgagtct ggtaaagaaa     120
ccgctgctgc gaaatttgaa                                                 140

<210> SEQ ID NO 41
<211> LENGTH: 203
<212> TYPE: PRT
<213> ORGANISM: Artificial sequence
<220> FEATURE:
<223> OTHER INFORMATION: Synthetic

<400> SEQUENCE: 41

Met Gly Val Gly Val Pro Gly Val Gly Val Pro Gly Val Gly Val Pro
1               5                   10                  15

Gly Val Gly Val Pro Gly Val Gly Val Pro Gly Val Gly Val Pro Gly
                20                  25                  30

Val Gly Val Pro Gly Val Gly Val Pro Gly Val Gly Val Pro Gly Val
            35                  40                  45

Gly Val Pro Gly Val Gly Val Pro Gly Val Gly Val Pro Gly Val Gly
        50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro Gly
                100                 105                 110

Val Gly Val Pro Gly Val Gly Val Pro Gly Val Gly Val Pro Gly Val
            115                 120                 125

Gly Val Pro Gly Val Gly Val Pro Gly Val Gly Val Pro Gly Val Gly
        130                 135                 140

Val Pro Gly Val Gly Val Pro Gly Val Gly Val Pro Gly Val Gly Val
145                 150                 155                 160
```

-continued

Pro Gly Val Gly Val Pro Gly Val Gly Val Pro Gly Val Gly Val Pro
            165                 170                 175

Gly Val Gly Val Pro Gly Val Gly Val Pro Gly Val Gly Val Pro Gly
            180                 185                 190

Val Gly Val Pro Gly Val Gly Val Pro Gly Tyr
        195                 200

<210> SEQ ID NO 42
<211> LENGTH: 215
<212> TYPE: PRT
<213> ORGANISM: Artificial sequence
<220> FEATURE:
<223> OTHER INFORMATION: Synthetic

<400> SEQUENCE: 42

Met Gly Ala Gly Ala Ser Arg Gly Gly Ser Gly Gly Ser Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
            115                 120                 125

Gly Val Gly Val Pro Gly Val Gly Val Pro Gly Val Gly Val Pro Gly
        130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
            195                 200                 205

Gly Val Gly Val Pro Gly Tyr
        210                 215

<210> SEQ ID NO 43
<211> LENGTH: 220
<212> TYPE: PRT
<213> ORGANISM: Artificial sequence
<220> FEATURE:
<223> OTHER INFORMATION: Synthetic

<400> SEQUENCE: 43

Met Gly Ala Gly Ala Gly Ala Tyr Arg Gly Gly Ser Gly Gly Ser Gly
1               5                   10                  15

Gly Ser Gly Val Gly Val Pro Gly Val Gly Val Pro Gly Val Gly Val
            20                  25                  30

Pro Gly Val Gly Val Pro Gly Val Gly Val Pro Gly Val Gly Val Pro

```
                35                  40                  45
Gly Val Gly Val Pro Gly Val Gly Val Pro Gly Val Gly Val Pro Gly
             50                  55                  60
Val Gly Val Pro Gly Val Gly Val Pro Gly Val Gly Val Pro Gly Val
 65                  70                  75                  80
Gly Val Pro Gly Val Gly Val Pro Gly Val Gly Val Pro Gly Val Gly
                 85                  90                  95
Val Pro Gly Val Gly Val Pro Gly Val Gly Val Pro Gly Val Gly Val
            100                 105                 110
Pro Gly Val Gly Val Pro Gly Val Gly Val Pro Gly Val Gly Val Pro
            115                 120                 125
Gly Val Gly Val Pro Gly Val Gly Val Pro Gly Val Gly Val Pro Gly
            130                 135                 140
Val Gly Val Pro Gly Val Gly Val Pro Gly Val Gly Val Pro Gly Val
145                 150                 155                 160
Gly Val Pro Gly Val Gly Val Pro Gly Val Gly Val Pro Gly Val Gly
                165                 170                 175
Val Pro Gly Val Gly Val Pro Gly Val Gly Val Pro Gly Val Gly Val
            180                 185                 190
Pro Gly Val Gly Val Pro Gly Val Gly Val Pro Gly Val Gly Val Pro
            195                 200                 205
Gly Val Gly Val Pro Gly Val Gly Val Pro Gly Tyr
            210                 215                 220

<210> SEQ ID NO 44
<211> LENGTH: 215
<212> TYPE: PRT
<213> ORGANISM: Artificial sequence
<220> FEATURE:
<223> OTHER INFORMATION: Synthetic

<400> SEQUENCE: 44

Met Gly Leu Ser Leu Ser Arg Gly Gly Ser Gly Gly Ser Gly Val Gly
 1               5                  10                  15
Val Pro Gly Val Gly Val Pro Gly Val Gly Val Pro Gly Val Gly Val
             20                  25                  30
Pro Gly Val Gly Val Pro Gly Val Gly Val Pro Gly Val Gly Val Pro
             35                  40                  45
Gly Val Gly Val Pro Gly Val Gly Val Pro Gly Val Gly Val Pro Gly
             50                  55                  60
Val Gly Val Pro Gly Val Gly Val Pro Gly Val Gly Val Pro Gly Val
 65                  70                  75                  80
Gly Val Pro Gly Val Gly Val Pro Gly Val Gly Val Pro Gly Val Gly
                 85                  90                  95
Val Pro Gly Val Gly Val Pro Gly Val Gly Val Pro Gly Val Gly Val
            100                 105                 110
Pro Gly Val Gly Val Pro Gly Val Gly Val Pro Gly Val Gly Val Pro
            115                 120                 125
Gly Val Gly Val Pro Gly Val Gly Val Pro Gly Val Gly Val Pro Gly
            130                 135                 140
Val Gly Val Pro Gly Val Gly Val Pro Gly Val Gly Val Pro Gly Val
145                 150                 155                 160
Gly Val Pro Gly Val Gly Val Pro Gly Val Gly Val Pro Gly Val Gly
                165                 170                 175
Val Pro Gly Val Gly Val Pro Gly Val Gly Val Pro Gly Val Gly Val
```

```
            180                 185                 190
Pro Gly Val Gly Val Pro Gly Val Gly Val Pro Gly Val Gly Val Pro
        195                 200                 205

Gly Val Gly Val Pro Gly Tyr
        210                 215

<210> SEQ ID NO 45
<211> LENGTH: 218
<212> TYPE: PRT
<213> ORGANISM: Artificial sequence
<220> FEATURE:
<223> OTHER INFORMATION: Synthetic

<400> SEQUENCE: 45

Met Gly Ala Gly Ala Ser Arg Gly Gly Ser Gly Gly Ser Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
                100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
                180                 185                 190

Pro Gly Val Gly Val Pro Gly Val Gly Val Pro Gly Val Gly Val Pro
        195                 200                 205

Gly Val Gly Val Pro Gly Gly Lys Gly Tyr
        210                 215

<210> SEQ ID NO 46
<211> LENGTH: 223
<212> TYPE: PRT
<213> ORGANISM: Artificial sequence
<220> FEATURE:
<223> OTHER INFORMATION: Synthetic

<400> SEQUENCE: 46

Met Gly Ala Gly Ala Gly Ala Tyr Arg Gly Gly Ser Gly Gly Ser Gly
1               5                   10                  15

Gly Ser Gly Val Gly Val Pro Gly Val Gly Val Pro Gly Val Gly Val
                20                  25                  30

Pro Gly Val Gly Val Pro Gly Val Gly Val Pro Gly Val Gly Val Pro
        35                  40                  45
```

Gly Val Gly Val Pro Gly Val Gly Val Pro Gly Val Gly Val Pro Gly
            50                  55                  60

Val Gly Val Pro Gly Val Gly Val Pro Gly Val Gly Val Pro Gly Val
 65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
        130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Gly Lys Gly Tyr
        210                 215                 220

<210> SEQ ID NO 47
<211> LENGTH: 218
<212> TYPE: PRT
<213> ORGANISM: Artificial sequence
<220> FEATURE:
<223> OTHER INFORMATION: Synthetic

<400> SEQUENCE: 47

Met Gly Leu Ser Leu Ser Arg Gly Gly Ser Gly Gly Ser Val Gly
 1               5                  10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Val
 65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
        130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

```
Pro Gly Val Gly Val Pro Gly Val Gly Val Pro Gly Val Gly Val Pro
            195                 200                 205
Gly Val Gly Val Pro Gly Lys Gly Tyr
    210                 215

<210> SEQ ID NO 48
<211> LENGTH: 6
<212> TYPE: PRT
<213> ORGANISM: Artificial sequence
<220> FEATURE:
<223> OTHER INFORMATION: Synthetic

<400> SEQUENCE: 48

Gly Ala Gly Ala Ser Arg
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic

<400> SEQUENCE: 49

Gly Ala Gly Ala Gly Ala Tyr Arg
1               5

<210> SEQ ID NO 50
<211> LENGTH: 6
<212> TYPE: PRT
<213> ORGANISM: Artificial sequence
<220> FEATURE:
<223> OTHER INFORMATION: Synthetic

<400> SEQUENCE: 50

Gly Leu Ser Leu Ser Arg
1               5

<210> SEQ ID NO 51
<211> LENGTH: 202
<212> TYPE: PRT
<213> ORGANISM: Artificial sequence
<220> FEATURE:
<223> OTHER INFORMATION: Synthetic

<400> SEQUENCE: 51

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
            35                  40                  45
Val Pro Gly Val Gly Val Pro Gly Val Gly Val Pro Gly Val Gly Val
        50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
                100                 105                 110
Gly Val Pro Gly Val Gly Val Pro Gly Val Gly Val Pro Gly Val Gly
            115                 120                 125
```

```
Val Pro Gly Val Gly Val Pro Gly Val Gly Val Pro Gly Val Gly Val
    130             135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
            180                 185                 190
Gly Val Pro Gly Val Gly Val Pro Gly Tyr
        195                 200

<210> SEQ ID NO 52
<211> LENGTH: 200
<212> TYPE: PRT
<213> ORGANISM: Artificial sequence
<220> FEATURE:
<223> OTHER INFORMATION: Synthetic

<400> SEQUENCE: 52

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
            20                  25                  30
Gly Val Pro Gly Val Gly Val Pro Gly Val Gly Val Pro Gly Val Gly
        35                  40                  45
Val Pro Gly Val Gly Val Pro Gly Val Gly Val Pro Gly Val Gly Val
    50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
            100                 105                 110
Gly Val Pro Gly Val Gly Val Pro Gly Val Gly Val Pro Gly Val Gly
        115                 120                 125
Val Pro Gly Val Gly Val Pro Gly Val Gly Val Pro Gly Val Gly Val
    130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
            180                 185                 190
Gly Val Pro Gly Val Gly Val Pro
        195                 200
```